United States Patent
Liu et al.

(10) Patent No.: US 11,767,323 B2
(45) Date of Patent: Sep. 26, 2023

(54) TRICYCLIC PYRIDONE COMPOUNDS AS JAK2 V617F INHIBITORS

(71) Applicant: Incyte Corporation, Wilmington, DE (US)

(72) Inventors: Kai Liu, Chadds Ford, PA (US); Onur Atasoylu, Wilmington, DE (US); Yu Bai, Claymont, DE (US); Andrew W. Buesking, Wilmington, DE (US); Leah C. Konkol, Newark, DE (US); Cheng-Tsung Lai, Wilmington, DE (US); Song Mei, Wilmington, DE (US); Jun Pan, Media, PA (US); Liangxing Wu, Wilmington, DE (US); Wenqing Yao, Chadds Ford, PA (US)

(73) Assignee: Incyte Corporation, Wilmington, DE (US)

(*) Notice: Subject to any disclaimer, the term of this patent is extended or adjusted under 35 U.S.C. 154(b) by 140 days.

(21) Appl. No.: 17/365,686

(22) Filed: Jul. 1, 2021

(65) Prior Publication Data
US 2022/0002299 A1    Jan. 6, 2022

Related U.S. Application Data

(60) Provisional application No. 63/047,509, filed on Jul. 2, 2020.

(51) Int. Cl.
 *C07D 471/14* (2006.01)
 *A61K 31/437* (2006.01)
 *C07D 519/00* (2006.01)

(52) U.S. Cl.
 CPC ......... *C07D 471/14* (2013.01); *C07D 519/00* (2013.01)

(58) Field of Classification Search
 CPC .. C07D 471/14; C07D 471/16; A61K 31/437; A61K 31/4375
 USPC ............................................ 546/82; 514/293
 See application file for complete search history.

(56) References Cited

U.S. PATENT DOCUMENTS

| | | | |
|---|---|---|---|
| 4,698,341 A | 10/1987 | Satzinger et al. | |
| 6,339,099 B1 | 1/2002 | Lam et al. | |
| 6,951,865 B2 | 10/2005 | Hibi et al. | |
| 7,429,456 B2 | 9/2008 | Vainchenker et al. | |
| 7,781,199 B2 | 8/2010 | Vainchenker et al. | |
| 7,879,844 B2 | 2/2011 | Inoue et al. | |
| 8,163,767 B2 | 4/2012 | Inoue et al. | |
| 8,524,867 B2 | 9/2013 | Bernett et al. | |
| 8,637,235 B2 | 1/2014 | Vainchenker et al. | |
| 8,785,639 B2 | 7/2014 | Wishart et al. | |
| 8,852,931 B2 | 10/2014 | Vainchenker et al. | |
| 9,115,133 B2* | 8/2015 | Barawkar | A61P 11/00 |
| 9,233,985 B2 | 1/2016 | Van Zandt et al. | |
| 9,321,730 B2 | 4/2016 | Chan et al. | |
| 9,493,419 B2 | 11/2016 | Tang et al. | |
| 10,065,974 B2 | 9/2018 | Sjogren et al. | |
| 10,155,987 B2 | 12/2018 | Sattler et al. | |
| 10,287,303 B2 | 4/2019 | Sjogren et al. | |
| 10,377,759 B2 | 8/2019 | Yamamoto et al. | |
| 2003/0139431 A1 | 7/2003 | Kawakami et al. | |
| 2004/0209902 A1 | 10/2004 | Lin et al. | |
| 2005/0182060 A1 | 8/2005 | Kelly et al. | |
| 2006/0004043 A1 | 1/2006 | Bhagwat et al. | |
| 2007/0049610 A1 | 3/2007 | Dillon et al. | |
| 2007/0161670 A1 | 7/2007 | Staab et al. | |
| 2008/0004297 A1 | 1/2008 | Cai et al. | |
| 2008/0004318 A1 | 1/2008 | Chelliah et al. | |
| 2008/0188467 A1 | 8/2008 | Wong et al. | |
| 2008/0280879 A1 | 11/2008 | Brickner et al. | |
| 2008/0293739 A1 | 11/2008 | Trede | |
| 2009/0246198 A1 | 10/2009 | Dong et al. | |
| 2010/0105661 A1 | 4/2010 | Shirakami et al. | |
| 2010/0160355 A1 | 6/2010 | DeGoey et al. | |
| 2011/0182812 A1 | 7/2011 | Szardenings et al. | |
| 2011/0269740 A1 | 11/2011 | Sunny et al. | |
| 2011/0313003 A1 | 12/2011 | Shi et al. | |
| 2012/0065188 A1 | 3/2012 | Brickner et al. | |
| 2012/0165370 A1 | 7/2012 | Tang et al. | |
| 2012/0214842 A1 | 8/2012 | Donello et al. | |
| 2012/0282233 A1 | 11/2012 | Rolshausen et al. | |
| 2013/0267521 A1 | 10/2013 | Castro et al. | |
| 2013/0281399 A1 | 10/2013 | McLure et al. | |
| 2013/0302248 A1 | 11/2013 | Gangadharmath et al. | |
| 2014/0142102 A1 | 4/2014 | Fairfax et al. | |
| 2014/0225082 A1 | 8/2014 | Park et al. | |
| 2014/0249204 A1 | 9/2014 | Vainchenker et al. | |
| 2014/0286964 A1 | 9/2014 | Hubbard et al. | |
| 2014/0288048 A1 | 9/2014 | Castro et al. | |
| 2016/0016914 A1 | 1/2016 | Ladziata et al. | |
| 2016/0118600 A1 | 4/2016 | Kim et al. | |

(Continued)

FOREIGN PATENT DOCUMENTS

| | | |
|---|---|---|
| CN | 102838600 | 12/2012 |
| CN | 102838601 | 12/2012 |

(Continued)

OTHER PUBLICATIONS

Atzrodt et al., "The Renaissance of H/D Exchange," Angew Chem Int Ed., 2007, 7744-7765.
Baxter et al., "Acquired mutation of the tyrosine kinase JAK2 in human myeloproliferative disorders," Lancet., 2005, 365:1054-1061.
Bennett et al., "Proposals for the classification of the myelodysplastic syndromes," Br J Haematol., 1982, 51:189-199.
Berge et al., "Pharmaceutical Salts," Journal of Pharmaceutical Science, 1977, 66:1-19 pages.

(Continued)

*Primary Examiner* — Charanjit Aulakh
(74) *Attorney, Agent, or Firm* — Fish & Richardson P.C.

(57) ABSTRACT

The present application provides tricyclic pyridone compounds that modulate the activity of the V617F variant of JAK2, which are useful in the treatment of various diseases, including cancer.

37 Claims, No Drawings
Specification includes a Sequence Listing.

(56) References Cited

U.S. PATENT DOCUMENTS

| | | | |
|---|---|---|---|
| 2016/0220592 A1 | 8/2016 | Franz et al. |
| 2017/0107216 A1 | 4/2017 | Wu et al. |
| 2017/0121346 A1 | 5/2017 | Sprengler et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0226095 A1 | 8/2017 | Tazi et al. |
| 2017/0298040 A1 | 10/2017 | Bennett et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0031557 A1 | 2/2018 | Scherrer et al. |
| 2018/0086719 A1 | 3/2018 | Chandrasekhar et al. |
| 2018/0104245 A1 | 4/2018 | Hansen |
| 2018/0179159 A1 | 6/2018 | Becknell et al. |
| 2018/0237797 A1 | 8/2018 | Loh |
| 2019/0152913 A1 | 5/2019 | Becknell et al. |
| 2019/0152988 A1 | 5/2019 | Sprengler et al. |
| 2019/0256492 A1 | 8/2019 | Tu et al. |
| 2021/0395251 A1 | 12/2021 | Shepard et al. |
| 2021/0395257 A1 | 12/2021 | Yu et al. |
| 2022/0064165 A1 | 3/2022 | Liu et al. |
| 2022/0169649 A1 | 6/2022 | Ai et al. |
| 2022/0213108 A1 | 7/2022 | Buesking et al. |
| 2022/0281887 A1 | 9/2022 | Shepard et al. |

FOREIGN PATENT DOCUMENTS

| | | |
|---|---|---|
| CN | 104311426 | 1/2015 |
| CN | 104725249 | 6/2015 |
| CN | 105461714 | 4/2016 |
| CN | 105481765 | 4/2016 |
| CN | 105732591 | 7/2016 |
| CN | 109575022 | 4/2019 |
| CN | 109608504 | 4/2019 |
| CN | 111484480 | 8/2020 |
| EP | 0329012 | 8/1989 |
| EP | 0481448 | 4/1992 |
| EP | 0652218 | 5/1995 |
| EP | 1692281 | 10/2005 |
| EP | 2309567 | 10/2010 |
| EP | 3277293 | 2/2018 |
| EP | 3277820 | 2/2018 |
| EP | 3578555 | 12/2019 |
| FR | 2996129 | 4/2014 |
| JP | 62209062 | 9/1987 |
| JP | 07089957 | 4/1995 |
| JP | 2000123973 | 4/2000 |
| JP | 2003107641 | 4/2003 |
| JP | 2004196702 | 7/2004 |
| KR | 20140111166 | 9/2014 |
| KR | 20150002266 | 1/2015 |
| KR | 20160123112 | 10/2016 |
| KR | 20170003469 | 6/2017 |
| WO | WO 93/17681 | 9/1993 |
| WO | WO 93/17682 | 9/1993 |
| WO | WO 95/18127 | 7/1995 |
| WO | WO 97/34893 | 9/1997 |
| WO | WO 97/47601 | 12/1997 |
| WO | WO 98/16184 | 4/1998 |
| WO | WO 98/40373 | 9/1998 |
| WO | WO 99/61444 | 12/1999 |
| WO | WO 99/64400 | 12/1999 |
| WO | WO 2000/041695 | 7/2000 |
| WO | WO 2000/067754 | 11/2000 |
| WO | WO 2000/068230 | 11/2000 |
| WO | WO 2001/023389 | 4/2001 |
| WO | WO 2001/042247 | 6/2001 |
| WO | WO 2001/047891 | 7/2001 |
| WO | WO 2001/058899 | 8/2001 |
| WO | WO 2001/070229 | 9/2001 |
| WO | WO 2002/000196 | 1/2002 |
| WO | WO 2002/091830 | 11/2002 |
| WO | WO 2003/062209 | 7/2003 |
| WO | WO 2003/074045 | 9/2003 |
| WO | WO 2004/014866 | 2/2004 |
| WO | WO 2004/024693 | 3/2004 |
| WO | WO 2004/030635 | 4/2004 |
| WO | WO 2004/031161 | 4/2004 |
| WO | WO 2004/039806 | 5/2004 |
| WO | WO 2004/055004 | 7/2004 |
| WO | WO 2004/080463 | 9/2004 |
| WO | WO 2005/003100 | 1/2005 |
| WO | WO 2005/007658 | 1/2005 |
| WO | WO 2005/009967 | 2/2005 |
| WO | WO 2005/028478 | 3/2005 |
| WO | WO 2005/061460 | 7/2005 |
| WO | WO 2005/072412 | 8/2005 |
| WO | WO 2005/080377 | 9/2005 |
| WO | WO 2005/082367 | 9/2005 |
| WO | WO 2005/110410 | 11/2005 |
| WO | WO 2005/112932 | 12/2005 |
| WO | WO 2005/117890 | 12/2005 |
| WO | WO 2005/121138 | 12/2005 |
| WO | WO 2006/021448 | 3/2006 |
| WO | WO 2006/032470 | 3/2006 |
| WO | WO 2006/039718 | 4/2006 |
| WO | WO 2006/045096 | 4/2006 |
| WO | WO 2006/045827 | 5/2006 |
| WO | WO 2006/065842 | 6/2006 |
| WO | WO 2006/072828 | 7/2006 |
| WO | WO 2006/074147 | 7/2006 |
| WO | WO 2006/108107 | 10/2006 |
| WO | WO 2006/122156 | 11/2006 |
| WO | WO 2007/002781 | 1/2007 |
| WO | WO 2007/007919 | 1/2007 |
| WO | WO 2007/016525 | 2/2007 |
| WO | WO 2007/022946 | 3/2007 |
| WO | WO 2007/038209 | 4/2007 |
| WO | WO 2007/047653 | 4/2007 |
| WO | WO 2007/051062 | 5/2007 |
| WO | WO 2007/076092 | 5/2007 |
| WO | WO 2007/077949 | 7/2007 |
| WO | WO 2007/110868 | 10/2007 |
| WO | WO 2007/112347 | 10/2007 |
| WO | WO 2007/113565 | 10/2007 |
| WO | WO 2007/125405 | 11/2007 |
| WO | WO 2007/133637 | 11/2007 |
| WO | WO 2007/136465 | 11/2007 |
| WO | WO 2007/140222 | 12/2007 |
| WO | WO 2007/147217 | 12/2007 |
| WO | WO 2008/000409 | 1/2008 |
| WO | WO 2008/005956 | 1/2008 |
| WO | WO 2008/007127 | 1/2008 |
| WO | WO 2008/011109 | 1/2008 |
| WO | WO 2008/011174 | 1/2008 |
| WO | WO 2008/021924 | 2/2008 |
| WO | WO 2008/024977 | 2/2008 |
| WO | WO 2008/046919 | 4/2008 |
| WO | WO 2008/060090 | 5/2008 |
| WO | WO 2008/064107 | 5/2008 |
| WO | WO 2008/079965 | 7/2008 |
| WO | WO 2008/084861 | 7/2008 |
| WO | WO 2008/092231 | 8/2008 |
| WO | WO 2008/112217 | 9/2008 |
| WO | WO 2008/113558 | 9/2008 |
| WO | WO 2008/124083 | 10/2008 |
| WO | WO 2008/135524 | 11/2008 |
| WO | WO 2008/151184 | 12/2008 |
| WO | WO 2009/024095 | 2/2009 |
| WO | WO 2009/042970 | 4/2009 |
| WO | WO 2009/114512 | 9/2009 |
| WO | WO 2010/006130 | 1/2010 |
| WO | WO 2010/026771 | 3/2010 |
| WO | WO 2010/039518 | 4/2010 |
| WO | WO 2010/042684 | 4/2010 |
| WO | WO 2010/077947 | 7/2010 |
| WO | WO 2010/078229 | 7/2010 |
| WO | WO 2010/080537 | 7/2010 |
| WO | WO 2010/101949 | 9/2010 |
| WO | WO 2010/106436 | 9/2010 |
| WO | WO 2010/107765 | 9/2010 |
| WO | WO 2010/107768 | 9/2010 |

(56) References Cited

FOREIGN PATENT DOCUMENTS

| | | |
|---|---|---|
| WO | WO 2010/123975 | 10/2010 |
| WO | WO 2010/125350 | 11/2010 |
| WO | WO 2010/129816 | 11/2010 |
| WO | WO 2010/141062 | 12/2010 |
| WO | WO 2010/143168 | 12/2010 |
| WO | WO 2010/143169 | 12/2010 |
| WO | WO 2010/143170 | 12/2010 |
| WO | WO 2011/004276 | 1/2011 |
| WO | WO 2011/022439 | 2/2011 |
| WO | WO 2011/028864 | 3/2011 |
| WO | WO 2011/047432 | 4/2011 |
| WO | WO 2011/050245 | 4/2011 |
| WO | WO 2011/053861 | 5/2011 |
| WO | WO 2011/068899 | 6/2011 |
| WO | WO 2011/072275 | 6/2011 |
| WO | WO 2011/075630 | 6/2011 |
| WO | WO 2011/078143 | 6/2011 |
| WO | WO 2011/078369 | 6/2011 |
| WO | WO 2011/086053 | 7/2011 |
| WO | WO 2011/097717 | 8/2011 |
| WO | WO 2011/103557 | 8/2011 |
| WO | WO 2011/112687 | 9/2011 |
| WO | WO 2011/123693 | 10/2011 |
| WO | WO 2011/137428 | 11/2011 |
| WO | WO 2011/146882 | 11/2011 |
| WO | WO 2012/061696 | 5/2012 |
| WO | WO 2012/066578 | 5/2012 |
| WO | WO 2012/078902 | 6/2012 |
| WO | WO 2012/085176 | 6/2012 |
| WO | WO 2012/089828 | 7/2012 |
| WO | WO 2012/097479 | 7/2012 |
| WO | WO 2012/116237 | 8/2012 |
| WO | WO 2012/127506 | 9/2012 |
| WO | WO 2013/007765 | 1/2013 |
| WO | WO 2013/033093 | 3/2013 |
| WO | WO 2013/033268 | 3/2013 |
| WO | WO 2013/033270 | 3/2013 |
| WO | WO 2013/033981 | 3/2013 |
| WO | WO 2013/049352 | 4/2013 |
| WO | WO 2013/062987 | 5/2013 |
| WO | WO 2013/067036 | 5/2013 |
| WO | WO 2013/086229 | 6/2013 |
| WO | WO 2013/156869 | 10/2013 |
| WO | WO 2013/158928 | 10/2013 |
| WO | WO 2013/167653 | 11/2013 |
| WO | WO 2013/175281 | 11/2013 |
| WO | WO 2013/191112 | 12/2013 |
| WO | WO 2014/018891 | 1/2014 |
| WO | WO 2014/023377 | 2/2014 |
| WO | WO 2014/051653 | 4/2014 |
| WO | WO 2014/074580 | 5/2014 |
| WO | WO 2014/087165 | 6/2014 |
| WO | WO 2014/120764 | 8/2014 |
| WO | WO 2014/203152 | 12/2014 |
| WO | WO 2014/204263 | 12/2014 |
| WO | WO 2015/001518 | 1/2015 |
| WO | WO 2015/009812 | 1/2015 |
| WO | WO 2015/025228 | 2/2015 |
| WO | WO 2015/036560 | 3/2015 |
| WO | WO 2015/049022 | 4/2015 |
| WO | WO 2015/086523 | 6/2015 |
| WO | WO 2015/124063 | 8/2015 |
| WO | WO 2015/144001 | 10/2015 |
| WO | WO 2015/168079 | 11/2015 |
| WO | WO 2016/009076 | 1/2016 |
| WO | WO 2016/116900 | 7/2016 |
| WO | WO 2016/123627 | 8/2016 |
| WO | WO 2016/128465 | 8/2016 |
| WO | WO 2016/160860 | 10/2016 |
| WO | WO 2016/190847 | 12/2016 |
| WO | WO 2016/197027 | 12/2016 |
| WO | WO 2017/003723 | 1/2017 |
| WO | WO 2017/004134 | 1/2017 |
| WO | WO 2017/029601 | 2/2017 |
| WO | WO 2017/059319 | 4/2017 |
| WO | WO 2017/072039 | 5/2017 |
| WO | WO 2017/072283 | 5/2017 |
| WO | WO 2017/075394 | 5/2017 |
| WO | WO 2017/090002 | 6/2017 |
| WO | WO 2017/103931 | 6/2017 |
| WO | WO 2017/205538 | 11/2017 |
| WO | WO 2017/223452 | 12/2017 |
| WO | WO 2018/009622 | 1/2018 |
| WO | WO 2018/046933 | 3/2018 |
| WO | WO 2018/057805 | 3/2018 |
| WO | WO 2018/068017 | 4/2018 |
| WO | WO 2018/083098 | 5/2018 |
| WO | WO 2018/112382 | 6/2018 |
| WO | WO 2018/140512 | 8/2018 |
| WO | WO 2018/140600 | 8/2018 |
| WO | WO 2018/144478 | 8/2018 |
| WO | WO 2018/204176 | 11/2018 |
| WO | WO 2018/204765 | 11/2018 |
| WO | WO 2018/222901 | 12/2018 |
| WO | WO 2018/231745 | 12/2018 |
| WO | WO 2018/237370 | 12/2018 |
| WO | WO 2019/060860 | 3/2019 |
| WO | WO 2019/070492 | 4/2019 |
| WO | WO 2019/129213 | 7/2019 |
| WO | WO 2019/135920 | 7/2019 |
| WO | WO 2019/177975 | 9/2019 |
| WO | WO 2019/201283 | 10/2019 |
| WO | WO 2019/214546 | 11/2019 |
| WO | WO 2021/018012 | 2/2021 |

OTHER PUBLICATIONS

Blom et al., "Preparative LC-MS Purification: Improved Compound Specific Method Optimization," J Combi Chem., 2004, 2004, 6:874-883.

Blom et al., "Optimizing Preparative LC-MS Configurations and Methods for Parallel Synthesis Purification," J Combi Chem., 2003, 5:670.

Blom et al., "Two-Pump at Column Dilution Configuration for Preparative LC-MS," J Combi Chem., 2002, 4:295.

Dommaraju et al., "An efficient catalyst- free chemoselective multicomponent reaction for the synthesis of pyrimidine functionalized pyrrolo-annelated derivatives," RSC Adv., Jan. 1, 2015, 5:24327-24335.

Eisenhauer et al., "New response evaluation criteria in solid tumours: Revised RECIST guideline (version 1.1)," European Journal of Cancer, Jan. 2009, 45(2):228-247.

Harris et al., "World Health Organization classification of neoplastic diseases of the hematopoietic and lymphoid tissues: report of the Clinical Advisory Committee meeting—Airlie House, Virginia, Nov. 1997," J Clin Oncol., 1999, 17:3835-3849.

Hart et al., "Structure-Based Design of Selective Janus Kinase 2 Imidazo[4,5-d]pyrrolo[2,3-b]pyridine Inhibitors," ACS Med Chem Lett., Aug. 13, 2015, 6(8):845-849.

International Search Report and Written Opinion in International Appln. No. PCT/US2021/037870, dated Aug. 13, 2021, 13 pages.

International Search Report and Written Opinion in International Appln. No. PCT/US2021/037877, dated Aug. 13, 2021, 10 pages.

International Search Report and Written Opinion in International Appln. No. PCT/US2021/040182, dated Sep. 22, 2021, 12 pages.

International Search Report and Written Opinion in International Appln. No. PCT/US2021/040185, dated Sep. 22, 2021, 15 pages.

International Search Report and Written Opinion in International Appln. No. PCT/US2021/047687, dated Nov. 19, 2021, 16 pages.

International Search Report and Written Opinion in International Appln. No. PCT/US2021/064295, dated Mar. 17, 2022, 15 pages.

International Search Report and Written Opinion in International Appln. No. PCT/US2022/017654, dated May 30, 2022, 22 pages.

James et al., "A unique clonal JAK2 mutation leading to constitutive signalling causes polycythaemia vera," Nature, 2005, 434:1144-1148.

Jisha et al., "Exploration of 3,6-dihydroimidazo(4,5-d)pyrrolo(2,3-b)pyridin-2(1H)-one derivatives as JAK inhibitors using various in silico techniques," In Silico Pharmacology, 2017, 5(1):1-23.

(56) References Cited

OTHER PUBLICATIONS

Kerekes et al., "Aurora kinase inhibitors based on the imidazo[1,2-a]pyrazine core: fluorine and deuterium incorporation improve oral absorption and exposure," J Med Chem., 2011, 54:201-210.
Khalaf et al., "Structure-based design and synthesis of antiparasitic pyrrolopyrimidines targeting pteridine reductase 1," J Med Chem., Jul. 9, 2014, 57(15):6479-6494.
Kralovics et al., "A gain-of-function mutation of JAK2 in myeloproliferative disorders," N Engl J Med., 2005, 352:1779-1790.
Kulagawski et al., "Identification of imidazo-pyrrolopyridines as novel and potent JAK1 inhibitors," J Med Chem., 2012, 55(12):5901-5921.
Labadie et al., "Design and evaluation of novel 8-oxo-pyridopyrimidine Jak1/2 inhibitors," Bioorg Med Chem Lett., Nov. 2013, 23(21):5923-5930.
Levine et al., "Activating mutation in the tyrosine kinase JAK2 in polycythemia vera, essential thrombocythemia, and myeloid metaplasia with myelofibrosis," Cancer Cell., 2005, 7:387-397.
Ma et al., "Mutation Profile of JAK2 Transcripts in Patients with Chronic Myeloproliferative Neoplasias," J. Mol. Diagn., Jan. 2009, 11(1):49-53.
Remington's Pharmaceutical Sciences, 17th ed., Mack Publishing Company, Easton, Pa., 1985, p. 1418.
STN Search Report, Conducted Dec. 10, 2019, 379 pages.
STN Search Report, Conducted Dec. 2020, 11 pages.
STN Search Report, Conducted Jun. 19, 2021, 236 pages.
STN Search Report, Conducted Jun. 2019, 316 pages.
STN Search Report, Conducted Oct. 2019, 14 pages.
STN Search Report, Conducted Sep. 2019, 236 pages.
STN Search Report, Conducted Sep. 2019, 5 pages.
Vardiman et al., "The 2008 revision of the World Health Organization (WHO) classification of myeloid neoplasms and acute leukemia: rationale and important changes," Blood 2009, 114:937-951.
Vardiman et al., "The World Health Organization (WHO) classification of the myeloid neoplasms," Blood 2002, 100:2292-2302.
Xu et al., "Design, synthesis and biological evaluation of deuterated nintedanib for improving pharmacokinetic properties," J Label Compd Radiopharm., 2015, 58:308-312.
Yamagishi et al., "Discovery of 3,6-dihydroimidazo[4,5-d]pyrrolo[2,3-b]pyridin-2(1H)-one derivatives as novel JAK inhibitors," Biorg & Med Chem., 2015, 23(15):4846-4859.
Yamagishi et al., "Discovery of tricyclic dipyrrolopyridine derivatives as novel JAK inhibitors," Biorg & Med Chem, 2017, 25(20):5311-5326.
Yang et al., "Three-component reaction for synthesis of 2-amino-6-aryl-5-(phenylamino)-3,7-dihydro-4H-pyrrolo[2,3-d]pyrimidin-4-one derivatives in water," J Hetero Chem., Sep. 2020, 57(9):3271-3278.
Zak et al., "Discovery and optimization of C-2 methyl imidazopyrrolopyridines as potent and orally bioavailable JAK1 inhibitors with selectivity over JAK2," J Med Chem., 2012, 55(13):6176-6193.
International Preliminary Report on Patentability in International Application No. PCT/US2021/037870, dated Dec. 29, 2022, 8 pages.
International Preliminary Report on Patentability in International Application No. PCT/US2021/037877, dated Dec. 29, 2022, 8 pages.
International Preliminary Report on Patentability in International Application No. PCT/US2021/040182, dated Jan. 12, 2023, 7 pages.
International Preliminary Report on Patentability in International Application No. PCT/US2021/040185, dated Jan. 12, 2023, 8 pages.
International Preliminary Report on Patentability in International Application No. PCT/US2021/047687, dated Mar. 9, 2023, 8 pages.
Scott et al., "JAK2 Exon 12 Mutations in Polycythemia Vera and Idiopathic Erythrocytosis," The New England Journal of Medicine, Feb. 1, 2007, 356:459-68.
Ceesay et al., "The JAK2 V617F mutation is rare in RARS but common in RARS-T," Leukemia, 2006, 20:2060-2061.
Leroy et al., "Differential effect of inhibitory strategies of the V617 mutant of JAK2 on cytokine receptor signaling," Journal of Allergy and Clinical Immunology, Jul. 2019, 144(1):224-235.
Vainchecker et al., "JAK inhibitors for the treatment of myeloproliferative neoplasms and other disorders," F1000Research., 2018, 7:82.
Wilmes et al., "Mechanism of homodimeric cytokine receptor activation and dysregulation by oncogenic mutations," Science, 2020, 367:643-652.
Woods et al., "Activation of JAK/STAT Signaling in Megakaryocytes Sustains Myeloproliferation In Vivo," Clin Cancer Res., 2019, 25(19):5901-5912.
Brunning et al., "Myelodysplastic syndrome/neoplasms," in Chapter 5, Swerdlow, et al, eds. WHO Classification of Tumours of Haematopoietic and Lymphoid Tissues., 4th edition, 2008, 21 pages.
Quiroga et al., "Generation of pyrrolo[2,3-d]pyrimidines. Unexpected products in the multicomponent reaction of 6-aminopyrimidines, dimedone, and arylglyoxal," Tetrahedron Letters, Oct. 2010, 51(41):5443-5447.
Dommaraju et al., "An efficient catalyst-free chemoselective multicomponent reaction for the synthesis of pyrimidine functionalized pyrrolo-annelated derivatives," Electronic Supplementary Information for RSC Adv., Jan. 1, 2015, 64 pages.

\* cited by examiner

TRICYCLIC PYRIDONE COMPOUNDS AS JAK2 V617F INHIBITORS

SEQUENCE LISTING

This application contains a Sequence Listing that has been submitted electronically as an ASCII text file named Sequence Listing. The ASCII text file, created on Aug. 24, 2021, is 4 kilobytes in size. The material in the ASCII text file is hereby incorporated by reference in its entirety.

TECHNICAL FIELD

The present invention provides tricyclic pyridone compounds that modulate the activity of the V617F variant of JAK2 and are useful in the treatment of diseases related to the V617F variant of JAK2, including cancer.

BACKGROUND

Janus kinase (JAK) 2 plays pivotal roles in signaling by several cytokine receptors. The mutant JAK2 V617F is the most common molecular event associated with myeloproliferative neoplasms. Selective targeting of the JAK2 V617F mutant may be useful for treating various pathologies, while sparing essential JAK2 functions. This application is directed to this need and others.

SUMMARY

The present invention relates to, inter alia, compounds of Formula I:

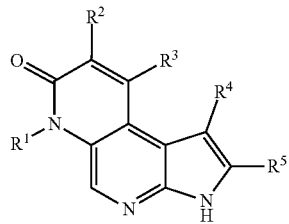

I or pharmaceutically acceptable salts thereof, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of the V617F variant of JAK2 kinase comprising contacting the kinase with a compound of Formula I, or a pharmaceutically acceptable salt thereof.

The present invention further provides methods of treating a disease or a disorder associated with expression or activity of the V617F variant of JAK2 kinase in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

The present application provides compounds of Formula I:

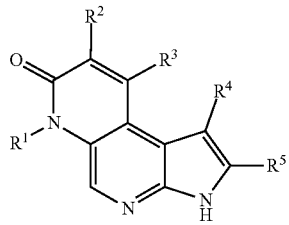

I or pharmaceutically acceptable salts thereof, wherein:

$R^1$ is selected from H, D, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^M$ substituents;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)R^{b2}$, $NR^{c2}S(O)NR^{c2}R^{d2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, and $OS(O)_2R^{b2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloal-

3 kyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)R^{b21}$, $NR^{c21}S(O)NR^{c21}R^{d21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloal-

4 kyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, 4, 5, 6, 7, or 8 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, 4, 5, 6, 7, or 8 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $C(=NR^{e22})NR^{c22}R^{d22}$, $NR^{c22}C(=NR^{e22})NR^{c22}R^{d22}$, $NR^{c22}C(=NR^{e22})R^{b22}$, $NR^{c22}S(O)R^{b22}$, $NR^{c22}S(O)NR^{c22}R^{d22}$, $NR^{c22}S(O)_2R^{b22}$, $NR^{c22}S(O)(=NR^{e22})R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, $OS(O)(=NR^{e22})R^{b22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, 4, 5, 6, 7, or 8 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, 4, 5, 6, 7, or 8 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, 4, 5, 6, 7, or 8 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a23}$, SR$^{a23}$, NHOR$^{a23}$, C(O)R$^{b23}$, C(O)NR$^{c23}$R$^{d23}$, C(O)NR$^{c23}$(OR$^{a23}$), C(O)OR$^{a23}$, OC(O)R$^{b23}$, OC(O)NR$^{c23}$R$^{d23}$, NR$^{c23}$R$^{d23}$, NR$^{c23}$NR$^{c23}$R$^{d23}$, NR$^{c23}$C(O)R$^{b23}$, NR$^{c23}$C(O)OR$^{a23}$, NR$^{c23}$C(O)NR$^{c23}$R$^{d23}$, C(=NR$^{e23}$)R$^{b23}$, C(=NR$^{e23}$)NR$^{c23}$R$^{d23}$, NR$^{c23}$C(=NR$^{e23}$)NR$^{c23}$R$^{d23}$, NR$^{c23}$C(=NR$^{e23}$)R$^{b23}$, NR$^{c23}$S(O)R$^{b23}$, NR$^{c23}$S(O)NR$^{c23}$R$^{d23}$, NR$^{c23}$S(O)$_2$R$^{b23}$, NR$^{c23}$S(O)(=NR$^{e23}$)R$^{b23}$, NR$^{c23}$S(O)$_2$NR$^{c23}$R$^{d23}$, S(O)R$^{b23}$, S(O)NR$^{c23}$R$^{d23}$, S(O)$_2$R$^{b23}$, S(O)$_2$NR$^{c23}$R$^{d23}$, OS(O)(=NR$^{e23}$)R$^{b23}$, and OS(O)$_2$R$^{b23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{2C}$ are each optionally substituted with 1, 2, 3, or 4 independently selected $R^M$ substituents;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a23}$, $R^{c23}$ and $R^{d23}$ are each optionally substituted with 1, 2, 3, or 4 independently selected $R^M$ substituents;

or, any $R^{c23}$ and $R^{d23}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b23}$ are each optionally substituted with 1, 2, 3, or 4 independently selected $R^M$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a3}$, SR$^{a3}$, NHOR$^{a3}$, C(O)R$^{b3}$, C(O)NR$^{c3}$R$^{d3}$, C(O)NR$^{c3}$(OR$^{a3}$), C(O)OR$^{a3}$, OC(O)R$^{b3}$, OC(O)NR$^{c3}$R$^{d3}$, NR$^{c3}$R$^{d3}$, NR$^{c3}$NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$C(=NR$^{e3}$)R$^{b3}$, NR$^{c3}$S(O)R$^{b3}$, NR$^{c3}$S(O)NR$^{c3}$R$^{d3}$, NR$^{c3}$S(O)$_2$R$^{b3}$, NR$^{c3}$S(O)(=NR$^{e3}$)R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, OS(O)(=NR$^{e3}$)R$^{b3}$, and OS(O)$_2$R$^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}C(O)NR^{c32}R^{d32}$, $C(=NR^{e32})R^{b32}$, $C(=NR^{e32})NR^{c32}R^{d32}$, $NR^{c32}C(=NR^{e32})NR^{c32}R^{d32}$, $NR^{c32}C(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)(=NR^{e32})R^{b32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(O)NR^{c33}R^{d33}$, $NR^{c33}S(O)_2R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, 6, 7, or 8 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{c4}$ and $R^{d4}$ are each optionally substituted with 1, 2, 3, 4, 5, 6, 7, or 8 independently selected $R^{4A}$ substituents;

or, any $R^{c4}$ and $R^{d4}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4A}$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b4}$ are each optionally substituted with 1, 2, 3, 4, 5, 6, 7, or 8 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}C(=NR^{e41})R^{b41}$, $NR^{c41}S(O)R^{b41}$, $NR^{c41}S(O)NR^{c41}R^{d41}$, $NR^{c41}S(O)_2R^{b41}$, $NR^{c41}S(O)(=NR^{e41})R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, $OS(O)(=NR^{e41})R^{b41}$, and $OS(O)_2R^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, 4, 5, 6, 7, or 8 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, 4, 5, 6, 7, or 8 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b41}$ are each optionally substituted with 1, 2, 3, 4, 5, 6, 7, or 8 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $NHOR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}NR^{c42}R^{d42}$, $NR^{c42}C(O)R^{b42}$, $NR^{c42}C(O)OR^{a42}$, $NR^{c42}C(O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}C(=NR^{e42})R^{b42}$, $NR^{c42}S(O)R^{b42}$, $NR^{c42}S(O)NR^{c42}R^{d42}$, $NR^{c42}S(O)(=NR^{e42})R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, $OS(O)(=NR^{e42})R^{b42}$, and $OS(O)_2R^{b42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, 4, 5, 6, 7, or 8 independently selected $R^{4C}$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{c42}$ and $R^{d42}$ are each optionally substituted with 1, 2, 3, 4, 5, 6, 7, or 8 independently selected $R^{4C}$ substituents;

or, any $R^{c42}$ and $R^{d42}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4C}$ substituents;

each $R^{b42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b42}$ are each optionally substituted with 1, 2, 3, 4, 5, 6, 7, or 8 independently selected $R^{4C}$ substituents;

each $R^{e42}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a43}$, $SR^{a43}$, $NHOR^{a43}$, $C(O)R^{b43}$, $C(O)NR^{c43}R^{d43}$, $C(O)NR^{c43}(OR^{a43})$, $C(O)OR^{a43}$, $OC(O)R^{b43}$, $OC(O)NR^{c43}R^{d43}$, $NR^{c43}R^{d43}$, $NR^{c43}NR^{c43}R^{d43}$, $NR^{c43}C(O)R^{b43}$, $NR^{c43}C(O)OR^{a43}$, $NR^{c43}C(O)NR^{c43}R^{d43}$, $C(=NR^{e43})R^{b43}$, $C(=NR^{e43})NR^{c43}R^{d43}$, $NR^{c43}C(=NR^{e43})NR^{c43}R^{d43}$, $NR^{c43}C(=NR^{e43})R^{b43}$, $NR^{c43}S(O)R^{b43}$, $NR^{c43}S(O)NR^{c43}R^{d43}$, $NR^{c43}S(O)_2R^{b43}$, $NR^{c43}S(O)(=NR^{e43})R^{b43}$, $NR^{c43}S(O)_2NR^{c43}R^{d43}$, $S(O)R^{b43}$, $S(O)NR^{c43}R^{d43}$, $S(O)_2R^{b43}$, $S(O)_2NR^{c43}R^{d43}$, $OS(O)(=NR^{e43})R^{b43}$, and $OS(O)_2R^{b43}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{4C}$ are each optionally substituted with 1, 2, 3, or 4 independently selected $R^M$ substituents;

each $R^{a43}$, $R^{c43}$, and $R^{d43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a43}$, $R^{c43}$ and $R^{d43}$ are each optionally substituted with 1, 2, 3, or 4 independently selected $R^M$ substituents;

or, any $R^{c43}$ and $R^{d43}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b43}$ are each optionally substituted with 1, 2, 3, or 4 independently selected $R^M$ substituents;

each $R^{e43}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^5$ is selected from H, D, halo, $C_{2-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, and $OS(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl- of $R^5$ are each optionally substituted with 1, 2, 3, 4, 5, 6, 7, or 8 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, 4, 5, 6, 7, or 8 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, 4, 5, 6, 7, or 8 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}C(=NR^{e51})R^{b51}$, $NR^{c51}S(O)R^{b51}$, $NR^{c51}S(O)NR^{c51}R^{d51}$, $NR^{c51}S(O)_2R^{b51}$, $NR^{c51}S(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)(=NR^{e51})R^{b51}$, and $OS(O)_2R^{b51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, 4, 5, 6, 7, or 8 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, 4, 5, 6, 7, or 8 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, 4, 5, 6, 7, or 8 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{c52}C(=NR^{e52})NR^{c52}R^{d52}$, $NR^{c52}C(=NR^{e52})R^{b52}$, $NR^{c52}S(O)R^{b52}$, $NR^{c52}S(O)NR^{c52}R^{d52}$, $NR^{c52}S(O)_2R^{b52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, and $OS(O)_2R^{b52}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5B}$ are each optionally substituted with 1, 2, 3, 4, 5, 6, 7, or 8 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a52}$, $R^{c52}$ and $R^{d52}$ are each optionally substituted with 1, 2, 3, 4, 5, 6, 7, or 8 independently selected $R^{5C}$ substituents;

or, any $R^{c52}$ and $R^{d52}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5C}$ substituents;

each $R^{b52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b52}$ are each optionally substituted with 1, 2, 3, 4, 5, 6, 7, or 8 independently selected $R^{5C}$ substituents;

each $R^{e52}$ is independently selected from H, OH, CN, $C_{1-6}$ alkyl, $C_{1-6}$ alkoxy, $C_{1-6}$ haloalkyl, $C_{1-6}$haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a53}$, $SR^{a53}$, $NHOR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}NR^{c53}R^{d53}$, $NR^{c53}C(O)R^{b53}$, $NR^{c53}C(O)OR^{a53}$, $NR^{c53}C(O)NR^{c53}R^{d53}$, $C(=NR^{e53})R^{b53}$, $C(=NR^{e53})NR^{c53}R^{d53}$, $NR^{c53}C(=NR^{e53})NR^{c53}R^{d53}$, $NR^{c53}C(=NR^{e53})R^{b53}$, $NR^{c53}S(O)R^{b53}$, $NR^{c53}S(O)NR^{c53}R^{d53}$, $NR^{c53}S(O)_2R^{b53}$, $NR^{c53}S(O)(=NR^{e53})R^{b53}$, $NR^{c53}S(O)_2NR^{c53}R^{d53}$, $S(O)R^{b53}$, $S(O)NR^{c53}R^{d53}$, $S(O)_2R^{b53}$, $S(O)_2NR^{c53}R^{d53}$, $OS(O)(=NR^{e53})R^{b53}$, and $OS(O)_2R^{b53}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{5C}$ are each optionally substituted with 1, 2, 3, or 4 independently selected $R^M$ substituents;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a53}$, $R^{c53}$ and $R^{d53}$ are each optionally substituted with 1, 2, 3, or 4 independently selected $R^M$ substituents;

or, any $R^{c53}$ and $R^{d53}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b53}$ are each optionally substituted with 1, 2, 3, or 4 independently selected $R^M$ substituents;

each $R^{e53}$ is independently selected from H, OH, CN, $C_{1-6}$ alkyl, $C_{1-6}$ alkoxy, $C_{1-6}$ haloalkyl, $C_{1-6}$haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-; and each $R^M$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$haloalkoxy, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments:

$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^M$ substituents;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{32}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)R^{b2}$, $NR^{c2}S(O)NR^{c2}R^{d2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, and $OS(O)_2R^{b2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)R^{b21}$, $NR^{c21}S(O)NR^{c21}R^{d21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, 4, 5, 6, 7, or 8 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, 4, 5, 6, 7, or 8 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $C(=NR^{e22})NR^{c22}R^{d22}$, $NR^{c22}C(=NR^{e22})NR^{c22}R^{d22}$, $NR^{c22}C(=NR^{e22})R^{b22}$, $NR^{c22}S(O)R^{b22}$, $NR^{c22}S(O)NR^{c22}R^{d22}$, $NR^{c22}S(O)_2R^{b22}$, $NR^{c22}S(O)(=NR^{e22})R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, $OS(O)(=NR^{e22})R^{b22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, 4, 5, 6, 7, or 8 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a22}$, R$^{c22}$ and R$^{d22}$ are each optionally substituted with 1, 2, 3, 4, 5, 6, 7, or 8 independently selected R$^{2C}$ substituents;

or, any R$^{c22}$ and R$^{d22}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected R$^{2C}$ substituents;

each R$^{b22}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b22}$ are each optionally substituted with 1, 2, 3, 4, 5, 6, 7, or 8 independently selected R$^{2C}$ substituents;

each R$^{e22}$ is independently selected from H, OH, CN, C$_{1-6}$ alkyl, C$_{1-6}$ alkoxy, C$_{1-6}$ haloalkyl, C$_{1-6}$haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{2C}$ is independently selected from halo, oxo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a23}$, SR$^{a23}$, NHOR$^{a23}$, C(O)R$^{b23}$, C(O)NR$^{c23}$R$^{d23}$, C(O)NR$^{c23}$(OR$^{a23}$), C(O)OR$^{a23}$, OC(O)R$^{b23}$, OC(O)NR$^{c23}$R$^{d23}$, NR$^{c23}$R$^{d23}$, NR$^{c23}$C(O)R$^{b23}$, NR$^{c23}$C(O)OR$^{a23}$, NR$^{c23}$C(O)NR$^{c23}$R$^{d23}$, C(=NR$^{e23}$)R$^{b23}$, C(=NR$^{e23}$)NR$^{c23}$R$^{d23}$, NR$^{c23}$C(=NR$^{e23}$)NR$^{c23}$R$^{d23}$, NR$^{c23}$C(=NR$^{e23}$)R$^{b23}$, NR$^{c23}$S(O)R$^{b23}$, NR$^{c23}$S(O)NR$^{c23}$R$^{d23}$, NR$^{c23}$S(O)$_2$R$^{b23}$, NR$^{c23}$S(O)(=NR$^{e23}$)R$^{b23}$, NR$^{c23}$S(O)$_2$NR$^{c23}$R$^{d23}$, S(O)R$^{b23}$, S(O)NR$^{c23}$R$^{d23}$, S(O)$_2$R$^{b23}$, S(O)$_2$NR$^{c23}$R$^{d23}$, OS(O)(=NR$^{e23}$)R$^{b23}$, and OS(O)$_2$R$^{b23}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{2C}$ are each optionally substituted with 1, 2, 3, or 4 independently selected R$^M$ substituents;

each R$^{a23}$, R$^{c23}$, and R$^{d23}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a23}$, R$^{c23}$ and R$^{d23}$ are each optionally substituted with 1, 2, 3, or 4 independently selected R$^M$ substituents;

or, any R$^{c23}$ and R$^{d23}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected R$^M$ substituents;

each R$^{b23}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{b23}$ are each optionally substituted with 1, 2, 3, or 4 independently selected R$^M$ substituents;

each R$^{e23}$ is independently selected from H, OH, CN, C$_{1-6}$ alkyl, C$_{1-6}$ alkoxy, C$_{1-6}$ haloalkyl, C$_{1-6}$haloalkoxy, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

R$^3$ is selected from H, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a3}$, SR$^{a3}$, NHOR$^{a3}$, C(O)R$^{b3}$, C(O)NR$^{c3}$R$^{d3}$, C(O)NR$^{c3}$(OR$^{a3}$), C(O)OR$^{a3}$, OC(O)R$^{b3}$, OC(O)NR$^{c3}$R$^{d3}$, NR$^{c3}$R$^{d3}$, NR$^{c3}$NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$C(=NR$^{e3}$)R$^{b3}$, NR$^{c3}$S(O)R$^{b3}$, NR$^{c3}$S(O)NR$^{c3}$R$^{d3}$, NR$^{c3}$S(O)$_2$R$^{b3}$, NR$^{c3}$S(O)(=NR$^{e3}$)R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, OS(O)(=NR$^{e3}$)R$^{b3}$, and OS(O)$_2$R$^{b3}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl-C$_{1-6}$ alkyl-, and (4-10 membered heterocycloalkyl)-C$_{1-6}$ alkyl- of R$^3$ are each optionally substituted with 1, 2, 3, 4, 5, 6, 7, or 8 independently selected R$^{3A}$ substituents;

each R$^{a3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl-C$_{1-6}$ alkyl-, and (4-10 membered heterocycloalkyl)-C$_{1-6}$ alkyl- of R$^{a3}$, R$^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}C(O)NR^{c32}R^{d32}$, $C(=NR^{e32})R^{b32}$, $C(=NR^{e32})NR^{c32}R^{d32}$, $NR^{c32}C(=NR^{e32})NR^{c32}R^{d32}$, $NR^{c32}C(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)(=NR^{e32})R^{b32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(O)NR^{c33}R^{d33}$, $NR^{c33}S(O)_2R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, 6, 7, or 8 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{c4}$ and $R^{d4}$ are each optionally substituted with 1, 2, 3, 4, 5, 6, 7, or 8 independently selected $R^{4A}$ substituents;

or, any $R^{c4}$ and $R^{d4}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4A}$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b4}$ are each optionally substituted with 1, 2, 3, 4, 5, 6, 7, or 8 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, (4-10 membered heterocycloalkyl)-$C_{1-6}$ alkyl-, CN, $NO_2$, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}C(=NR^{e41})R^{b41}$, $NR^{c41}S(O)R^{b41}$, $NR^{c41}S(O)NR^{c41}R^{d41}$, $NR^{c41}S(O)_2R^{b41}$, $NR^{c41}S(O)(=NR^{e41})R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, $OS(O)(=NR^{e41})R^{b41}$, and $OS(O)_2R^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, 4, 5, 6, 7, or 8 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, 4, 5, 6, 7, or 8 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b41}$ are each optionally substituted with 1, 2, 3, 4, 5, 6, 7, or 8 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $NHOR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}NR^{c42}R^{d42}$, $NR^{c42}C(O)R^{b42}$, $NR^{c42}C(O)OR^{a42}$, $NR^{c42}C(O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}C(=NR^{e42})R^{b42}$, $NR^{c42}S(O)R^{b42}$, $NR^{c42}S(O)NR^{c42}R^{d42}$, $NR^{c42}S(O)_2R^{b42}$, $NR^{c42}S(O)(=NR^{e42})R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, $OS(O)(=NR^{e42})R^{b42}$, and $OS(O)_2R^{b42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, 4, 5, 6, 7, or 8 independently selected $R^{4C}$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{c42}$ and $R^{d42}$ are each optionally substituted with 1, 2, 3, 4, 5, 6, 7, or 8 independently selected $R^{4C}$ substituents;

or, any $R^{c42}$ and $R^{d42}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4C}$ substituents;

each $R^{b42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b42}$ are each optionally substituted with 1, 2, 3, 4, 5, 6, 7, or 8 independently selected $R^{4C}$ substituents;

each $R^{e42}$ is independently selected from H, OH, CN, $C_{1-6}$ alkyl, $C_{1-6}$ alkoxy, $C_{1-6}$ haloalkyl, $C_{1-6}$haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl-$C_{1-6}$ alkyl-, (4-7 membered heterocycloalkyl)-$C_{1-6}$ alkyl-, CN, $NO_2$, $OR^{a43}$, $SR^{a43}$, $NHOR^{a43}$, $C(O)R^{b43}$, $C(O)NR^{c43}R^{d43}$, $C(O)NR^{c43}(OR^{a43})$, $C(O)OR^{a43}$, $OC(O)R^{b43}$, $OC(O)NR^{c43}R^{d43}$, $NR^{c43}R^{d43}$, $NR^{c43}NR^{c43}R^{d43}$, $NR^{c43}C(O)R^{b43}$, $NR^{c43}C(O)OR^{a43}$, $NR^{c43}C(O)NR^{c43}R^{d43}$, $C(=NR^{e43})R^{b43}$, $C(=NR^{e43})NR^{c43}R^{d43}$, $NR^{c43}C(=NR^{e43})NR^{c43}R^{d43}$, $NR^{c43}C(=NR^{e43})R^{b43}$, $NR^{c43}S(O)R^{b43}$, $NR^{c43}S(O)NR^{c43}R^{d43}$, $NR^{c43}S(O)_2R^{b43}$, $NR^{c43}S(O)(=NR^{e43})R^{b43}$, $NR^{c43}S(O)_2NR^{c43}R^{d43}$, $S(O)R^{b43}$, $S(O)NR^{c43}R^{d43}$, $S(O)_2R^{b43}$, $S(O)_2NR^{c43}R^{d43}$, $OS(O)(=NR^{e43})R^{b43}$, and $OS(O)_2R^{b43}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{4C}$ are each optionally substituted with 1, 2, 3, or 4 independently selected $R^M$ substituents;

each $R^{a43}$, $R^{c43}$, and $R^{d43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a43}$, $R^{c43}$ and $R^{d43}$ are each optionally substituted with 1, 2, 3, or 4 independently selected $R^M$ substituents;

or, any $R^{c43}$ and $R^{d43}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b43}$ are each optionally substituted with 1, 2, 3, or 4 independently selected $R^M$ substituents;

each $R^{e43}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^5$ is selected from H, halo, $C_{2-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, and $OS(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, 4, 5, 6, 7, or 8 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, 4, 5, 6, 7, or 8 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, 4, 5, 6, 7, or 8 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl-;

each $R^{5A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}C(=NR^{e51})R^{b51}$, $NR^{c51}S(O)R^{b51}$, $NR^{c51}S(O)NR^{c51}R^{d51}$, $NR^{c51}S(O)_2R^{b51}$, $NR^{c51}S(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)(=NR^{e51})R^{b51}$, and $OS(O)_2R^{b51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, 4, 5, 6, 7, or 8 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, 4, 5, 6, 7, or 8 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, 4, 5, 6, 7, or 8 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{c52}C(=NR^{e52})NR^{c52}R^{d52}$, $NR^{c52}C(=NR^{e52})R^{b52}$, $NR^{c52}S(O)R^{b52}$, $NR^{c52}S(O)NR^{c52}R^{d52}$, $NR^{c52}S(O)_2R^{b52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, and $OS(O)_2R^{b52}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5B}$ are each optionally substituted with 1, 2, 3, 4, 5, 6, 7, or 8 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a52}$, $R^{c52}$ and $R^{d52}$ are each optionally substituted with 1, 2, 3, 4, 5, 6, 7, or 8 independently selected $R^{5C}$ substituents;

or, any $R^{c52}$ and $R^{d52}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5C}$ substituents;

each $R^{b52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b52}$ are each optionally substituted with 1, 2, 3, 4, 5, 6, 7, or 8 independently selected $R^{5C}$ substituents;

each $R^{e52}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a53}$, SR$^{a53}$, NHOR$^{a53}$, C(O)R$^{b53}$, C(O)NR$^{c53}$R$^{d53}$, C(O)NR$^{c53}$(OR$^{a53}$), C(O)OR$^{a53}$, OC(O)R$^{b53}$, OC(O)NR$^{c53}$R$^{d53}$, NR$^{c53}$R$^{d53}$, NR$^{c53}$NR$^{c53}$R$^{d53}$, NR$^{c53}$C(O)R$^{b53}$, NR$^{c53}$C(O)OR$^{a53}$, NR$^{c53}$C(O)NR$^{c53}$R$^{d53}$, C(=NR$^{e53}$)R$^{b53}$, C(=NR$^{e53}$)NR$^{c53}$R$^{d53}$, NR$^{c53}$C(=NR$^{e53}$)NR$^{c53}$R$^{d53}$, NR$^{c53}$C(=NR$^{e53}$)R$^{b53}$, NR$^{c53}$S(O)R$^{b53}$, NR$^{c53}$S(O)NR$^{c53}$R$^{d53}$, NR$^{c53}$S(O)$_2$R$^{b53}$, NR$^{c53}$S(O)(=NR$^{e53}$)R$^{b53}$, NR$^{c53}$S(O)$_2$NR$^{c53}$R$^{d53}$, S(O)R$^{b53}$, S(O)NR$^{c53}$R$^{d53}$, S(O)$_2$R$^{b53}$, S(O)$_2$NR$^{c53}$R$^{d53}$, OS(O)(=NR$^{e53}$)R$^{b53}$, and OS(O)$_2$R$^{b53}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{5C}$ are each optionally substituted with 1, 2, 3, or 4 independently selected $R^M$ substituents;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a53}$, $R^{c53}$ and $R^{d53}$ are each optionally substituted with 1, 2, 3, or 4 independently selected $R^M$ substituents;

or, any $R^{c53}$ and $R^{d53}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b53}$ are each optionally substituted with 1, 2, 3, or 4 independently selected $R^M$ substituents;

each $R^{e53}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-; and each $R^M$ is independently selected from H, OH, halo, oxo, CN, C(O)OH, NH$_2$, NO$_2$, SF$_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments:

$R^1$ is selected from H, $C_{1-6}$ alkyl, $C_{1-6}$ haloalkyl, $C_{2-6}$ alkenyl, and $C_{2-6}$ alkynyl;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{32}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)NR$^{c2}$R$^{d2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, or 4 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)NR^{c21}R^{d21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, or 4 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, or 4 independently selected $R^{2B}$ substituents;

each $R^{2B}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)R^{b22}$, $NR^{c22}S(O)NR^{c22}R^{d22}$, $NR^{c22}S(O)_2R^{b22}$, $NR^{c22}S(O)_2NR^{c22}R^{d22}$, $S(O)R^{b22}$, $S(O)NR^{c22}R^{d22}$, $S(O)_2R^{b22}$, and $S(O)_2NR^{c22}R^{d22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, or 4 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, or 4 independently selected $R^{2C}$ substituents;

each $R^{2C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a23}$, $C(O)R^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}NR^{c23}R^{d23}$, $NR^{c23}C(O)$ $R^{b23}$, $NR^{c23}C(O)OR^{a23}$, $NR^{c23}C(O)NR^{c23}R^{d23}$, $NR^{c23}S(O)R^{b23}$, $NR^{c23}S(O)NR^{c23}R^{d23}$, $NR^{c23}S(O)_2R^{b23}$, $NR^{c23}S(O)_2NR^{c23}R^{d23}$, $S(O)R^{b23}$, $S(O)NR^{c23}R^{d23}$, $S(O)_2R^{b23}$, and $S(O)_2NR^{c23}R^{d23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{2C}$ are each optionally substituted with 1, 2, 3, or 4 independently selected $R^M$ substituents;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a23}$, $R^{c23}$ and $R^{d23}$ are each optionally substituted with 1, 2, 3, or 4 independently selected $R^M$ substituents;

or, any $R^{c23}$ and $R^{d23}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b23}$ are each optionally substituted with 1, 2, 3, or 4 independently selected $R^M$ substituents;

$R^3$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, $NO_2$, and $OR^{a3}$;

each $R^{a3}$ is independently selected from H, $C_{1-6}$ alkyl, $C_{1-6}$ haloalkyl, $C_{2-6}$ alkenyl, and $C_{2-6}$ alkynyl;

$R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, $NO_2$, and $OR^{a4}$;

each $R^{a4}$ is independently selected from H, $C_{1-6}$ alkyl, $C_{1-6}$ haloalkyl, $C_{2-6}$ alkenyl, and $C_{2-6}$ alkynyl;

$R^5$ is selected from H, halo, $C_{2-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, or 4 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, or 4 independently selected $R^{5A}$ substituents;

each $R^{5A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)NR^{c51}R^{d51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, or 4 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, or 4 independently selected $R^{5B}$ substituents;

each $R^{5B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)NR^{c52}R^{d52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, and $S(O)_2NR^{c52}R^{d52}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5B}$ are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a52}$, $R^{c52}$ and $R^{d52}$ are each optionally substituted with 1, 2, 3, or 4 independently selected $R^{5C}$ substituents;

or, any $R^{c52}$ and $R^{d52}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5C}$ substituents;

each $R^{b52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b52}$ are each optionally substituted with 1, 2, 3, or 4 independently selected $R^{5C}$ substituents;

each $R^{5C}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}C(O)R^{b53}$, $NR^{c53}C(O)OR^{a53}$, $NR^{c53}C(O)NR^{c53}R^{d53}$, $NR^{c53}S(O)R^{b53}$, $NR^{c53}S(O)NR^{c53}R^{d53}$, $NR^{c53}S(O)_2R^{b53}$, $NR^{c53}S(O)_2NR^{c53}R^{d53}$, $S(O)R^{b53}$, $S(O)NR^{c53}R^{d53}$, $S(O)_2R^{b53}$, and $S(O)_2NR^{c53}R^{d53}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{5C}$ are each optionally substituted with 1, 2, 3, or 4 independently selected $R^M$ substituents;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a53}$, $R^{c53}$ and $R^{d53}$ are each optionally substituted with 1, 2, 3, or 4 independently selected $R^M$ substituents;

or, any $R^{c53}$ and $R^{d53}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b53}$ are each optionally substituted with 1, 2, 3, or 4 independently selected $R^M$ substituents; and each $R^M$ is independently selected from H, OH, halo, oxo, CN, C(O)OH, NH$_2$, NO$_2$, SF$_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments:

$R^1$ is selected from H, D, $C_{1-6}$ alkyl, $C_{1-6}$ haloalkyl, $C_{2-6}$ alkenyl, and $C_{2-6}$ alkynyl;

$R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)NR$^{c2}$R$^{d2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, or 4 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, or 4 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a21}$, C(O)R$^{b21}$, C(O)NR$^{c21}$R$^{d21}$, C(O)OR$^{a21}$, OC(O)R$^{b21}$, OC(O)NR$^{c21}$R$^{d21}$, NR$^{c21}$R$^{d21}$, NR$^{c21}$C(O)R$^{b21}$, NR$^{c21}$C(O)OR$^{a21}$, NR$^{c21}$C(O)NR$^{c21}$R$^{d21}$, NR$^{c21}$S(O)R$^{b21}$, NR$^{c21}$S(O)NR$^{c21}$R$^{d21}$, NR$^{c21}$S(O)$_2$R$^{b21}$, NR$^{c21}$S(O)$_2$NR$^{c21}$R$^{d21}$, S(O)R$^{b21}$, S(O)NR$^{c21}$R$^{d21}$, S(O)$_2$R$^{b21}$, and S(O)$_2$NR$^{c21}$R$^{d21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, or 4 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, or 4 independently selected $R^{2B}$ substituents;

each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a22}$, C(O)R$^{b22}$, C(O)NR$^{c22}$R$^{d22}$, C(O)NR$^{c22}$(OR$^{a22}$), C(O)OR$^{a22}$, OC(O)R$^{b22}$, OC(O)NR$^{c22}$R$^{d22}$, NR$^{c22}$R$^{d22}$, NR$^{c22}$NR$^{c22}$R$^{d22}$, NR$^{c22}$C(O)R$^{b22}$, NR$^{c22}$C(O)OR$^{a22}$, NR$^{c22}$C(O)NR$^{c22}$R$^{d22}$, NR$^{c22}$S(O)R$^{b22}$, NR$^{c22}$S(O)NR$^{c22}$R$^{d22}$, NR$^{c22}$S(O)$_2$R$^{b22}$, NR$^{c22}$S(O)$_2$NR$^{c22}$R$^{d22}$, S(O)R$^{b22}$, S(O)NR$^{c22}$R$^{d22}$, S(O)$_2$R$^{b22}$, and S(O)$_2$NR$^{c22}$R$^{d22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{2B}$ are each optionally substituted with 1, 2, 3, or 4 independently selected R$^{2C}$ substituents;

each R$^{a22}$, R$^{c22}$, and R$^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{a22}$, R$^{c22}$ and R$^{d22}$ are each optionally substituted with 1, 2, 3, or 4 independently selected R$^{2C}$ substituents;

or, any R$^{c22}$ and R$^{d22}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected R$^{2C}$ substituents;

each R$^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{b22}$ are each optionally substituted with 1, 2, 3, or 4 independently selected R$^{2C}$ substituents;

each R$^{2C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a23}$, C(O)R$^{b23}$, C(O)NR$^{c23}$R$^{d23}$, C(O)NR$^{c23}$(OR$^{a23}$), C(O)OR$^{a23}$, OC(O)R$^{b23}$, OC(O)NR$^{c23}$R$^{d23}$, NR$^{c23}$R$^{d23}$, NR$^{c23}$NR$^{c23}$R$^{d23}$, NR$^{c23}$C(O)R$^{b23}$, NR$^{c23}$C(O)OR$^{a23}$, NR$^{c23}$C(O)NR$^{c23}$R$^{d23}$, NR$^{c23}$S(O)R$^{b23}$, NR$^{c23}$S(O)NR$^{c23}$R$^{d23}$, NR$^{c23}$S(O)$_2$R$^{b23}$, NR$^{c23}$S(O)$_2$NR$^{c23}$R$^{d23}$, S(O)R$^{b23}$, S(O)NR$^{c23}$R$^{d23}$, S(O)$_2$R$^{b23}$, and S(O)$_2$NR$^{c23}$R$^{d23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{2C}$ are each optionally substituted with 1, 2, 3, or 4 independently selected R$^M$ substituents;

each R$^{a23}$, R$^{c23}$, and R$^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{a23}$, R$^{c23}$ and R$^{d23}$ are each optionally substituted with 1, 2, 3, or 4 independently selected R$^M$ substituents;

or, any R$^{c23}$ and R$^{d23}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected R$^M$ substituents;

each R$^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{b23}$ are each optionally substituted with 1, 2, 3, or 4 independently selected R$^M$ substituents;

R$^3$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, NO$_2$, and OR$^{a3}$;

each R$^{a3}$ is independently selected from H, $C_{1-6}$ alkyl, $C_{1-6}$ haloalkyl, $C_{2-6}$ alkenyl, and $C_{2-6}$ alkynyl;

R$^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, CN, NO$_2$, and OR$^{a4}$;

each R$^{a4}$ is independently selected from H, $C_{1-6}$ alkyl, $C_{1-6}$ haloalkyl, $C_{2-6}$ alkenyl, and $C_{2-6}$ alkynyl;

R$^5$ is selected from H, D, halo, $C_{2-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, $OR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, or 4 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, or 4 independently selected $R^{5A}$ substituents;

each $R^{5A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)NR^{c51}R^{d51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, or 4 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, or 4 independently selected $R^{5B}$ substituents;

each $R^{5B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)NR^{c52}R^{d52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, and $S(O)_2NR^{c52}R^{d52}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5B}$ are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, and (4-10 membered heterocycloalkyl)-$C_{1-6}$ alkyl- of $R^{a52}$, $R^{c52}$ and $R^{d52}$ are each optionally substituted with 1, 2, 3, or 4 independently selected $R^{5C}$ substituents;

or, any $R^{c52}$ and $R^{d52}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5C}$ substituents;

each $R^{b52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b52}$ are each optionally substituted with 1, 2, 3, or 4 independently selected $R^{5C}$ substituents;

each $R^{5C}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}C(O)R^{b53}$, $NR^{c53}C(O)OR^{a53}$, $NR^{c53}C(O)NR^{c53}R^{d53}$, $NR^{c53}S(O)R^{b53}$, $NR^{c53}S(O)NR^{c53}R^{d53}$, $NR^{c53}S(O)_2R^{b53}$, $NR^{c53}S(O)_2NR^{c53}R^{d53}$, $S(O)R^{b53}$, $S(O)NR^{c53}R^{d53}$, $S(O)_2R^{b53}$, and $S(O)_2NR^{c53}R^{d53}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{5C}$ are each optionally substituted with 1, 2, 3, or 4 independently selected $R^M$ substituents;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a53}$, $R^{c53}$ and $R^{d53}$ are each optionally substituted with 1, 2, 3, or 4 independently selected $R^M$ substituents;

or, any $R^{c53}$ and $R^{d53}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b53}$ are each optionally substituted with 1, 2, 3, or 4 independently selected $R^M$ substituents; and each $R^M$ is independently selected from H, D, OH, halo, oxo, CN, C(O)OH, $NH_2$, $NO_2$, $SF_5$, $C_{1-6}$ alkyl, $C_{1-6}$alkoxy, $C_{1-6}$haloalkoxy, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments, $R^1$ is selected from H, $C_{1-6}$ alkyl, $C_{1-6}$ haloalkyl, $C_{2-6}$ alkenyl, and $C_{2-6}$ alkynyl.

In some embodiments, $R^1$ is selected from H, D, $C_{1-6}$ alkyl, $C_{1-6}$ haloalkyl, $C_{2-6}$ alkenyl, and $C_{2-6}$ alkynyl.

In some embodiments, $R^1$ is selected from H and $C_{1-6}$ alkyl.

In some embodiments, $R^1$ is selected from H, methyl, and ethyl.

In some embodiments, $R^1$ is H.

In some embodiments, $R^1$ is methyl.

In some embodiments, $R^1$ is ethyl.

In some embodiments, $R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, and $C(O)OR^{a2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

In some embodiments, $R^2$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, and $C(O)OR^{a2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

In some embodiments, $R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, and $C(O)OR^{a2}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, $C(O)OR^{a2}$, and $NR^{c2}R^{d2}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from $C(O)NR^{c2}R^{d2}$ and $NR^{c2}R^{d2}$, wherein each $R^{c2}$ and $R^{d2}$ are independently selected from H, $C_{1-6}$ alkyl, $C_{6-10}$ aryl, and $C_{3-10}$ cycloalkyl, wherein the $C_{1-6}$ alkyl, $C_{6-10}$ aryl and $C_{3-10}$ cycloalkyl of $R^{c2}$ and $R^{d2}$ are each optionally substituted with 1, 2, 3, 4, 5, 6, 7, or 8 independently selected $R^{2A}$ substituents.

In some embodiments, $R^2$ is selected from H, phenyl, $C_{3-6}$ cycloalkyl, 5-6 membered heteroaryl, 5-6 membered heterocycloalkyl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (8-10 membered heterocycloalkyl)-$C_{1-6}$ alkyl-, CN, $C(O)NR^{c2}R^{d2}$, and $NR^{c2}R^{d2}$, wherein the phenyl, $C_{3-6}$ cycloalkyl, 5-6 membered heteroaryl, 5-6 membered heterocycloalkyl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (8-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, phenyl, pyrrolidinyl, piperidinyl, benzodioxolyl, dihydrobenzodioxinyl, pyrazolyl, tetrazolyl, oxa-azaspiro[4.5]decanyl, isoxazolyl, pyridinyl, CN, $C(O)NR^{c2}R^{d2}$, and $NR^{c2}R^{d2}$, wherein the phenyl, pyrrolidinyl, piperidinyl, benzodioxolyl, dihydrobenzodioxinyl, oxa-azaspiro[4.5]decanyl, isoxazolyl, and pyridinyl of $R^2$ are each optionally substituted with 1, 2, 3, or 4 independently selected $R^{2A}$ substituents.

In some embodiments, $R^2$ is selected from H, phenyl, pyrrolidinyl, piperidinyl, benzodioxolyl, dihydrobenzodioxinyl, pyrazolyl, tetrazolyl, oxa-azaspiro[4.5]decanyl, isoxazolyl, pyridinyl, CN, $C(O)NR^{c2}R^{d2}$, and $NR^{c2}R^{d2}$, wherein the phenyl, pyrrolidinyl, piperidinyl, benzodioxolyl, dihydrobenzodioxinyl, oxa-azaspiro[4.5]decanyl, isoxazolyl, and pyridinyl of $R^2$ are each optionally substituted with 1, 2, 3, or 4 independently selected $R^{2A}$ substituents, wherein each $R^{c2}$ and $R^{d2}$ are independently selected from H, methyl, phenyl, and cyclohexyl, wherein the phenyl and cyclohexyl of $R^{c2}$ and $R^{d2}$ are each optionally substituted with 1, 2, 3, 4, 5, 6, 7, or 8 independently selected $R^{2A}$ substituents.

In some embodiments, $R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (8-10 membered heterocycloalkyl)-$C_{1-6}$ alkyl-, and CN, wherein the phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (8-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (8-10 membered heterocycloalkyl)-$C_{1-6}$ alkyl-, and CN, wherein the phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (8-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, phenyl, benzodioxolyl, dihydrobenzodioxinyl, and CN, wherein the phenyl, benzodioxolyl, and dihydrobenzodioxinyl of $R^2$ are each optionally substituted with 1, 2, 3, or 4 independently selected $R^{2A}$ substituents.

In some embodiments, $R^2$ is selected from H, phenyl, and CN, wherein the phenyl is optionally substituted with 1, 2, 3, or 4 independently selected $R^{2A}$ substituents.

In some embodiments, $R^2$ is selected from H or CN.

In some embodiments, $R^2$ is phenyl, which is optionally substituted with 1, 2, 3, or 4 independently selected $R^{2A}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $C(O)R^{b21}$, $C(O)NR^{c21}R^{d21}$, $C(O)OR^{a21}$, and $S(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $C(O)R^{b21}$, $C(O)NR^{c21}R^{d21}$, and $C(O)OR^{a21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, CN, $NO_2$, $OR^{a21}$, $C(O)R^{b21}$, $C(O)NR^{c21}R^{d21}$, and $C(O)OR^{a21}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, 5-10 membered heteroaryl, CN, $NO_2$, $OR^{a21}$, and $C(O)OR^{a21}$, wherein the $C_{1-6}$ alkyl and 5-10 membered heteroaryl of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, 5-6 membered heteroaryl, CN, $NO_2$, $OR^{a21}$, $C(O)R^{b21}$, $C(O)OR^{a21}$, and $S(O)_2R^{b21}$, wherein the $C_{1-6}$ alkyl and 5-6 membered heteroaryl of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, 5-6 membered heteroaryl, CN, $NO_2$, $OR^{a21}$, and $C(O)OR^{a21}$, wherein the $C_{1-6}$ alkyl and 5-6 membered heteroaryl of $R^{2A}$ are each optionally substituted with 1, 2, 3, or 4 independently selected $R^{2B}$ substituents.

In some embodiments, each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl of $R^{a21}$, $R^{b21}$, $R^{c21}$, and $R^{d21}$ are each optionally substituted with 1, 2, 3, 4, 5, 6, 7, or 8 independently selected $R^{2B}$ substituents.

In some embodiments, each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a21}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2A}$ is independently selected from chloro, fluoro, methyl, trifluoromethyl, methoxy, cyanomethyl, pyrazolyl, tetrazolyl, tetrazolylmethyl, CN, $NO_2$, $C(O)CH_3$, $C(O)OH$, methylsulfonyl, and methoxyethylsulfonyl, wherein the pyrazolyl and tetrazolyl of $R^{2A}$ are each optionally substituted with 1 or 2 independently selected $R^{2B}$ substituents.

In some embodiments, each $R^{2A}$ is independently selected from halo, $C_{1-6}$ alkyl, $C_{1-6}$ haloalkyl, 5-10 membered heteroaryl, CN, $NO_2$, $OR^{a21}$, and $C(O)OR^{a21}$, wherein the $C_{1-6}$ alkyl and 5-10 membered heteroaryl of $R^{2A}$ are each optionally substituted with 1, 2, 3, or 4 independently selected $R^{2B}$ substituents, and wherein each $R^{a21}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2A}$ is independently selected from halo, $C_{1-6}$ alkyl, $C_{1-6}$ haloalkyl, 5-6 membered heteroaryl, CN, $NO_2$, $OR^{a21}$, and $C(O)OR^{a21}$, wherein the $C_{1-6}$ alkyl and 5-6 membered heteroaryl of $R^{2A}$ are each optionally substituted with 1, 2, 3, or 4 independently selected $R^{2B}$ substituents, and wherein each $R^{a21}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2A}$ is independently selected from chloro, fluoro, methyl, trifluoromethyl, methoxy, pyrazolyl, tetrazolyl, CN, $NO_2$, and $C(O)OH$, wherein the pyrazolyl and tetrazolyl of $R^{2A}$ are each optionally substituted with 1 or 2 independently selected $R^{2B}$ substituents.

In some embodiments, each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, CA-10 cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a22}$, wherein each $R^{a22}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2B}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a22}$, wherein each $R^{a22}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments, each $R^{2B}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments, each $R^{2B}$ is independently selected from D, halo, $C_{1-6}$ alkyl, $C_{1-6}$ haloalkyl, $C_{2-6}$ alkenyl, and $C_{2-6}$ alkynyl.

In some embodiments, each $R^{2B}$ is independently selected from halo, $C_{1-6}$ alkyl, $C_{1-6}$ haloalkyl, $C_{2-6}$ alkenyl, and $C_{2-6}$ alkynyl.

In some embodiments, each $R^{2B}$ is independently selected from D, $C_{1-6}$ alkyl, and $C_{1-6}$ haloalkyl.

In some embodiments, each $R^{2B}$ is independently selected from $C_{1-6}$ alkyl, and $C_{1-6}$ haloalkyl.

In some embodiments, each $R^{2B}$ is an independently selected $C_{1-6}$ alkyl group.

In some embodiments, each $R^{2A}$ is independently selected from chloro, fluoro, methyl, trifluoromethyl, methoxy, pyrazolyl, tetrazolyl, CN, $NO_2$, and $C(O)OH$, wherein the pyrazolyl and tetrazolyl of $R^{2A}$ are each optionally substituted with 1 or 2 independently selected $C_{1-6}$ alkyl substituents.

In some embodiments, each $R^{2A}$ is independently selected from chloro, methyl, methoxy, CN, and $C(O)OH$.

In some embodiments, $R^2$ is selected from H, phenyl, benzodioxolyl, dihydrobenzodioxinyl, and CN, wherein the phenyl, benzodioxolyl, and dihydrobenzodioxinyl of $R^2$ are each optionally substituted with 1, 2, 3, or 4 $R^{2A}$ substituents independently selected from chloro, fluoro, methyl, trifluoromethyl, methoxy, pyrazolyl, tetrazolyl, CN, $NO_2$, and $C(O)OH$, wherein the pyrazolyl and tetrazolyl of $R^{2A}$ are each optionally substituted with 1 or 2 independently selected $C_{1-6}$ alkyl substituents.

In some embodiments, $R^2$ is selected from H, phenyl, and CN, wherein the phenyl is optionally substituted with 1 or 2 substituents independently selected from chloro, methyl, methoxy, CN, and $C(O)OH$.

In some embodiments, $R^3$ is selected from H, D, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 4-10 membered heterocycloalkyl, and $OR^{a3}$, wherein the $C_{6-10}$ aryl, $C_{3-10}$ cycloalkyl, and 4-10 membered heterocycloalkyl of $R^3$ are each optionally substituted with 1, 2, 3, 4, 5, 6, 7, or 8 independently selected $R^{3A}$ substituents; and wherein $R^{a3}$ is selected from H, $C_{1-6}$ alkyl, $C_{1-6}$ haloalkyl, $C_{2-6}$ alkenyl, and $C_{2-6}$ alkynyl.

In some embodiments, $R^3$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 4-10 membered heterocycloalkyl, and $OR^{a3}$, wherein the $C_{6-10}$ aryl, $C_{3-10}$ cycloalkyl, and 4-10 membered heterocycloalkyl of $R^3$ are each optionally substituted with 1, 2, 3, 4, 5, 6, 7, or 8 independently selected $R^{3A}$ substituents; and wherein $R^{a3}$ is selected from H, $C_{1-6}$ alkyl, $C_{1-6}$ haloalkyl, $C_{2-6}$ alkenyl, and $C_{2-6}$ alkynyl.

In some embodiments, $R^3$ is selected from H, D, $C_{1-6}$ alkyl, $C_{1-6}$ haloalkyl, $C_{2-6}$ alkenyl, $C_{2-6}$ alkynyl, phenyl, $C_{3-6}$ cycloalkyl, tetrahydropyranyl, pyrrolidinyl, and $OR^{a3}$, wherein the phenyl, $C_{3-6}$ cycloalkyl, tetrahydropyranyl, and pyrrolidinyl of $R^3$ are each optionally substituted with 1, 2, 3, or 4 independently selected $R^{3A}$ substituents; and wherein $R^{a3}$ is selected from H, $C_{1-6}$ alkyl, $C_{1-6}$ haloalkyl, $C_{2-6}$ alkenyl, and $C_{2-6}$ alkynyl.

In some embodiments, $R^3$ is selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, tetrahydropyranyl, pyrrolidinyl, and $OR^{a3}$, wherein the phenyl, $C_{3-6}$ cycloalkyl, tetrahydropyranyl, and pyrrolidinyl of $R^3$ are each optionally substituted with 1, 2, 3, or 4 independently selected $R^{3A}$ substituents; and wherein $R^{a3}$ is selected from H, $C_{1-6}$ alkyl, $C_{1-6}$ haloalkyl, $C_{2-6}$ alkenyl, and $C_{2-6}$ alkynyl.

In some embodiments, each $R^{3A}$ is independently selected from $C_{1-6}$ alkyl, 5-10 membered heteroaryl, $OR^{a31}$, $C(O)NR^{c31}R^{d31}$, $NR^{c31}R^{d31}$, and $S(O)_2R^{b31}$, wherein the $C_{1-6}$ alkyl and 5-10 membered heteroaryl of $R^{3A}$ are each optionally substituted with 1, 2, 3, 4, 5, 6, 7, or 8 independently selected $R^{3B}$ substituents.

In some embodiments, each $R^{a31}$, $R^{b31}$, $R^{c31}$, and $R^{d31}$ is independently selected from H, $C_{1-6}$ alkyl, 5-10 membered heteroaryl, and 4-10 membered heterocycloalkyl, wherein the $C_{1-6}$ alkyl, 5-10 membered heteroaryl, and 4-10 membered heterocycloalkyl of $R^{a31}$, $R^{b31}$, $R^{c31}$, and $R^{d31}$ are each optionally substituted with 1, 2, 3, 4, 5, 6, 7, or 8 independently selected $R^{3B}$ substituents.

In some embodiments, each $R^{3B}$ is independently selected from $C_{1-6}$ alkyl, $OR^{a32}$, and $NR^{c32}R^{d32}$, wherein the $C_{1-6}$ alkyl of $R^{3B}$ are each optionally substituted with 1, 2, 3, 4, 5, 6, 7, or 8 independently selected $R^{3C}$ substituents.

In some embodiments, each $R^{a32}$, $R^{c32}$, and $R^{d32}$ are independently selected from H, $C_{1-6}$ alkyl, and 4-10 membered heterocycloalkyl, wherein the $C_{1-6}$ alkyl and 4-10 membered heterocycloalkyl of $R^{a32}$, $R^{c32}$, and $R^{d32}$ are each optionally substituted with 1, 2, 3, 4, 5, 6, 7, or 8 independently selected $R^{3C}$ substituents.

In some embodiments, each $R^{3C}$ is $OR^{a33}$, wherein $R^{a33}$ is H.

In some embodiments, $R^3$ is selected from H, methyl, ethyl, methoxy, phenyl, cyclohexyl, pyrrolidino, and tetrahydropyranyl, wherein the phenyl, cyclohexyl, and pyrrolidino of $R^3$ are each optionally substituted with 1, 2, 3, or 4 independently selected $R^{3A}$ substituents.

In some embodiments, $R^3$ is selected from H, D, $C_{1-6}$ alkyl, $C_{1-6}$ haloalkyl, $C_{2-6}$ alkenyl, $C_{2-6}$ alkynyl, and $OR^{a3}$, wherein $R^{a3}$ is selected from H, $C_{1-6}$ alkyl, $C_{1-6}$ haloalkyl, $C_{2-6}$ alkenyl, and $C_{2-6}$ alkynyl.

In some embodiments, $R^3$ is selected from H, $C_{1-6}$ alkyl, $C_{1-6}$ haloalkyl, $C_{2-6}$ alkenyl, $C_{2-6}$ alkynyl, and $OR^{a3}$, wherein $R^{a3}$ is selected from H, $C_{1-6}$ alkyl, $C_{1-6}$ haloalkyl, $C_{2-6}$ alkenyl, and $C_{2-6}$ alkynyl.

In some embodiments, $R^3$ is selected from H, D, $C_{1-6}$ alkyl, $C_{1-6}$ haloalkyl, $C_{2-6}$ alkenyl, $C_{2-6}$ alkynyl, and $C_{1-6}$ alkoxy.

In some embodiments, $R^3$ is selected from H, $C_{1-6}$ alkyl, $C_{1-6}$ haloalkyl, $C_{2-6}$ alkenyl, $C_{2-6}$ alkynyl, and $C_{1-6}$ alkoxy.

In some embodiments, $R^3$ is selected from H, $C_{1-6}$ alkyl, $C_{1-6}$ haloalkyl, and $C_{1-6}$ alkoxy.

In some embodiments, $R^3$ is selected from H, $C_{1-6}$ alkyl, and $C_{1-6}$ alkoxy.

In some embodiments, $R^3$ is selected from H, methyl, ethyl, and methoxy.

In some embodiments, $R^3$ is H.

In some embodiments, $R^3$ is methyl.

In some embodiments, $R^3$ is ethyl.

In some embodiments, $R^3$ is methoxy.

In some embodiments, $R^4$ is selected from H, D, $C_{1-6}$ alkyl, $C_{1-6}$ haloalkyl, $C_{2-6}$ alkenyl, $C_{2-6}$ alkynyl, $C_{6-10}$ aryl, and 5-10 membered heteroaryl, wherein the $C_{1-6}$ alkyl, $C_{2-6}$ alkenyl, $C_{2-6}$ alkynyl, $C_{6-10}$ aryl, and 5-10 membered heteroaryl of $R^4$ are each optionally substituted with 1, 2, 3, 4, 5, 6, 7, or 8 independently selected $R^{4A}$ substituents.

In some embodiments, $R^4$ is selected from H, $C_{1-6}$ alkyl, $C_{1-6}$ haloalkyl, $C_{2-6}$ alkenyl, $C_{2-6}$ alkynyl, $C_{6-10}$ aryl, and 5-10 membered heteroaryl, wherein the $C_{1-6}$ alkyl, $C_{2-6}$ alkenyl, $C_{2-6}$ alkynyl, $C_{6-10}$ aryl, and 5-10 membered heteroaryl of $R^4$ are each optionally substituted with 1, 2, 3, 4, 5, 6, 7, or 8 independently selected $R^{4A}$ substituents.

In some embodiments, $R^4$ is selected from H, D, $C_{1-6}$ alkyl, $C_{1-6}$ haloalkyl, $C_{2-6}$ alkenyl, $C_{2-6}$ alkynyl, phenyl, and 8-10 membered heteroaryl, wherein the $C_{1-6}$ alkyl, $C_{2-6}$ alkenyl, $C_{2-6}$ alkynyl, phenyl, and 8-10 membered heteroaryl of $R^4$ are each optionally substituted with 1, 2, 3, 4, 5, 6, 7, or 8 independently selected $R^{4A}$ substituents.

In some embodiments, $R^4$ is selected from H, $C_{1-6}$ alkyl, $C_{1-6}$ haloalkyl, $C_{2-6}$ alkenyl, $C_{2-6}$ alkynyl, phenyl, and 8-10 membered heteroaryl, wherein the $C_{1-6}$ alkyl, $C_{2-6}$ alkenyl, $C_{2-6}$ alkynyl, phenyl, and 8-10 membered heteroaryl of $R^4$ are each optionally substituted with 1, 2, 3, 4, 5, 6, 7, or 8 independently selected $R^{4A}$ substituents.

In some embodiments, $R^4$ is selected from H, $C_{1-6}$ alkyl, $C_{1-6}$ haloalkyl, $C_{2-6}$ alkenyl, $C_{2-6}$ alkynyl, $C_{6-10}$ aryl, and 5-10 membered heteroaryl, wherein the $C_{1-6}$ alkyl, $C_{2-6}$ alkenyl, $C_{2-6}$ alkynyl, $C_{6-10}$ aryl, and 5-10 membered heteroaryl of $R^4$ are each optionally substituted with 1, 2, 3, 4, 5, 6, 7, or 8 independently selected $R^{4A}$ substituents.

In some embodiments, $R^4$ is selected from H, $C_{1-6}$ alkyl, $C_{1-6}$ haloalkyl, $C_{2-6}$ alkenyl, $C_{2-6}$ alkynyl, phenyl, and 8-10 membered heteroaryl, wherein the $C_{1-6}$ alkyl, $C_{2-6}$ alkenyl, $C_{2-6}$ alkynyl, phenyl, and 8-10 membered heteroaryl of $R^4$ are each optionally substituted with 1, 2, 3, 4, 5, 6, 7, or 8 independently selected $R^{4A}$ substituents.

In some embodiments, $R^4$ is selected from H, $C_{1-6}$ alkyl, phenyl, and indazolyl, wherein the $C_{1-6}$ alkyl, phenyl, and indazolyl of $R^4$ are each optionally substituted with 1, 2, 3, or 4 independently selected $R^{4A}$ substituents.

In some embodiments, each $R^{4A}$ is independently selected from $C_{1-6}$ alkyl, $C_{3-10}$ cycloalkyl, $OR^{a41}$, and $C(O)NR^{c41}R^{d41}$, wherein the $C_{1-6}$ alkyl and $C_{3-10}$ cycloalkyl of $R^{4A}$ are each optionally substituted with 1, 2, 3, 4, 5, 6, 7, or 8 independently selected $R^{4B}$ substituents; and wherein each $R^{a41}$, $R^{c41}$, and $R^{d41}$ are independently selected from H and $C_{1-6}$ alkyl.

In some embodiments, each $R^{4B}$ is independently selected from $C_{1-6}$ alkyl and CN.

In some embodiments, $R^4$ is selected from H, $C_{1-6}$ alkyl, phenyl, and indazolyl, wherein the phenyl and indazolyl of $R^4$ are each optionally substituted with methyl, methoxy, cyanocyclopropyl, or $C(O)N(CH_3)_2$.

In some embodiments, $R^4$ is selected from H, D, $C_{1-6}$ alkyl, $C_{1-6}$ haloalkyl, $C_{2-6}$ alkenyl, and $C_{2-6}$ alkynyl.

In some embodiments, $R^4$ is selected from H, $C_{1-6}$ alkyl, $C_{1-6}$ haloalkyl, $C_{2-6}$ alkenyl, and $C_{2-6}$ alkynyl.

In some embodiments, $R^4$ is selected from H, D, $C_{1-6}$ alkyl, and $C_{1-6}$ haloalkyl.

In some embodiments, $R^4$ is selected from H, $C_{1-6}$ alkyl, and $C_{1-6}$ haloalkyl.

In some embodiments, $R^4$ is selected from H and $C_{1-6}$ alkyl.

In some embodiments, $R^4$ is H or D.

In some embodiments, $R^4$ is H.

In some embodiments, $R^5$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

In some embodiments, $R^5$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $R^5$ are each optionally substituted with 1, 2, 3, or 4 independently selected $R^{5A}$ substituents.

In some embodiments, $R^5$ is selected from phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of $R^5$ are each optionally substituted with 1, 2, 3, or 4 independently selected $R^{5A}$ substituents.

In some embodiments, $R^5$ is selected from $C_{6-10}$ aryl and pyrazolyl, wherein the $C_{6-10}$ aryl and pyrazolyl of $R^5$ are each optionally substituted with 1, 2, 3, or 4 independently selected $R^{5A}$ substituents.

In some embodiments, $R^5$ is selected from phenyl and pyrazolyl, wherein the phenyl and pyrazolyl of $R^5$ are each optionally substituted with 1, 2, or 3 independently selected $R^{5A}$ substituents.

In some embodiments, $R^5$ is selected from phenyl and pyrazolyl, wherein the phenyl and pyrazolyl of $R^5$ are each optionally substituted with 1 or 2 independently selected $R^{5A}$ substituents.

In some embodiments, $R^5$ is selected from phenyl and pyrazolyl, wherein the phenyl and pyrazolyl of $R^5$ are each optionally substituted with 1 $R^{5A}$ substituent.

In some embodiments, $R^5$ is $C_{6-10}$ aryl, which is optionally substituted with 1, 2, 3, or 4 independently selected $R^{5A}$ substituents.

In some embodiments, $R^5$ is $C_{6-10}$ aryl, which is optionally substituted with 1 or 2 independently selected $R^{5A}$ substituents.

In some embodiments, $R^5$ is $C_{6-10}$ aryl, which is optionally substituted with 1 $R^{5A}$ substituent.

In some embodiments, $R^5$ is phenyl which is optionally substituted by 1 or 2 independently selected $R^{5A}$ substituents.

In some embodiments, $R^5$ is phenyl which is optionally substituted by 1 $R^{5A}$ substituent.

In some embodiments, each $R^{5A}$ is independently selected from $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents.

In some embodiments, each $R^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents.

In some embodiments, each $R^{5A}$ is independently selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents.

In some embodiments, each $R^{5A}$ is independently selected from phenyl-$C_{1-6}$ alkyl-, $C_{3-6}$cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1, 2, 3, or 4 independently selected $R^{5B}$ substituents.

In some embodiments, each $R^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1 or 2 independently selected $R^{5B}$ substituents.

In some embodiments, each $R^{5A}$ is (4-6 membered heterocycloalkyl)-$C_{1-6}$ alkyl-, wherein the (4-6 membered heterocycloalkyl)-$C_{1-6}$ alkyl- is optionally substituted with 1 or 2 independently selected $R^{5B}$ substituents.

In some embodiments, each $R^{5A}$ is piperidinylmethyl, which is optionally substituted by 1 or 2 independently selected $R^{5B}$ groups.

In some embodiments, each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$.

In some embodiments, each $R^{a52}$, $R^{b52}$, $R^{c52}$, and $R^{d52}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a52}$, $R^{b52}$, $R^{c52}$, and $R^{d52}$ is independently selected from H and $C_{1-6}$ alkyl.

In some embodiments, each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$; and each $R^{a52}$, $R^{b52}$, $R^{c52}$, and $R^{d52}$ is independently selected from H, $C_{1-6}$ alkyl, $C_{1-6}$ haloalkyl, $C_{2-6}$ alkenyl, and $C_{2-6}$ alkynyl.

In some embodiments, each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$; and each $R^{a52}$, $R^{b52}$, $R^{c52}$, and $R^{d52}$ is independently selected from H and $C_{1-6}$ alkyl.

In some embodiments, each $R^{5B}$ is independently selected from $S(O)R^{b52}$, $S(O)NR^{c52}R^{d52}$ and $S(O)_2R^{b52}$.

In some embodiments, each $R^{5B}$ is independently selected from $S(O)R^{b52}$, $S(O)NR^{c52}R^{d52}$ and $S(O)_2R^{b52}$; and each $R^{b52}$, $R^{c52}$, and $R^{d52}$ is independently selected from H and $C_{1-6}$ alkyl.

In some embodiments, each $R^{5B}$ is $S(O)_2R^{b52}$.

In some embodiments, each $R^{5B}$ is $S(O)_2R^{b52}$, wherein each $R^{b52}$ is independently selected from H and $C_{1-6}$ alkyl.

In some embodiments, each $R^{5B}$ is $S(O)_2R^{b52}$, wherein each $R^{b52}$ is an independently selected $C_{1-6}$ alkyl group.

In some embodiments, each $R^{5B}$ is methylsulfonyl.

In some embodiments, $R^5$ is selected from pyrazolyl or phenyl, wherein the pyrazolyl and phenyl are each optionally substituted by methyl or piperidinylmethyl, wherein the piperidinylmethyl is optionally substituted by $S(O)_2R^{b52}$; and $R^{b52}$ is selected from H and $C_{1-6}$ alkyl.

In some embodiments, $R^5$ is selected from methylpyrazolyl and 4-((4-(methylsulfonyl)piperidin-1-yl)methyl)phenyl.

In some embodiments, $R^5$ is phenyl, which is optionally substituted by piperidinylmethyl, wherein the piperidinylmethyl is optionally substituted by $S(O)_2R^{b52}$; and $R^{b52}$ is selected from H and $C_{1-6}$ alkyl.

In some embodiments, $R^5$ is phenyl, which is optionally substituted by piperidinylmethyl, wherein the piperidinylmethyl is optionally substituted by methylsulfonyl.

In some embodiments, $R^5$ is 4-((4-(methylsulfonyl)piperidin-1-yl)methyl)phenyl.

In some embodiments:

$R^1$ is selected from H, D, $C_{1-6}$ alkyl, $C_{1-6}$ haloalkyl, $C_{2-6}$ alkenyl, and $C_{2-6}$ alkynyl;

$R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, $C(O)OR^{a2}$, and $NR^{c2}R^{d2}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{6-10}$ aryl, $C_{2-6}$ alkenyl, $C_{2-6}$ alkynyl, and $C_{3-10}$ cycloalkyl, wherein the $C_{1-6}$ alkyl, $C_{6-10}$ aryl and $C_{3-10}$ cycloalkyl of $R^{a2}$, $R^{b2}$, $R^{c2}$, and $R^{d2}$ are each optionally substituted with 1, 2, 3, 4, 5, 6, 7, or 8 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $C(O)R^{b21}$, $C(O)NR^{c21}R^{d21}$, $C(O)OR^{a21}$, and $S(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl of $R^{a21}$, $R^{b21}$, $R^{c21}$, and $R^{d21}$ are each optionally substituted with 1, 2, 3, 4, 5, 6, 7, or 8 independently selected $R^{2B}$ substituents;

each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a22}$, wherein each $R^{a22}$ is independently selected from H, $C_{1-6}$ alkyl, $C_{1-6}$ haloalkyl, $C_{2-6}$ alkenyl, and $C_{2-6}$ alkynyl;

$R^3$ is selected from $R^3$ is selected from H, D, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 4-10 membered heterocycloalkyl, and $OR^{a3}$, wherein the $C_{6-10}$ aryl, $C_{3-10}$ cycloalkyl, and 4-10 membered heterocycloalkyl of $R^3$ are each optionally substituted with 1, 2, 3, 4, 5, 6, 7, or 8 independently selected $R^{3A}$ substituents;

each $R^{a3}$ is selected from H, $C_{1-6}$ alkyl, $C_{1-6}$ haloalkyl, $C_{2-6}$ alkenyl, and $C_{2-6}$ alkynyl;

each $R^{3A}$ is independently selected from $C_{1-6}$ alkyl, 5-10 membered heteroaryl, $OR^{a31}$, $C(O)NR^{c31}R^{d31}$, $NR^{c31}R^{d31}$, and $S(O)_2R^{b31}$, wherein the $C_{1-6}$ alkyl and 5-10 membered heteroaryl of $R^{3A}$ are each optionally substituted with 1, 2, 3, 4, 5, 6, 7, or 8 independently selected $R^{3B}$ substituents;

each $R^{a31}$, $R^{b31}$, $R^{c31}$, and $R^{d31}$ is independently selected from H, $C_{1-6}$ alkyl, 5-10 membered heteroaryl, and 4-10 membered heterocycloalkyl, wherein the $C_{1-6}$ alkyl, 5-10 membered heteroaryl, and 4-10 membered heterocycloalkyl of $R^{a31}$, $R^{b31}$, $R^{c31}$, and $R^{d31}$ are each optionally substituted with 1, 2, 3, 4, 5, 6, 7, or 8 independently selected $R^{3B}$ substituents;

each $R^{3B}$ is independently selected from $C_{1-6}$ alkyl, $OR^{a32}$, and $NR^{c32}R^{d32}$, wherein the $C_{1-6}$ alkyl of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ are independently selected from H, $C_{1-6}$ alkyl, and 4-10 membered heterocycloalkyl, wherein the $C_{1-6}$ alkyl and 4-10 membered heterocycloalkyl of $R^{a32}$, $R^{c32}$, and $R^{d32}$ are each optionally substituted with 1, 2, 3, 4, 5, 6, 7, or 8 independently selected $R^{3C}$ substituents;

each $R^{3C}$ is $OR^{a33}$, wherein $R^{a33}$ is H;

$R^4$ is selected from H, D, $C_{1-6}$ alkyl, $C_{1-6}$ haloalkyl, $C_{2-6}$ alkenyl, $C_{2-6}$ alkynyl, $C_{6-10}$ aryl, and 5-10 membered heteroaryl, wherein the $C_{1-6}$ alkyl, $C_{2-6}$ alkenyl, $C_{2-6}$ alkynyl, $C_{6-10}$ aryl, and 5-10 membered heteroaryl of R⁴ are each optionally substituted with 1, 2, 3, 4, 5, 6, 7, or 8 independently selected $R^{4A}$ substituents;

each $R^{4A}$ is independently selected from $C_{1-6}$ alkyl, $C_{3-10}$ cycloalkyl, $OR^{a41}$, and $C(O)NR^{c41}R^{d41}$, wherein the $C_{1-6}$ alkyl and $C_{3-10}$ cycloalkyl of $R^{4A}$ are each optionally substituted with 1, 2, 3, 4, 5, 6, 7, or 8 independently selected $R^{4B}$ substituents;

each $R^{a41}$, $R^{c41}$, and $R^{d41}$ are independently selected from H and $C_{1-6}$ alkyl;

each $R^{4B}$ is independently selected from $C_{1-6}$ alkyl and CN;

$R^5$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{5A}$ is independently selected from $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$; and each $R^{a52}$, $R^{b52}$, $R^{c52}$, and $R^{d52}$ is independently selected from H and $C_{1-6}$ alkyl.

In some embodiments:

$R^1$ is selected from H, $C_{1-6}$ alkyl, $C_{1-6}$ haloalkyl, $C_{2-6}$ alkenyl, and $C_{2-6}$ alkynyl;

$R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, $C(O)OR^{a2}$, and $NR^{c2}R^{d2}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{6-10}$ aryl, $C_{2-6}$ alkenyl, $C_{2-6}$ alkynyl, and $C_{3-10}$ cycloalkyl, wherein the $C_{1-6}$ alkyl, $C_{6-10}$ aryl and $C_{3-10}$ cycloalkyl of $R^{a2}$, $R^{b2}$, $R^{c2}$, and $R^{d2}$ are each optionally substituted with 1, 2, 3, 4, 5, 6, 7, or 8 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $C(O)R^{b21}$, $C(O)NR^{c21}R^{d21}$, $C(O)OR^{a21}$, and $S(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl of $R^{a21}$, $R^{b21}$, $R^{c21}$, and $R^{d21}$ are each optionally substituted with 1, 2, 3, 4, 5, 6, 7, or 8 independently selected $R^{2B}$ substituents;

each $R^{2B}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_3U0$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a22}$, wherein each $R^{a22}$ is independently selected from H, $C_{1-6}$ alkyl, $C_{1-6}$ haloalkyl, $C_{2-6}$ alkenyl, and $C_{2-6}$ alkynyl;

$R^3$ is selected from $R^3$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 4-10 membered heterocycloalkyl, and $OR^{a3}$, wherein the $C_{6-10}$ aryl, $C_{3-10}$ cycloalkyl, and 4-10 membered heterocycloalkyl of $R^3$ are each optionally substituted with 1, 2, 3, 4, 5, 6, 7, or 8 independently selected $R^{3A}$ substituents;

each $R^{a3}$ is selected from H, $C_{1-6}$ alkyl, $C_{1-6}$ haloalkyl, $C_{2-6}$ alkenyl, and $C_{2-6}$ alkynyl;

each $R^{3A}$ is independently selected from $C_{1-6}$ alkyl, 5-10 membered heteroaryl, $OR^{a31}$, $C(O)NR^{c31}R^{d31}$, $NR^{c31}R^{d31}$, and $S(O)_2R^{b31}$, wherein the $C_{1-6}$ alkyl and 5-10 membered heteroaryl of $R^{3A}$ are each optionally substituted with 1, 2, 3, 4, 5, 6, 7, or 8 independently selected $R^{3B}$ substituents;

each $R^{a31}$, $R^{b31}$, $R^{c31}$, and $R^{d31}$ is independently selected from H, $C_{1-6}$ alkyl, 5-10 membered heteroaryl, and 4-10 membered heterocycloalkyl, wherein the $C_{1-6}$ alkyl, 5-10 membered heteroaryl, and 4-10 membered heterocycloalkyl of $R^{a31}$, $R^{b31}$, $R^{c31}$, and $R^{d31}$ are each optionally substituted with 1, 2, 3, 4, 5, 6, 7, or 8 independently selected $R^{3B}$ substituents;

each $R^{3B}$ is independently selected from $C_{1-6}$ alkyl, $OR^{a32}$, and $NR^{c32}R^{d32}$, wherein the $C_{1-6}$ alkyl of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ are independently selected from H, $C_{1-6}$ alkyl, and 4-10 membered heterocycloalkyl, wherein the $C_{1-6}$ alkyl and 4-10 membered heterocycloalkyl of $R^{a32}$, $R^{c32}$, and $R^{d32}$ are each optionally substituted with 1, 2, 3, 4, 5, 6, 7, or 8 independently selected $R^{3C}$ substituents;

each $R^{3C}$ is $OR^{a33}$, wherein $R^{a33}$ is H;

$R^4$ is selected from H, $C_{1-6}$ alkyl, $C_{1-6}$ haloalkyl, $C_{2-6}$ alkenyl, $C_{2-6}$ alkynyl, $C_{6-10}$ aryl, and 5-10 membered heteroaryl, wherein the $C_{1-6}$ alkyl, $C_{2-6}$ alkenyl, $C_{2-6}$ alkynyl, $C_{6-10}$ aryl, and 5-10 membered heteroaryl of $R^4$ are each optionally substituted with 1, 2, 3, 4, 5, 6, 7, or 8 independently selected $R^{4A}$ substituents;

each $R^{4A}$ is independently selected from $C_{1-6}$ alkyl, $C_{3-10}$ cycloalkyl, $OR^{a41}$, and $C(O)NR^{c41}R^{d41}$, wherein the $C_{1-6}$ alkyl and $C_{3-10}$ cycloalkyl of $R^{4A}$ are each optionally substituted with 1, 2, 3, 4, 5, 6, 7, or 8 independently selected $R^{4B}$ substituents;

each $R^{a41}$, $R^{c41}$, and $R^{d41}$ are independently selected from H and $C_{1-6}$ alkyl;

each $R^{4B}$ is independently selected from $C_{1-6}$ alkyl and CN;

$R^5$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{5A}$ is independently selected from $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$; and each $R^{a52}$, $R^{b52}$, $R^{c52}$, and $R^{d52}$ is independently selected from H and $C_{1-6}$ alkyl.

In some embodiments:

$R^1$ is selected from H, D, $C_{1-6}$ alkyl, $C_{1-6}$ haloalkyl, $C_{2-6}$ alkenyl, and $C_{2-6}$ alkynyl;

$R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, and $C(O)OR^{a2}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, and $C_{2-6}$ alkynyl;

each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $C(O)R^{b21}$, $C(O)NR^{c21}R^{d21}$, and $C(O)OR^{a21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl;

each $R^{2B}$ is independently selected from $C_{1-6}$ alkyl, $C_{1-6}$ haloalkyl, $C_{2-6}$ alkenyl, and $C_{2-6}$ alkynyl;

$R^3$ is selected from H, D, $C_{1-6}$ alkyl, $C_{1-6}$ haloalkyl, $C_{2-6}$ alkenyl, $C_{2-6}$ alkynyl, and $OR^{a3}$;

$R^{a3}$ is selected from H, $C_{1-6}$ alkyl, $C_{1-6}$ haloalkyl, $C_{2-6}$ alkenyl, and $C_{2-6}$ alkynyl;

$R^4$ is selected from H, D, $C_{1-6}$ alkyl, $C_{1-6}$ haloalkyl, $C_{2-6}$ alkenyl, and $C_{2-6}$ alkynyl;

$R^5$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$; and each $R^{a52}$, $R^{b52}$, $R^{c52}$, and $R^{d52}$ is independently selected from H and $C_{1-6}$ alkyl.

In some embodiments:

$R^1$ is selected from H, $C_{1-6}$ alkyl, $C_{1-6}$ haloalkyl, $C_{2-6}$ alkenyl, and $C_{2-6}$ alkynyl;

$R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, and $C(O)OR^{a2}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{32}$, $R^{b2}$, $R^{c2}$, and $R^{d2}$ is independently selected from H, $C_{1-6}$ alkyl, $C_{1-6}$ haloalkyl, $C_{2-6}$ alkenyl, and $C_{2-6}$ alkynyl;

each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a21}$, C(O)R$^{b21}$, C(O)NR$^{c21}$R$^{d21}$, and C(O)OR$^{a21}$, wherein the $C_{1-6}$ alkyl, $C_{1-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{2A}$ are each optionally substituted with 1, 2, 3, or 4 independently selected R$^{2B}$ substituents;

each R$^{a21}$, R$^{b21}$, R$^{c21}$, and R$^{d21}$ is independently selected from H, $C_{1-6}$ alkyl, $C_{1-6}$ haloalkyl, $C_{2-6}$ alkenyl, and $C_{2-6}$ alkynyl;

each R$^{2B}$ is independently selected from $C_{1-6}$ alkyl, $C_{1-6}$ haloalkyl, $C_{2-6}$ alkenyl, and $C_{2-6}$ alkynyl;

R$^3$ is selected from H, $C_{1-6}$ alkyl, $C_{1-6}$ haloalkyl, $C_{2-6}$ alkenyl, $C_{2-6}$ alkynyl, and OR$^{a3}$;

R$^{a3}$ is selected from H, $C_{1-6}$ alkyl, $C_{1-6}$ haloalkyl, $C_{2-6}$ alkenyl, and $C_{2-6}$ alkynyl;

R$^4$ is selected from H, $C_{1-6}$ alkyl, $C_{1-6}$ haloalkyl, $C_{2-6}$ alkenyl, and $C_{2-6}$ alkynyl;

R$^5$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^5$ are each optionally substituted with 1, 2, 3, or 4 independently selected R$^{5A}$ substituents;

each R$^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{5A}$ are each optionally substituted with 1, 2, 3, or 4 independently selected R$^{5B}$ substituents;

each R$^{5B}$ is independently selected from C(O)R$^{b52}$, C(O)NR$^{c52}$R$^{d52}$, C(O)OR$^{a52}$, NR$^{c52}$S(O)R$^{b52}$, NR$^{c52}$S(O)$_2$R$^{b52}$, S(O)R$^{b52}$, S(O)NR$^{c52}$R$^{d52}$, S(O)$_2$R$^{b52}$, and S(O)$_2$NR$^{c52}$R$^{d52}$; and each R$^{a52}$, R$^{b52}$, R$^{c52}$, and R$^{d52}$ is independently selected from H and $C_{1-6}$ alkyl.

In some embodiments:

R$^1$ is selected from H, D, $C_{1-6}$ alkyl, $C_{1-6}$ haloalkyl, $C_{2-6}$ alkenyl, and $C_{2-6}$ alkynyl;

R$^2$ is selected from H, phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (8-10 membered heterocycloalkyl)-$C_{1-6}$ alkyl-, and CN, wherein the phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (8-10 membered heterocycloalkyl)-$C_{1-6}$ alkyl- of R$^2$ are each optionally substituted with 1, 2, 3, or 4 independently selected R$^{2A}$ substituents;

each R$^{2A}$ is independently selected from halo, $C_{1-6}$ alkyl, $C_{1-6}$ haloalkyl, 5-6 membered heteroaryl, CN, NO$_2$, OR$^{a21}$, and C(O)OR$^{a21}$, wherein the $C_{1-6}$ alkyl and 5-6 membered heteroaryl of R$^{2A}$ are each optionally substituted with 1, 2, 3, or 4 independently selected R$^{2B}$ substituents;

each R$^{a21}$ is independently selected from H, $C_{1-6}$ alkyl, $C_{1-6}$ haloalkyl, $C_{2-6}$ alkenyl, and $C_{2-6}$ alkynyl;

R$^3$ is selected from H, D, $C_{1-6}$ alkyl, $C_{1-6}$ haloalkyl, $C_{2-6}$ alkenyl, $C_{2-6}$ alkynyl, and OR$^{a3}$;

R$^{a3}$ is selected from H, $C_{1-6}$ alkyl, $C_{1-6}$ haloalkyl, $C_{2-6}$ alkenyl, and $C_{2-6}$ alkynyl;

R$^4$ is selected from H, D, $C_{1-6}$ alkyl, $C_{1-6}$ haloalkyl, $C_{2-6}$ alkenyl, and $C_{2-6}$ alkynyl;

R$^5$ is selected from phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of R$^5$ are each optionally substituted with 1, 2, 3, or 4 independently selected R$^{5A}$ substituents;

each R$^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of R$^{5A}$ are each optionally substituted with 1, 2, 3, or 4 independently selected R$^{5B}$ substituents;

each R$^{5B}$ is independently selected from S(O)R$^{b52}$ and S(O)$_2$R$^{b52}$; and each R$^{b52}$ is independently selected from H and $C_{1-6}$ alkyl.

In some embodiments:

R$^1$ is selected from H, $C_{1-6}$ alkyl, $C_{1-6}$ haloalkyl, $C_{2-6}$ alkenyl, and $C_{2-6}$ alkynyl;

R$^2$ is selected from H, phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (8-10 membered heterocycloalkyl)-$C_{1-6}$ alkyl-, and CN, wherein the phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (8-10 membered heterocycloalkyl)-$C_{1-6}$ alkyl- of R$^2$ are each optionally substituted with 1, 2, 3, or 4 independently selected R$^{2A}$ substituents;

each R$^{2A}$ is independently selected from halo, $C_{1-6}$ alkyl, $C_{1-6}$ haloalkyl, 5-6 membered heteroaryl, CN, NO$_2$, OR$^{a21}$, and C(O)OR$^{a21}$, wherein the $C_{1-6}$ alkyl and 5-6 membered heteroaryl of R$^{2A}$ are each optionally substituted with 1, 2, 3, or 4 independently selected R$^{2B}$ substituents;

each R$^{a21}$ is independently selected from H, $C_{1-6}$ alkyl, $C_{1-6}$ haloalkyl, $C_{2-6}$ alkenyl, and $C_{2-6}$ alkynyl;

R$^3$ is selected from H, $C_{1-6}$ alkyl, $C_{1-6}$ haloalkyl, $C_{2-6}$ alkenyl, $C_{2-6}$ alkynyl, and OR$^{a3}$;

R$^{a3}$ is selected from H, $C_{1-6}$ alkyl, $C_{1-6}$ haloalkyl, $C_{2-6}$ alkenyl, and $C_{2-6}$ alkynyl;

R$^4$ is selected from H, $C_{1-6}$ alkyl, $C_{1-6}$ haloalkyl, $C_{2-6}$ alkenyl, and $C_{2-6}$ alkynyl;

R$^5$ is selected from phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of R$^5$ are each optionally substituted with 1, 2, 3, or 4 independently selected R$^{5A}$ substituents;

each R$^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1, 2, 3, or 4 independently selected $R^{5B}$ substituents;
each $R^{5B}$ is independently selected from $S(O)R^{b52}$ and $S(O)_2R^{b52}$; and
each $R^{b52}$ is independently selected from H and $C_{1-6}$ alkyl.

In some embodiments:
$R^1$ is selected from H and $C_{1-6}$ alkyl;
$R^2$ is selected from H, phenyl, benzodioxolyl, dihydrobenzodioxinyl, and CN, wherein the phenyl, benzodioxolyl, and dihydrobenzodioxinyl of $R^2$ are each optionally substituted with 1, 2, 3, or 4 independently selected $R^{2A}$ substituents;
$R^{2A}$ is independently selected from chloro, fluoro, methyl, trifluoromethyl, methoxy, pyrazolyl, tetrazolyl, CN, $NO_2$, and $C(O)OH$, wherein the pyrazolyl and tetrazolyl of $R^{2A}$ are each optionally substituted with 1 or 2 independently selected $C_{1-6}$ alkyl substituents;
$R^3$ is selected from H, $C_{1-6}$ alkyl, and $C_{1-6}$ alkoxy;
$R^4$ is selected from H and $C_{1-6}$ alkyl;
$R^5$ is phenyl, which is optionally substituted by piperidinylmethyl, wherein the piperidinylmethyl is optionally substituted by $S(O)_2R^{b52}$; and
each $R^{b52}$ is independently selected from H and $C_{1-6}$ alkyl.

In some embodiments:
$R^1$ is selected from H and $C_{1-6}$ alkyl;
$R^2$ is selected from H, phenyl, pyrrolidinyl, piperidinyl, benzodioxolyl, dihydrobenzodioxinyl, pyrazolyl, tetrazolyl, oxa-azaspiro[4.5]decanyl, isoxazolyl, pyridinyl, CN, $C(O)NR^{c2}R^{d2}$, and $NR^{c2}R^{d2}$, wherein the phenyl, pyrrolidinyl, piperidinyl, benzodioxolyl, dihydrobenzodioxinyl, oxa-azaspiro[4.5]decanyl, isoxazolyl, and pyridinyl of $R^2$ are each optionally substituted with 1, 2, 3, or 4 independently selected $R^{2A}$ substituents;
each $R^{c2}$ and $R^{d2}$ are independently selected from H, methyl, phenyl, and cyclohexyl, wherein the phenyl and cyclohexyl of $R^{c2}$ and $R^{d2}$ are each optionally substituted with 1, 2, 3, 4, 5, 6, 7, or 8 independently selected $R^{2A}$ substituents;
$R^{2A}$ is independently selected from chloro, fluoro, methyl, trifluoromethyl, methoxy, cyanomethyl, pyrazolyl, tetrazolyl, tetrazolylmethyl, CN, $NO_2$, $C(O)CH_3$, $C(O)OH$, methylsulfonyl, and methoxyethylsulfonyl, wherein the pyrazolyl and tetrazolyl of $R^{2A}$ are each optionally substituted with 1 or 2 independently selected $R^{2B}$ substituents;
$R^3$ is selected from H, methyl, ethyl, methoxy, phenyl, cyclohexyl, pyrrolidino, and tetrahydropyranyl, wherein the phenyl, cyclohexyl, and pyrrolidino of $R^3$ are each optionally substituted with 1, 2, 3, or 4 independently selected $R^{3A}$ substituents;
$R^4$ is selected from H, $C_{1-6}$ alkyl, phenyl, and indazolyl, wherein the phenyl and indazolyl of $R^4$ are each optionally substituted with methyl, methoxy, cyanocyclopropyl, or $C(O)N(CH_3)_2$; and
$R^5$ is selected from methylpyrazolyl and 4-((4-(methylsulfonyl)piperidin-1-yl)methyl)phenyl.

In some embodiments:
$R^1$ is selected from H and $C_{1-6}$ alkyl;
$R^2$ is selected from H, phenyl, benzodioxolyl, dihydrobenzodioxinyl, and CN, wherein the phenyl, benzodioxolyl, and dihydrobenzodioxinyl of $R^2$ are each optionally substituted with 1, 2, 3, or 4 independently selected $R^{2A}$ substituents;
$R^{2A}$ is independently selected from chloro, fluoro, methyl, trifluoromethyl, methoxy, pyrazolyl, tetrazolyl, CN, $NO_2$, and $C(O)OH$, wherein the pyrazolyl and tetrazolyl of $R^{2A}$ are each optionally substituted with 1 or 2 independently selected $C_{1-6}$ alkyl substituents;
$R^3$ is selected from H, methyl, ethyl, and methoxy;
$R^4$ is selected from H and $C_{1-6}$ alkyl; and
$R^5$ is 4-((4-(methylsulfonyl)piperidin-1-yl)methyl)phenyl.

In some embodiments, the compound of Formula I is a compound of Formula II:

II or a pharmaceutically acceptable salt thereof, wherein variables $R^1$, $R^2$, $R^3$, and $R^{5A}$ are defined according to the definitions provided herein for compounds of Formula I.

In some embodiments, the compound of Formula I is a compound of Formula III:

III or a pharmaceutically acceptable salt thereof, wherein n is 0, 1, 2, 3, or 4, and variables $R^1$, $R^{2A}$, $R^3$, and $R^{5A}$ are defined according to the definitions provided herein for compounds of Formula I.

In some embodiments, the compound of Formula I is a compound of Formula IV:

IV or a pharmaceutically acceptable salt thereof, wherein:
n is 0, 1, 2, 3, or 4;
m is 0, 1 or 2;
and variables $R^1$, $R^{2A}$, $R^3$, and $R^{5B}$ are defined according to the definitions provided herein for compounds of Formula I.

In some embodiments, the compound provided herein (e.g., a compound of Formula I) is selected from:

2-(4-((4-(methylsulfonyl)piperidin-1-yl)methyl)phenyl)-8-phenyl-3,6-dihydro-7H-pyrrolo[3,2-f][1,7]naphthyridin-7-one;

4-(2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

2-(4-((4-(methylsulfonyl)piperidin-1-yl)methyl)phenyl)-7-oxo-6,7-dihydro-3H-pyrrolo[3,2-f][1,7]naphthyridine-8-carbonitrile;

8-(1-methyl-1H-pyrazol-5-yl)-2-(4-((4-(methylsulfonyl)piperidin-1-yl)methyl)phenyl)-3,6-dihydro-7H-pyrrolo[3,2-f][1,7]naphthyridin-7-one;

2-(4-((4-(methylsulfonyl)piperidin-1-yl)methyl)phenyl)-8-(1H-tetrazol-5-yl)-3,6-dihydro-7H-pyrrolo[3,2-f][1,7]naphthyridin-7-one;

4-(9-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

8-(4-(1H-tetrazol-1-yl)phenyl)-9-methyl-2-(4-((4-(methylsulfonyl)piperidin-1-yl)methyl)phenyl)-3,6-dihydro-7H-pyrrolo[3,2-f][1,7]naphthyridin-7-one;

4-(6,9-dimethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

6,9-dimethyl-2-(4-((4-(methylsulfonyl)piperidin-1-yl)methyl)phenyl)-8-(p-tolyl)-3,6-dihydro-7H-pyrrolo[3,2-f][1,7]naphthyridin-7-one;

8-(4-chlorophenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one;

8-(3-chlorophenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one;

8-(4-methoxyphenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one;

4-(6,9-dimethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzonitrile;

4-(6-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

4-(6-ethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

4-(9-ethyl-6-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

9-methyl-2-(4-((4-(methylsulfonyl)piperidin-1-yl)methyl)phenyl)-3,6-dihydro-7H-pyrrolo[3,2-f][1,7]naphthyridin-7-one;

9-methyl-2-(4-((4-(methylsulfonyl)piperidin-1-yl)methyl)phenyl)-8-(4-nitrophenyl)-3,6-dihydro-7H-pyrrolo[3,2-f][1,7]naphthyridin-7-one;

8-(2,3-dihydrobenzo[b][1,4]dioxin-6-yl)-9-methyl-2-(4-((4-(methylsulfonyl)piperidin-1-yl)methyl)phenyl)-3,6-dihydro-7H-pyrrolo[3,2-f][1,7]naphthyridin-7-one;

9-methoxy-6-methyl-2-(4-((4-(methylsulfonyl)piperidin-1-yl)methyl)phenyl)-8-phenyl-3,6-dihydro-7H-pyrrolo[3,2-f][1,7]naphthyridin-7-one;

6-Methyl-8-(3-methylisoxazol-5-yl)-2-(4-((4-(methylsulfonyl)piperidin-1-yl)methyl)phenyl)-9-(tetrahydro-2H-pyran-4-yl)-3,6-dihydro-7H-pyrrolo[3,2-f][1,7]naphthyridin-7-one;

9-(4-Methoxycyclohexyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;

6-methyl-2-(1-methyl-1H-pyrazol-4-yl)-8-(3-methylisoxazol-5-yl)-9-phenyl-3,6-dihydro-7H-pyrrolo[3,2-f][1,7]naphthyridin-7-one;

9-(4-methoxycyclohexyl)-6-methyl-2-(1-methyl-1H-pyrazol-4-yl)-3,6-dihydro-7H-pyrrolo[3,2-f][1,7]naphthyridin-7-one;

N-(2-hydroxyethyl)-4-(6-methyl-2-(1-methyl-1H-pyrazol-4-yl)-8-(3-methylisoxazol-5-yl)-7-oxo-6,7-dihydro-3H-pyrrolo[3,2-f][1,7]naphthyridin-9-yl)benzamide;

4-(6-Methyl-2-(1-methyl-1H-pyrazol-4-yl)-8-(3-methylisoxazol-5-yl)-7-oxo-6,7-dihydro-3H-pyrrolo[3,2-f][1,7]naphthyridin-9-yl)-N-(2-methylbenzo[d]oxazol-5-yl)benzamide;

9-(4-(Methoxymethyl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;

6-Methyl-2-(1-methyl-1H-pyrazol-4-yl)-8-(3-methylisoxazol-5-yl)-9-(4-(((tetrahydro-2H-pyran-3-yl)amino)methyl)phenyl)-3,6-dihydro-7H-pyrrolo[3,2-f][1,7]naphthyridin-7-one;

9-(4-((2-Methoxyethyl)(methyl)amino)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;

6-Methyl-2-(1-methyl-1H-pyrazol-4-yl)-8-(3-methylisoxazol-5-yl)-9-(4-((tetrahydro-2H-pyran-4-yl)amino)phenyl)-3,6-dihydro-7H-pyrrolo[3,2-f][1,7]naphthyridin-7-one;

9-(4-(1,5-Dimethyl-1H-pyrazol-4-yl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;

9-(4-(5-(Hydroxymethyl)-1-methyl-1H-pyrazol-4-yl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;

6-Methyl-2-(1-methyl-1H-pyrazol-4-yl)-8-(3-methylisoxazol-5-yl)-9-(1-(methylsulfonyl)pyrrolidin-3-yl)-3,6-dihydro-7H-pyrrolo[3,2-f][1,7]naphthyridin-7-one;

4-(8-((3-(1H-tetrazol-5-yl)phenyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide;

4-(8-((4-((1H-tetrazol-5-yl)methyl)phenyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide;

N,N-dimethyl-4-(6-methyl-2-(1-methyl-1H-pyrazol-4-yl)-8-(4-methylpyridin-3-yl)-7-oxo-6,7-dihydro-3H-pyrrolo[3,2-f][1,7]naphthyridin-1-yl)benzamide;

(A)-8-(1-acetylpyrrolidin-3-yl)-6-methyl-2-(4-((4-(methylsulfonyl)piperidin-1-yl)methyl)phenyl)-1-phenyl-3,6-dihydro-7H-pyrrolo[3,2-f][1,7]naphthyridin-7-one;

4-(8-((4-(cyanomethyl)cyclohexyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide;

N,N-dimethyl-4-(6-methyl-2-(1-methyl-1H-pyrazol-4-yl)-8-(4-(methylsulfonyl)piperidin-1-yl)-7-oxo-6,7-dihydro-3H-pyrrolo[3,2-f][1,7]naphthyridin-1-yl)benzamide;

4-(8-(4-((2-Methoxyethyl)sulfonyl)piperidin-1-yl)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide;

N,N-dimethyl-4-(6-methyl-2-(1-methyl-1H-pyrazol-4-yl)-7-oxo-8-(2-oxa-8-azaspiro[4.5]decan-8-yl)-6,7-dihydro-3H-pyrrolo[3,2-f][1,7]naphthyridin-1-yl)benzamide;

1-(4-Methoxyphenyl)-N,N,6-trimethyl-2-(1-methyl-1H-pyrazol-4-yl)-7-oxo-6,7-dihydro-3H-pyrrolo[3,2-f][1,7]naphthyridine-8-carboxamide;

N,N,6-trimethyl-1-(1-methyl-1H-indazol-5-yl)-2-(1-methyl-1H-pyrazol-4-yl)-7-oxo-6,7-dihydro-3H-pyrrolo[3,2-f][1,7]naphthyridine-8-carboxamide; and 1-(4-(1-cyanocyclopropyl)phenyl)-N,N,6-trimethyl-2-(1-methyl-1H-pyrazol-4-yl)-7-oxo-6,7-dihydro-3H-pyrrolo[3,2-f][1,7]naphthyridine-8-carboxamide;

or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "Cn-m" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, the term "thio" refers to a group of formula —SH.

As used herein, the term "carbonyl", employed alone or in combination with other terms, refers to a —C(O)— group.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1] heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S, and B. In some embodiments, the heteroaryl is a 5-6 monocyclic heteroaryl having 1 or 2 heteroatom ring members independently selected from N, O, and S. In some embodiments, the heteroaryl group contains 3 to 10, 4 to 10, 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzoxazolyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a]pyridinyl, 1H-pyrrolo[3,2-b]pyridinyl, 1H-pyrrolo[2,3-b]pyridinyl, pyrazolo[1,5-a]pyridinyl, indazolyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or $S(O)_2$, etc.). When a ring-forming carbon atom or heteroatom of a heterocycloalkyl group is optionally substituted by one or more oxo or sulfide, the O or S of said group is in addition to the number of ring-forming atoms specified herein (e.g., a 1-methyl-6-oxo-1,6-dihydropyridazin-3-yl is a 6-membered heterocycloalkyl group, wherein a ring-forming carbon atom is substituted with an oxo group, and wherein the 6-membered heterocycloalkyl group is further substituted with a methyl group). Heterocycloalkyl groups include monocyclic and polycyclic (e.g., having 2 fused rings) systems. Included in heterocycloalkyl are monocyclic and polycyclic 3 to 10, 4 to 10, 5 to 10, 4 to 7, 5 to 7, or 5 to 6 membered heterocycloalkyl groups. Heterocycloalkyl groups can also include spirocycles and bridged rings (e.g., a 5 to 10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 5-10 membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Example heterocycloalkyl groups include pyrrolidin-2-one (or 2-oxopyrrolidinyl), 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, benzazapene, dihydrobenzodioxinyl, 2,3-dihydrobenzo[b][1,4]dioxinyl, azabicyclo[3.1.0]hexanyl, diazabicyclo[3.1.0]hexanyl, oxobicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxobicyclo[2.2.2]octanyl, azabicyclo[2.2.2] octanyl, azaadamantanyl, diazaadamantanyl, oxoadamantanyl, azaspiro[3.3]heptanyl, diazaspiro[3.3] heptanyl, oxo-azaspiro[3.3]heptanyl, azaspiro[3.4]octanyl, diazaspiro[3.4]octanyl, oxo-azaspiro[3.4]octanyl, azaspiro

[2.5]octanyl, diazaspiro[2.5]octanyl, azaspiro[4.4]nonanyl, diazaspiro[4.4]nonanyl, oxo-azaspiro[4.4]nonanyl, azaspiro[4.5]decanyl, oxa-azaspiro[4.5]decanyl, diazaspiro[4.5]decanyl, diazaspiro[4.4]nonanyl, oxo-diazaspiro[4.4]nonanyl, oxo-dihydropyridazinyl, oxo-2,6-diazaspiro[3.4]octanyl, oxohexahydropyrrolo[1,2-a]pyrazinyl, 3-oxopiperazinyl, oxo-pyrrolidinyl, oxo-pyridinyl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-dilyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl, or sulfonyl group.

As used herein, the term "independently selected from" means that each occurrence of a variable or substituent (e.g., each $R^M$), are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula I, Formula Ia, etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and A forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and Journal of Pharmaceutical Science, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula I can be prepared, for example, according to the procedures described in Scheme 1 (e.g., Compound 1-A of Scheme 1). The 4-chloro-5-nitro-1H-pyrrolo[2,3-b]pyridine with a suitable protection group such as, but not limited to benzenesulfonyl group (compound 1-1) can be treated with lithium diisopropyl amide solution and suitable bromination reagent (e.g. dibromotetrachloroethane) to generate desired compound 1-2. Compound 1-3 can be prepared by metal-catalyzed cross coupling reactions (such as Suzuki coupling) of compound 1-2 in the presence of a palladium catalyst (e.g. [1,1'-bis(diphenylphosphino)ferrocene]dichloropalladium(II)) and a base (e.g. cesium carbonate or potassium phosphate, tribasic). Compound 1-4 can be prepared by metal-catalyzed cross coupling reactions (such as Suzuki coupling) of compound 1-3 with vinylboronic acid in the presence of a palladium catalyst (e.g. [1,1'-bis(diphenylphosphino)ferrocene]dichloropalladium (II)) and a base (e.g. cesium carbonate or potassium phosphate, tribasic). Compound 1-5 can be prepared by oxidative cleavage conditions such as potassium osmate dihydrate in the presence of sodium periodate. Compound 1-5 can be then converted to compound 1-6 using reduction conditions such as but not limited to iron in combination with ammonium chloride. Amide coupling between compound 1-6 and acid 1-7 using coupling reagents (e.g. 1-[bis(dimethylamino)methylene]-1H-1,2,3-triazolo[4,5-b]pyridinium 3-oxid hexafluorophosphate) in the presence of base (e.g. diisopropylethylamine) gives corresponding amide which will either cyclize spontaneously or cyclizes upon heating to afford compound 1-8. Compound 1-9 can be prepared by treating compound 1-8 with suitable base (e.g. sodium hydride) and methylation reagent such as but not limited to, iodomethane. Compound I can be prepared by treating compound 1-9 in suitable deprotection conditions (e.g. when benzene sulfonyl was used as protection group, sodium hydroxide was used with water and methanol as co-solvent).

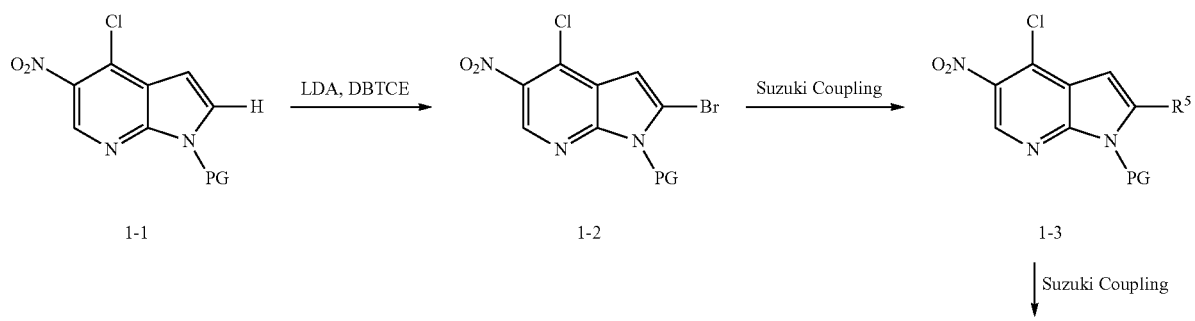

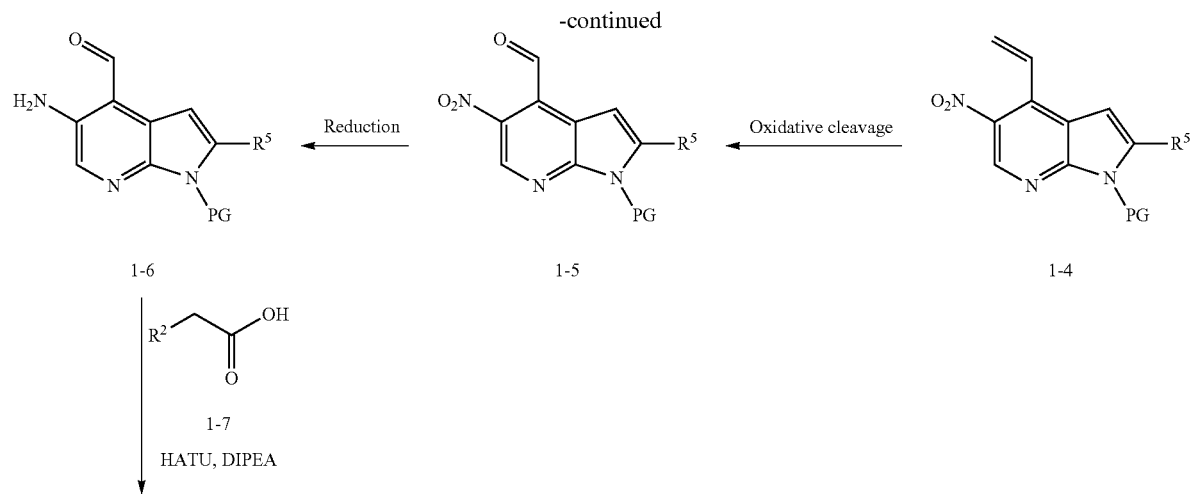

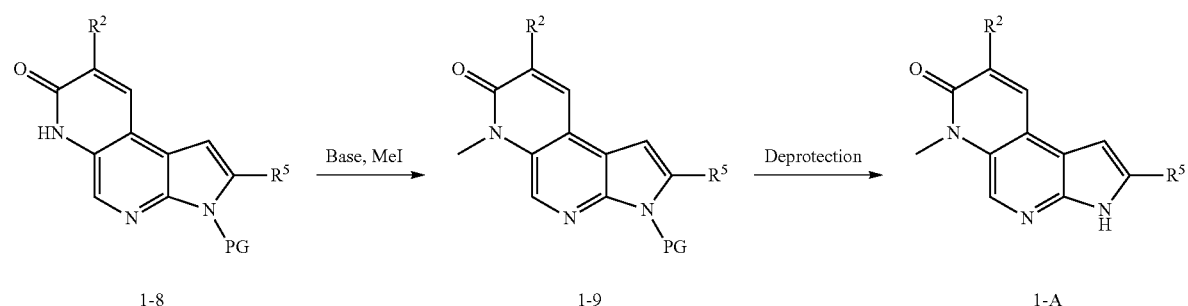

Compound of Formula I can also be prepared, for example, according to the procedures described in Scheme 2 (e.g., Compound 2-A of Scheme 2). The 4-chloro-5-nitro-1H-pyrrolo[2,3-b]pyridine with a suitable protection group such as, but not limited to benzenesulfonyl group (compound 2-1) can be treated with lithium diisopropyl amide solution and suitable bromination reagent (e.g. dibromotetrachloroethane) to generate desired compound 2-2. Compound 2-3 can be prepared by metal-catalyzed cross coupling reactions (such as Suzuki coupling) of compound 2-2 in the presence of a palladium catalyst (e.g. [1,1'-bis(diphenylphosphino)ferrocene]dichloropalladium(II)) and a base (e.g. cesium carbonate or potassium phosphate, tribasic). Compound 2-4 can be prepared by metal-catalyzed cross coupling reactions (such as Stille coupling) of compound 2-3 with tributyl(1-ethoxyvinyl)tin in the presence of a palladium catalyst (e.g. bis(triphenylphosphine)palladium (II) dichloride). The resulting intermediate can be converted to compound 2-4 by treating with acid in one pot. Compound 2-5 can be prepared by treating compound 2-4 with reduction conditions such as but not limited to iron in combination with hydrochloric acid. Amide coupling between compound 2-5 and acid 2-6 using coupling reagents (e.g. 1-[bis(dimethylamino)methylene]-1H-1,2,3-triazolo[4,5-b]pyridinium 3-oxid hexafluorophosphate) in the presence of base (e.g. diisopropylethylamine) gives corresponding amide which will either cyclize spontaneously or cyclizes upon heating to afford compound 2-7. Compound 2-8 can be prepared by treating compound 2-7 with suitable base (e.g. sodium hydride) and methylation reagent such as but not limited to, iodomethane. Compound II can be prepared by treating compound 2-8 in suitable deprotection conditions (e.g. when benzene sulfonyl was used as protection group, sodium hydroxide was used with water and methanol as co-solvent).

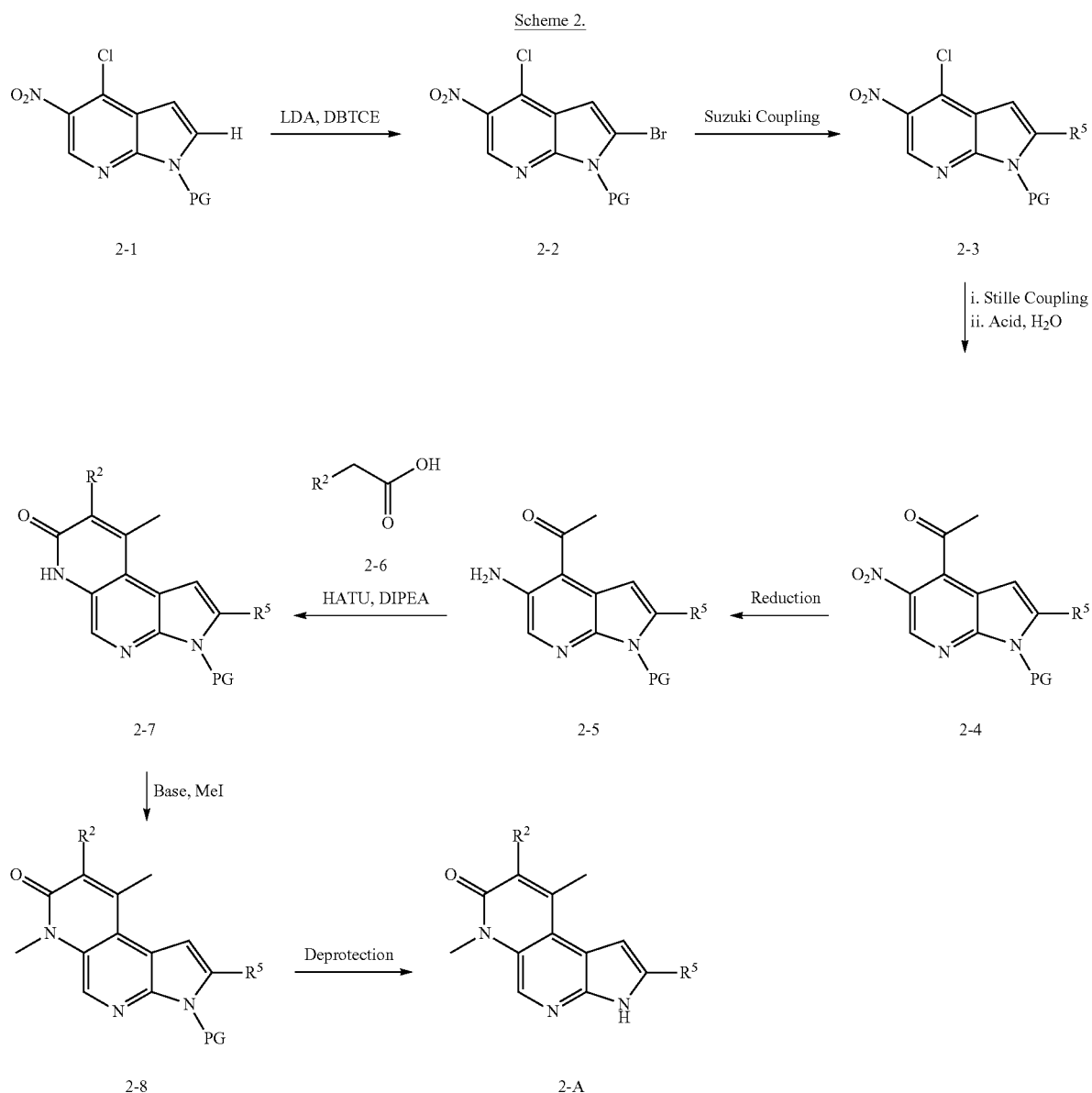

Scheme 2.

Compound of Formula I can also be prepared, for example, according to the procedures described in Scheme 3 (e.g., Compound 3-A of Scheme 3). The 4-chloro-5-nitro-1H-pyrrolo[2,3-b]pyridine with a suitable protection group such as, but not limited to benzenesulfonyl group (compound 3-1) can be treated with potassium iodide to generate compound 3-2. Compound 3-3 can be prepared by treating compound 3-2 with Grignard reagent (e.g. phenylmagnesium bromide) followed by addition of copper cyanide, lithium chloride and corresponding acyl chloride. Compound 3-4 can be prepared by treating compound 3-3 with reduction conditions such as but not limited to iron in combination with hydrochloric acid. Amide coupling between compound 3-4 and acid 3-5 using coupling reagents (e.g. 1-[bis(dimethylamino)methylene]-1H-1,2,3-triazolo[4,5-b]pyridinium 3-oxid hexafluorophosphate) in the presence of base (e.g. diisopropylethylamine) gives corresponding amide which will either cyclize spontaneously or cyclizes upon heating to afford compound 3-6. Compound 3-7 can be prepared by treating compound 3-6 with suitable base (e.g. sodium hydride) and methylation reagent such as but not limited to, iodomethane. Compound 3-7 can be treated with lithium diisopropyl amide solution and suitable bromination reagent (e.g. dibromotetrachloroethane) to generate desired compound 3-8. Compound 3-9 can be prepared by metal-catalyzed cross coupling reactions (such as Suzuki coupling) of compound 3-8 in the presence of a palladium catalyst (e.g. [1,1'-bis(diphenylphosphino)ferrocene]dichloropalladium (II)) and a base (e.g. cesium carbonate or potassium phosphate, tribasic). Compound III can be prepared by treating compound 3-9 in suitable deprotection conditions (e.g. when benzene sulfonyl was used as protection group, sodium hydroxide was used with water and methanol as co-solvent).

Scheme 3.

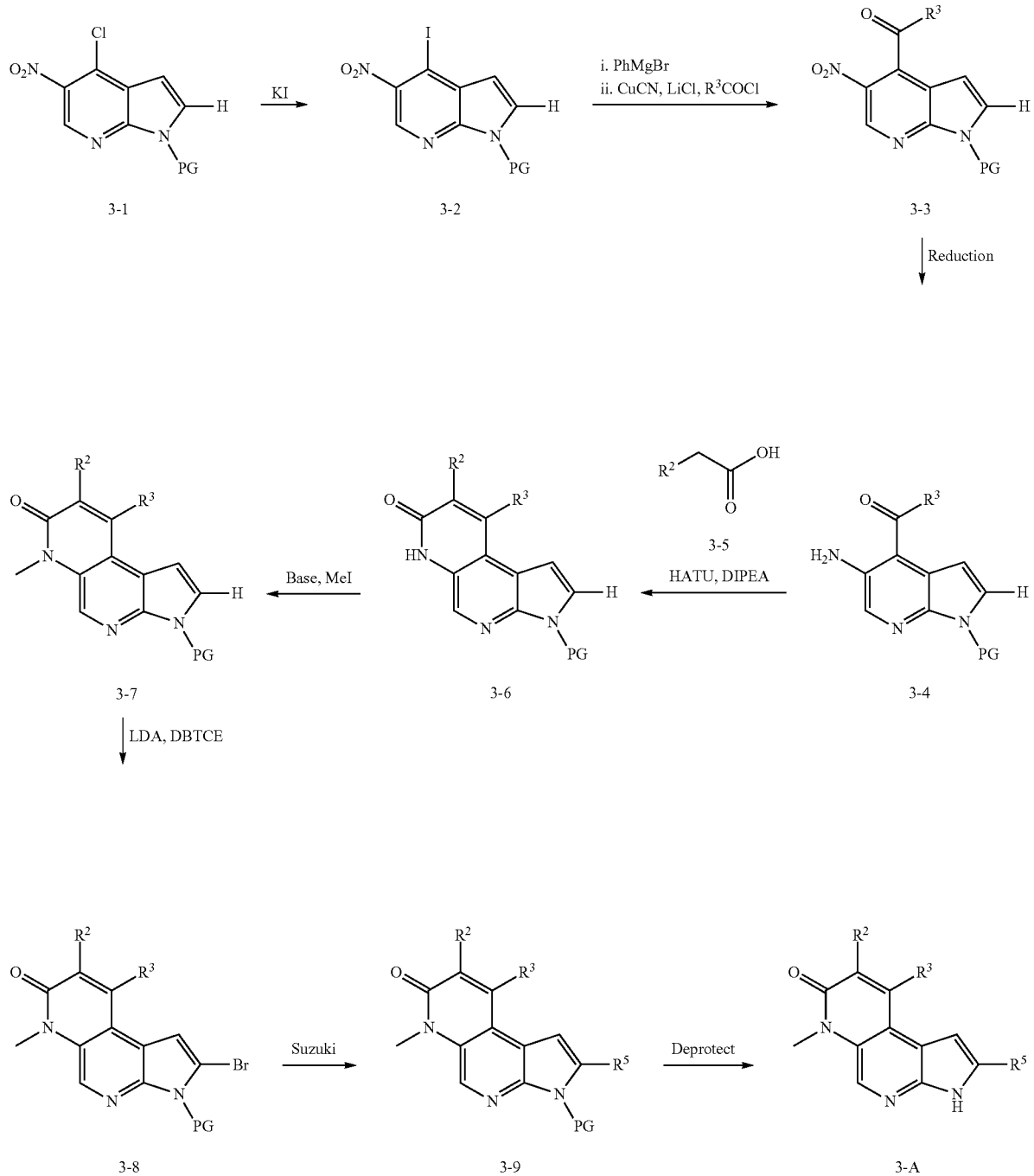

Compound of Formula I can also be prepared, for example, according to the procedures described in Scheme 4 (e.g., Compound 4-A of Scheme 4). The 4-chloro-5-nitro-1H-pyrrolo[2,3-b]pyridine with a suitable protection group such as, but not limited to benzenesulfonyl group (compound 4-1) can be treated with lithium diisopropyl amide solution and suitable bromination reagent (e.g. dibromotetrachloroethane) to generate desired compound 4-2. Compound 4-3 can be prepared by metal-catalyzed cross coupling reactions (such as Suzuki coupling) of compound 4-2 in the presence of a palladium catalyst (e.g. [1,1-bis(diphenylphosphino)ferrocene]dichloropalladium(II)) and a base (e.g. cesium carbonate or potassium phosphate, tribasic). Compound 4-4 can be prepared by metal-catalyzed cross coupling reactions (such as Suzuki coupling) of compound 4-3 in the presence of a palladium catalyst (e.g., Dichlorobis (triphenylphosphine)-palladium(II)) and a base (e.g. potassium phosphate, tribasic). Compound 4-5 can be prepared by treating compound 4-4 with reduction conditions such as but not limited to iron in combination with ammonium chloride. Compound IV can be prepared by concomitant ring closure and deprotection of 4-5 with sodium ethoxide.

Scheme 4.

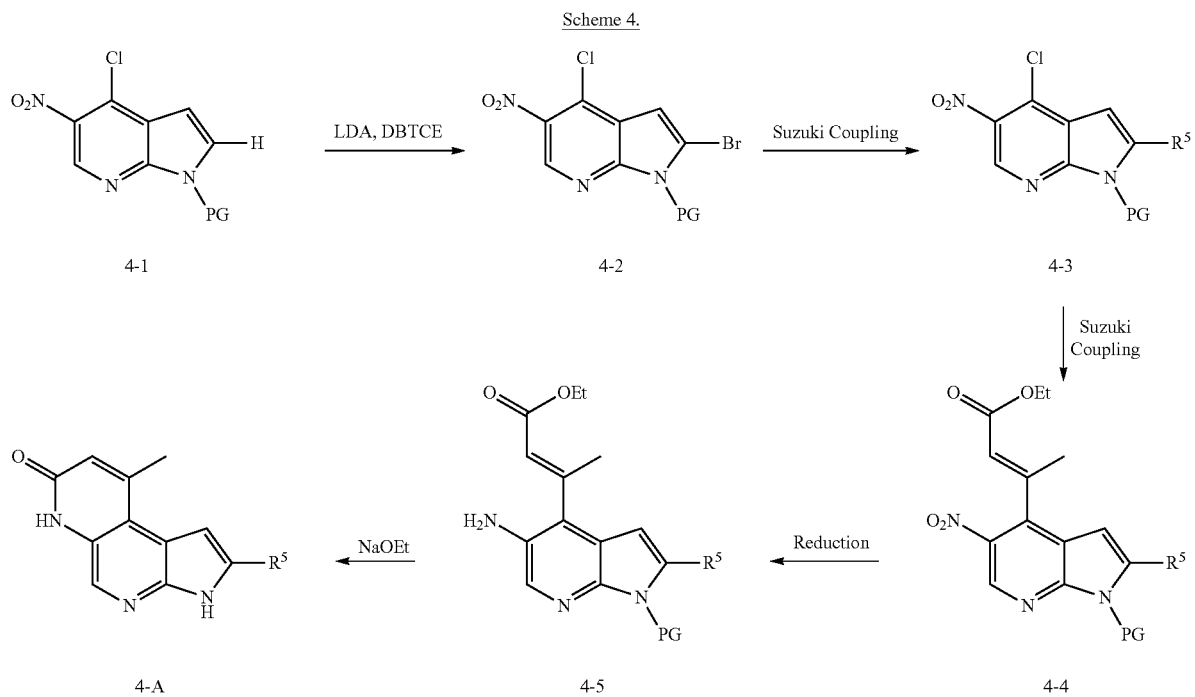

Compound of Formula I can also be prepared, for example, according to the procedures described in Scheme 5 (e.g., Compound 5-A of Scheme 5). The 4-chloro-5-nitro-1H-pyrrolo[2,3-b]pyridine with a suitable protection group such as, but not limited to benzenesulfonyl group (compound 5-1) can be treated with cyanoacetamide and hydrogenperoxide to generate compound 5-2. Compound 5-3 can be prepared by treating compound 5-2 with base and methylation reagent (e.g. dimethyl sulfate). Compound 5-4 can be prepared by treating compound 5-3 with reduction conditions such as but not limited to iron in combination with hydrochloric acid. Amide coupling between compound 5-4 and acid 5-5 using coupling reagents (e.g. 1-[bis(dimethylamino)methylene]-1H-1,2,3-triazolo[4,5-b]pyridinium 3-oxid hexafluorophosphate) in the presence of base (e.g. diisopropylethylamine) gives corresponding amide which will cyclize upon heating to afford compound 5-6. Compound 5-7 can be prepared by treating compound 5-6 with suitable base (e.g. sodium hydride) and alkylation reagent such as but not limited to, iodomethane. This alkylation of nitrogen and oxygen can be done in one step or can be done stepwise so that different alklyl on $R_3$ can be synthesized other than bis-methylation. Compound 5-7 can be treated with lithium diisopropyl amide solution and suitable bromination reagent (e.g. dibromotetrachloroethane) to generate desired compound 5-8. Compound 5-9 can be prepared by metal-catalyzed cross coupling reactions (such as Suzuki coupling) of compound 5-8 in the presence of a palladium catalyst (e.g. [1,1'-bis(diphenylphosphino)ferrocene]dichloropalladium(II)) and a base (e.g. cesium carbonate or potassium phosphate, tribasic). Compound V can be prepared by treating compound 5-9 in suitable deprotection conditions (e.g. when benzene sulfonyl was used as protection group, sodium hydroxide was used with water and methanol as co-solvent).

Scheme 5.

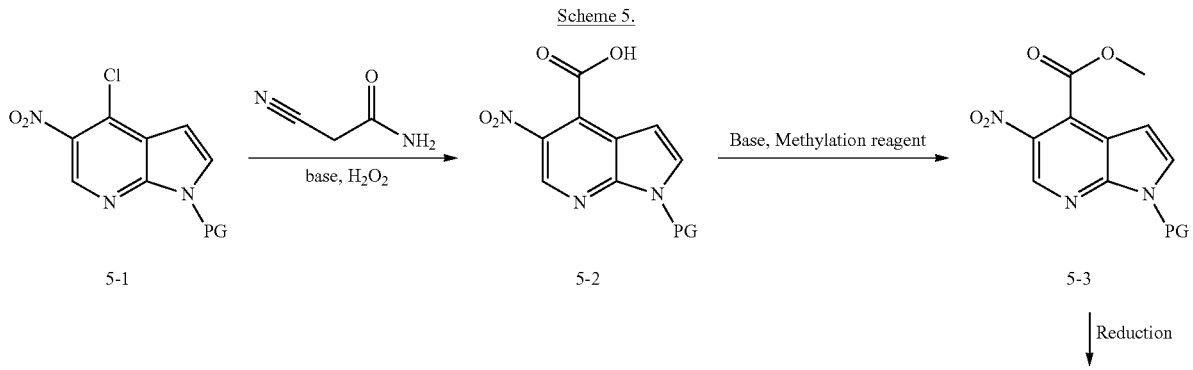

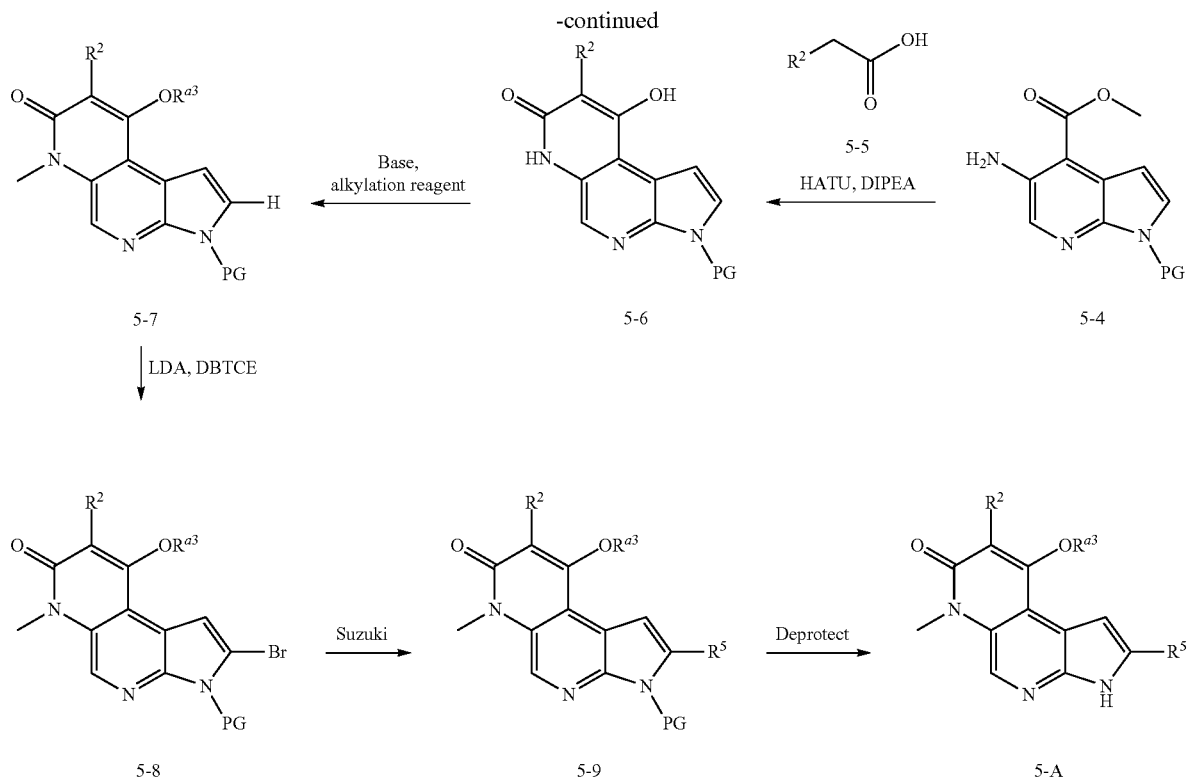

Compound of Formula I can also be prepared, for example, according to the procedures described in Scheme 6 (e.g., Compound 6-A of Scheme 6). The 4-chloro-5-nitro-1H-pyrrolo[2,3-b]pyridine with a suitable protection group such as, but not limited to benzenesulfonyl group (compound 6-1) can be converted to compound 6-2 via Suzuki coupling with 4,4,5,5-tetramethyl-2-vinyl-1,3,2-dioxaborolane. Treating compound 6-2 with lithium diisopropyl amide solution and a suitable bromination reagent (e.g. dibromotetrachloroethane) affords compound 6-3. Compound 6-3 can be subsequently converted to compound 6-4 by a metal-catalyzed cross coupling reaction (such as Suzuki coupling). Compound 6-4 can then be converted into compound 6-5 using oxidative cleavage conditions such as osmium tetroxide in the presence of sodium periodate. Treating compound 6-5 with a bromination reagent (e.g. bromine) affords compound 6-6 which can be subsequently converted to compound 6-7 under reductive conditions (such as but not limited to, iron powder in the presence of ammonium chloride). Compound 6-7 can be subsequently converted to compound 6-8 by a metal-catalyzed cross coupling reaction (such as Suzuki coupling). Treating compound 6-8 with diethyl (1,2-dichloro-2-oxoethyl)phosphonate in the presence of pyridine affords compound 6-9. Compound 6-9 can then be converted to compound 6-10 by treating with lithium chloride in the presence of DBU. Treating compound 6-10 with a suitable base (e.g. cesium carbonate) and an alkylation reagent (such as but not limited to, iodomethane) affords compound 6-11. Finally, compound 6-11 can be converted to the desired compound 6-A by a metal-catalyzed cross coupling reaction followed by deprotection.

Scheme 6.

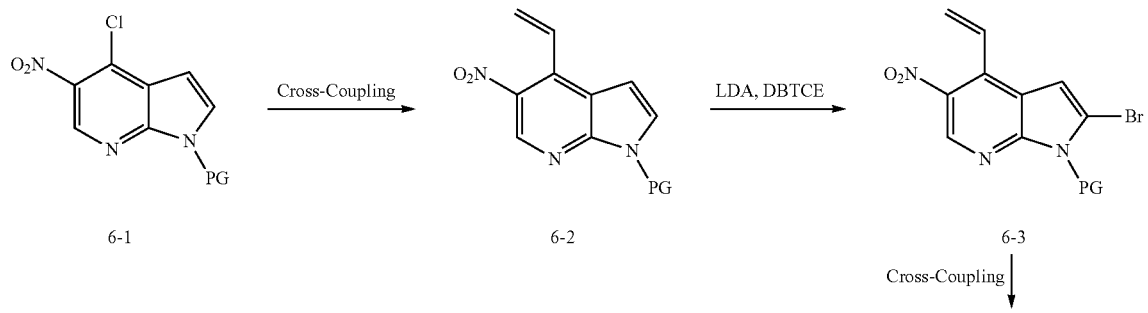

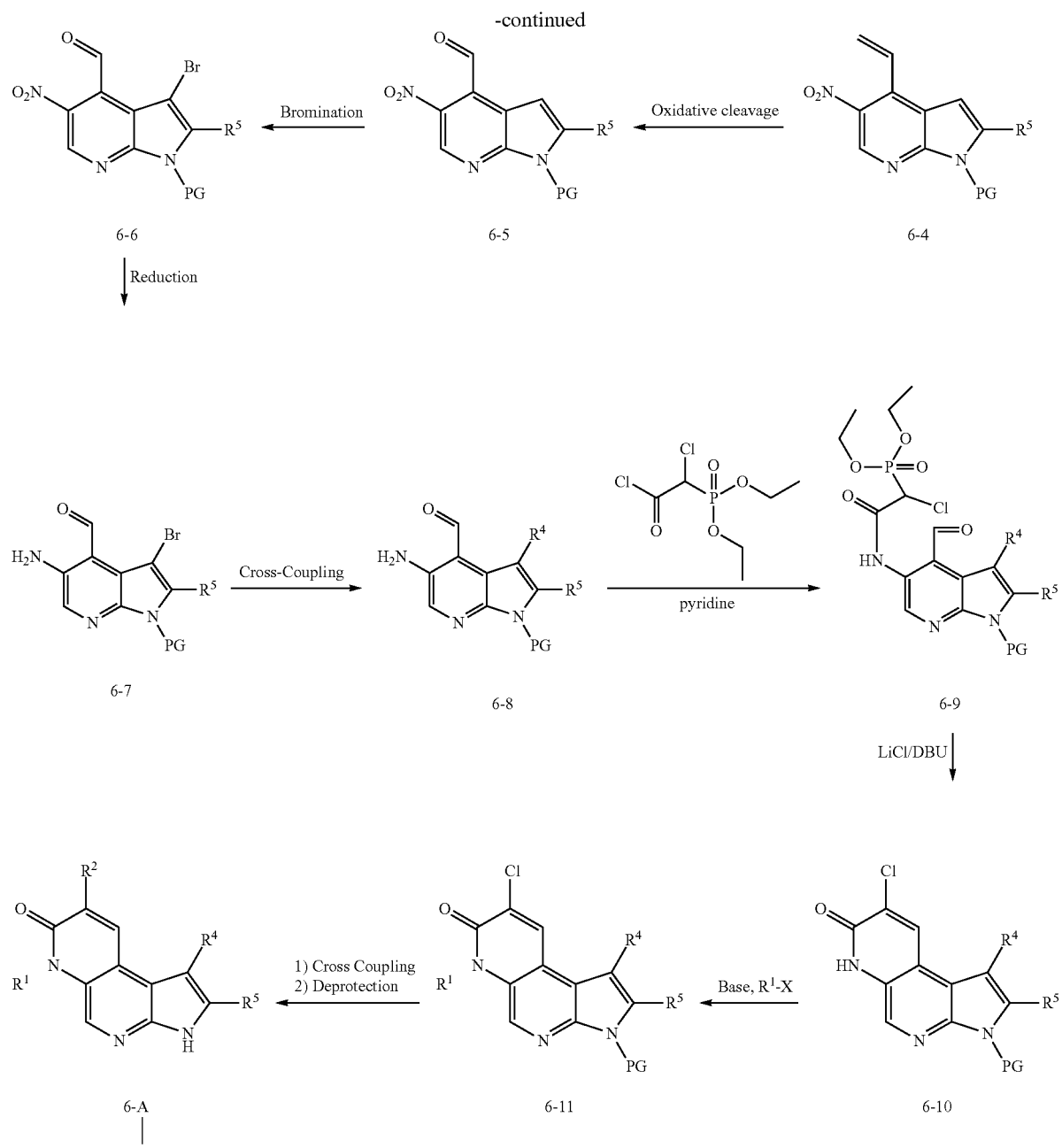

Compound of Formula I can also be prepared, for example, according to the procedures described in Scheme 7 (e.g., Compound 7-A of Scheme 7). The 4-chloro-5-nitro-1,3-dihydro-2H-pyrrolo[2,3-b]pyridin-2-one (Compound 7-1) can be converted to compound 7-2 by treating with phosphorus(V) oxychloride. Protecting the NH group of compound 7-2 with a suitable protection group (such as, but not limited to, SEM group) affords compound 7-3 which can be subsequently converted to compound 7-4 via Suzuki coupling with 4,4,5,5-tetramethyl-2-vinyl-1,3,2-dioxaborolane. Compound 7-4 can then be converted into compound 7-5 using oxidative cleavage conditions such as osmium tetroxide in the presence of sodium periodate. Compound 7-5 can be converted into 7-6 under reductive conditions (such as, but not limited to, iron powder in the presence of ammonium chloride). Treating compound 7-6 with ethyl 3-chloro-3-oxopropanoate in the presence of pyridine affords compound 7-7. Treating compound 7-7 with a suitable base (e.g. cesium carbonate) and an alkylation reagent (such as, but not limited to, iodomethane) affords compound 7-8 which can be subsequently converted to compound 7-9 upon hydrolysis. Compound 7-9 can be converted to amide 7-10 using an amide coupling reagent (e.g. 1-[bis(dimethylamino)methylene]-1H-1,2,3-triazolo[4,5-b]pyridinium 3-oxid hexafluorophosphate (HATU)) with a suitable amine. Treating compound 7-10 with a bromination reagent (e.g. NBS) affords compound 7-11 which can be subsequently converted to compound 7-12 by a metal-catalyzed cross coupling reaction (such as Suzuki coupling). Finally, compound 7-12 can be converted to the desired compound 7-A by a metal-catalyzed cross coupling reaction followed by deprotection.

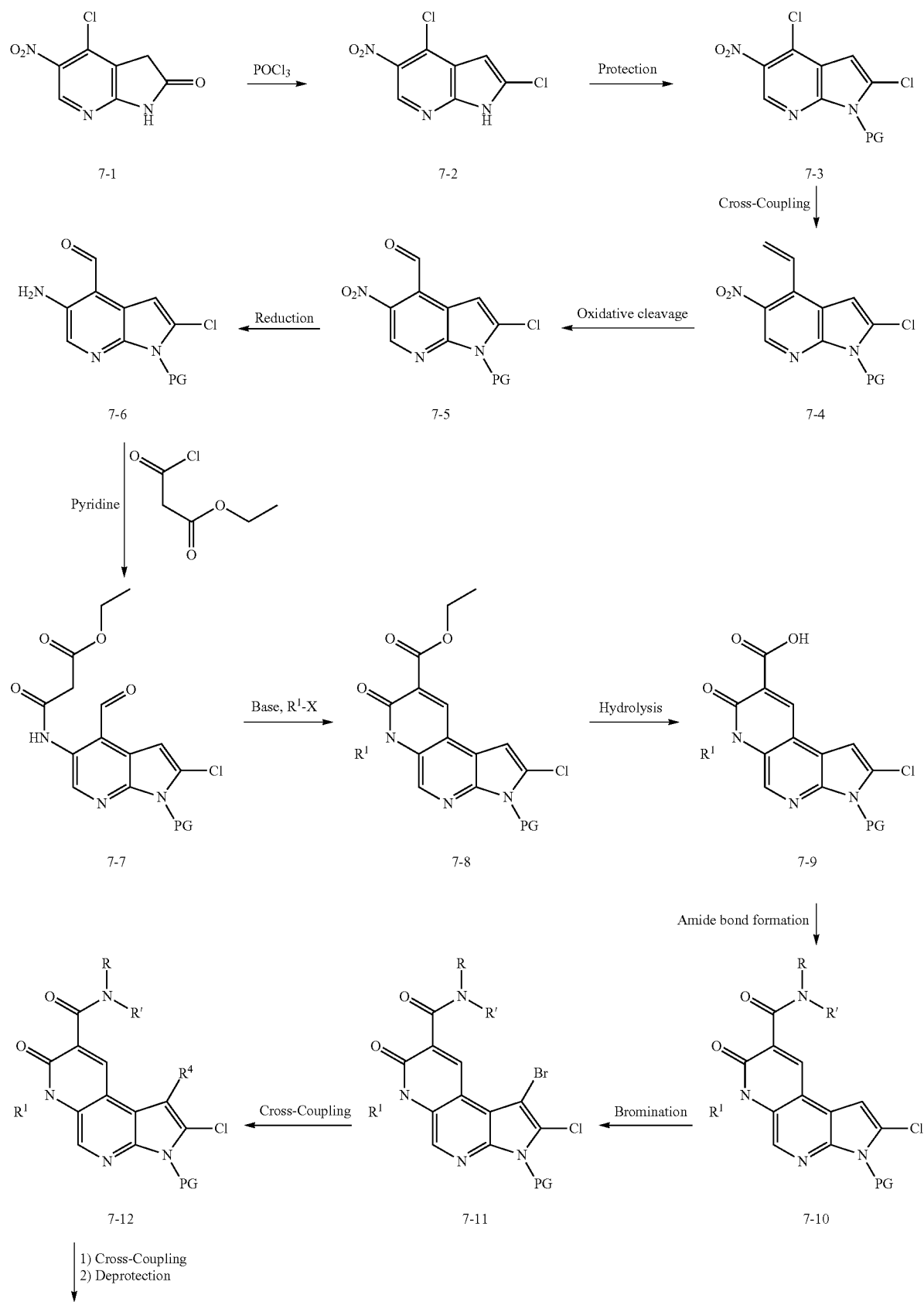
Scheme 7.

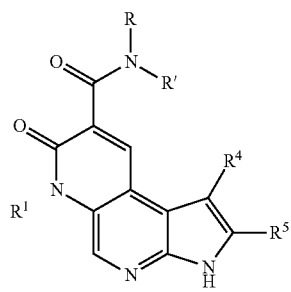

7-A

Compound of Formula I can also be prepared, for example, according to the procedures described in Scheme 8 (e.g., Compound 8-A of Scheme 8). Compound 7-3 (synthesized according to procedures described in Scheme 7) can be converted to compound 8-1 by a nucleophilic aromatic substitution reaction using an iodine source such as potassium iodide. The intermediate 8-2 can be synthesized by treating 8-1 with phenylmagnesium bromide followed by addition of lithium chloride, copper (I) cyanide and corresponding acid chloride. Metal-catalyzed cross coupling reactions (such as Suzuki couplings) can convert 8-2 to 8-3, which after reduction using a suitable reductant (e.g., iron powder) affords intermediate 8-4. Intermediate 8-5 can be synthesized by amide coupling reaction between 8-4 and suitable carboxylic acid followed by treatment of suitable base (such as cesium carbonate) under elevated temperature. Finally, compound 8-5 can be converted to compound 8-A by first reacting with alkyl halide $R^1$—X (such as iodomethane) under suitable base (such as cesium carbonate) and then followed by subsequent deprotection (e.g. when trimethylsilylethoxymethyl was used as protection group, TFA was used for deprotection).

Scheme 8.

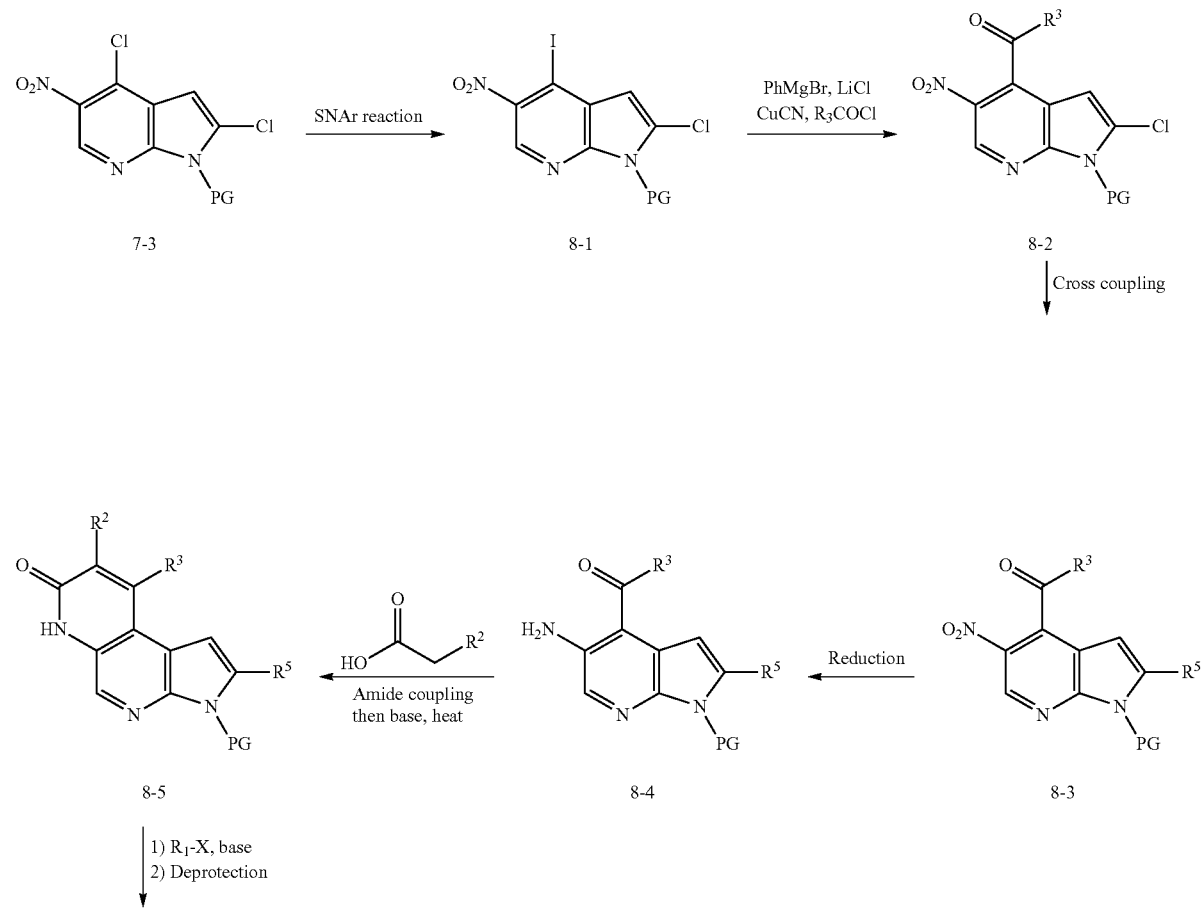

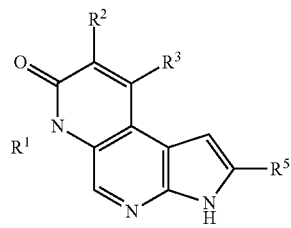

8-A

Compound of Formula I can also be prepared, for example, according to the procedures described in Scheme 9 (e.g., Compound 9-A of Scheme 9). Compound 8-2a (synthesized according to procedures described in Scheme 8 for Compound 8-2, using 4-bromobenzoyl chloride as $R^3COCl$ in step 2) can be converted to compound 9-1 by treatment with suitable reductant (such as iron powder). Compound 9-2 can be synthesized by amide coupling reaction between 9-1 and corresponding carboxylic acid using an amide coupling reagent (such as HATU). Treating compound 9-2 with base (e.g. cesium carbonate) at elevated temperature followed by treatment of alkyl halide (e.g. iodomethane) could afford compound 9-3. Metal catalyzed cross coupling reaction between 9-3 and bis(pinacolato)diboron using suitable catalyst such as [1,1'-bis(diphenylphosphino)ferrocene]dichloropalladium(II) complex with dichloromethane can give compound 9-4. Compound 9-5 can be prepared by Suzuki coupling between 9-4 and suitable coupling partners such as 1-methyl-4-(4,4,5,5-tetramethyl-1,3,2-dioxaborolan-2-yl)-1H-pyrazole. Finally, compound 9-5 can be converted to compound 9-A by a metal-catalyzed cross coupling reaction (such as Suzuki coupling) or Chan-Lam reaction followed by deprotection (e.g. when trimethylsilylethoxymethyl was used as protection group, TFA was used for deprotection).

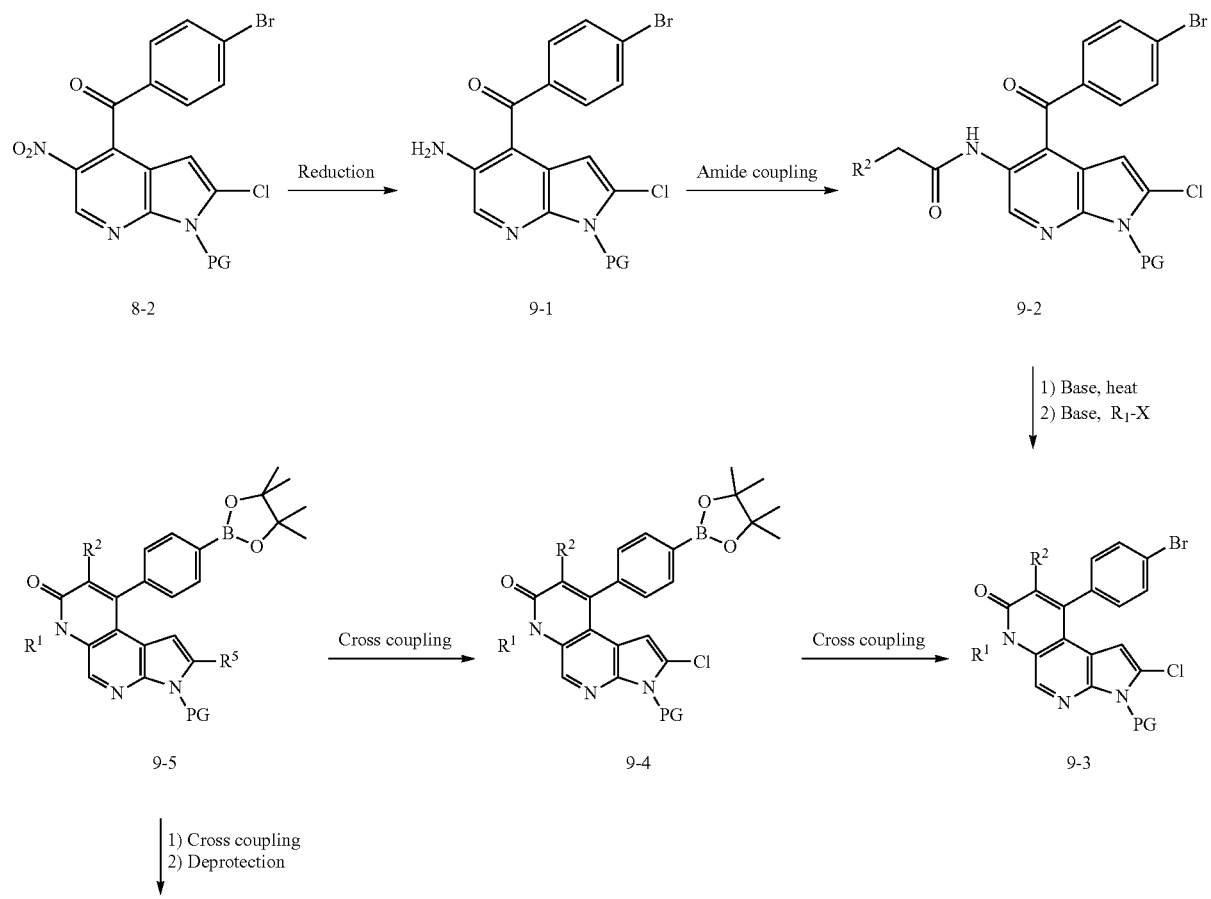

Scheme 9.

-continued

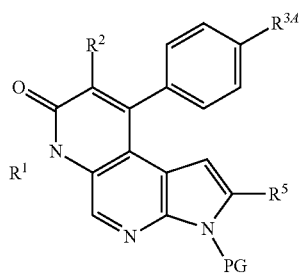

9-A

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds described herein can inhibit the activity of the V617F variant of the protein-tyrosine kinase JAK2 (i.e., "V617F" or "JAK2V617F"). Compounds which inhibit V617F are useful in providing a means of preventing the growth or inducing apoptosis in tumors, particularly by inhibiting angiogenesis. It is therefore anticipated that the compounds of the disclosure are useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the disclosure provides a method for treating a V617F-related disorder in a patient in need thereof, comprising the step of administering to said patient a compound of the disclosure, or a pharmaceutically acceptable composition thereof.

Myeloproliferative diseases (MPD) are multipotent hematopoietic stem cell disorders characterized by excess production of various blood cells. MPNs include polycythemia vera (PV), essential thrombocythemia (ET), and idiopathic myelofibrosis (IMF). JAK2 V617F mutation is reported in about 95% of patients with PV, in 35% to 70% of patients with ET, and 50% of patients with IMF. Also, JAK2 exon 12 mutations are detected in some of the V617F-negative PV patients (Ma et al., J. Mol. Diagn., 11: 49-53, 2009). In some embodiments, the compounds of the disclosure can be useful in the treatment of myeloproliferative disorders (e.g., myeloproliferative neoplasms) in a patient in need thereof, such as polycythemia vera, essential thrombocythemia, myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like.

In some embodiments, the myeloproliferative disorder is a myeloproliferative neoplasm.

In some embodiments, the myeloproliferative disorder is myelofibrosis (e.g., primary myelofibrosis (PMF) or post polycythemia vera/essential thrombocythemia myelofibrosis (Post-PV/ET MF)).

In some embodiments, the myeloproliferative disorder is primary myelofibrosis (PMF).

In some embodiments, the myeloproliferative disorder is post-essential thrombocythemia myelofibrosis (Post-ET MF).

In some embodiments, the myeloproliferative disorder is post polycythemia vera myelofibrosis (Post-PV MF).

In some embodiments, the myeloproliferative disorder is selected from primary myelofibrosis (PMF), polycythemia vera (PV), and essential thrombocythemia (ET).

In some embodiments, the myeloproliferative neoplasm is primary myelofibrosis (PMF).

In some embodiments, the myeloproliferative neoplasm is polycythemia vera (PV).

In some embodiments, the myeloproliferative neoplasm is essential thrombocythemia (ET).

Myeloproliferative diseases include disorders of a bone marrow or lymph node-derived cell type, such as a white blood cell. A myeloproliferative disease can manifest by abnormal cell division resulting in an abnormal level of a particular hematological cell population. The abnormal cell division underlying a proliferative hematological disorder is typically inherent in the cells and not a normal physiological response to infection or inflammation. Leukemia is a type of myeloproliferative disease. Exemplary myeloproliferative diseases include, but are not limited to, acute myeloid leukemia (AML), acute lymphoblastic leukemia (ALL), chronic lymphocytic leukemia (CLL), myelodysplastic syndrome (MDS), chronic myeloid leukemia (CML), hairy cell leukemia, leukemic manifestations of lymphomas, multiple myeloma, polycythemia vera (PV), essential thrombocythemia (ET), idiopathic myelofibrosis (IMF), hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, systemic mastocytosis (SM), and unclassified myeloproliferative diseases (UMPD or MPD-NC). Lymphoma is a type of proliferative disease that mainly involves lymphoid organs, such as lymph nodes, liver, and spleen. Exemplary proliferative lymphoid disorders include lymphocytic lymphoma (also called chronic lymphocytic leukemia), follicular lymphoma, large cell lymphoma, Burkitt's lymphoma, marginal zone lymphoma, lymphoblastic lymphoma (also called acute lymphoblastic lymphoma).

For example, the compounds of the disclosure are useful in the treatment of cancer. Example cancers include bladder cancer (e.g., urothelial carcinoma, squamous cell carcinoma, adenocarcinoma), breast cancer (e.g., hormone R positive, triple negative), cervical cancer, colorectal cancer, cancer of the small intestine, colon cancer, rectal cancer, cancer of the anus, endometrial cancer, gastric cancer (e.g., gastrointestinal stromal tumors), head and neck cancer (e.g., cancers of the larynx, hypopharynx, nasopharynx, oropharynx, lips, and mouth, squamous head and neck cancers), kidney cancer (e.g., renal cell carcinoma, urothelial carcinoma, sarcoma, Wilms tumor), liver cancer (e.g., hepatocellular carcinoma, cholangiocellular carcinoma (e.g., intrahepatic, hilar or perihilar, distal extrahepatic), liver angiosarcoma, hepatoblastoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, neuroendocrine cancer (e.g., pheochromocytoma, Merkel cell cancer, neuroendocrine carcinoma), skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, acute myeloid leukemia (AML), B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera (PV), essential thrombocythemia (ET), and primary myelofibrosis (PMF)), myelodysplastic syndrome, chronic eosinophilic leukemia, Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating cancer comprising administering to a patient in need thereof a therapeutically effect amount of a compound of the disclosure. In certain embodiments, the cancer is selected from T lymphoblastic lymphoma, glioblastoma, melanoma, rhabdosarcoma, lymphosarcoma, and osteosarcoma.

Other cancers treatable with the compounds of the disclosure include tumors of the eye, glioblastoma, melanoma, leiomyosarcoma, and urothelial carcinoma (e.g., ureter, urethra, bladder, urachus).

The compounds of the disclosure can also be useful in the inhibition of tumor metastases.

In some embodiments, the compounds of the disclosure as described herein can be used to treat Alzheimer's disease, HIV, or tuberculosis.

In some embodiments, the compounds of the disclosure can be useful in the treatment of myelodysplastic syndrome (MDS) in a patient in need thereof. In some embodiments, said patient having the myelodysplastic syndrome (MDS) is red blood cell transfusion dependent.

As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br. J. Haematol.* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114:937-951; Swerdlow, et al., *WHO Classification of Tumours of Haematopoietic and Lymphoid Tissues.* 4th Edition. Lyon France: IARC Press; 2008:88-103; Bunning and Germing, "Myelodysplastic syndromes/neoplasms" in Chapter 5, Swerdlow, et al, eds. WHO Classification of Tumours of Haematopoietic and Lymphoid Tissues, (ed. 4th edition): Lyon, France: IARC Press; 2008:88-103).

TABLE 1

2008 WHO Classification for De Novo Myelodysplastic Syndrome

| Subtype | Blood | Bone Marrow |
| --- | --- | --- |
| Refractory cytopenia with unilineage dysplasia (RCUD) | Single or Bicytopenia | Dysplasia in ≥10% of 1 cell line, <5% blasts |

TABLE 1-continued

2008 WHO Classification for De Novo Myelodysplastic Syndrome

| Subtype | Blood | Bone Marrow |
| --- | --- | --- |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × $10^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × $10^9$/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × $10^9$/L monocytes | Unilineage or multilineage dysplasia, ± Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del(5q) | Anemia, platelets normal or increased | Unilineage erythroid. Isolated del(5q), <5% blasts |

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory anemia with ring sideroblasts associated with thrombocytosis (RARS-T).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

In some embodiments, the compounds of the disclosure can be useful in the treatment of myeloproliferative disorder/myelodysplastic overlap syndrome (MPD/MDS overlap syndrome).

In some embodiments, the compounds of the disclosure can be useful in the treatment of leukemia.

In some embodiments, the compounds of the disclosure can be useful in the treatment of acute myeloid leukemia (AML).

In addition to oncogenic neoplasms, the compounds of the disclosure can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds provided herein may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

In some embodiments, the compounds provided herein can be used in the treatment of a hypophosphatemia disorder such as, for example, X-linked hypophosphatemic rickets, autosomal recessive hypophosphatemic rickets, and autosomal dominant hypophosphatemic rickets, or tumor-induced osteromalacia.

In some embodiments, provided herein is a method of increasing survival or progression-free survival in a patient, comprising administering a compound provided herein to the patient. In some embodiments, the patient has cancer. In some embodiments, the patient has a disease or disorder described herein. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a V617F variant with a compound described herein includes the administration of a compound described herein to an individual or patient, such as a human, having a V617F variant, as well as, for example, introducing a compound described herein into a sample containing a cellular or purified preparation containing the V617F variant.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., Remington; The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed; Ash and Ash Eds.; Gower Publishing Company: 2007; Pharmaceutical Preformulation and Formulation, 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment or prevention of V617F-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD19, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (ruxolitinib, additional JAK1/2 and JAK1-selective, baricitinib or itacitinib), Pim kinase inhibitors (e.g., LGH447, INCB053914 and SGI-1776), PI3 kinase inhibitors including PI3K-delta selective and broad spectrum PI3K inhibitors (e.g., INCB50465 and INCB50797), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfdzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibitors (e.g., olaparib or rucaparib), and inhibitors of BTK such as ibrutinib.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2.

In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012, nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012. In some embodiments, the anti-PD1 antibody is SHR-1210. Other anti-cancer agent (s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO 1, TDO, or arginase. Examples of IDO 1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2′,3′-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with inhibitors described herein. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with compounds described herein. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide, ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alphaethinylestradiol, diethylstilbestrol, testosterone, prednisone, fluoxymesterone, methylprednisolone, methyltestosterone, prednisolone, triamcinolone, chiorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (e.g., vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel, mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin (see e.g., U.S. Pat. Nos. 9,233,985, 10,065,974, 10,287,303, 8,524,867, the disclosures of which are incorporated by reference herein in their entireties).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating V617F in tissue samples, including human, and for identifying V617F inhibitors by binding of a labeled compound. Substitution of one or more of the atoms of the compounds of the present disclosure can also be useful in generating differentiated ADME (Adsorption, Distribution, Metabolism and Excretion.) Accordingly, the present disclosure includes V617F assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula I can be optionally substituted with deuterium atoms, such as —$CD_3$ (i.e., trideuteromethyl) being substituted for —$CH_3$). In some embodiments, alkyl groups of the disclosed Formulas (e.g., Formula I) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, 1-6, 1-8, 1-10, 1-12, 1-14, 1-16, 1-18, or 1-20 deuterium atoms. In some embodiments, all of the hydrogen atoms in a compound can be replaced or substituted by deuterium atoms.

In some embodiments, each hydrogen atom of the compounds provided herein, such as hydrogen atoms attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, is optionally replaced by deuterium atoms.

In some embodiments, each hydrogen atom of the compounds provided herein, such as hydrogen atoms to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, is replaced by deuterium atoms (i.e., the alkyl, alkenyl, alkynyl, aryl, phenyl, cycloalkyl, heterocycloalkyl, or heteroaryl substituents, or —$C_{1-4}$ alkyl-, alkylene, alkenylene, and alkynylene linking groups are perdeuterated).

In some embodiments, 1, 2, 3, 4, 5, 6, 7, 8, 9, 10, 11, or 12 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, are optionally replaced by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene and alkynylene linking groups, as described herein, are optionally replaced by deuterium atoms.

In some embodiments, the compound provided herein (e.g., the compound of any of Formulas I-IV), or a pharmaceutically acceptable salt thereof, comprises at least one deuterium atom.

In some embodiments, the compound provided herein (e.g., the compound of any of Formulas I-IV), or a pharmaceutically acceptable salt thereof, comprises two or more deuterium atoms.

In some embodiments, the compound provided herein (e.g., the compound of any of Formulas I-IV), or a pharmaceutically acceptable salt thereof, comprises three or more deuterium atoms.

In some embodiments, for a compound provided herein (e.g., the compound of any of Formulas I-IV), or a pharmaceutically acceptable salt thereof, all of the hydrogen atoms are replaced by deuterium atoms (i.e., the compound is "perdeuterated").

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances, (see e.g., A. Kerekes et. al. *J. Med Chem.* 2011, 54, 201-210; R. Xu et. al. *J. Label Compd Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro V617F labeling and competition assays, compounds that incorporate $^3H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind V617F by monitoring its concentration variation when contacting with V617F, through tracking of the labeling. For example, a test compound (labeled) can be evaluated for its ability to reduce binding of another compound which is known to bind to V617F (i.e., standard compound). Accordingly, the ability of a test compound to compete with the standard compound for binding to V617F directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of V617F-associated diseases or disorders as described herein, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 30×100 mm or Waters XBridge™ $C_{18}$ 5 µm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 µm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Example 1. 2-(4-((4-(Methylsulfonyl)piperidin-1-yl)methyl)phenyl)-8-phenyl-3,6-dihydro-7H-pyrrolo[3,2-f][1,7]naphthyridin-7-one

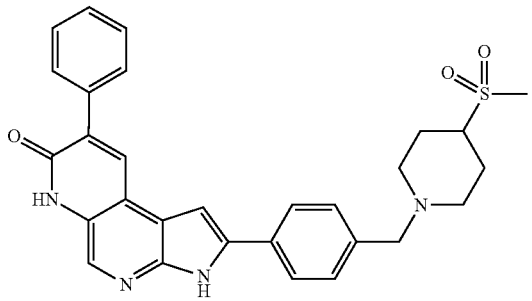 [SMILES: CS(=O)(=O)C1CCN(Cc2ccc(-c3cc4c(ncc5[nH]c(=O)c(-c6ccccc6)cc54)[nH]3)cc2)CC1]

Step 1. 4-(Methylsulfonyl)-1-(4-(4,4,5,5-tetramethyl-1,3,2-dioxaborolan-2-yl)benzyl)piperidine

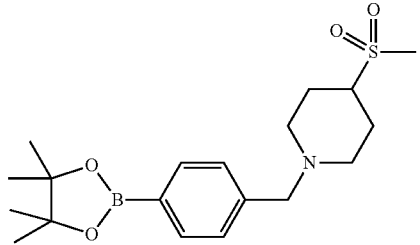

To a solution of 2-(4-(bromomethyl)phenyl)-4,4,5,5-tetramethyl-1,3,2-dioxaborolane (3000 mg, 10.10 mmol, Combi Blocks cat #BB-2488) in dimethylformamide (40 ml) was added cesium carbonate (9873 mg, 30.3 mmol) and 4-(methylsulfonyl)piperidine (1814 mg, 11.11 mmol). The resulting solution was stirred at room temperature (r.t.) for 1 hour. After this time, the mixture was diluted with ethyl acetate and then washed with water and brine. The organic layer was dried over $MgSO_4$, filtered, and then concentrated to dryness. The residue was used in the next step without purification. LC-MS calculated for $C_{19}H_{31}BNO_4S$ $(M+H)^+$: m/z=380.2. found 380.2.

Step 2. 2-Bromo-4-chloro-5-nitro-1-(phenylsulfonyl)-1H-pyrrolo[2,3-b]pyridine

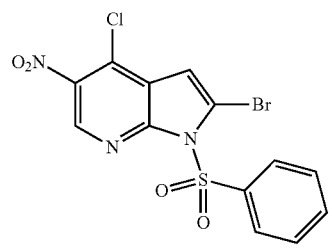 [SMILES: O=[N+]([O-])c1cnc2c(cc(Br)n2S(=O)(=O)c2ccccc2)c1Cl]

To a solution of 4-chloro-5-nitro-1-(phenylsulfonyl)-1H-pyrrolo[2,3-b]pyridine (20 g, 59.2 mmol, Astatech Inc. cat #P12207) in tetrahydrofuran (250 ml) was added lithium diisopropylamide solution (2.0M in tetrahydrofuran/heptane/ethylbenzene, 89 mL, 178 mmol) over 10 minutes at −78° C. The resulting solution was stirred at −78° C. for 30 minutes then 1,2-dibromo-1,1,2,2-tetrachloroethane (38.6 g, 118 mmol) in tetrahydrofuran was added and the resulting solution was then warmed up r.t. over 30 minutes and stirred at r.t. for 1 hour. After this time, the reaction was quenched by addition of 1N HCl and then extracted by ethyl acetate. The organic layer was then washed with water and brine, dried over $MgSO_4$, filtered, and then concentrated to dryness. The residue was purified by silica gel chromatography using 0-100% ethyl acetate in hexanes to afford the desired product (14.2 g, 34.1 mmol) as brownish solid. LC-MS calculated for $C_{13}H_8BrClN_3O_4S$ $(M+H)^+$: m/z=415.9. found 415.9.

Step 3. 4-Chloro-2-(4-((4-((methylsulfonyl)piperidin-1-yl)methyl)phenyl)-5-nitro-1-(phenylsulfonyl)-1H-pyrrolo[2,3-b]pyridine

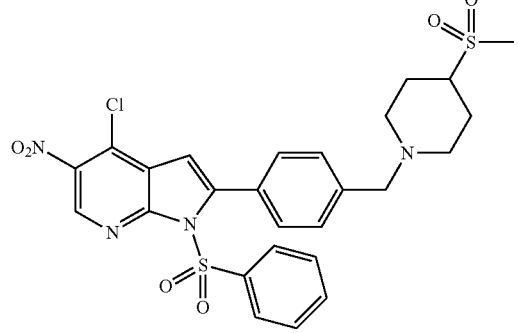

To a solution of 2-bromo-4-chloro-5-nitro-1-(phenylsulfonyl)-1H-pyrrolo[2,3-b]pyridine (2.5 g, 6.00 mmol) and 4-(methylsulfonyl)-1-(4-(4,4,5,5-tetramethyl-1,3,2-dioxaborolan-2-yl)benzyl)piperidine (1.366 g, 3.60 mmol) in dioxane (50 mL) and water (12.50 mL) was added cesium carbonate (7.82 g, 24.00 mmol) and [1,1'-bis(diphenylphosphino)ferrocene]dichloropalladium(II) (0.980 g, 1.20 mmol). $N_2$ was bubbled through the mixture for 5 minutes then the mixture was stirred at 70° C. for 2 hours. The resulting solution was then cooled to r.t., water was removed, the resulting mixture was concentrated to dryness and then purified by silica gel chromatography using 0-5% methanol in dichloromethane with 1% triethylamine to afford the desired product as brownish oil (1.40 g, 2.38 mmol). LC-MS calculated for $C_{28}H_{29}N_4O_6S_2$ $(M+H)^+$: m/z=589.2. found 589.2.

Step 4. 2-(4-((4-(Methylsulfonyl)piperidin-1-yl)methyl)phenyl)-5-nitro-1-(phenylsulfonyl)-4-vinyl-1H-pyrrolo[2,3-b]pyridine

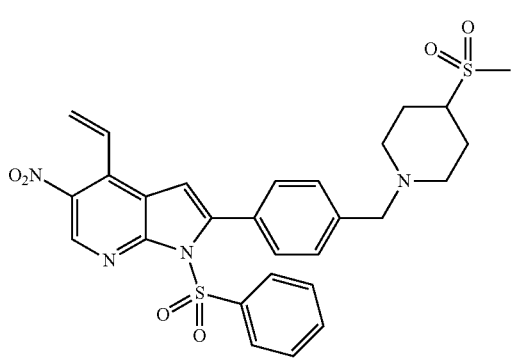 [SMILES: C=Cc1c([N+](=O)[O-])cnc2c1cc(-c1ccc(CN3CCC(S(C)(=O)=O)CC3)cc1)n2S(=O)(=O)c1ccccc1]

To a solution of 4-chloro-2-(4-((4-(methylsulfonyl)piperidin-1-yl)methyl)phenyl)-5-nitro-1-(phenylsulfonyl)-1H-pyrrolo[2,3-b]pyridine (1100 mg, 1.867 mmol) and 4,4,5,5-tetramethyl-2-vinyl-1,3,2-dioxaborolane (345 mg, 2.241 mmol, Combi Blocks cat #PN-8602) in dioxane (10 mL) and water (2.500 mL) was added chloro(2-dicyclohexylphosphino-2',4',6'-triisopropyl-1,1'-biphenyl) [2-(2'-amino-1,1'-biphenyl)]palladium(II) (73.5 mg, 0.093 mmol) and potassium carbonate (774 mg, 5.60 mmol). $N_2$ was bubbled through the mixture for 5 minutes then the mixture was stirred at 70° C. for 2 hours. After this time, the mixture was cooled to r.t., diluted with dichloromethane, then washed with water and brine. The organic layer was dried over $MgSO_4$, filtered, concentrated to dryness, and then purified by silica gel chromatography using 0-5% methanol in dichloromethane with 1% triethylamine to afford desired product as brownish solid (0.64 g, 1.10 mmol). LC-MS calculated for $C_{28}H_{29}N_4O_6S_2$ $(M+H)^+$: m/z=595.2. found 595.2.

Step 5. 2-(4-((4-(Methylsulfonyl)piperidin-1-yl)methyl)phenyl)-5-nitro-1-(phenylsulfonyl)-1H-pyrrolo[2,3-b]pyridine-4-carbaldehyde

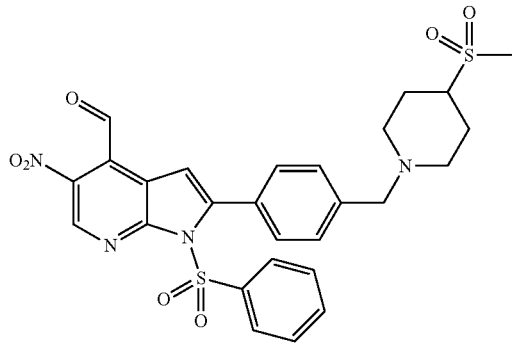 [SMILES: CS(=O)(=O)C1CCN(Cc2ccc(-c3cc4c(C=O)c([N+](=O)[O-])cnc4n3S(=O)(=O)c3ccccc3)cc2)CC1]

To a solution of 2-(4-((4-(methylsulfonyl)piperidin-1-yl)methyl)phenyl)-5-nitro-1-(phenylsulfonyl)-4-vinyl-1H-pyrrolo[2,3-b]pyridine (2.1 g, 3.6 mmol) in tetrahydrofuran (10 mL) and water (5.0 mL) was added sodium periodate (2.32 g, 10.8 mmol) and potassium osmate dihydrate (0.013 g, 0.036 mmol) then the resulting mixture was stirred at r.t. for 15 hours. After this time, the mixture was diluted with 5% methanol in dichloromethane and then washed with water and brine. The organic layer was dried over $MgSO_4$, filtered, and then concentrated to dryness. The residue was purified by silica gel chromatography using 0-30% methanol in dichloromethane to afford the desired product (1.65 g, 2.83 mmol). LC-MS calculated for $C_{27}H_{27}N_4O_7S_2$ $(M+H)^+$: m/z=583.2. found 583.2.

Step 6. 5-Amino-2-(4-((4-(methylsulfonyl)piperidin-1-yl)methyl)phenyl)-1-(phenylsulfonyl)-1H-pyrrolo[2,3-b]pyridine-4-carbaldehyde

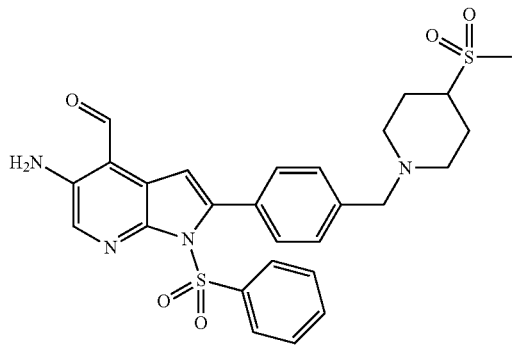

To a solution of 2-(4-((4-(methylsulfonyl)piperidin-1-yl)methyl)phenyl)-5-nitro-1-(phenylsulfonyl)-1H-pyrrolo[2,3-b]pyridine-4-carbaldehyde (300 mg, 0.515 mmol) in tetrahydrofuran (2 mL), methanol (2.000 mL), and water (2.000 mL), was added iron (288 mg, 5.15 mmol) and ammonium chloride (275 mg, 5.15 mmol), and the resulting mixture was stirred at 80° C. for 15 hours. After this time, the mixture was cooled to r.t., diluted with methanol, filtered, and then concentrated to dryness. The residue was purified by silica gel chromatography using 0-40% methanol in dichloromethane to afford the desired product as brownish oil (100 mg, 0.181 mmol). LC-MS calculated for $C_{27}H_{29}N_4O_5S_2$ (M+H)$^+$: m/z=553.2. found 553.1.

Step 7. 2-(4-((4-(Methylsulfonyl)piperidin-1-yl)methyl)phenyl)-8-phenyl-3-(phenylsulfonyl)-3,6-dihydro-7H-pyrrolo[3,2-f][1,7]naphthyridin-7-one

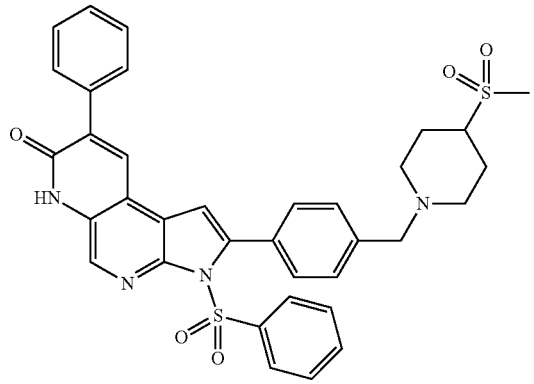 [SMILES: CS(=O)(=O)C1CCN(Cc2ccc(-c3cc4c5cc(-c6ccccc6)c(=O)[nH]c5cnc4n3S(=O)(=O)c3ccccc3)cc2)CC1]

To a solution of 5-amino-2-(4-((4-(methylsulfonyl)piperidin-1-yl)methyl)phenyl)-1-(phenylsulfonyl)-1H-pyrrolo[2,3-b]pyridine-4-carbaldehyde (50 mg, 0.090 mmol) in dimethylformamide (2 mL) was added 2-phenylacetic acid (18.48 mg, 0.136 mmol) and N,N'-diisopropylethylamine (47.4 μL, 0.271 mmol), followed by addition of (1-[bis(dimethylamino)methylene]-1H-1,2,3-triazolo[4,5-b]pyridinium 3-oxide hexafluorophosphate (68.8 mg, 0.181 mmol). The resulting solution was stirred at r.t. for 24 hours then purified by prep-LCMS (XBridge C18 column, eluting with a gradient of acetonitrile/water containing 0.1% TFA, at flow rate of 60 mL/min) to obtain the desired product as a yellowish powder. LC-MS calculated for $C_{35}H_{33}N_4O_5S_2$ (M+H)$^+$: m/z=653.2. found 653.2. $^1$H NMR (500 MHz, DMSO-d6) δ 12.33 (s, 1H), 8.51 (s, 1H), 8.46 (s, 1H), 7.79 (q, J=8.1 Hz, 6H), 7.67 (d, J=7.8 Hz, 3H), 7.57-7.51 (m, 3H), 7.49-7.41 (m, 3H), 4.46 (d, J=4.3 Hz, 2H), 3.61 (d, J=12.3 Hz, 2H), 3.45 (tt, J=12.4, 3.7 Hz, 1H), 3.09 (d, J=11.8 Hz, 2H), 3.02 (s, 3H), 2.32 (d, J=13.6 Hz, 2H), 1.91 (qd, J=13.6, 4.1 Hz, 2H).

Step 8. 2-(4-((4-(Methylsulfonyl)piperidin-1-yl)methyl)phenyl)-8-phenyl-3,6-dihydro-7H-pyrrolo[3,2-f][1,7]naphthyridin-7-one

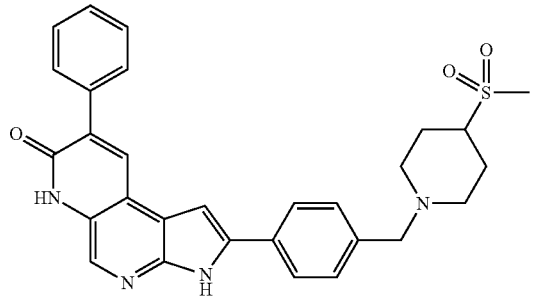 [SMILES: CS(=O)(=O)C1CCN(Cc2ccc(-c3cc4c(ncc5[nH]c(=O)c(-c6ccccc6)cc54)[nH]3)cc2)CC1]

2-(4-((4-(methylsulfonyl)piperidin-1-yl)methyl)phenyl)-8-phenyl-3-(phenylsulfonyl)-3,6-dihydro-7H-pyrrolo[3,2-f][1,7]naphthyridin-7-one was dissolved in 1 mL methanol and 1 mL 2.5 M sodium hydroxide solution then stirred at 60° C. for 1 hour. After this time, the mixture was cooled to r.t., diluted with methanol, then purified by prep-LCMS (XBridge C18 column, eluting with a gradient of acetonitrile/water containing 0.1% TFA, at flow rate of 60 mL/min) to give the desired compound. LC-MS calculated for $C_{29}H_{29}N_4O_3S$ (M+H)$^+$: m/z=513.2. found 513.4.

Example 2. 4-(2-(4-((4-(Methylsulfonyl)piperidin-1-yl)methyl)phenyl)-7-oxo-6,7-dihydro-3H-pyrrolo[3,2-f][1,7]naphthyridin-8-yl)benzoic acid

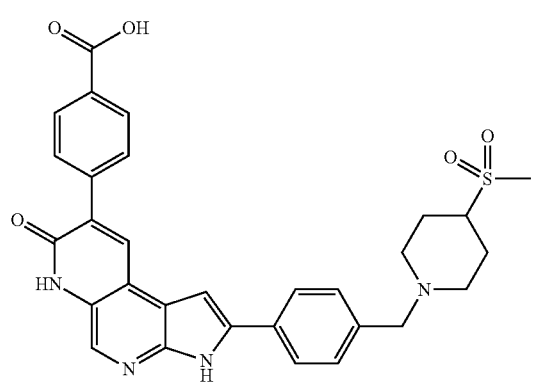

The title compound was prepared according to the procedures described in Example 1, using 2-(4-(methoxycarbonyl)phenyl)acetic acid instead of 2-phenylacetic acid in Step 7 as starting material. LC-MS calculated for $C_{30}H_{29}N_4O_5S$ (M+H)$^+$: m/z=557.2. found 557.2.

Example 3. 2-(4-((4-(Methylsulfonyl)piperidin-1-yl)methyl)phenyl)-7-oxo-6,7-dihydro-3H-pyrrolo[3,2-f][1,7]naphthyridine-8-carbonitrile

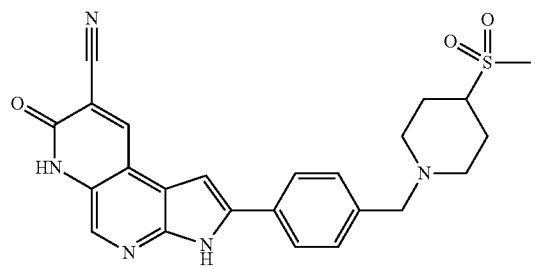 [SMILES: CS(=O)(=O)C1CCN(Cc2ccc(-c3cc4c(ncc5[nH]c(=O)c(C#N)cc54)[nH]3)cc2)CC1]

The title compound was prepared according to the procedures described in Example 1, using 2-cyanoacetic acid instead of 2-phenylacetic acid in Step 7 as starting material. LC-MS calculated for $C_{24}H_{24}N_5O_3S$ (M+H)$^+$: m/z=462.2. found 462.2.

Example 4. 8-(1-Methyl-1H-pyrazol-5-yl)-2-(4-((4-(methylsulfonyl)piperidin-1-yl)methyl)phenyl)-3,6-dihydro-7H-pyrrolo[3,2-f][1,7]naphthyridin-7-one

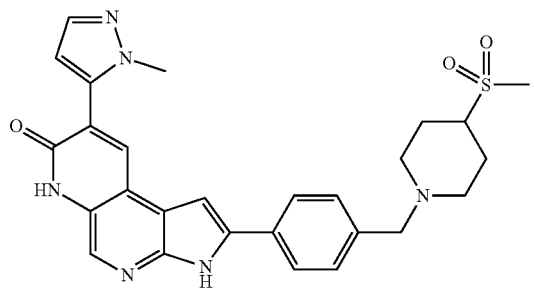 [SMILES: Cn1nccc1-c1cc2c(cnc3[nH]c(-c4ccc(CN5CCC(S(C)(=O)=O)CC5)cc4)cc32)[nH]c1=O]

The title compound was prepared according to the procedures described in Example 1, using 2-(1-methyl-1H-pyrazol-5-yl)acetic acid instead of 2-phenylacetic acid in Step 7 as starting material. LC-MS calculated for $C_{27}H_{29}N_6O_3S$ (M+H)$^+$: m/z=517.2; found 517.2.

Example 5. 2-(4-((4-(Methylsulfonyl)piperidin-1-yl)methyl)phenyl)-8-(1H-tetrazol-5-yl)-3,6-dihydro-7H-pyrrolo[3,2-f][1,7]naphthyridin-7-one

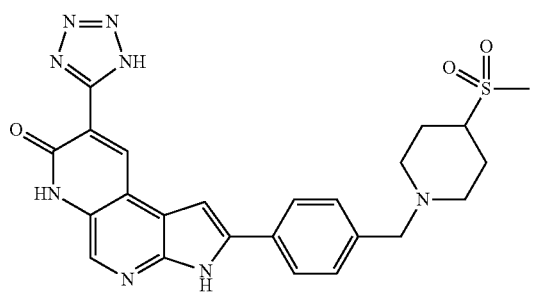 [SMILES: CS(=O)(=O)C1CCN(Cc2ccc(-c3cc4c(ncc5[nH]c(=O)c(-c6nnn[nH]6)cc54)[nH]3)cc2)CC1]

The title compound was prepared according to the procedures described in Example 1, using 2-(1H-tetrazol-5-yl)acetic acid instead of 2-phenylacetic acid in Step 7 as starting material. LC-MS calculated for $C_{24}H_{25}N_8O_3S$ (M+H)$^+$: m/z=505.2; found 505.2.

Example 6. 4-(9-Methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid

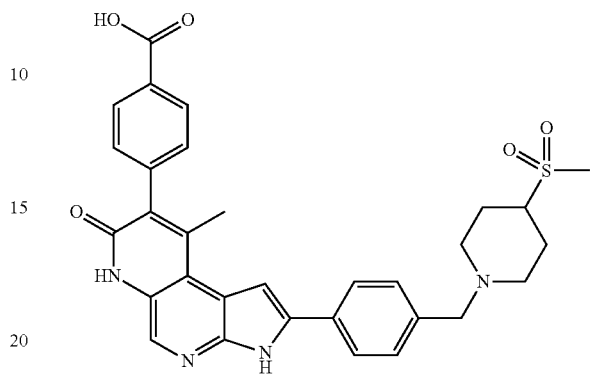

Step 1. 1-(2-(4-((4-(Methylsulfonyl)piperidin-1-yl)methyl)phenyl)-5-nitro-1-(phenylsulfonyl)-1H-pyrrolo[2,3-b]pyridin-4-yl)ethan-1-one

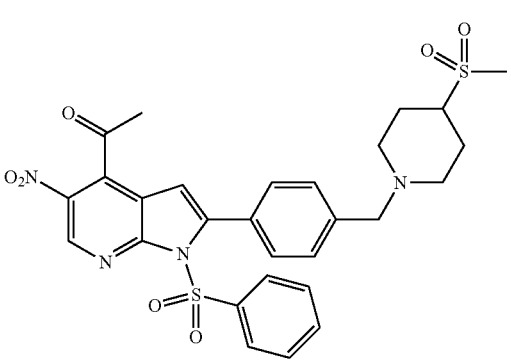

To a solution of 4-chloro-2-(4-((4-(methylsulfonyl)piperidin-1-yl)methyl)phenyl)-5-nitro-1-(phenylsulfonyl)-1H-pyrrolo[2,3-b]pyridine (Example 1, Step 3; 1600 mg, 2.72 mmol) in dioxane (20 mL) was added 1-ethoxyvinyltri-n-butyltin (1101 μL, 3.26 mmol) and triphenylphosphine palladium chloride (381 mg, 0.543 mmol), and the resulting mixture was stirred at 100° C. for 2 hours. After this time, the mixture was cooled to r.t. then 2 mL water and 2 mL concentrated hydrochloric acid were added and the mixture was then stirred for 1 hour at r.t. After this time, the pH was adjusted to 7 then the mixture was diluted with water and extracted with dichloromethane. The organic layer was dried over MgSO$_4$, filtered, and then concentrated to dryness. The resulting residue was purified by silica gel chromatography using 0-10% methanol in DCM with 1% triethylamine (TEA) to afford the desired product (1.33 g, 2.23 mmol). LC-MS calculated for $C_{28}H_{29}N_4O_7S_2$ (M+H)$^+$: m/z=597.2. found 597.2.

Step 2. 1-(5-Amino-2-(4-((4-(methylsulfonyl)piperidin-1-yl)methyl)phenyl)-1-(phenylsulfonyl)-1H-pyrrolo[2,3-b]pyridin-4-yl)ethan-1-one

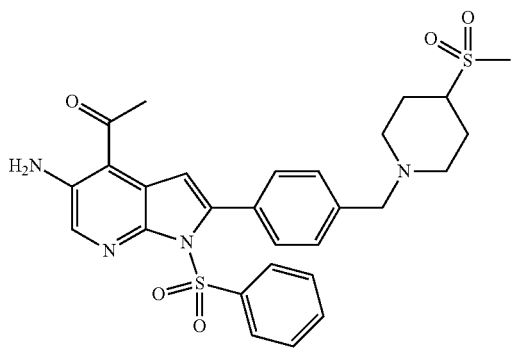 [SMILES: CC(=O)c1c([N+](=O)[O-])cnc2c1cc(-c1ccc(CN3CCC(S(C)(=O)=O)CC3)cc1)n2S(=O)(=O)c1ccccc1]

To a solution of 1-(2-(4-((4-(methylsulfonyl)piperidin-1-yl)methyl)phenyl)-5-nitro-1-(phenylsulfonyl)-1H-pyrrolo[2,3-b]pyridin-4-yl)ethan-1-one (400 mg, 0.670 mmol) in tetrahydrofuran (4.00 mL), methanol (4.00 mL) and water (4.00 mL) was added iron (187 mg, 3.35 mmol) and ammonium chloride (179 mg, 3.35 mmol), and the resulting mixture was stirred at 80° C. for 2 hours. After this time, the mixture was cooled to r.t., filtered, and the solid was washed with dichloromethane and methanol. The filtrate was concentrated to dryness then purified by silica gel chromatography using 0-50% methanol in dichloromethane.

Step 3. Methyl 4-(2-((4-acetyl-2-(4-((4-(methylsulfonyl)piperidin-1-yl)methyl)phenyl)-1-(phenylsulfonyl)-1H-pyrrolo[2,3-b]pyridin-5-yl)amino)-2-oxoethyl)benzoate

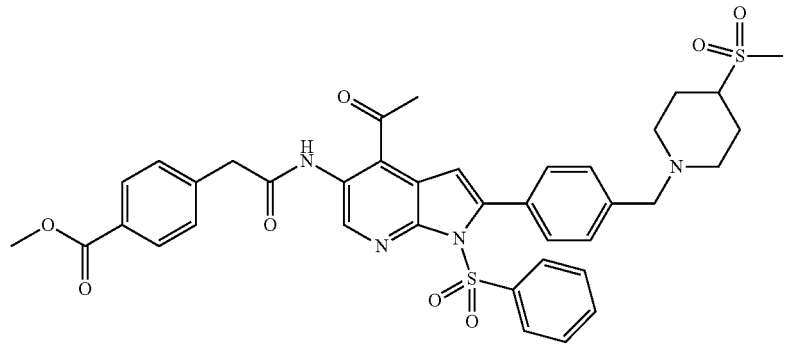

To a solution of 1-(5-amino-2-(4-((4-(methylsulfonyl)piperidin-1-yl)methyl)phenyl)-1-(phenylsulfonyl)-1H-pyrrolo[2,3-b]pyridin-4-yl)ethan-1-one (250 mg, 0.442 mmol) in dimethylformamide (4 mL) was added 2-(4-(methoxycarbonyl)phenyl)acetic acid (325 mg, 1.676 mmol), (1-[bis(dimethylamino)methylene]-1H-1,2,3-triazolo[4,5-b]pyridinium 3-oxide hexafluorophosphate (765 mg, 2.011 mmol) and N,N'-diisopropylethylamine (351 µL, 2.01 mmol), and the resulting mixture was heated to 50° C., then stirred at r.t. for 15 hours. After this time, the mixture was diluted in acetonitrile and then filtered and purified by prep-LCMS (XBridge C18 column, eluting with a gradient of acetonitrile/water containing 0.1% trifluoroacetic acid (TFA), at flow rate of 60 mL/min).

Step 4. 4-(9-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid

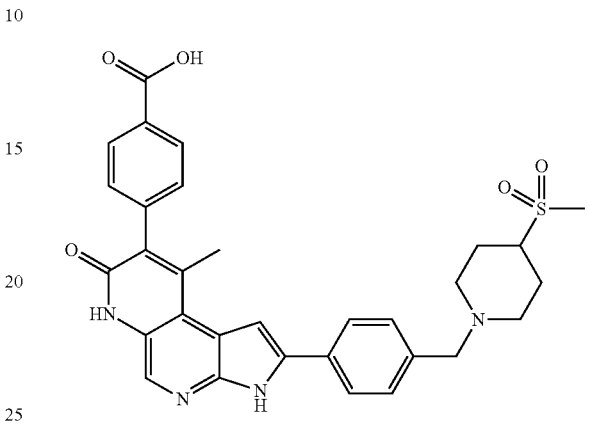

To a solution of methyl 4-(2-((4-acetyl-2-(4-((4-(methylsulfonyl)piperidin-1-yl)methyl)phenyl)-1-(phenylsulfonyl)-1H-pyrrolo[2,3-b]pyridin-5-yl)amino)-2-oxoethyl)benzoate in dimethylformamide (2.00 mL) was added N,N'-diisopropylethylamine (351 µL, 2.01 mmol), and the resulting mixture was stirred at 120° C. for 15 hours. The reaction mixture was then cooled to r.t., diluted with dichloromethane then washed twice with water. The organic layer was concentrated to dryness, diluted with 1 mL methanol and 1 mL 2.5M sodium hydroxide solution, and then stirred at 80° C. for 4 hours. After this time, the mixture was cooled to r.t. then diluted with methanol and purified by prep-LCMS (XBridge C18 column, eluting with a gradient of acetonitrile/water containing 0.1% ammonium hydroxide, at flow rate of 60 mL/min) to afford the desired product. LC-MS calculated for $C_{31}H_{31}N_4O_5S$ (M+H)$^+$: m/z=571.2; found 571.2. $^1$H NMR (500 MHz, DMSO-d6) δ 8.38 (s, 1H), 7.98 (d, J=7.9 Hz, 2H), 7.90 (d, J=7.7 Hz, 2H), 7.39 (d, J=7.9 Hz, 2H), 7.33 (s, 1H), 7.17 (d, J=7.7 Hz, 2H), 3.53 (s, 2H), 3.06 (t, J=12.3 Hz, 1H), 2.97 (d, J=11.8 Hz, 2H), 2.92 (s, 3H), 2.60 (s, 3H), 2.01 (t, J=11.6 Hz, 4H), 1.70-1.58 (m, 2H).

Example 7. 8-(4-(1H-Tetrazol-1-yl)phenyl)-9-methyl-2-(4-((4-((methylsulfonyl)piperidin-1-yl)methyl)phenyl)-3,6-dihydro-7H-pyrrolo[3,2-f][1,7]naphthyridin-7-one

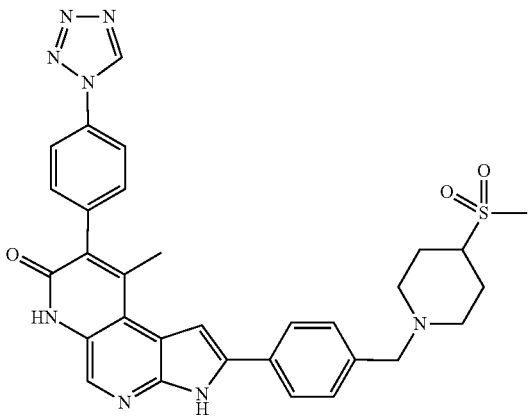 [SMILES: Cc1c(-c2ccc(-n3cnnn3)cc2)c(=O)[nH]c2cnc3[nH]c(-c4ccc(CN5CCC(S(C)(=O)=O)CC5)cc4)cc3c12]

The title compound was prepared according to the procedures described in Example 6, using 2-(4-(1H-tetrazol-1-yl)phenyl)acetic acid instead of 2-(4-(methoxycarbonyl)phenyl)acetic acid as starting material in Step 3. LC-MS calculated for $C_{31}H_{31}N_8O_3S$ (M+H)$^+$: m/z=595.2. found 595.2.

Example 8. 4-(6,9-Dimethyl-2-(4-((4-((methylsulfonyl)piperidin-1-yl)methyl)phenyl)-7-oxo-6,7-dihydro-3H-pyrrolo[3,2-f][1,7]naphthyridin-8-yl)benzoic acid

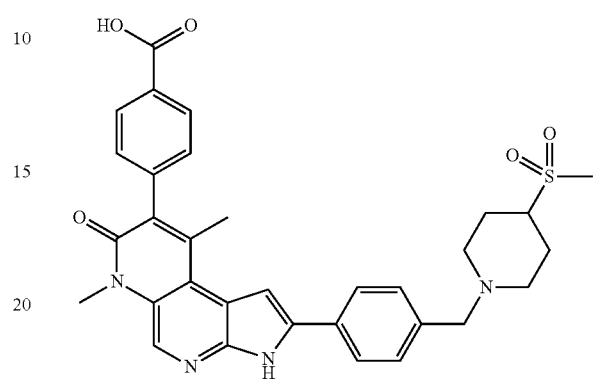

Step 1. Methyl 4-(2-((4-acetyl-2-(4-((4-(methylsulfonyl)piperidin-1-yl)methyl)phenyl)-1-(phenylsulfonyl)-1H-pyrrolo[2,3-b]pyridin-5-yl)amino)-2-oxoethyl)benzoate

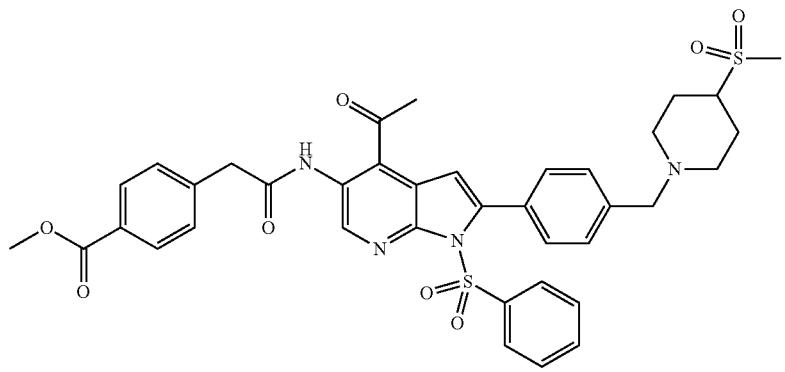

To a solution of 1-(5-amino-2-(4-((4-(methylsulfonyl)piperidin-1-yl)methyl)phenyl)-1-(phenylsulfonyl)-1H-pyrrolo[2,3-b]pyridin-4-yl)ethan-1-one (Example 6, Step 2, 250 mg, 0.442 mmol) in dimethylformamide (4 mL) was added 2-(4-(methoxycarbonyl)phenyl)acetic acid (325 mg, 1.676 mmol), (1-[bis(dimethylamino)methylene]-1H-1,2,3-triazolo[4,5-b]pyridinium 3-oxide hexafluorophosphate (765 mg, 2.011 mmol) and N,N'-diisopropylethylamine (351 µL, 2.011 mmol), and the resulting mixture was heated to 50° C. and stirred for 15 hours. After this time, the mixture was diluted in acetonitrile and then filtered and purified by prep-LCMS (XBridge C18 column, eluting with a gradient of acetonitrile/water containing 0.1% TFA, at flow rate of 60 mL/min).

Step 2. Methyl 4-(9-methyl-2-(4-((4-(methylsulfonyl)piperidin-1-yl)methyl)phenyl)-7-oxo-3-(phenylsulfonyl)-6,7-dihydro-3H-pyrrolo[3,2-f][1,7]naphthyridin-8-yl)benzoate

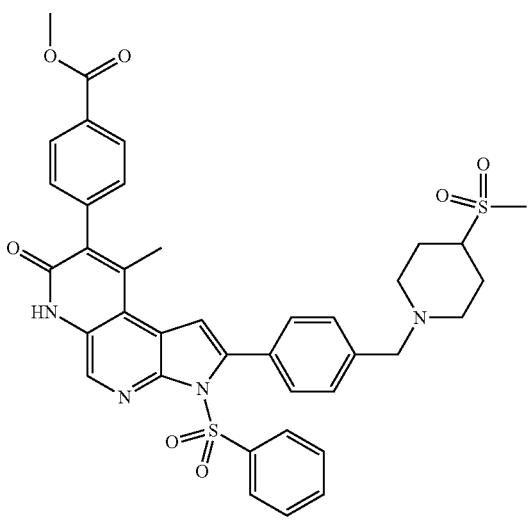 [SMILES: COC(=O)c1ccc(-c2c(C)c3c(cnc4c3cc(-c3ccc(CN5CCC(S(C)(=O)=O)CC5)cc3)n4S(=O)(=O)c3ccccc3)[nH]c2=O)cc1]

To a solution of methyl 4-(2-((4-acetyl-2-(4-((4-(methylsulfonyl)piperidin-1-yl)methyl)phenyl)-1-(phenylsulfonyl)-1H-pyrrolo[2,3-b]pyridin-5-yl)amino)-2-oxoethyl)benzoate in dimethylformamide (2.00 mL) was added N,N'-diisopropylethylamine (351 µL, 2.011 mmol), then the resulting mixture was stirred at 120° C. for 15 hours. The reaction mixture was then cooled to r.t., diluted with ethyl acetate then washed twice with water. The organic layer was concentrated to dryness to afford desired crude product which was used for next step without purification.

Step 3. 4-(6,9-dimethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid

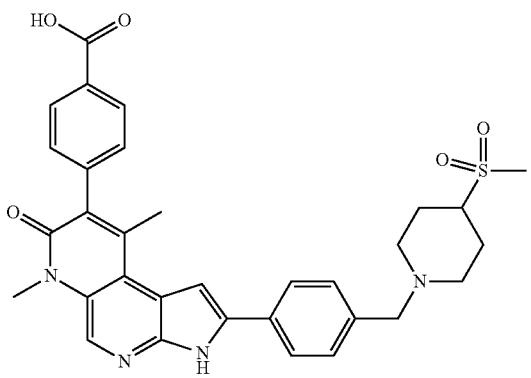 [SMILES: Cc1c(-c2ccc(C(=O)O)cc2)c(=O)n(C)c2cnc3[nH]c(-c4ccc(CN5CCC(S(C)(=O)=O)CC5)cc4)cc3c12]

To a solution of methyl 4-(9-methyl-2-(4-((4-(methylsulfonyl)piperidin-1-yl)methyl)phenyl)-7-oxo-3-(phenylsulfonyl)-6,7-dihydro-3H-pyrrolo[3,2-f][1,7]naphthyridin-8-yl)benzoate in tetrahydrofuran (5 mL) was added cesium carbonate (129 mg, 0.396 mmol) and iodomethane (37.1 µL, 0.593 mmol), and the resulting mixture was stirred at 60° C. for 2 hours. After this time, the mixture was cooled to r.t., filtered, and then concentrated to dryness. The residue was diluted with 1 mL methanol and 1 mL 2.5M sodium hydroxide solution and then stirred at 80° C. for 4 hours. After this time, the mixture was cooled to r.t. then diluted with methanol and purified by prep-LCMS (XBridge C18 column, eluting with a gradient of acetonitrile/water containing 0.1% ammonium hydroxide, at flow rate of 60 mL/min) to afford the desired product.

Example 9. 6,9-Dimethyl-2-(4-((4-(methylsulfonyl)piperidin-1-yl)methyl)phenyl)-8-(p-tolyl)-3,6-dihydro-7H-pyrrolo[3,2-f][1,7]naphthyridin-7-one

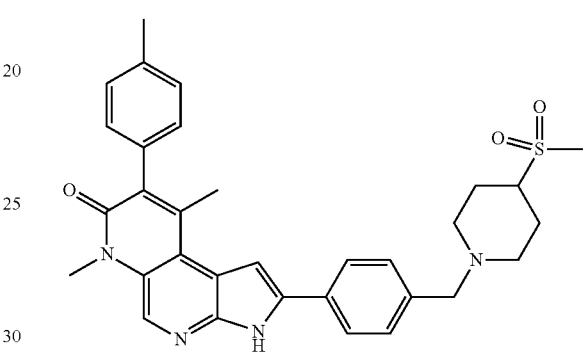

The title compound was prepared according to the procedures described in Example 8, using 2-(p-tolyl)acetic acid instead of 2-(4-(methoxycarbonyl)phenyl)acetic acid as starting material in Step 1. LC-MS calculated for $C_{32}H_{34}N_4O_3S$ (M+H)$^+$: m/z=555.2. found 555.2.

Example 10. 8-(4-Chlorophenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one

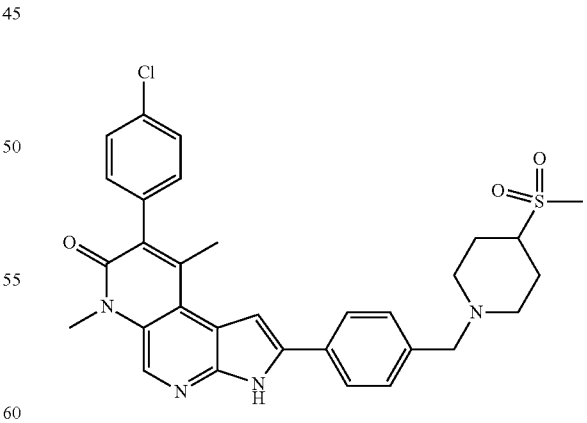

The title compound was prepared according to the procedures described in Example 8, using 2-(4-chlorophenyl)acetic acid instead of 2-(4-(methoxycarbonyl)phenyl)acetic acid as starting material in Step 1. LC-MS calculated for $C_{31}H_{32}ClN_4O_3S$ (M+H)$^+$: m/z=575.2. found 575.2.

Example 11. 8-(3-Chlorophenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one

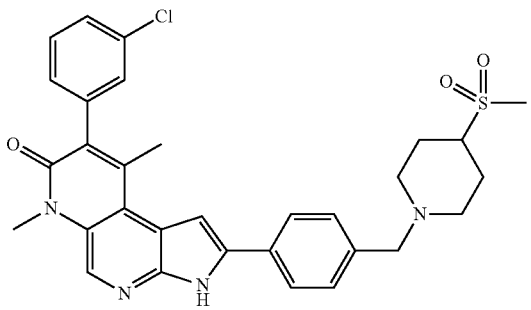 [SMILES: Cc1c(-c2cccc(Cl)c2)c(=O)n(C)c2cnc3[nH]c(-c4ccc(CN5CCC(S(C)(=O)=O)CC5)cc4)cc3c12]

The title compound was prepared according to the procedures described in Example 8, using 2-(3-chlorophenyl)acetic acid instead of 2-(4-(methoxycarbonyl)phenyl)acetic acid as starting material in Step 1. LC-MS calculated for $C_{31}H_{32}ClN_4O_3S$ (M+H)$^+$: m/z=575.2. found 575.2.

Example 12. 8-(4-Methoxyphenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one

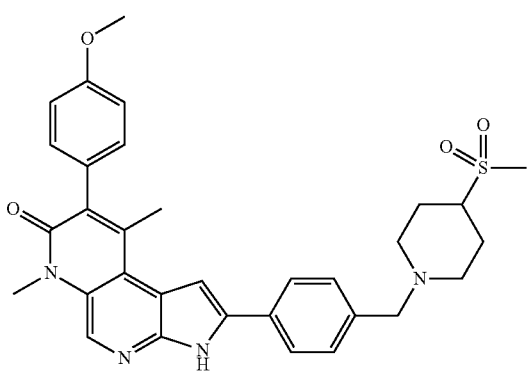 [SMILES: COc1ccc(-c2c(C)c3c4cc(-c5ccc(CN6CCC(S(C)(=O)=O)CC6)cc5)[nH]c4ncc3n(C)c2=O)cc1]

The title compound was prepared according to the procedures described in Example 8, using 2-(4-methoxyphenyl)acetic acid instead of 2-(4-(methoxycarbonyl)phenyl)acetic acid as starting material in Step 1. LC-MS calculated for $C_{32}H_{35}N_4O_4S$ (M+H)$^+$: m/z=571.2. found 571.2.

Example 13. 4-(6,9-Dimethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzonitrile

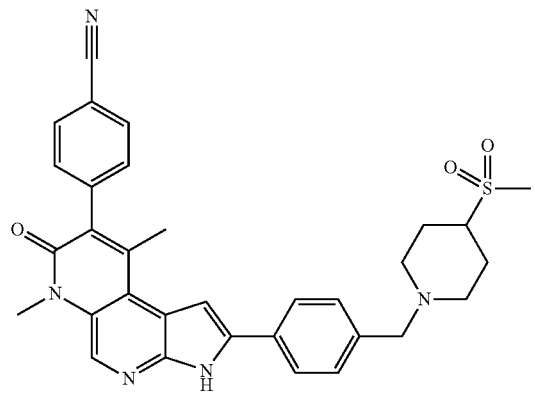 [SMILES: Cc1c(-c2ccc(C#N)cc2)c(=O)n(C)c2cnc3[nH]c(-c4ccc(CN5CCC(S(C)(=O)=O)CC5)cc4)cc3c12]

The title compound was prepared according to the procedures described in Example 8, using 2-(4-cyanophenyl)acetic acid instead of 2-(4-(methoxycarbonyl)phenyl)acetic acid as starting material in Step 1. LC-MS calculated for $C_{32}H_{32}N_5O_3S$ (M+H)$^+$: m/z=566.2. found 566.2.

Example 14. 4-(6-Methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid

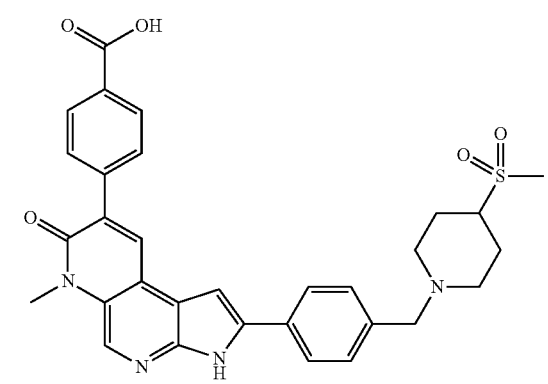 [SMILES: Cn1c(=O)c(-c2ccc(C(=O)O)cc2)cc2c3cc(-c4ccc(CN5CCC(S(C)(=O)=O)CC5)cc4)[nH]c3ncc21]

Step 1. Methyl 4-(2-(4-((4-(methylsulfonyl)piperidin-1-yl)methyl)phenyl)-7-oxo-3-(phenylsulfonyl)-6,7-dihydro-3H-pyrrolo[3,2-f][1,7]naphthyridin-8-yl)benzoate

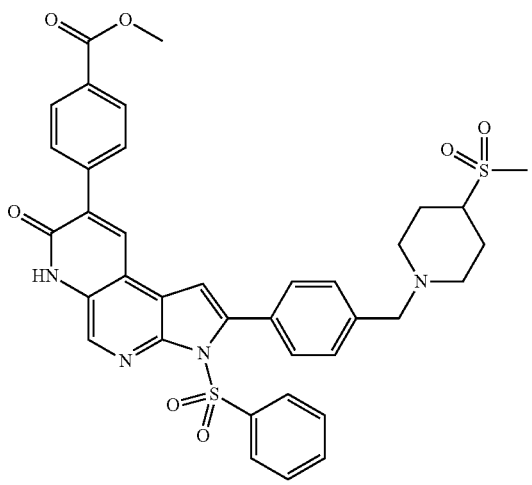 [SMILES: COC(=O)c1ccc(-c2cc3c(cnc4c3cc(-c3ccc(CN5CCC(S(C)(=O)=O)CC5)cc3)n4S(=O)(=O)c3ccccc3)[nH]c2=O)cc1]

The title compound was prepared according to the procedures described in Example 1, Step 7, using 2-(4-(methoxycarbonyl)phenyl)acetic acid instead of phenyl acetic acid as starting material. LC-MS calculated for $C_{37}H_{35}N_4O_7S_2$ (M+H)$^+$: m/z=711.2. found 711.2.

Step 2. 4-(6-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid

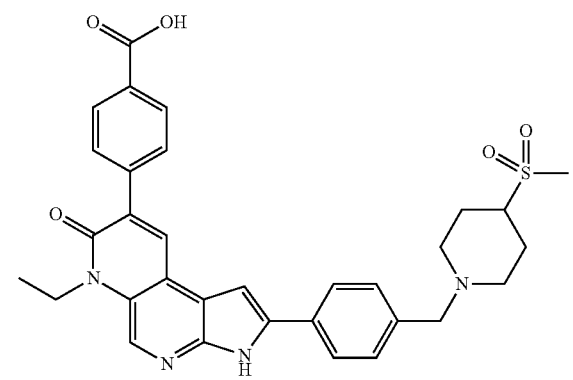 [SMILES: CCn1c(=O)c(-c2ccc(C(=O)O)cc2)cc2c3cc(-c4ccc(CN5CCC(S(C)(=O)=O)CC5)cc4)[nH]c3ncc21]

Methyl 4-(2-(4-((4-(methylsulfonyl)piperidin-1-yl)methyl)phenyl)-7-oxo-3-(phenylsulfonyl)-6,7-dihydro-3H-pyrrolo[3,2-f][1,7]naphthyridin-8-yl)benzoate (57 mg, 0.080 mmol) was dissolved in dimethylformamide (1 mL) then iodomethane (8.49 μL, 0.136 mmol) was added, followed by addition of sodium hydride (5.43 mg, 0.136 mmol). The resulting solution was stirred at r.t. for 10 minutes then quenched with water and extracted with ethyl acetate. The organic layer was dried over MgSO$_4$, filtered, and then concentrated to dryness. The residue was dissolved in 1 mL methanol and 1 mL 2.5M sodium hydroxide solution then stirred at 60° C. for 1 hour. After this time, the mixture was cooled to r.t., diluted with methanol, then purified by prep-LCMS (XBridge C18 column, eluting with a gradient of acetonitrile/water containing 0.1% ammonium hydroxide, at flow rate of 60 mL/min). LC-MS calculated for $C_{31}H_{31}N_4O_5S$ (M+H)$^+$: m/z=571.2. found 571.2.

Example 15. 4-(6-Ethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid

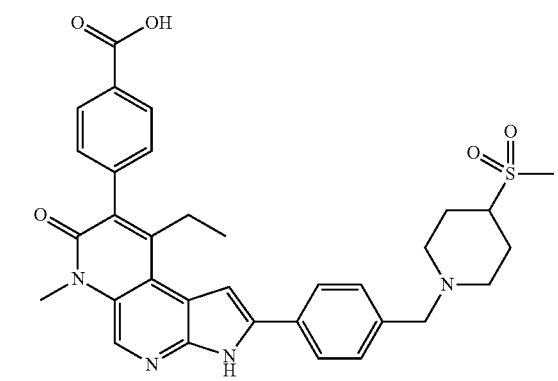 [SMILES: CCc1c(-c2ccc(C(=O)O)cc2)c(=O)n(C)c2cnc3[nH]c(-c4ccc(CN5CCC(S(C)(=O)=O)CC5)cc4)cc3c12]

The title compound was prepared according to the procedures described in Example 14, using iodoethane instead of iodomethane as starting material in Step 2. LC-MS calculated for $C_{32}H_{33}N_4O_5S$ (M+H)$^+$: m/z=585.2. found 585.2.

Example 16. 4-(9-Ethyl-6-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid

Step 1. 4-Iodo-5-nitro-1-(phenylsulfonyl)-1H-pyrrolo[2,3-b]pyridine

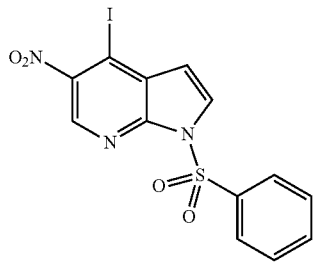 [SMILES: O=[N+]([O-])c1cnc2c(ccn2S(=O)(=O)c2ccccc2)c1I]

To a solution of 4-chloro-5-nitro-1-(phenylsulfonyl)-1H-pyrrolo[2,3-#]pyridine (2.00 g, 5.92 mmol, Astatech Inc. cat #P12207) in dimethylformamide (29.6 mL) was added potassium iodide (3932 mg, 23.69 mmol) then the mixture was stirred at 100° C. for 15 hours. After this time, the mixture was cooled to r.t. then poured into water and filtered. The solid was dried over air and vacuum then collected to afford the desired product as pale yellowish solid (2.41 g, 5.92 mmol). LC-MS calculated for $C_{13}H_9IN_3O_4S$ (M+H)$^+$: m/z=429.9. found 430.1.

Step 2. 1-(5-Nitro-1-(phenylsulfonyl)-1H-pyrrolo[2,3-b]pyridin-4-yl)propan-1-one

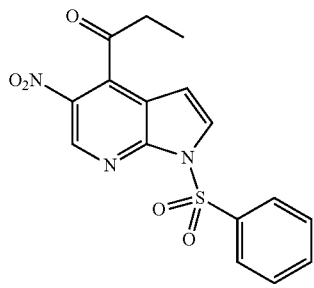 [SMILES: CCC(=O)c1c([N+](=O)[O-])cnc2c1ccn2S(=O)(=O)c1ccccc1]

To a suspension of 4-iodo-5-nitro-1-(phenylsulfonyl)-1H-pyrrolo[2,3-b]pyridine (600 mg, 1.40 mmol) in tetrahydrofuran (9 mL) was added phenylmagnesium bromide (513 µL, 1.54 mmol) at −40° C. then the mixture was stirred for 10 minutes until the solution become clear. To the resulting solution was then added a solution of copper(I) cyanide (138 mg, 1.54 mmol) and lithium chloride (119 mg, 2.80 mmol) in tetrahydrofuran (1 mL). Propionyl chloride (259 mg, 2.80 mmol) was then added, the cooling bath was removed, and the reaction mixture was warmed to r.t. and stirred for 20 minutes. After this time, the reaction was quenched with water and ammonium hydroxide then extracted with ethyl acetate. The organic layer was dried over $MgSO_4$, filtered, and then concentrated to dryness. The residue was purified by silica gel chromatography using 0-70% ethyl acetate in hexanes to afford the desired product as a mixture with side products. The crude product mixture was taken to the next step without purification. LC-MS calculated for $C_{16}H_{14}N_3O_5S$ (M+H)$^+$: m/z=360.2. found 360.2.

Step 3. 1-(5-Amino-1-(phenylsulfonyl)-1H-pyrrolo[2,3-b]pyridin-4-yl)propan-1-one

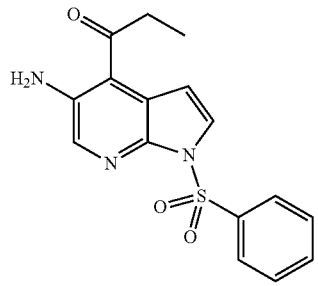

To a solution of 1-(5-nitro-1-(phenylsulfonyl)-1H-pyrrolo[2,3-b]pyridin-4-yl)propan-1-one in tetrahydrofuran (9 mL) and ethanol (9.00 mL) was added iron (234 mg, 4.19 mmol) and 1N HCl (2.00 mL, 2.00 mmol) then the mixture was stirred at 60° C. for 1 hour. After this time, the mixture was cooled to r.t. then diluted with dichloromethane. The resulting suspension was stirred for 15 minutes, filtered, and the filtrate was concentrated to dryness. The resulting residue was used for next step without purification. LC-MS calculated for $C_{16}H_{16}N_3O_3S$ (M+H)$^+$: m/z=330.1. found 330.1.

Step 4. Methyl 4-(2-oxo-2-((1-(phenylsulfonyl)-4-propionyl-1H-pyrrolo[2,3-b]pyridin-5-yl)amino)ethyl)benzoate

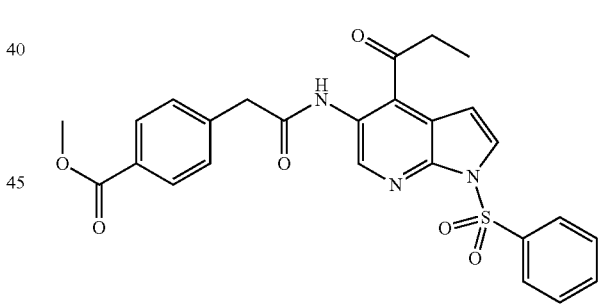

1-(5-Amino-1-(phenylsulfonyl)-1H-pyrrolo[2,3-b]pyridin-4-yl)propan-1-one was dissolved in dimethylformamide (9.00 mL) then 2-(4-(methoxycarbonyl)phenyl)acetic acid (326 mg, 1.678 mmol) was added, followed by addition of (1-[bis(dimethylamino)methylene]-1H-1,2,3-triazolo[4,5-b])pyridinium 3-oxide hexafluorophosphate (1595 mg, 4.19 mmol) and N,N-diisopropylethylamine (733 µL, 4.19 mmol). The resulting solution was stirred at r.t. for 30 minutes then diluted with methanol and acetonitrile, filtered, and then purified by prep-LCMS (XBridge C18 column, eluting with a gradient of acetonitrile/water containing 0.1% TFA, at flow rate of 60 mL/min). LC-MS calculated for $C_{26}H_{24}N_3O_6S$ (M+H)$^+$: m/z=506.2. found 506.2.

Step 5. Methyl 4-(9-ethyl-6-methyl-7-oxo-3-(phenylsulfonyl)-6,7-dihydro-5H-pyrrolo[3,2-f][1,7]naphthyridin-8-yl)benzoate

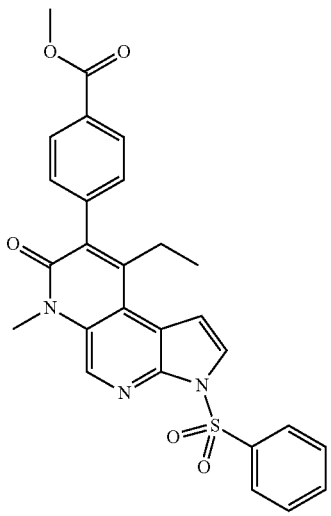 [SMILES: CCc1c(-c2ccc(C(=O)OC)cc2)c(=O)n(C)c2cnc3c(ccn3S(=O)(=O)c3ccccc3)c12]

To a solution of methyl 4-(2-oxo-2-((1-(phenylsulfonyl)-4-propionyl-1H-pyrrolo[2,3-b]pyridin-5-yl)amino)ethyl)benzoate (100 mg, 0.198 mmol) in tetrahydrofuran (5 mL) was added cesium carbonate (129 mg, 0.396 mmol), then the mixture was stirred at 90° C. for 2 hours. After this time, iodomethane (37.1 µL, 0.593 mmol) was added and the mixture was stirred at 60° C. for 2 hours. After this time, the mixture was cooled to r.t., filtered, and then concentrated to dryness. The resulting residue was purified by silica gel chromatography using 0-80% ethyl acetate in hexanes to afford the desired product as yellowish oil (58 mg, 0.12 mmol). LC-MS calculated for $C_{27}H_{24}N_3O_5S$ (M+H)$^+$: m/z=502.1. found 502.1.

Step 6. Methyl 4-(2-bromo-9-ethyl-6-methyl-7-oxo-3-(phenylsulfonyl)-6,7-dihydro-3H-pyrrolo[3,2-f][1,7]naphthyridin-8-yl)benzoate

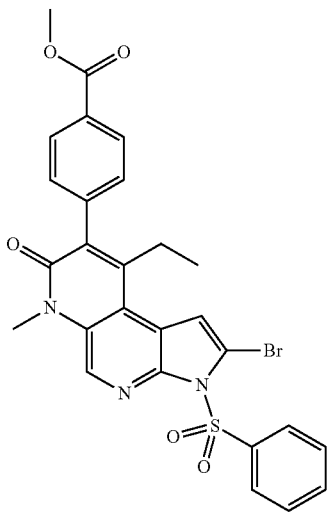 [SMILES: CCc1c(-c2ccc(C(=O)OC)cc2)c(=O)n(C)c2cnc3c(cc(Br)n3S(=O)(=O)c3ccccc3)c12]

To a solution of methyl 4-(9-ethyl-6-methyl-7-oxo-3-(phenylsulfonyl)-6,7-dihydro-3H-pyrrolo[3,2-f][1,7]naphthyridin-8-yl)benzoate (58 mg, 0.116 mmol) in tetrahydrofuran (2 mL) was added lithium diisopropylamide solution (2.0 M in tetrahydrofuran/heptane/ethylbenzene, 116 µL, 0.231 mmol) at −78° C. then the mixture was stirred for 30 minutes at −78° C. Next, a solution of 1,2-dibromo-1,1,2,2-tetrachloroethane (75 mg, 0.23 mmol) in tetrahydrofuran (0.5 mL) was added. The resulting solution was warmed to r.t., stirred for 15 minutes, then quenched with 1N HCl and extracted with ethyl acetate. The organic layer was washed with brine then concentrated to dryness. The residue was purified by silica gel chromatography using 0-100% ethyl acetate in hexanes to afford the desired product (25 mg, 0.12 mmol). LC-MS calculated for $C_{27}H_{23}BrN_3O_5S$ (M+H)$^+$: m/z=580.0. found 580.1.

Step 7. 4-(9-Ethyl-6-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid

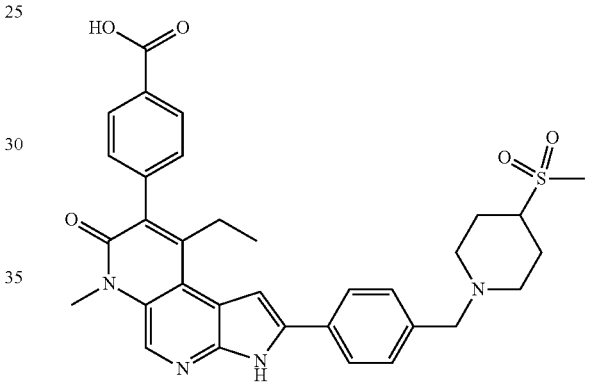

To a solution of methyl 4-(2-bromo-9-ethyl-6-methyl-7-oxo-3-(phenylsulfonyl)-6,7-dihydro-3H-pyrrolo[3,2-f][1,7]naphthyridin-8-yl)benzoate in dioxane (2.0 mL) and water (0.5 mL) was added 4-(methylsulfonyl)-1-(4-(4,4,5,5-tetramethyl-1,3,2-dioxaborolan-2-yl)benzyl)piperidine (Example 1, Step 1, 65.8 mg, 0.173 mmol) followed by addition of potassium carbonate (32.0 mg, 0.231 mmol) and [1,1'-bis(diphenylphosphino)ferrocene]dichloropalladium(II) (18.89 mg, 0.023 mmol). N$_2$ was bubbled through the mixture for 1 minute then the mixture was warmed up to 100° C. and stirred for 1 hour. After this time, the mixture was cooled to r.t., diluted with methanol (1 mL) and 1N sodium hydroxide (1 mL), then stirred at 60° C. for 1 hour. The resulting solution was diluted with water and methanol then filtered and purified by prep-LCMS (XBridge C18 column, eluting with a gradient of acetonitrile/water containing 0.1% ammonium hydroxide, at flow rate of 60 mL/min). LC-MS calculated for $C_{33}H_{35}N_4O_5S$ (M+H)$^+$: m/z=599.2. found 599.4. $^1$H NMR (600 MHz, DMSO-d6) δ 8.67 (s, 1H), 7.99 (t, J=5.9 Hz, 4H), 7.41 (d, J=8.1 Hz, 2H), 7.25 (d, J=10.5 Hz, 3H), 3.82 (s, 3H), 3.55 (s, 2H), 3.05 (tt, J=11.8, 3.6 Hz, 1H), 3.00-2.93 (m, 4H), 2.91 (s, 3H), 2.02 (ddd, J=18.6, 13.2, 5.8 Hz, 4H), 1.64 (qd, J=12.5, 4.1 Hz, 3H), 1.21 (t, J=7.4 Hz, 3H).

Example 17. 9-Methyl-2-(4-((4-(methylsulfonyl)piperidin-1-yl)methyl)phenyl)-3,6-dihydro-7H-pyrrolo[3,2-f][1,7]naphthyridin-7-one

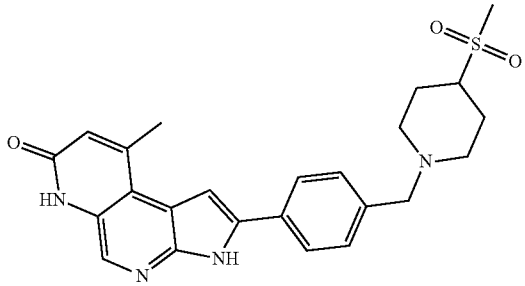 [SMILES: Cc1cc(=O)[nH]c2cnc3[nH]c(-c4ccc(CN5CCC(S(C)(=O)=O)CC5)cc4)cc3c12]

Step 1: Ethyl (E)-3-(2-(4-((4-(methylsulfonyl)piperidin-1-yl)methyl)phenyl)-5-nitro-1-(phenylsulfonyl)-1H-pyrrolo[2,3-b]pyridin-4-yl) but-2-enoate

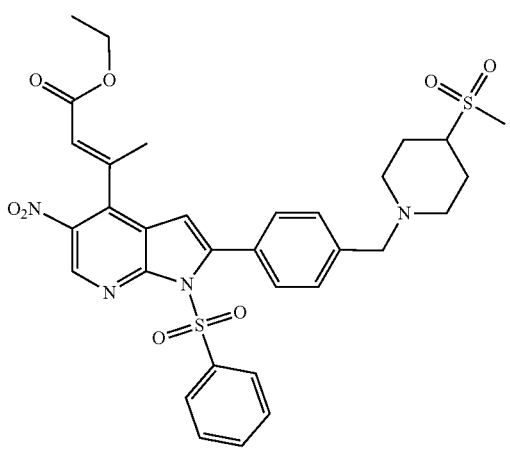 [SMILES: CCOC(=O)/C=C(\C)c1c([N+](=O)[O-])cnc2c1cc(-c1ccc(CN3CCC(S(C)(=O)=O)CC3)cc1)n2S(=O)(=O)c1ccccc1]

4-Chloro-2-(4-((4-(methylsulfonyl)piperidin-1-yl)methyl)phenyl)-5-nitro-1-(phenylsulfonyl)-1H-pyrrolo[2,3-b]pyridine (Example 1, Step 3; 950 mg, 1.613 mmol) was dissolved in a mixture of 1:1 dioxane:ethanol (10 mL). To this solution was added ethyl (Z)-3-(4,4,5,5-tetramethyl-1,3,2-dioxaborolan-2-yl)but-2-enoate (465 mg, 1.935 mmol, Combi Blocks cat #QV-2471), dichlorobis(triphenylphosphine)-palladium(II) (67.9 mg, 0.097 mmol) and potassium phosphate tribasic (342 mg, 1.613 mmol). $N_2$ was then bubbled through for 1 minute, then the mixture was warmed to 90° C. and stirred for 1 hour. The crude reaction mixture was cooled to room temperature, quenched with water, and extracted with ethyl acetate. The combined organic layers were washed with brine, dried over magnesium sulfate, and then concentrated under reduced pressure. The residue was purified by silica gel chromatography using 0-100% ethyl acetate in hexanes to afford desired product. LC-MS calculated for $C_{32}H_{35}N_4O_8S_2$ (M+H)$^+$: m/z=667.2; found 667.4.

Step 2: Ethyl (E)-3-(5-amino-2-(4-((4-(methylsulfonyl)piperidin-1-yl)methyl)phenyl)-1-(phenylsulfonyl)-1H-pyrrolo[2,3-b]pyridin-4-yl) but-2-enoate

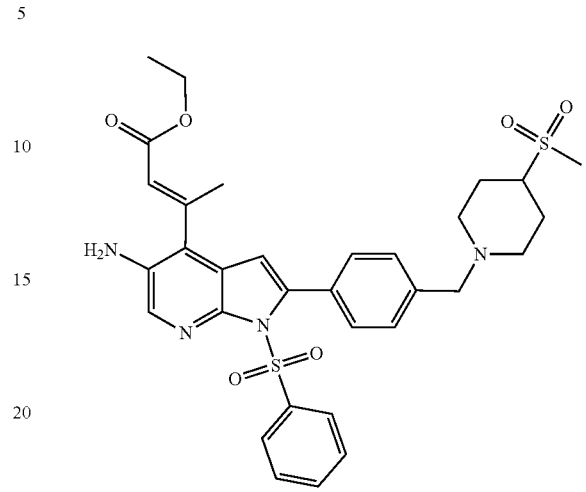

Ethyl (E)-3-(2-(4-((4-(methylsulfonyl)piperidin-1-yl)methyl)phenyl)-5-nitro-1-(phenylsulfonyl)-1H-pyrrolo[2,3-b]pyridin-4-yl)but-2-enoate (475 mg, 0.57 mmol) was diluted with a 3:1 mixture of methanol and water (6 mL). To this mixture was sequentially added ammonium chloride (152 mg, 2.85 mmol) and iron (95 mg, 1.71 mmol) and the resulting mixture was then heated at 85° C. overnight. The crude reaction mixture was cooled to room temperature and filtered over celite with aid of methanol and DCM. The filtrate was concentrated under reduced pressure. The crude residue was purified by prep-LCMS (XBridge C18 column, eluting with a gradient of acetonitrile/water containing 0.1% TFA, at flow rate of 60 mL/min) to afford the desired product. LC-MS calculated for $C_{32}H_{37}N_4O_6S_2$ (M+H)$^+$: m/z=637.2. found 637.2.

Step 3: 9-Methyl-2-(4-((4-(methylsulfonyl)piperidin-1-yl)methyl)phenyl)-3,6-dihydro-7H-pyrrolo[3,2-f][1,7]naphthyridin-7-one

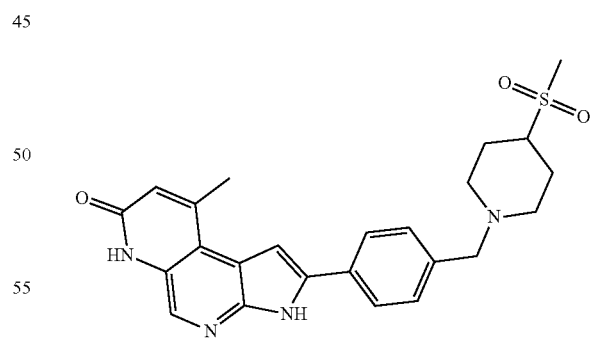

Ethyl (E)-3-(5-amino-2-(4-((4-(methylsulfonyl)piperidin-1-yl)methyl)phenyl)-1-(phenylsulfonyl)-1H-pyrrolo[2,3-b]pyridin-4-yl)but-2-enoate (18 mg, 0.029 mmol) was diluted with ethanol (EtOH, 0.30 mL) and then a solution of 21 wt % NaOEt in EtOH (43 uL, 0.116 mmol) was added, and the resulting mixture was heated at 85° C. overnight. The crude reaction mixture was cooled to room temperature and purified by prep-LCMS (XBridge C18 column, eluting with a gradient of acetonitrile/water containing 0.1% TFA, at flow

Example 18. 9-Methyl-2-(4-((4-(methylsulfonyl)piperidin-1-yl)methyl)phenyl)-8-(4-nitrophenyl)-3,6-dihydro-7H-pyrrolo[3,2-f][1,7]naphthyridin-7-one

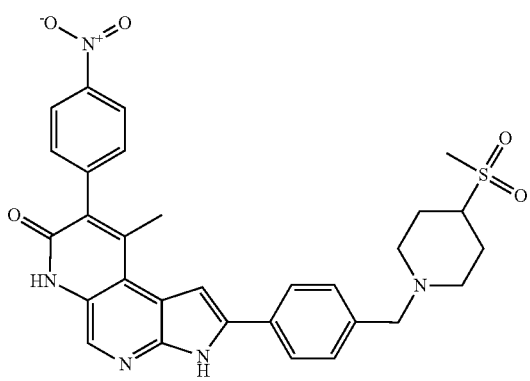

The title compound was prepared according to the procedures described in Example 6, using 2-(4-nitrophenyl)acetic acid instead of 2-(4-(methoxycarbonyl)phenyl)acetic acid as starting material in Step 3. LC-MS calculated for $C_{30}H_{30}N_5O_5S$ (M+H)$^+$: m/z=572.2. found 572.2.

Example 19. 8-(2,3-Dihydrobenzo[6][1,4]dioxin-6-yl)-9-methyl-2-(4-((4-(methylsulfonyl)piperidin-1-yl)methyl)phenyl)-3,6-dihydro-7H-pyrrolo[3,2-f][1,7]naphthyridin-7-one

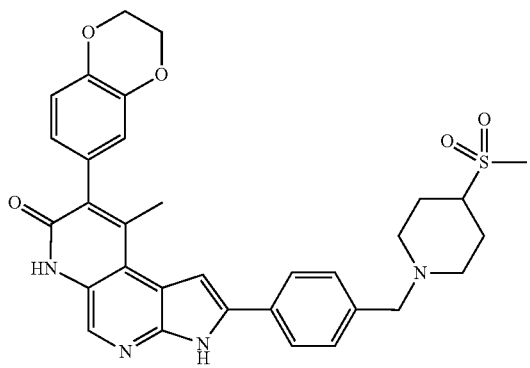 [SMILES: Cc1c(-c2ccc3c(c2)OCCO3)c(=O)[nH]c2cnc3[nH]c(-c4ccc(CN5CCC(S(C)(=O)=O)CC5)cc4)cc3c12]

The title compound was prepared according to the procedures described in Example 6, using 2-(2,3-dihydrobenzo[b][1,4]dioxin-6-yl)acetic acid instead of 2-(4-(methoxycarbonyl)phenyl)acetic acid as starting material in Step 3. LC-MS calculated for $C_{32}H_{33}N_4O_5S$ (M+H)$^+$: m/z=585.2. found 585.2.

Example 20. 9-Methoxy-6-methyl-2-(4-((4-(methylsulfonyl)piperidin-1-yl)methyl)phenyl)-8-phenyl-3,6-dihydro-7H-pyrrolo[3,2-f][1,7]naphthyridin-7-one

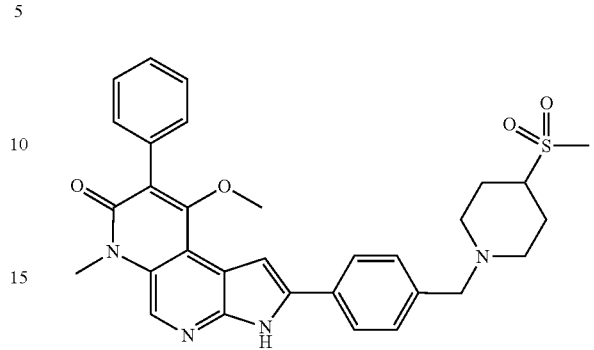

Step 1. Methyl 5-nitro-1-(phenylsulfonyl)-1H-pyrrolo[2,3-b]pyridine-4-carboxylate

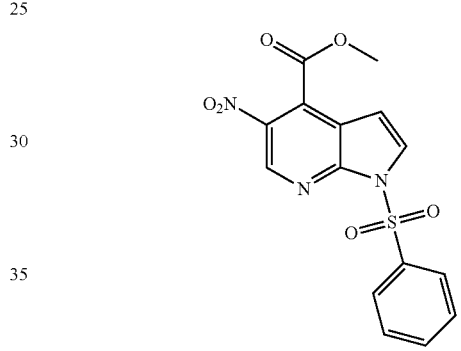

To a solution of 4-chloro-5-nitro-1-(phenylsulfonyl)-1H-pyrrolo[2,3-b]pyridine (5.0 g, 14.80 mmol, Astatech Inc. cat #P12207) in DMF (70 ml) was added 2-cyanoacetamide (1.494 g, 17.77 mmol) and potassium carbonate (7.16 g, 51.8 mmol). The resulting solution was stirred at 50° C. for 2 hours then hydrogen peroxide (9.07 ml, 89 mmol) was added and then stirred at the same temperature for another 1 hour. After this time it was cooled to r.t. then quenched by sodium bisulfite solution. The resulting solution was then extracted with ethyl acetate. The organic layer was discarded and the aqueous layer was poured onto excess 1N HCl then extracted with ethyl acetate 2 times. The organic layer was washed with brine then dried over MgSO$_4$, filtered and then concentrated to dryness. The obtained intermediate was then dissolved in DMF (70 ml) and sodium hydride (1.18 g, 29.6 mmol) was added and stirred for 15 minutes before benzenesulfonyl chloride (0.954 ml, 7.40 mmol) was added. The reaction was then stirred at r.t. for 15 minutes then dimethyl sulfate (2.80 g, 22.21 mmol) was added and stirred for another 15 hours. After this time it was diluted with water and 1N NaOH then extracted with ethyl acetate. The organic layer was washed with brine then dried over MgSO4, filtered and then concentrated to dryness. The residue was purified by silica gel chromatography using 0-100% ethyl acetate in hexanes to afford desired product as pale yellowish solid. LC-MS calculated for $C_{15}H_{12}N_3O_6S$ (M+H)$^+$: m/z=362.2. found 362.2.

Step 2. Methyl 5-amino-1-(phenylsulfonyl)-1H-pyrrolo[2,3-b]pyridine-4-carboxylate

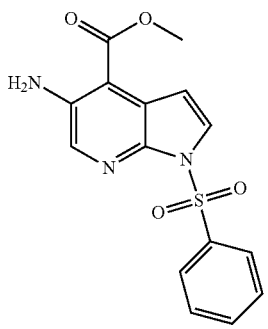 [SMILES: COC(=O)c1c(N)cnc2c1ccn2S(=O)(=O)c1ccccc1]

To a solution of methyl 5-nitro-1-(phenylsulfonyl)-1H-pyrrolo[2,3-b]pyridine-4-carboxylate (1500 mg, 4.15 mmol) in THF (5 ml) and ethanol (10.00 ml) was added iron (695 mg, 12.45 mmol) and HCl (6227 µl, 6.23 mmol) then it was stirred at 50° C. for 1 hour. After this time it was filtered and then residue was washed with methanol and DCM. The combined filtrate was concentrated to dryness then purified by silica gel chromatography using 0-10% methanol in DCM to afford the desired intermediate as yellowish solid. LC-MS calculated for $C_{15}H_{14}N_3O_4S$ (M+H)$^+$: m/z=332.2. found 332.2.

Step 3. Methyl 5-(2-phenylacetamido)-1-(phenylsulfonyl)-1H-pyrrolo[2,3-b]pyridine-4-carboxylate

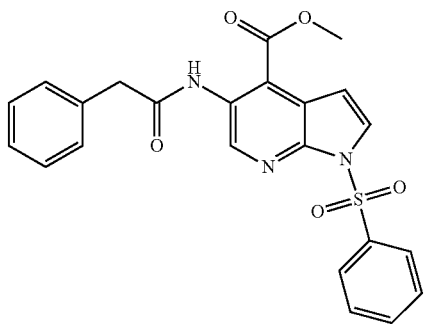 [SMILES: COC(=O)c1c(NC(=O)Cc2ccccc2)cnc2c1ccn2S(=O)(=O)c1ccccc1]

Methyl 5-amino-1-(phenylsulfonyl)-1H-pyrrolo[2,3-b]pyridine-4-carboxylate (1.21 g, 3.64 mmol) was dissolved in DMF (15.00 ml) and then 2-phenylacetic acid (1696 mg, 12.45 mmol) was added and followed by addition of 1-[bis(dimethylamino)methylene]-1H-1,2,3-triazolo[4,5-b]pyridinium 3-oxid hexafluorophosphate (4735 mg, 12.45 mmol) and DIPEA (3625 µl, 20.76 mmol). The resulting solution was stirred at 50° C. for 15 hours then cooled to r.t., diluted with ethyl acetate then washed with water and brine. The organic layer was dried over MgSO$_4$, filtered and then concentrated to dryness. The residue was purified by silica gel chromatography using 0-10% methanol in DCM. LC-MS calculated for $C_{23}H_{20}N_3O_5S$ (M+H)$^+$: m/z=450.2. found 450.2.

Step 4. 9-hydroxy-8-phenyl-3-(phenylsulfonyl)-3,6-dihydro-7H-pyrrolo[3,2-f][1,7]naphthyridin-7-one

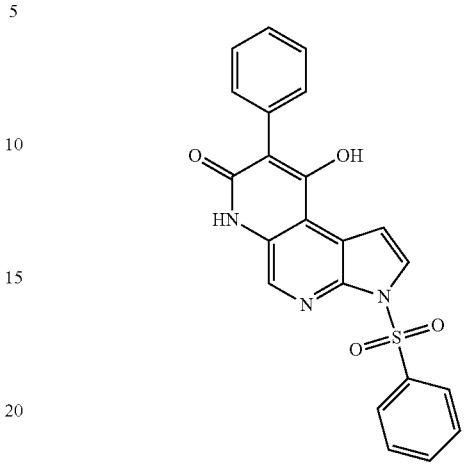

To a solution of methyl 5-(2-phenylacetamido)-1-(phenylsulfonyl)-1H-pyrrolo[2,3-b]pyridine-4-carboxylate (1500 mg, 3.34 mmol) in DMF (33.4 ml) was added cesium carbonate (3262 mg, 10.01 mmol) then it was stirred at 50° C. for 15 hours. After this time it was cooled to r.t. then diluted with DCM and washed with water and brine. The organic layer was dried over MgSO$_4$, filtered and then concentrated to dryness. The residue was purified by silica gel chromatography using 0-10% methanol in DCM. LC-MS calculated for $C_{22}H_{16}N_3O_4S$ (M+H)$^+$: m/z=418.2. found 418.2.

Step 5. 9-Methoxy-6-methyl-8-phenyl-3-(phenylsulfonyl)-3,6-dihydro-7H-pyrrolo[3,2-f][1,7]naphthyridin-7-one

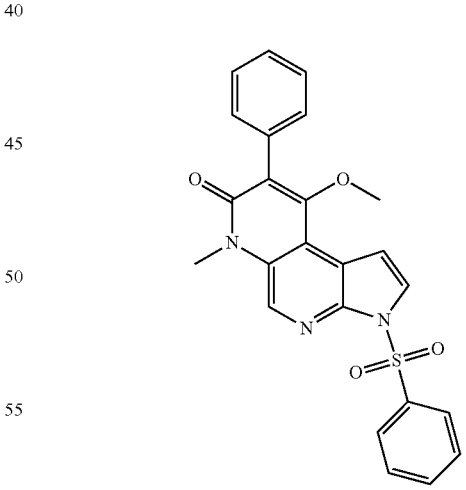

To a solution of 9-hydroxy-8-phenyl-3-(phenylsulfonyl)-3,6-dihydro-7H-pyrrolo[3,2-f][1,7]naphthyridin-7-one (150 mg, 0.359 mmol) in DMF (2 ml) was added cesium carbonate (585 mg, 1.797 mmol) and iodomethane (67.4 µl, 1.078 mmol) then it was stirred at 60° C. for 2 hours. After this time it was quenched with water and extracted with ethyl acetate. The organic layer was washed with brine then dried over MgSO$_4$, filtered and then concentrated to dryness.

The residue was purified by silica gel chromatography using 0-10% methanol in DCM to afford desired product. LC-MS calculated for $C_{24}H_{20}N_3O_4S$ (M+H)⁺: m/z=446.2. found 446.2.

Step 6. 2-Bromo-9-methoxy-6-methyl-8-phenyl-3-(phenylsulfonyl)-3,6-dihydro-7H-pyrrolo[3,2-f][1,7]naphthyridin-7-one

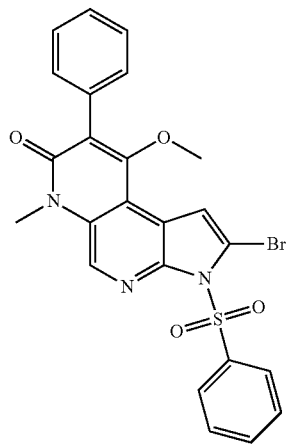 [SMILES: COc1c(-c2ccccc2)c(=O)n(C)c2cnc3c(cc(Br)n3S(=O)(=O)c3ccccc3)c12]

To a solution of 9-methoxy-6-methyl-8-phenyl-3-(phenylsulfonyl)-3,6-dihydro-7H-pyrrolo[3,2-f][1,7]naphthyridin-7-one (50 mg, 0.112 mmol) in THF (1.5 ml) was added LDA (140 µl, 0.281 mmol) at −78° C. then it was stirred for 30 minutes at that temperature then a solution of 1,2-dibromo-1,1,2,2-tetrachloroethane (73.1 mg, 0.224 mmol) in 0.5 mL THF was added. The resulting solution was allowed to warm up to r.t. then stirred for another 15 minutes then quenched with 1N HCl and extracted with ethyl acetate. The organic layer was washed with brine then concentrated to dryness. The residue was purified by silica gel chromatography using 0-100% ethyl acetate in hexanes. LC-MS calculated for $C_{24}H_{19}BrN_3O_4S$ (M+H)⁺: m/z=524.0. found 524.2.

Step 7. 9-Methoxy-6-methyl-2-(4-((4-(methylsulfonyl)piperidin-1-yl)methyl)phenyl)-8-phenyl-3,6-dihydro-7H-pyrrolo[3,2-f][1,7]naphthyridin-7-one

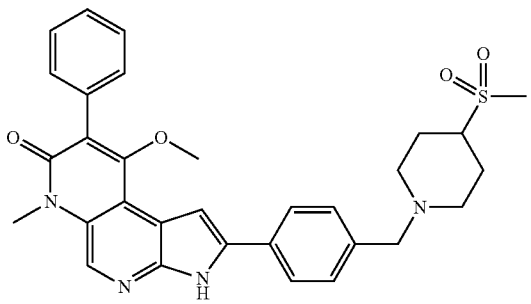 [SMILES: COc1c(-c2ccccc2)c(=O)n(C)c2cnc3[nH]c(-c4ccc(CN5CCC(S(C)(=O)=O)CC5)cc4)cc3c12]

To a solution of above intermediate in dioxane (1.500 ml) and water (0.5 ml) was added 4-(methylsulfonyl)-1-(4-(4,4,5,5-tetramethyl-1,3,2-dioxaborolan-2-yl)benzyl)piperidine (63.9 mg, 0.168 mmol, step 1, example 1) followed by addition of potassium carbonate (31.0 mg, 0.224 mmol) and [1,1'-bis(diphenylphosphino)ferrocene]dichloropalladium (II) (18.33 mg, 0.022 mmol) then N₂ was bubbled through for 1 minute before it was warmed up to 100° C. and stirred for 1 hour at this temperature. After this time it was cooled to r.t. then diluted with 1 mL MeOH and 1 mL 1N NaOH then stirred at 60° C. for another 1 hour. The resulting solution was diluted with water and methanol then filtered and purified by prep-LCMS (XBridge C18 column, eluting with a gradient of acetonitrile/water containing 0.1% NH₄OH, at flow rate of 60 mL/min). LC-MS calculated for $C_{31}H_{33}N_4O_4S$ (M+H)⁺: m/z=557.2; found 557.2.

Example 21. 6-Methyl-8-(3-methylisoxazol-5-yl)-2-(4-((4-(methylsulfonyl)piperidin-1-yl)methyl)phenyl)-9-(tetrahydro-2H-pyran-4-yl)-3,6-dihydro-7H-pyrrolo[3,2-f][1,7]naphthyridin-7-one

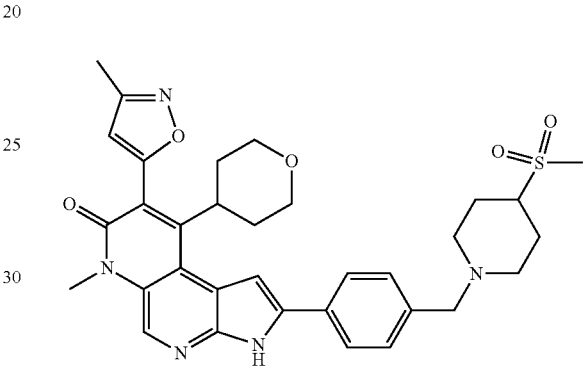

Step 1. 2-chloro-4-iodo-5-nitro-1-((2-(trimethylsilyl)ethoxy)methyl)-1H-pyrrolo[2,3-b]pyridine

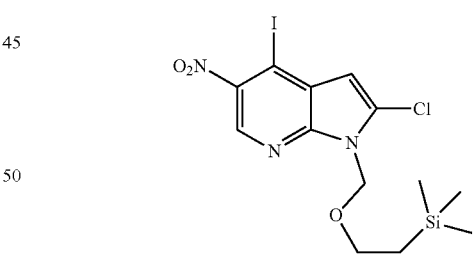

To a solution of 2,4-dichloro-5-nitro-1-((2-(trimethylsilyl)ethoxy)methyl)-1H-pyrrolo[2,3-b]pyridine (850 mg, 2.346 mmol) in DMF (15.64 mL was added potassium iodide (7790 mg, 46.9 mmol) and then it was stirred at 90° C. for 72 hours. After this time it was cooled to r.t., diluted with ethyl acetate, and then washed with water and brine. The organic layer was dried over MgSO₄, filtered, and then concentrated to dryness. The residue was purified by silica gel chromatography using 0-30% ethyl acetate in hexanes to afford desired product as light yellowish solid (445 mg, 41.8%). LCMS calculated for $C_{13}H_{18}ClIN_3O_3Si$ (M+H)+: m/z=453.9. Found: 453.9.

Step 2. (2-chloro-5-nitro-1-((2-(trimethylsilyl)ethoxy)methyl)-1H-pyrrolo[2,3-b]pyridin-4-yl)(tetrahydro-2H-pyran-4-yl)methanone

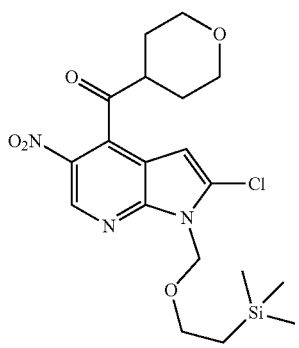 [SMILES: C[Si](C)(C)CCOCn1c(Cl)cc2c(C(=O)C3CCOCC3)c([N+](=O)[O-])cnc21]

To a solution of 2-chloro-4-iodo-5-nitro-1-((2-(trimethylsilyl)ethoxy)methyl)-1H-pyrrolo[2,3-b]pyridine (440 mg, 0.970 mmol) in tetrahydrofuran (8 mL) was added phenylmagnesium bromide (873 µL, 0.873 mmol) dropwise at −40° C. The resulting solution was stirred for 20 minutes at this temperature before a solution of copper(I) cyanide (29.7 µL, 0.970 mmol) and lithium chloride (41.1 mg, 0.970 mmol) in tetrahydrofuran (0.800 mL) was added followed by immediate addition of tetrahydro-2H-pyran-4-carbonyl chloride (432 mg, 2.91 mmol). The resulting solution was then allowed to warm up to r.t. and was stirred for another 30 minutes, then diluted with ethyl acetate and washed with NH$_4$OH solution in water and brine. The organic layer was dried over MgSO$_4$, filtered, and then concentrated to dryness. The residue was purified by silica gel chromatography using 0-40% ethyl acetate in hexanes to afford desired product (96 mg, 23%). LCMS calculated for C$_{19}$H$_{27}$ClN$_3$O$_5$Si (M+H)+: m/z=440.2. Found: 440.2.

Step 3. (2-(4-((4-(methylsulfonyl)piperidin-1-yl)methyl)phenyl)-5-nitro-1-((2-(trimethylsilyl)ethoxy)methyl)-1H-pyrrolo[2,3-b]pyridin-4-yl) (tetrahydro-2H-pyran-4-yl)methanone

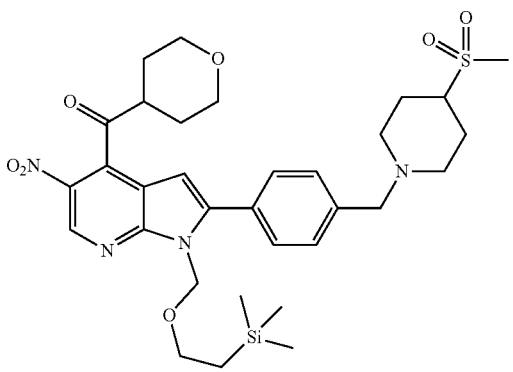

To a solution of (2-chloro-5-nitro-1-((2-(trimethylsilyl)ethoxy)methyl)-1H-pyrrolo[2,3-b]pyridin-4-yl)(tetrahydro-2H-pyran-4-yl)methanone (96 mg, 0.218 mmol) in dioxane (3 mL) and water (0.75 mL) was added 4-(methylsulfonyl)-1-(4-(4,4,5,5-tetramethyl-1,3,2-dioxaborolan-2-yl)benzyl) piperidine (124 mg, 0.327 mmol), Xphos-Pd-G2 (51.5 mg, 0.065 mmol), and cesium carbonate (213 mg, 0.655 mmol), then it was stirred at 80° C. for 2 hours. After this time it was filtered and concentrated to dryness. The residue was purified by silica gel chromatography using 0-100% ethyl acetate in hexanes to afford desired product as yellowish oil (87 mg, 67%). LCMS calculated for C$_{32}$H$_{45}$N$_4$O$_7$SSi (M+H)+: m/z=657.2. Found: 657.2.

Step 4. (5-amino-2-(4-((4-(methylsulfonyl)piperidin-1-yl)methyl)phenyl)-1-((2-(trimethylsilyl)ethoxy)methyl)-1H-pyrrolo[2,3-b]pyridin-4-yl) (tetrahydro-2H-pyran-4-yl)methanone

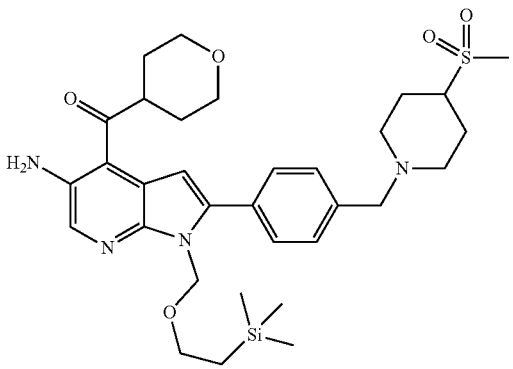 [SMILES: C[Si](C)(C)CCOCn1c(-c2ccc(CN3CCC(S(C)(=O)=O)CC3)cc2)cc2c(C(=O)C3CCOCC3)c([N+](=O)[O-])cnc21]

To a solution of (2-(4-((4-(methylsulfonyl)piperidin-1-yl)methyl)phenyl)-5-nitro-1-((2-(trimethylsilyl)ethoxy)methyl)-1H-pyrrolo[2,3-b]pyridin-4-yl)(tetrahydro-2H-pyran-4-yl)methanone (87 mg, 0.132 mmol) in tetrahydrofuran (1 mL), Methanol (1.000 mL) and water (1.000 mL), was added iron (51.8 mg, 0.927 mmol) and ammonium chloride (49.6 mg, 0.927 mmol). The resulting solution was stirred at 80° C. for 1 hour. After this time it was cooled to r.t., then diluted with 10% methanol in dichloromethane solution and then stirred for another 10 minutes, filtered, and then concentrated to dryness. The residue was purified by silica gel chromatography using 0-10% methanol in dichloromethane (61 mg, 74%). LCMS calculated for C$_{32}$H$_{47}$N$_4$O$_5$SSi (M+H)+: m/z=627.2. Found: 627.2.

Step 5. 2-(3-methylisoxazol-5-yl)-N-(2-(4-((4-(methylsulfonyl)piperidin-1-yl)methyl)phenyl)-4-(tetrahydro-2H-pyran-4-carbonyl)-1-((2-(trimethylsilyl)ethoxy)methyl)-1H-pyrrolo[2,3-b]pyridin-5-yl)acetamide

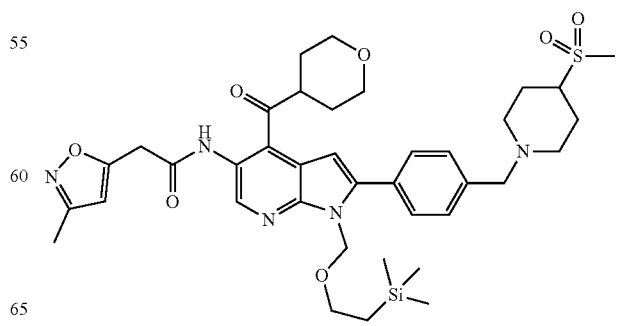

To a solution of (5-amino-2-(4-((4-(methylsulfonyl)piperidin-1-yl)methyl)phenyl)-1-((2-(trimethylsilyl)ethoxy)methyl)-1H-pyrrolo[2,3-b]pyridin-4-yl)(tetrahydro-2H-pyran-4-yl)methanone (22 mg, 0.035 mmol) in DMF (1 mL) was added 2-(3-methylisoxazol-5-yl)acetic acid (20 mg, 0.14 mmol) followed by addition of HATU (53.4 mg, 0.140 mmol) and diisopropylethylamine (36.8 μL, 0.211 mmol). The resulting solution was stirred at 50° C. for 2 hours then cooled to r.t., diluted with water and MeCN, then purified by prep-LCMS (XBridge C18 column, eluting with a gradient of acetonitrile/water containing 0.1% NH$_4$OH, at flow rate of 60 mL/min). LCMS calculated for C$_{38}$H$_{52}$N$_5$O$_7$SSi (M+H)+: m/z=750.3. Found: 750.2.

Step 6. 6-methyl-8-(3-methylisoxazol-5-yl)-2-(4-((4-(methylsulfonyl)piperidin-1-yl)methyl)phenyl)-9-(tetrahydro-2H-pyran-4-yl)-3,6-dihydro-7H-pyrrolo[3,2-f][1,7]naphthyridin-7-one

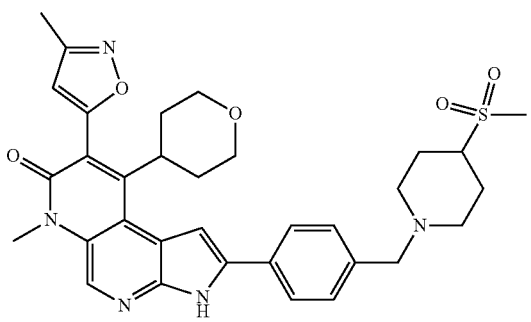

To a solution of 2-(3-methylisoxazol-5-yl)-A-(2-(4-((4-(methylsulfonyl)piperidin-1-yl)methyl)phenyl)-4-(tetrahydro-2H-pyran-4-carbonyl)-1-((2-(trimethylsilyl)ethoxy)methyl)-1H-pyrrolo[2,3-b]pyridin-5-yl)acetamide (8 mg, 10.81 μmol) in tetrahydrofuran (2 mL) was added cesium carbonate (17.61 mg, 0.054 mmol) and then it was stirred at 80° C. for 3 hours. After this time it was cooled to 50° C. then methyl iodide (2.028 μL, 0.032 mmol) was added. The resulting solution was stirred at this temperature for 30 minutes then cooled to r.t. and concentrated to dryness. The residue was dissolved in 1 mL dichloromethane and 1 mL TFA then stirred for 30 minutes before concentrated to dryness. The residue was dissolved in 5 mL 1:1:1 MeCN/Methanol/Water solution and then 0.3 mL ethylene diamine was added and then the resulting mixture was filtered and purified by prep-LCMS (XBridge C18 column, eluting with a gradient of acetonitrile/water containing 0.1% TFA, at flow rate of 60 mL/min) to afford the title compound. LCMS calculated for C$_{33}$H$_{38}$N$_5$O$_5$S (M+H)+: m/z=616.2. Found: 616.2.

Example 22. 9-(4-Methoxycyclohexyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one

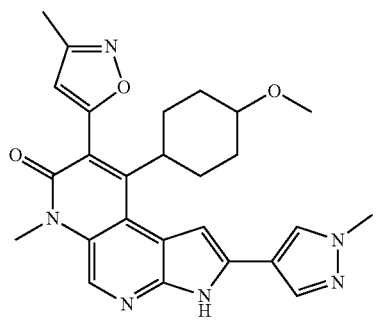

The title compound was prepared according to the procedure described in example 21, using 4-methoxycyclohexane-1-carbonyl chloride instead of tetrahydro-2H-pyran-4-carbonyl chloride in step 2 and using 1-methyl-4-(4,4,5,5-tetramethyl-1,3,2-dioxaborolan-2-yl)-1H-pyrazole instead of 4-(methylsulfonyl)-1-(4-(4,4,5,5-tetramethyl-1,3,2-dioxaborolan-2-yl)benzyl)piperidine as starting material in step 3. LC-MS calculated for C$_{26}$H$_{29}$N$_6$O$_3$ (M+H)$^+$: m/z=473.2. found 473.2.

Example 23. 6-methyl-2-(1-methyl-1H-pyrazol-4-yl)-8-(3-methylisoxazol-5-yl)-9-phenyl-3,6-dihydro-7H-pyrrolo[3,2-f][1,7]naphthyridin-7-one

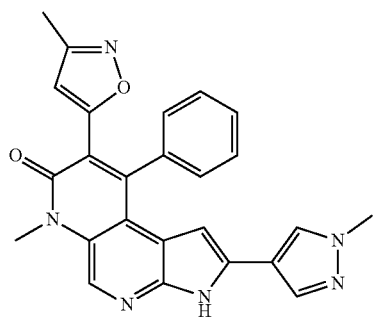

The title compound was prepared according to the procedure described in example 21, using benzoyl chloride instead of tetrahydro-2H-pyran-4-carbonyl chloride in step 2 and using 1-methyl-4-(4,4,5,5-tetramethyl-1,3,2-dioxaborolan-2-yl)-1H-pyrazole instead of 4-(methylsulfonyl)-1-(4-(4,4,5,5-tetramethyl-1,3,2-dioxaborolan-2-yl)benzyl)piperidine as starting material in step 3. LC-MS calculated for C$_{25}$H$_{21}$N$_6$O$_2$ (M+H)$^+$: m/z=437.2. found 437.2.

149

Example 24. 9-(4-methoxycyclohexyl)-6-methyl-2-(1-methyl-1H-pyrazol-4-yl)-3,6-dihydro-7H-pyrrolo[3,2-f][1,7]naphthyridin-7-one

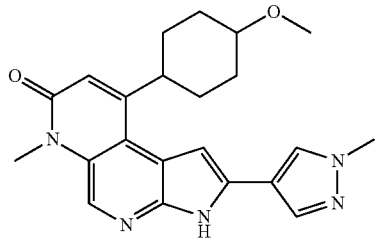

The title compound was prepared according to the procedure described in example 21, using 4-methoxycyclohexane-1-carbonyl chloride instead of tetrahydro-2H-pyran-4-carbonyl chloride in step 2, using 1-methyl-4-(4,4,5,5-tetramethyl-1,3,2-dioxaborolan-2-yl)-1H-pyrazole instead of 4-(methylsulfonyl)-1-(4-(4,4,5,5-tetramethyl-1,3,2-dioxaborolan-2-yl)benzyl)piperidine as starting material in step 3 and using 2-(diethoxyphosphoryl)acetic acid instead of 2-(3-methylisoxazol-5-yl)acetic acid in step 5. LC-MS calculated for $C_{22}H_{26}N_5O_2$ (M+H)$^+$: m/z=392.2. found 392.2.

Example 25. N-(2-hydroxyethyl)-4-(6-methyl-2-(1-methyl-1H-pyrazol-4-yl)-8-(3-methylisoxazol-5-yl)-7-oxo-6,7-dihydro-3H-pyrrolo[3,2-f][1,7]naphthyridin-9-yl)benzamide

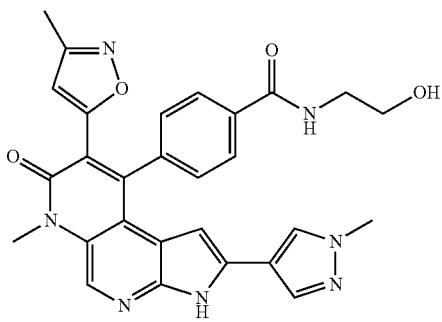 [SMILES: Cc1cc(-c2c(-c3ccc(C(=O)NCCO)cc3)c3c4cc(-c5cnn(C)c5)[nH]c4ncc3n(C)c2=O)on1]

150

Step 1. methyl 4-(6-methyl-2-(1-methyl-1H-pyrazol-4-yl)-8-(3-methylisoxazol-5-yl)-7-oxo-3-((2-(trimethylsilyl)ethoxy)methyl)-6,7-dihydro-3H-pyrrolo[3,2-f][1,7]naphthyridin-9-yl)benzoate

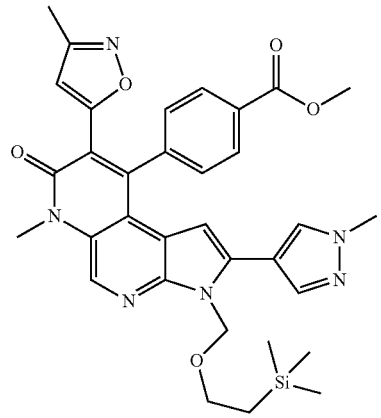

The title compound was prepared according to the procedure described in example 21, using methyl 4-(chlorocarbonyl)benzoate instead of tetrahydro-2H-pyran-4-carbonyl chloride in step 2 and using 1-methyl-4-(4,4,5,5-tetramethyl-1,3,2-dioxaborolan-2-yl)-1H-pyrazole instead of 4-(methylsulfonyl)-1-(4-(4,4,5,5-tetramethyl-1,3,2-dioxaborolan-2-yl)benzyl)piperidine as starting material in step 3. The dichloromethane/TFA treatment in step 6 was not performed so the protection group is still on the desired product. LC-MS calculated for $C_{33}H_{37}N_6O_5Si$ (M+H)$^+$: m/z=625.2; found 625.2.

Step 2. 4-(6-methyl-2-(1-methyl-1H-pyrazol-4-yl)-8-(3-methylisoxazol-5-yl)-7-oxo-3-((2-(trimethylsilyl)ethoxy)methyl)-6,7-dihydro-3H-pyrrolo[3,2-f][1,7]naphthyridin-9-yl)benzoic acid

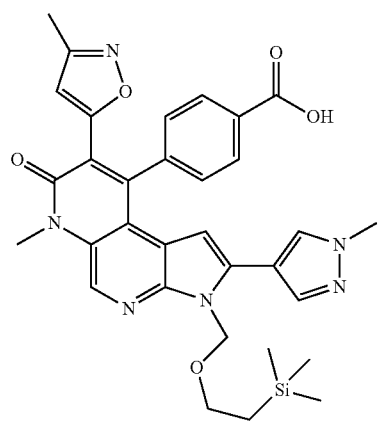

To a solution of methyl 4-(6-methyl-2-(1-methyl-1H-pyrazol-4-yl)-8-(3-methylisoxazol-5-yl)-7-oxo-3-((2-(trimethylsilyl)ethoxy)methyl)-6,7-dihydro-3H-pyrrolo[3,2-f][1,7]naphthyridin-9-yl)benzoate (386 mg, 0.618 mmol) in tetrahydrofuran (5 mL) and water (5.00 mL) was added lithium hydroxide (148 mg, 6.18 mmol) and it was then stirred at 80° C. for 2 hours. After this time it was cooled to r.t., acidified with 1N HCl then extracted with ethyl acetate. The organic layer was dried over MgSO₄, filtered and then concentrated to dryness. The residue was purified by silica gel chromatography using 0-10% methanol in dichloromethane to afford desired product as brownish solid (354 mg, 94%). LC-MS calculated for C₃₂H₃₅N₆O₅Si (M+H)⁺: m/z=611.2. found 611.2.

Step 3. N-(2-hydroxyethyl)-4-(6-methyl-2-(1-methyl-1H-pyrazol-4-yl)-8-(3-methylisoxazol-5-yl)-7-oxo-6,7-dihydro-3H-pyrrolo[3,2-f][1,7]naphthyridin-9-yl)benzamide

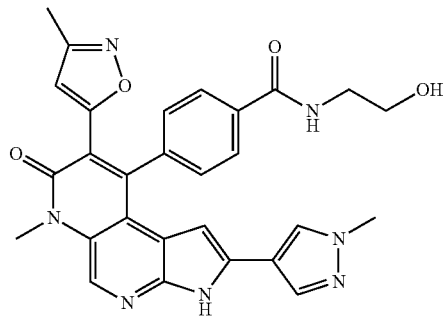 [SMILES: Cc1cc(-c2c(-c3ccc(C(=O)NCCO)cc3)c3c4cc(-c5cnn(C)c5)[nH]c4ncc3n(C)c2=O)on1]

To a solution of 4-(6-methyl-2-(1-methyl-1H-pyrazol-4-yl)-8-(3-methylisoxazol-5-yl)-7-oxo-3-((2-(trimethyl silyl)ethoxy)methyl)-6,7-dihydro-3H-pyrrolo[3,2-f][1,7]naphthyridin-9-yl)benzoic acid (15 mg, 0.025 mmol) in dichloromethane (1 mL) was added 2-aminoethan-1-ol (6.0 mg, 0.098 mmol) and HATU (37.4 mg, 0.098 mmol) followed by addition of diisopropylethylamine (25.7 μL, 0.147 mmol). The resulting solution was stirred at r.t. for 15 hours. After this time 1 mL TFA was added then it was stirred for another 30 minutes before concentrated to dryness. The residue was dissolved in 1:1:1 MeCN/water/Methanol solution and then 0.3 mL ethylene diamine was added. The resulting solution was then filtered and then purified by prep-LCMS (XBridge C18 column, eluting with a gradient of acetonitrile/water containing 0.1% TFA, at flow rate of 60 mL/min) to afford the title compound. LC-MS calculated for C₂₈H₂₆N₇O₄ (M+H)⁺: m/z=524.2. found 524.2.

Example 26. 4-(6-Methyl-2-(1-methyl-1H-pyrazol-4-yl)-8-(3-methylisoxazol-5-yl)-7-oxo-6,7-dihydro-3H-pyrrolo[3,2-f][1,7]naphthyridin-9-yl)-A-(2-methylbenzo[d]oxazol-5-yl)benzamide

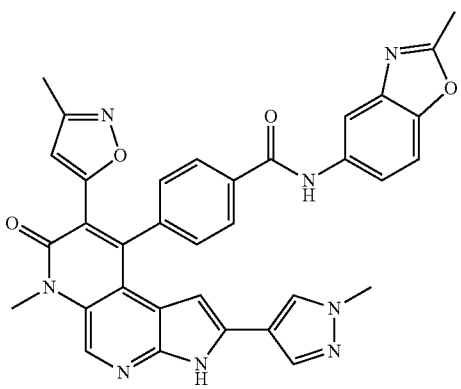

The title compound was prepared according to the procedure described in example 25, using 2-methylbenzo[t/]oxazol-5-amine instead of 2-aminoethan-1-ol in step 3. LC-MS calculated for C₃₄H₂₇N₈O₄ (M+H)⁺: m/z=611.2. found 611.2.

Example 27. 9-(4-(Methoxymethyl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one

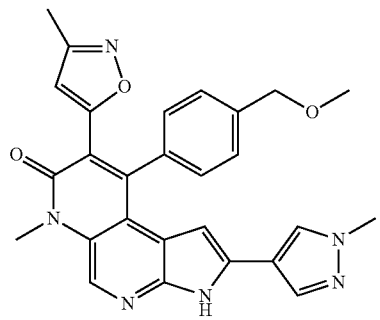

Step 1. 9-(4-(hydroxymethyl)phenyl)-6-methyl-2-(1-methyl-1H-pyrazol-4-yl)-8-(3-methylisoxazol-5-yl)-3-((2-(trimethylsilyl)ethoxy)methyl)-3,6-dihydro-7H-pyrrolo[3,2-f][1,7]naphthyridin-7-one

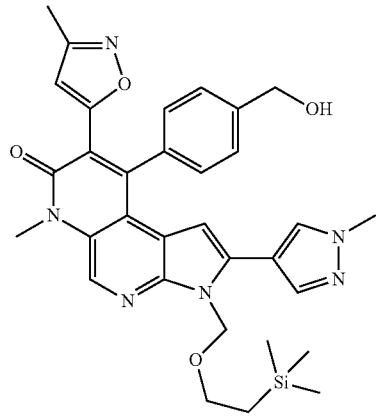

To a solution of methyl 4-(6-methyl-2-(1-methyl-1H-pyrazol-4-yl)-8-(3-methylisoxazol-5-yl)-7-oxo-3-((2-(trimethylsilyl)ethoxy)methyl)-6,7-dihydro-3H-pyrrolo[3,2-f][1,7]naphthyridin-9-yl)benzoate (400 mg, 0.640 mmol. Step 1, example 25) in tetrahydrofuran (10 mL) was added lithium aluminum hydride (640 μL, 0.640 mmol) at r.t. then it was stirred for 30 minutes. After this time it was diluted with ethyl acetate and then washed with sodium potassium tartrate solution followed by washing with brine. The organic layer was dried over MgSO₄, filtered and then concentrated to dryness. The residue was purified by silica gel chromatography using 0-10% methanol in dichloromethane to afford desired product (211 mg, 55.2%). LC-MS calculated for C₃₂H₃₇N₆O₄Si (M+H)⁺: m/z=597.2. found 597.2.

Step 2. 9-(4-(methoxymethyl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one

Step 1. 4-(6-methyl-2-(1-methyl-1H-pyrazol-4-yl)-8-(3-methylisoxazol-5-yl)-7-oxo-3-((2-(trimethylsilyl)ethoxy)methyl)-6,7-dihydro-3H-pyrrolo[3,2-f][1,7]naphthyridin-9-yl)benzaldehyde

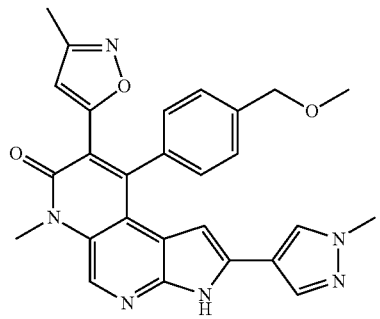

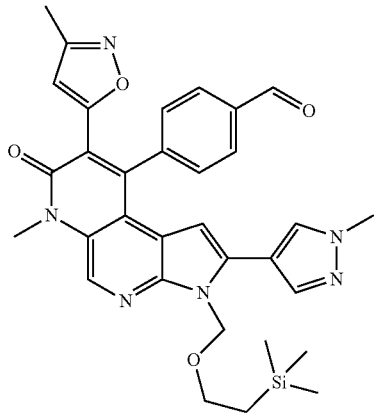

To a solution of 9-(4-(hydroxymethyl)phenyl)-6-methyl-2-(1-methyl-1H-pyrazol-4-yl)-8-(3-methylisoxazol-5-yl)-3-((2-(trimethylsilyl)ethoxy)methyl)-3,6-dihydro-7H-pyrrolo[3,2-f][1,7]naphthyridin-7-one (20 mg, 0.034 mmol) in tetrahydrofuran (1 mL) was added sodium hydride (1.340 mg, 0.034 mmol) and then it was stirred at r.t. for 10 minutes before addition of iodomethane (2.096 μL, 0.034 mmol). The resulting solution was stirred at r.t. for 1 hour then concentrated to dryness. The residue was dissolved in 1 mL dichloromethane and 1 mL TFA then it was stirred for 30 minutes before concentrated to dryness. The residue was dissolved in 1:1:1 MeCN/water/Methanol and then 0.3 mL ethylene diamine was added and the resulting solution was filtered and purified by prep-LCMS (XBridge C18 column, eluting with a gradient of acetonitrile/water containing 0.1% TFA, at flow rate of 60 mL/min) to afford the title compound. LC-MS calculated for $C_{27}H_{25}N_6O_3$ (M+H)$^+$: m/z=481.2. found 481.2.

To a solution of 9-(4-(hydroxymethyl)phenyl)-6-methyl-2-(1-methyl-1H-pyrazol-4-yl)-8-(3-methylisoxazol-5-yl)-3-((2-(trimethyl silyl)ethoxy)methyl)-3,6-dihydro-7H-pyrrolo[3,2-f][1,7]naphthyridin-7-one (150 mg, 0.251 mmol, step 1 Example 27) in tetrahydrofuran (8 mL) was added dess-martinperiodinane (320 mg, 0.754 mmol) and it was then stirred at r.t. for 2 hours. After this time it was diluted with tetrahydrofuran and then filtered. The filtrate was concentrated to dryness and then purified by silica gel chromatography using 0-10% methanol in dichloromethane to afford desired product (135 mg, 90%). LC-MS calculated for $C_{32}H_{35}N_6O_4Si$ (M+H)$^+$: m/z=595.2. found 595.2.

Step 2. 6-methyl-2-(1-methyl-1H-pyrazol-4-yl)-8-(3-methylisoxazol-5-yl)-9-(4-(((tetrahydro-2H-pyran-3-yl)amino)methyl)phenyl)-3,6-dihydro-7H-pyrrolo[3,2-f][1,7]naphthyridin-7-one

Example 28. 6-Methyl-2-(1-methyl-1H-pyrazol-4-yl)-8-(3-methylisoxazol-5-yl)-9-(4-(((tetrahydro-2H-pyran-3-yl)amino)methyl)phenyl)-3,6-dihydro-7H-pyrrolo[3,2-f][1,7]naphthyridin-7-one

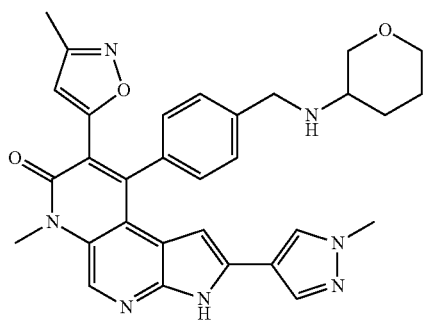 [SMILES: Cc1cc(-c2c(-c3ccc(CNC4CCCOC4)cc3)c3c4cc(-c5cnn(C)c5)[nH]c4ncc3n(C)c2=O)on1]

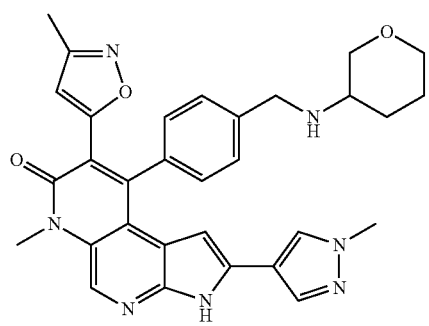

To a solution of 4-(6-methyl-2-(1-methyl-1H-pyrazol-4-yl)-8-(3-methylisoxazol-5-yl)-7-oxo-3-((2-(trimethyl silyl)ethoxy)methyl)-6,7-dihydro-3H-pyrrolo[3,2-f][1,7]naphthyridin-9-yl)benzaldehyde (20 mg, 0.034 mmol) in dichloromethane (1 mL) was added tetrahydro-2H-pyran-3-amine (10.20 mg, 0.101 mmol), acetic acid (5.78 μL, 0.101 mmol) and sodium triacetoxyborohydride (21.38 mg, 0.101 mmol) then it was stirred at r.t. for 1 hour. After this time 1 mL TFA was added and it was stirred for another 30 minutes before concentrated to dryness. The residue was dissolved in 1:1:1 MeCN/water/Methanol solution and then 0.3 mL ethylene diamine was added. The resulting solution was then purified by prep-LCMS (XBridge C18 column, eluting with a gradient of acetonitrile/water containing 0.1% TFA, at flow rate of 60 mL/min) to afford the title compound. LC-MS calculated for $C_{31}H_{32}N_7O_3$ (M+H)$^+$: m/z=550.2; found 550.2.

Example 29. 9-(4-((2-Methoxyethyl)(methyl)amino)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one

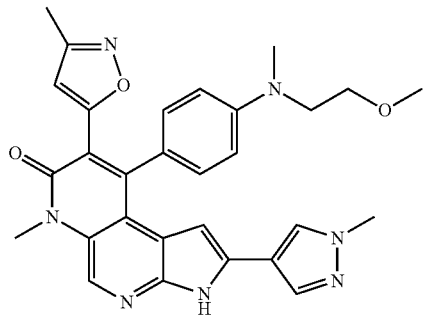

Step 1. (4-bromophenyl)(2-chloro-5-nitro-1-((2-(trimethylsilyl)ethoxy)methyl)-1H-pyrrolo[2,3-b]pyridin-4-yl)methanone

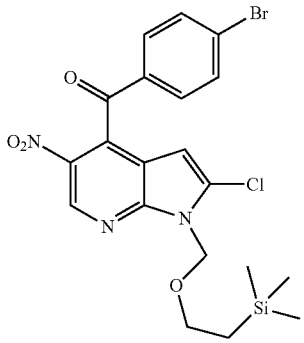 [SMILES: C[Si](C)(C)CCOCn1c(Cl)cc2c(C(=O)c3ccc(Br)cc3)c([N+](=O)[O-])cnc21]

The title compound was prepared according to the procedure described in example 21, using 4-bromobenzoyl chloride instead of tetrahydro-2H-pyran-4-carbonyl chloride in step 2. LC-MS calculated for $C_{20}H_{22}BrClN_3O_4Si$ (M+H)$^+$: m/z=512.0; found 512.0.

Step 2. (5-amino-2-chloro-1-((2-(trimethylsilyl)ethoxy)methyl)-1H-pyrrolo[2,3-b]pyridin-4-yl)(4-bromophenyl)methanone

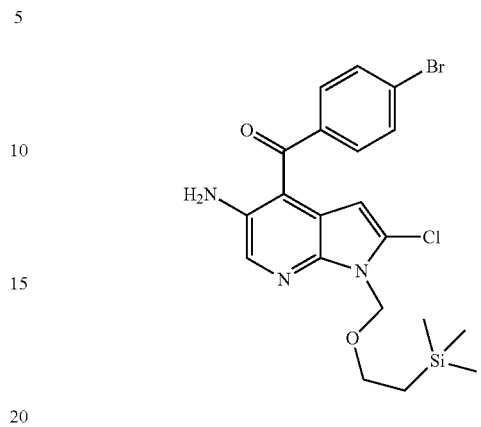

To a solution of (4-bromophenyl)(2-chloro-5-nitro-1-((2-(trimethylsilyl)ethoxy)methyl)-1H-pyrrolo[2,3-b]pyridin-4-yl)methanone (2.25 g, 4.41 mmol) in tetrahydrofuran (10.0 mL) and EtOH (20 mL) was added iron (1231 mg, 22.04 mmol) and HCl (6612 µL, 6.61 mmol) then it was stirred at 80° C. for 1 hour. After this time it was cooled to r.t., diluted with dichloromethane and methanol then filtered and concentrated to dryness. The residue was purified by silica gel chromatography using 0-10% methanol in dichloromethane to afford desired product (1.84 g, 87%). LC-MS calculated for $C_{20}H_{24}BrClN_3O_2Si$ (M+H)$^+$: m/z=482.0. found 482.0.

Step 3. 9-(4-bromophenyl)-2-chloro-8-(3-methylisoxazol-5-yl)-3-((2-(trimethylsilyl)ethoxy)methyl)-3,6-dihydro-7H-pyrrolo[3,2-f][1,7]naphthyridin-7-one

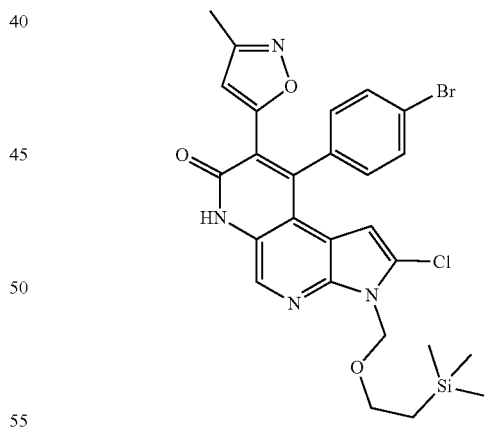

To a solution of (5-amino-2-chloro-1-((2-(trimethylsilyl)ethoxy)methyl)-1H-pyrrolo[2,3-b]pyridin-4-yl)(4-bromophenyl)methanone (1.89 g, 3.93 mmol) in DMF (20 mL) was added diisopropylethylamine (4.12 mL, 23.58 mmol), 2-(3-methylisoxazol-5-yl)acetic acid (1.664 g, 11.79 mmol) and HATU (5.98 g, 15.72 mmol) and then it was stirred at 50° C. for 15 hour. After this time it was diluted with ethyl acetate and then washed with water and brine. The organic layer was dried over MgSO$_4$, filtered and then concentrated to dryness. The residue was purified by silica gel chromatography using 0-10% methanol in dichloromethane to afford desired product (2.11 g, 92%). LC-MS calculated for $C_{26}H_{27}BrClN_4O_3Si$ (M+H)+: m/z=587.0. found 587.0.

Step 4. 9-(4-bromophenyl)-2-chloro-6-methyl-8-(3-methylisoxazol-5-yl)-3-((2-(trimethylsilyl)ethoxy)methyl)-3,6-dihydro-7H-pyrrolo[3,2-f][1,7]naphthyridin-7-one

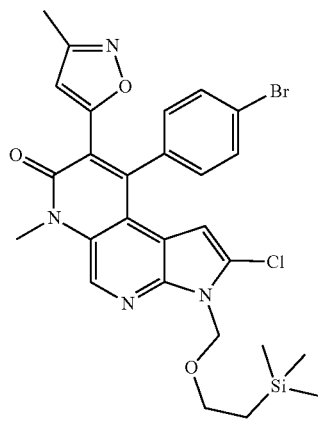 [SMILES: Cc1cc(-c2c(-c3ccc(Br)cc3)c3c4cc(Cl)n(COCC[Si](C)(C)C)c4ncc3n(C)c2=O)on1]

To a solution of 9-(4-bromophenyl)-2-chloro-8-(3-methylisoxazol-5-yl)-3-((2-(trimethylsilyl)ethoxy)methyl)-3,6-dihydro-7H-pyrrolo[3,2-f][1,7]naphthyridin-7-one (2.11 g, 3.61 mmol) in tetrahydrofuran (20 mL) was added cesium carbonate (3.84 g, 11.79 mmol) then iodomethane (0.492 mL, 7.86 mmol) was added and stirred for 1 hour at 50° C. After this time it was cooled to r.t., filtered and then concentrated to dryness. The residue was purified by silica gel chromatography using 0-10% methanol in dichloromethane to afford desired product (2.01 g, 93%). LC-MS calculated for $C_{27}H_{29}BrClN_4O_3Si$ (M+H)+: m/z=599.0. found 599.0.

Step 5. 2-chloro-6-methyl-8-(3-methylisoxazol-5-yl)-9-(4-(4,4,5,5-tetramethyl-1,3,2-dioxaborolan-2-yl)phenyl)-3-((2-(trimethylsilyl)ethoxy)methyl)-3,6-dihydro-7H-pyrrolo[3,2-f][1,7]naphthyridin-7-one

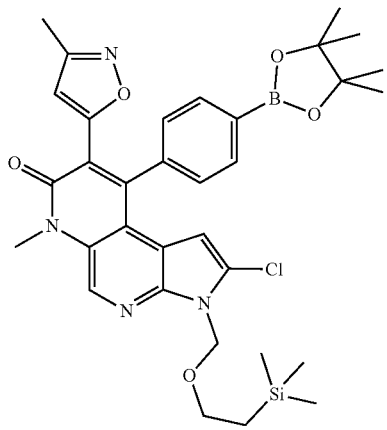 [SMILES: Cc1cc(-c2c(-c3ccc(B4OC(C)(C)C(C)(C)O4)cc3)c3c4cc(Cl)n(COCC[Si](C)(C)C)c4ncc3n(C)c2=O)on1]

To a solution of 9-(4-bromophenyl)-2-chloro-6-methyl-8-(3-methylisoxazol-5-yl)-3-((2-(trimethylsilyl)ethoxy)methyl)-3,6-dihydro-7H-pyrrolo[3,2-f][1,7]naphthyridin-7-one (1.46 g, 2.433 mmol) in dioxane (30 mL) was added bis(pinacolato)diboron (0.927 g, 3.65 mmol), Pd-dppf (0.596 g, 0.730 mmol) and potassium acetate (0.478 g, 4.87 mmol) then it was stirred at 100° C. for 3 hours. After this time it was cooled to r.t., filtered and then concentrated to dryness. The residue was purified by silica gel chromatography using 0-100% ethyl acetate in hexanes to afford desired product as brownish oil (0.978 g, 62.1%). LC-MS calculated for $C_{33}H_{41}BClN_4O_5Si$ (M+H)+: m/z=647.0. found 647.0.

Step 6. 9-(4-bromophenyl)-6-methyl-2-(1-methyl-1H-pyrazol-4-yl)-8-(3-methylisoxazol-5-yl)-3-((2-(trimethylsilyl)ethoxy)methyl)-3,6-dihydro-7H-pyrrolo[3,2-f][1,7]naphthyridin-7-one

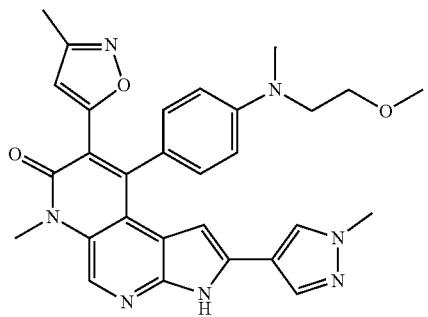 [SMILES: COCCN(C)c1ccc(-c2c(-c3cc(C)no3)c(=O)n(C)c3cnc4[nH]c(-c5cnn(C)c5)cc4c23)cc1]

To a solution of 6-methyl-2-(1-methyl-1H-pyrazol-4-yl)-8-(3-methylisoxazol-5-yl)-9-(4-(4,4,5,5-tetramethyl-1,3,2-dioxaborolan-2-yl)phenyl)-3-((2-(trimethylsilyl)ethoxy)methyl)-3,6-dihydro-7H-pyrrolo[3,2-f][1,7]naphthyridin-7-one (20 mg, 0.029 mmol) in acetonitrile (0.5 mL) was added copper (II) acetate (7.87 mg, 0.043 mmol), triethylamine (16.10 µL, 0.115 mmol) and activated 4 Å molecular sieves. The mixture was stirred at r.t. for 5 minutes before 2-methoxy-A-methylethan-1-amine (7.72 mg, 0.087 mmol) was added and then it was stirred at 80° C. for 5 hours. After this time it was cooled to r.t., diluted with MeCN and then filtered and concentrated to dryness. The residue was dissolved in 1:1 dichloromethane/TFA and then stirred at r.t. for 30 minutes before concentrated to dryness. The residue was dissolved in 5 mL 1:1:1 MeCN/water/Methanol and then 0.5 mL ethylenediamine was added and it was purified by prep-LCMS (XBridge C18 column, eluting with a gradient of acetonitrile/water containing 0.1% TFA, at flow rate of 60 mL/min) to afford desired product. LC-MS calculated for $C_{29}H_{30}N_7O_3$ (M+H)+: m/z=524.0. found 524.0.

Example 30. 6-Methyl-2-(1-methyl-1H-pyrazol-4-yl)-8-(3-methylisoxazol-5-yl)-9-(4-((tetrahydro-2H-pyran-4-yl)amino)phenyl)-3,6-dihydro-7H-pyrrolo[3,2-f][1,7]naphthyridin-7-one

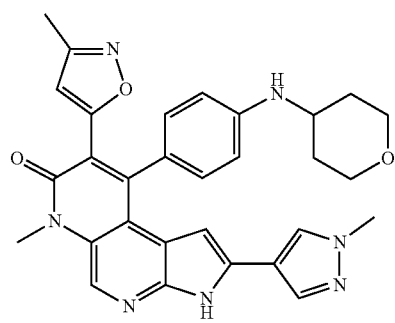 [SMILES: Cc1cc(-c2c(-c3ccc(NC4CCOCC4)cc3)c3c4cc(-c5cnn(C)c5)[nH]c4ncc3n(C)c2=O)on1]

The title compound was prepared according to the procedure described in example 29, using tetrahydro-2H-pyran-4-amine instead of 2-methoxy-N-methylethan-1-amine in step 6. LC-MS calculated for $C_{30}H_{30}N_7O_3$ $(M+H)^+$: m/z=536.0. found 536.0.

Example 31. 9-(4-(1,5-Dimethyl-1H-pyrazol-4-yl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one

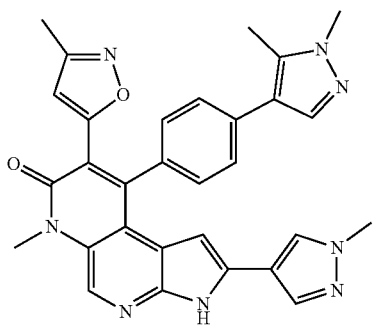 [SMILES: Cc1cc(-c2c(-c3ccc(-c4cnn(C)c4C)cc3)c3c4cc(-c5cnn(C)c5)[nH]c4ncc3n(C)c2=O)on1]

To a solution of 6-methyl-2-(1-methyl-1H-pyrazol-4-yl)-8-(3-methylisoxazol-5-yl)-9-(4-(4,4,5,5-tetramethyl-1,3,2-dioxaborolan-2-yl)phenyl)-3-((2-(trimethylsilyl)ethoxy)methyl)-3,6-dihydro-7H-pyrrolo[3,2-f][1,7]naphthyridin-7-one (20 mg, 0.029 mmol, example 29, step 5) in dioxane (1 mL) and water (0.250 mL) was added 4-iodo-1,5-dimethyl-1H-pyrazole (6.41 mg, 0.029 mmol), cesium carbonate (47.0 mg, 0.144 mmol). Nitrogen gas was bubbled through for 1 minute then it was stirred at 80° C. for 1 hour. After this time it was cooled to r.t. then concentrated to dryness. The residue was dissolved in 1:1 TFA/dichloromethane and then stirred for another 1 hour. After this time it was concentrated to dryness then diluted with MeCN/water/Methanol then 0.5 mL ethylenediamine was added. The resulting solution was then filtered and then purified by prep-LCMS (XBridge C18 column, eluting with a gradient of acetonitrile/water containing 0.1% TFA, at flow rate of 60 mL/min) to afford desired product. LC-MS calculated for $C_{30}H_{27}N_8O_2$ $(M+H)^+$: m/z=531.2. found 531.2.

Example 32. 9-(4-(5-(Hydroxymethyl)-1-methyl-1H-pyrazol-4-yl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one

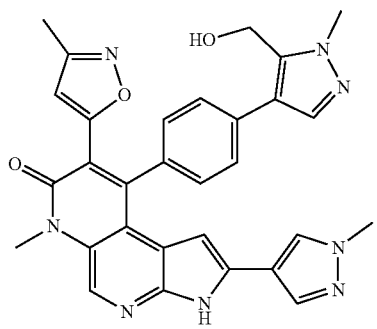 [SMILES: Cc1cc(-c2c(-c3ccc(-c4cnn(C)c4CO)cc3)c3c4cc(-c5cnn(C)c5)[nH]c4ncc3n(C)c2=O)on1]

The title compound was prepared according to the procedure described in example 31, using (4-bromo-1-methyl-1H-pyrazol-5-yl)methanol instead of 4-iodo-1,5-dimethyl-1H-pyrazole. LC-MS calculated for $C_{30}H_{27}N_8O_3$ $(M+H)^+$: m/z=547.2; found 547.2.

Example 33. 6-Methyl-2-(1-methyl-1H-pyrazol-4-yl)-8-(3-methylisoxazol-5-yl)-9-(1-(methylsulfonyl)pyrrolidin-3-yl)-3,6-dihydro-7H-pyrrolo[3,2-f][1,7]naphthyridin-7-one

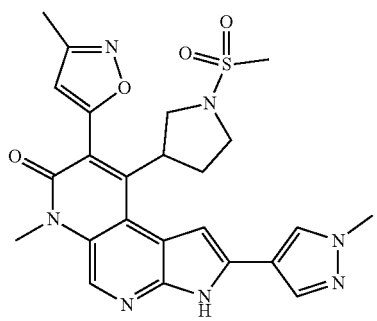 [SMILES: Cc1cc(-c2c(C3CCN(S(C)(=O)=O)C3)c3c4cc(-c5cnn(C)c5)[nH]c4ncc3n(C)c2=O)on1]

Step 1. tert-butyl 3-((2-chloro-5-nitro-1-((2-(trimethylsilyl)ethoxy)methyl)-1H-pyrrolo[2,3-b]pyridin-4-yl)(hydroxy)methyl)pyrrolidine-1-carboxylate

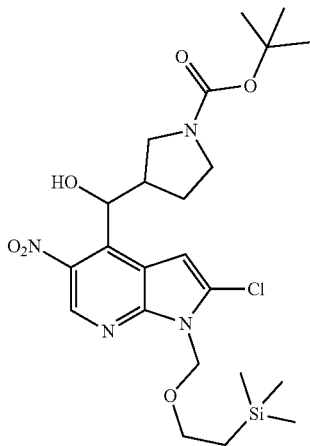 [SMILES: CC(C)(C)OC(=O)N1CCC(C(O)c2c([N+](=O)[O-])cnc3c2cc(Cl)n3COCC[Si](C)(C)C)C1]

To a solution of 2-chloro-4-iodo-5-nitro-1-((2-(trimethylsilyl)ethoxy)methyl)-1H-pyrrolo[2,3-b]pyridine (2400 mg, 5.29 mmol, step 1, example 21) in tetrahydrofuran (30 mL) was added phenylmagnesium bromide (5818 µL, 5.82 mmol) at −40° C. then it was stirred for 20 minutes. In a separate flask tert-butyl 3-formylpyrrolidine-1-carboxylate (1265 mg, 6.35 mmol) and lithium bromide (689 mg, 7.93 mmol) was dissolved in tetrahydrofuran (10.0 mL) then cooled to 0° C. The previously made Grignard reagent was added slowly to the aldehyde solution then stirred for 20 minutes at this temperature, then slowly warmed up to r.t. The resulting solution was then quenched with 1N HCl and extracted with ethyl acetate. The organic layer was then washed with brine, dried over MgSO₄, filtered and then concentrated to dryness. The residue was purified by silica gel chromatography using 0-100% ethyl acetate in hexanes to afford desired product as brownish oil (1.41 g, 50.5%). LC-MS calculated for $C_{23}H_{36}ClN_4O_6Si$ (M+H⁺): m/z=527.2. found 527.2.

Step 2. tert-butyl 3-(2-chloro-5-nitro-1-((2-(trimethylsilyl)ethoxy)methyl)-1H-pyrrolo[2,3-b]pyridine-4-carbonyl)pyrrolidine-1-carboxylate

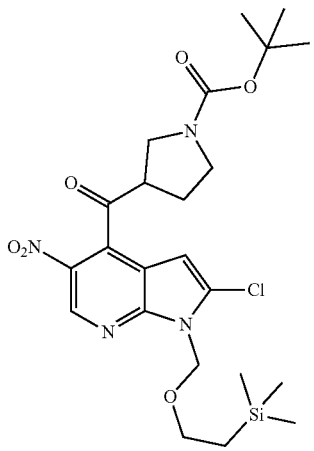 [SMILES: CC(C)(C)OC(=O)N1CCC(C(=O)c2c([N+](=O)[O-])cnc3c2cc(Cl)n3COCC[Si](C)(C)C)C1]

To a solution of tert-butyl 3-((2-chloro-5-nitro-1-((2-(trimethylsilyl)ethoxy)methyl)-1H-pyrrolo[2,3-b]pyridin-4-yl)(hydroxy)methyl)pyrrolidine-1-carboxylate (1.4 g, 2.66 mmol) in tetrahydrofuran (26.6 mL) was added sodium bicarbonate (2.231 g, 26.6 mmol) and dess-martinperiodinane (1.690 g, 3.98 mmol) then it was stirred at r.t. for 90 minutes then filtered and concentrated to dryness. The residue was purified by silica gel chromatography using 0-100% ethyl acetate in hexanes to afford desired product as brownish solid (1.40 g, 100%). LC-MS calculated for $C_{23}H_{34}ClN_4O_6Si$ (M+H⁺): m/z=525.2. found 525.2.

Step 3. tert-butyl 3-(2-(1-methyl-1H-pyrazol-4-yl)-5-nitro-1-((2-(trimethylsilyl)ethoxy)methyl)-1H-pyrrolo[2,3-b]pyridine-4-carbonyl)pyrrolidine-1-carboxylate

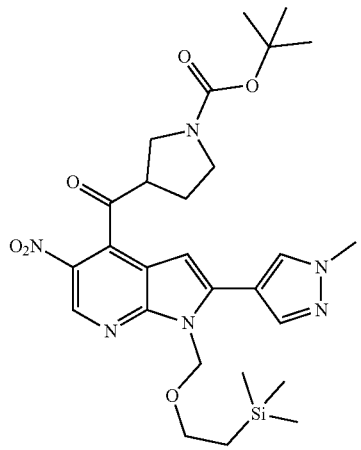

To a solution of tert-butyl 3-(2-chloro-5-nitro-1-((2-(trimethylsilyl)ethoxy)methyl)-1H-pyrrolo[2,3-b]pyridine-4-carbonyl)pyrrolidine-1-carboxylate (1.397 g, 2.66 mmol) in dioxane (10.64 mL) and water (2.66 mL) was added 1-methyl-4-(4,4,5,5-tetramethyl-1,3,2-dioxaborolan-2-yl)-1H-pyrazole (0.664 g, 3.19 mmol), chloro(2-dicyclohexylphosphino-2',4',6'-triisopropyl-1,1'-biphenyl)[2-(2'-amino-1,1'-biphenyl)]palladium(II) (Xphos-Pd-G2, 0.105 g, 0.133 mmol) and cesium carbonate (2.60 g, 7.98 mmol) then it was stirred at 80° C. for 2 hours. After this time it was cooled to r.t. and then concentrated to dryness. The residue was purified by silica gel chromatography using 0-100% ethyl acetate in hexanes to afford desired product as brownish solid (1.33 g, 88%). LC-MS calculated for $C_{27}H_{39}N_6O_6Si$ (M+H⁺): m/z=571.2; found 571.2.

Step 3. tert-butyl 3-(5-amino-2-(1-methyl-1H-pyrazol-4-yl)-1-((2-(trimethylsilyl)ethoxy)methyl)-1H-pyrrolo[2,3-b]pyridine-4-carbonyl)pyrrolidine-1-carboxylate

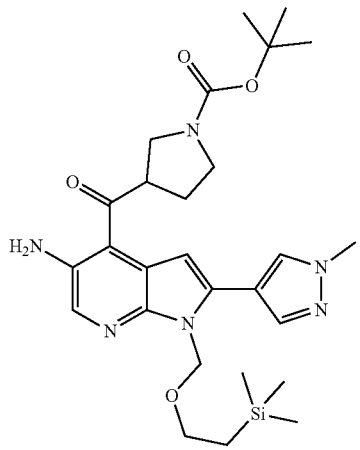 [SMILES: Cn1cc(-c2cc3c(C(=O)C4CCN(C(=O)OC(C)(C)C)C4)c([N+](=O)[O-])cnc3n2COCC[Si](C)(C)C)cn1]

To a solution of tert-butyl 3-(2-(1-methyl-1H-pyrazol-4-yl)-5-nitro-1-((2-(trimethylsilyl)ethoxy)methyl)-1H-pyrrolo[2,3-b]pyridine-4-carbonyl)pyrrolidine-1-carboxylate (1.33 g, 2.330 mmol) in tetrahydrofuran (4 mL) and ethanol (8.00 mL) was added iron (0.651 g, 11.65 mmol) and HCl (2.80 mL, 2.80 mmol) then it was stirred at 80° C. for 3 hours then cooled to r.t., diluted with dichloromethane and methanol, filtered and then concentrated to dryness. The residue was purified by silica gel chromatography using 0-10% methanol in dichloromethane (1.17 g, 93%). LC-MS calculated for $C_{27}H_{41}N_6O_4Si$ (M+H$^+$): m/z=541.2. found 541.2.

Step 4. tert-butyl 3-(6-methyl-2-(1-methyl-1H-pyrazol-4-yl)-8-(3-methylisoxazol-5-yl)-7-oxo-3-((2-(trimethylsilyl)ethoxy)methyl)-6,7-dihydro-3H-pyrrolo[3,2-f][1,7]naphthyridin-9-yl)pyrrolidine-1-carboxylate

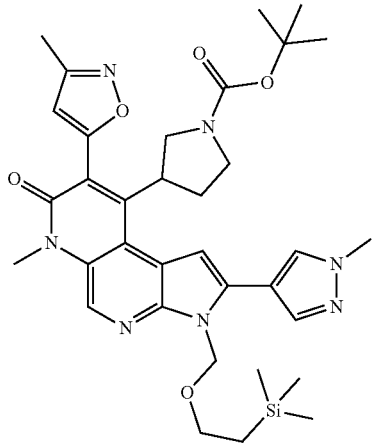 [SMILES: Cc1cc(-c2c(C3CCN(C(=O)OC(C)(C)C)C3)c3c4cc(-c5cnn(C)c5)n(COCC[Si](C)(C)C)c4ncc3n(C)c2=O)on1]

To a solution of tert-butyl 3-(5-amino-2-(1-methyl-1H-pyrazol-4-yl)-1-((2-(trimethylsilyl)ethoxy)methyl)-1H-pyrrolo[2,3-b]pyridine-4-carbonyl)pyrrolidine-1-carboxylate (580 mg, 1.073 mmol) in DMF (10 mL) was added 2-(3-methylisoxazol-5-yl)acetic acid (303 mg, 2.145 mmol), HATU (1224 mg, 3.22 mmol) and diisopropylethylamine (749 μL, 4.29 mmol) then it was stirred at 50° C. for 15 hours. After this time it was diluted with ethyl acetate, washed with water and brine then the organic layer was dried over MgSO$_4$, filtered and then concentrated to dryness. The residue was washed through a column of silica gel eluting with 0-10% methanol in dichloromethane to afford a mixture of intermediates. The above intermediate mixture was dissolved in tetrahydrofuran (10.00 mL) then cesium carbonate (1048 mg, 3.22 mmol) was added and stirred at 80° C. for 2 hours. After this time it was cooled to 50° C. and then iodomethane (101 μL, 1.609 mmol) was added and stirred for another 1 hour. After this time it was filtered and concentrated to dryness. The residue was purified by silica gel chromatography using 0-10% methanol in dichloromethane to afford desired product as brownish oil (580 mg, 82%). LC-MS calculated for $C_{34}H_{46}N_7O_5Si$ (M+H$^+$): m/z=660.3. found 660.3.

Step 5. 6-methyl-2-(1-methyl-1H-pyrazol-4-yl)-8-(3-methylisoxazol-5-yl)-9-(pyrrolidin-3-yl)-3-((2-(trimethylsilyl)ethoxy)methyl)-3,6-dihydro-7H-pyrrolo[3,2-f][1,7]naphthyridin-7-one

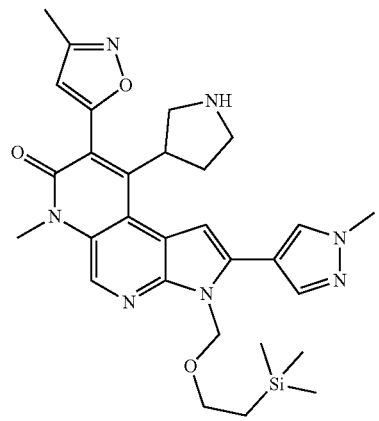 [SMILES: Cc1cc(-c2c(C3CCNC3)c3c4cc(-c5cnn(C)c5)n(COCC[Si](C)(C)C)c4ncc3n(C)c2=O)on1]

To a solution of tert-butyl 3-(6-methyl-2-(1-methyl-1H-pyrazol-4-yl)-8-(3-methylisoxazol-5-yl)-7-oxo-3-((2-(trimethylsilyl)ethoxy)methyl)-6,7-dihydro-3H-pyrrolo[3,2-f][1,7]naphthyridin-9-yl)pyrrolidine-1-carboxylate (580 mg, 0.879 mmol) in dichloromethane (15 mL) was added trifluoroacetic acid (3 mL, 38.9 mmol) then it was stirred at r.t. for 15 minutes then concentrated to dryness immediately. The residue was re-dissolved in dichloromethane and toluene and then concentrated and this process was repeated for 5 times then the residue was concentrated to afford the desired product as TFA salt. LC-MS calculated for $C_{29}H_{38}N_7O_3Si$ (M+H$^+$): m/z=560.3. found 560.3.

Step 6. 6-methyl-2-(1-methyl-1H-pyrazol-4-yl)-8-(3-methylisoxazol-5-yl)-9-(1-(methylsulfonyl)pyrrolidin-3-yl)-3,6-dihydro-7H-pyrrolo[3,2-f][1,7]naphthyridin-7-one

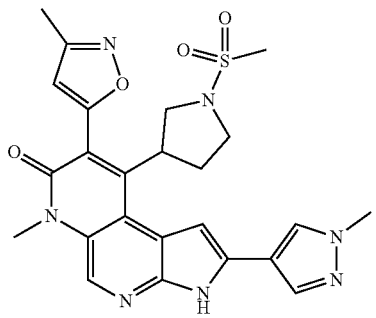 [SMILES: Cc1cc(-c2c(C3CCN(S(C)(=O)=O)C3)c3c4cc(-c5cnn(C)c5)[nH]c4ncc3n(C)c2=O)on1]

To a solution of 6-methyl-2-(1-methyl-1H-pyrazol-4-yl)-8-(3-methylisoxazol-5-yl)-9-(pyrrolidin-3-yl)-3-((2-(trimethylsilyl)ethoxy)methyl)-3,6-dihydro-7H-pyrrolo[3,2-f][1,7]naphthyridin-7-one (20 mg, 0.036 mmol) in dichloromethane (1 mL) was added diisopropylethylamine (31.2 µL, 0.179 mmol) and methanesulfonyl chloride (13.78 mg, 0.107 mmol) then it was stirred at r.t. for 1 hour. After this time 1 mL TFA was added and it was then stirred at r.t. for another 1 hour. The resulting solution was concentrated to dryness then dissolved in MeCN and then 0.5 mL ethylene diamine was added and stirred for 10 minutes at r.t. before purified by prep-LCMS (XBridge C18 column, eluting with a gradient of acetonitrile/water containing 0.1% TFA, at flow rate of 60 mL/min) to afford the title compound. LC-MS calculated for $C_{24}H_{26}N_7O_4S$ $(M+H)^+$: m/z=508.0; found 508.0.

Example 34. 4-(8-((3-(1H-tetrazol-5-yl)phenyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide

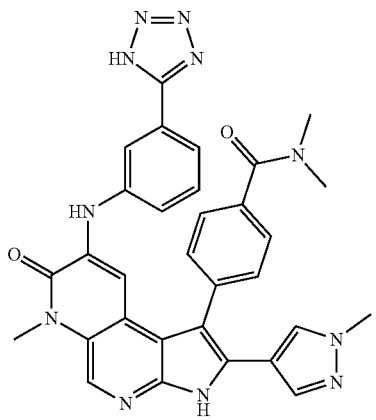 [SMILES: CN(C)C(=O)c1ccc(-c2c(-c3cnn(C)c3)[nH]c3ncc4c(cc(Nc5cccc(-c6nnn[nH]6)c5)c(=O)n4C)c23)cc1]

Step 1: 5-nitro-1-(phenylsulfonyl)-4-vinyl-1H-pyrrolo[2,3-b]pyridine

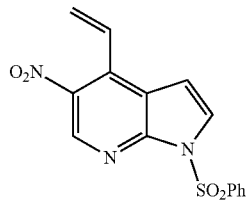

To a round bottom flask equipped with a magnetic stir bar was added 4-chloro-5-nitro-1-(phenylsulfonyl)-1H-pyrrolo[2,3-b]pyridine (7.64 g, 22.62 mmol), dichloro[1,1'-bis(diphenylphosphino)ferrocene]palladium (II) dichloromethane adduct (3.66 g, 4.48 mmol) and $CS_2CO_3$ (19.48 g, 59.8 mmol). The flask was sealed with a rubber septum, evacuated and backfilled with nitrogen (this process was repeated a total of three times). A solution of 4,4,5,5-tetramethyl-2-vinyl-1,3,2-dioxaborolane (4.604 g, 29.9 mmol) in 1,4-dioxane (60.0 mL) was added, followed by water (12.0 mL). The reaction was heated at 80° C. for 16 h. After cooling to room temperature, the reaction mixture was concentrated. The residue was diluted with dichloromethane and filtered. The filtrate was concentrated. The resulting residue was purified on silica gel (240 g, 0-50% EtOAc in dichloromethane) to give the desired product as a yellow solid (4.96 g, 67%). LCMS calculated for $C_{15}H_{12}N_3O_4S$ $(M+H)^+$ m/z=330.1. found 330.1.

Step 2: 2-bromo-5-nitro-1-(phenylsulfonyl)-4-vinyl-1H-pyrrolo[2,3-b]pyridine

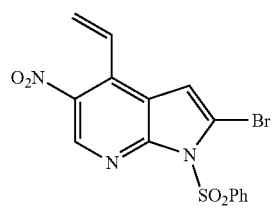

To a solution of diisopropylamine (3.595 g, 35.5 mmol) in tetrahydrofuran (100.0 mL) at −78° C. was added n-BuLi solution (1.6 M in hexanes, 19.0 mL, 30.4 mmol). The resulting solution was stirred at −78° C. for 10 min. Then a solution of 5-nitro-1-(phenylsulfonyl)-4-vinyl-1H-pyrrolo[2,3-b]pyridine (4.96 g, 15.06 mmol) in tetrahydrofuran (80.0 mL) was added. The resulting mixture was stirred at −78° C. for 60 min. A solution of 1,2-dibromo-1,1,2,2-tetrachloroethane (7.88 g, 24.20 mmol) in tetrahydrofuran (50.0 mL) was added. After stirring at −78° C. for another 30 min, the reaction mixture was poured into the mixture of EtOAc and 1N HCl (aq). The separated organic layer was dried over anhydrous $Na_2SO_4$, filtered and concentrated. The residue was purified on silica gel (240 g, 0-100% EtOAc in dichloromethane) to give the desired product as a yellow solid (5.264 g, 86%). LCMS calculated for $C_{15}H_{11}BrN_3O_4S$ $(M+H)^+$ m/z=408.0. found 408.0.

Step 3: 2-(1-methyl-1H-pyrazol-4-yl)-5-nitro-1-(phenylsulfonyl)-4-vinyl-1H-pyrrolo[2,3-b]pyridine

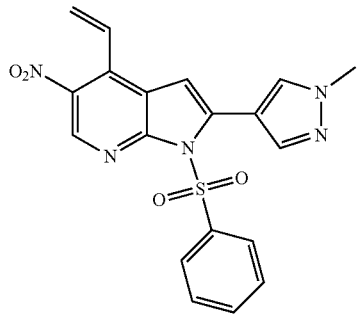 [SMILES: C=Cc1c([N+](=O)[O-])cnc2c1cc(-c1cnn(C)c1)n2S(=O)(=O)c1ccccc1]

To a round bottom flask equipped with a magnetic stir bar was added 2-bromo-5-nitro-1-(phenylsulfonyl)-4-vinyl-1H-pyrrolo[2,3-b]pyridine (5.264 g, 12.89 mmol), 1-methyl-4-(4,4,5,5-tetramethyl-1,3,2-dioxaborolan-2-yl)-1H-pyrazole (4.355 g, 20.93 mmol), dichloro[1,1'-bis(diphenylphosphino)ferrocene]palladium (II) dichloromethane adduct (2.436 g, 2.98 mmol) and cesium carbonate (14.93 g, 45.8 mmol). The flask was sealed with a rubber septum, evacuated and backfilled with nitrogen (this process was repeated a total of three times). 1,4-Dioxane (100.0 mL) was added, followed by water (20.0 mL). The reaction was heated at 80° C. for 1 h. After cooling to room temperature, the reaction mixture was concentrated. The residue was diluted with dichloromethane and filtered. The filtrate was concentrated. The resulting residue was purified on silica gel (240 g, 0-100% EtOAc in dichloromethane) to give the desired product as a yellow solid (3.85 g, 73%). LCMS calculated for $C_{19}H_{16}N_5O_4S$ $(M+H)^+$ m/z=410.1. found 410.1.

Step 4: 2-(1-methyl-1H-pyrazol-4-yl)-5-nitro-1-(phenylsulfonyl)-1H-pyrrolo[2,3-b]pyridine-4-carbaldehyde

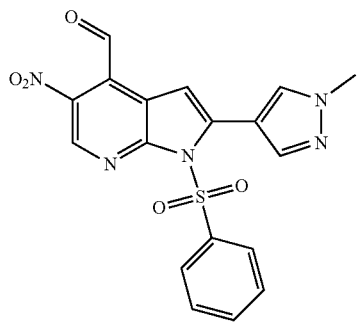 [SMILES: Cn1cc(-c2cc3c(C=O)c([N+](=O)[O-])cnc3n2S(=O)(=O)c2ccccc2)cn1]

To a mixture of 2-(1-methyl-1H-pyrazol-4-yl)-5-nitro-1-(phenylsulfonyl)-4-vinyl-1H-pyrrolo[2,3-b]pyridine (3.85 g, 9.40 mmol) and sodium periodate (9.10 g, 42.5 mmol) was added acetone (120.0 mL) followed by water (20.0 mL). A solution osmium tetroxide (4 wt % in water) (6.16 g, 0.969 mmol) was added dropwise. After stirring at room temperature for 16 h, the reaction was diluted with water and extracted with EtOAc. The separated organic layer was dried over anhydrous $Na_2SO_4$, filtered and concentrated. The residue was purified on silica gel (120 g, 0-100% EtOAc in dichloromethane) to give the desired product as a yellow solid (2.58 g, 67%). LCMS calculated for $C_{18}H_{14}N_5O_5S$ $(M+H)^+$ m/z=412.1. found 412.1.

Step 5: 3-bromo-2-(1-methyl-1H-pyrazol-4-yl)-5-nitro-1-(phenylsulfonyl)-1H-pyrrolo[2,3-b]pyridine-4-carbaldehyde

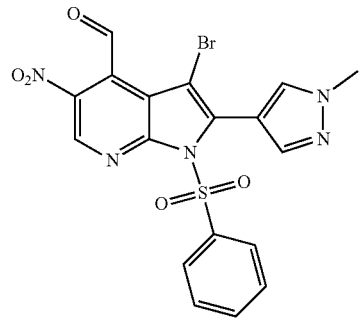

To a suspension of 2-(1-methyl-1H-pyrazol-4-yl)-5-nitro-1-(phenylsulfonyl)-1H-pyrrolo[2,3-b]pyridine-4-carbaldehyde (2.58 g, 6.27 mmol) in acetonitrile (100.0 mL) was added bromine (5.531 g, 34.6 mmol). After stirring at room temperature for 10 minutes, the reaction was concentrated. The residue was dissolved in dichloromethane and washed with sat. NaHCCh(aq). The separated organic layer was dried over anhydrous $Na_2SO_4$, filtered and concentrated. The residue was purified by silica gel chromatography (120 g, 0-100% EtOAc in dichloromethane) to give the desired product as a yellow solid (2.63 g, 86%). LCMS calculated for $C_{18}H_{13}BrN_5O_5S$ $(M+H)^+$ m/z=490.0. found 490.0.

Step 6: 5-amino-3-bromo-2-(1-methyl-1H-pyrazol-4-yl)-1-(phenylsulfonyl)-1H-pyrrolo[2,3-b]pyridine-4-carbaldehyde

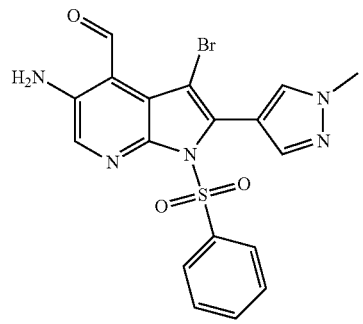 [SMILES: Cn1cc(-c2c(Br)c3c(C=O)c([N+](=O)[O-])cnc3n2S(=O)(=O)c2ccccc2)cn1]

To a solution of 3-bromo-2-(1-methyl-1H-pyrazol-4-yl)-5-nitro-1-(phenylsulfonyl)-1H-pyrrolo[2,3-b]pyridine-4-carbaldehyde (2.63 g, 5.36 mmol) in tetrahydrofuran (50.0 mL) was added methanol (50.0 mL) and water (50.0 mL). Then iron powder (1.572 g, 28.1 mmol) was added, followed by ammonium chloride (2.142 g, 40.0 mmol). The mixture was stirred at 65° C. for 1 h. After cooling to room temperature, the mixture was concentrated. The residue was diluted with dichloromethane and filtered. The filtrate was concentrated. The resulting residue was purified on silica gel (40 g, 0-100% EtOAc in dichloromethane) to afford desired product as a yellow solid (1.642 g, 67%). LCMS calculated for $C_{18}H_{15}BrN_5O_3S$ (M+H)$^+$ m/z=460.0. found 460.0.

Step 7: 4-(5-amino-4-formyl-2-(1-methyl-1H-pyrazol-4-yl)-1-(phenylsulfonyl)-1H-pyrrolo[2,3-b]pyridin-3-yl)-N,N-dimethylbenzamide

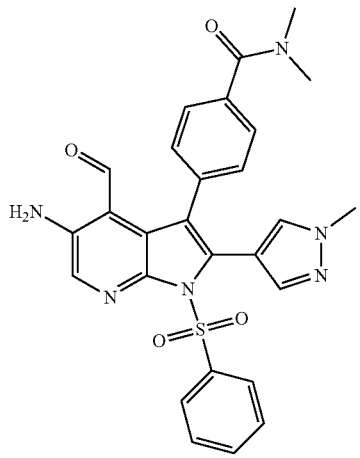 [SMILES: CN(C)C(=O)c1ccc(-c2c(-c3cnn(C)c3)n(S(=O)(=O)c3ccccc3)c3ncc(N)c(C=O)c23)cc1]

To a screw-cap vial equipped with a magnetic stir bar was added 5-amino-3-bromo-2-(1-methyl-1H-pyrazol-4-yl)-1-(phenylsulfonyl)-1H-pyrrolo[2,3-b]pyridine-4-carbaldehyde (510.1 mg, 1.108 mmol), N,N-dimethyl-4-(4,4,5,5-tetramethyl-1,3,2-dioxaborolan-2-yl)benzamide (464.1 mg, 1.687 mmol), cesium carbonate (1262 mg, 3.87 mmol) and dichloro[1,1'-bis(diphenylphosphino)ferrocene]palladium (II) dichloromethane adduct (222.0 mg, 0.272 mmol). The vial was sealed with a Teflon-lined septum, evacuated and backfilled with nitrogen (this process was repeated a total of three times). 1,4-Dioxane (12.0 mL) was added, followed by degassed water (2.0 mL). The reaction was heated at 80° C. for 2 h. After cooling to room temperature, the reaction was concentrated. The resulting residue was purified on silica gel (40 g, 0-100% EtOAc in dichloromethane, then 5% methanol in dichloromethane) to afford desired product as a yellow solid (500.9 mg, 86%). LCMS calculated for $C_{27}H_{25}N_6O_4S$ (M+H)$^+$ m/z=529.2; found 529.2.

Step 8: diethyl (1,2-dichloro-2-oxoethyl)phosphonate

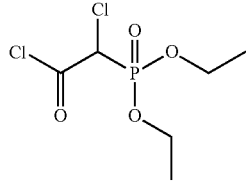

To a solution of 2-chloro-2-(diethoxyphosphoryl)acetic acid (1193 mg, 5.17 mmol) in dichloromethane (20.0 mL) under N$_2$ atmosphere was added DMF (40.0 µL). Then oxalyl chloride (2026 mg, 15.96 mmol) was added dropwise. The reaction was stirred at room temperature under N$_2$ atmosphere for 16 h. The reaction was then concentrated to give the desired product which was used directly in the next step without further purification (1.043 g).

Step 9: diethyl (1-chloro-2-((3-(4-(dimethylcarbamoyl)phenyl)-4-formyl-2-(1-methyl-1H-pyrazol-4-yl)-1-(phenylsulfonyl)-1H-pyrrolo[2,3-b]pyridin-5-yl)amino)-2-oxoethyl)phosphonate

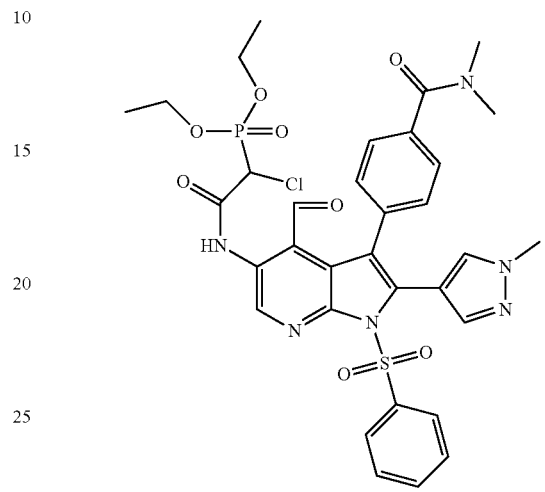

To a solution of 4-(5-amino-4-formyl-2-(1-methyl-1H-pyrazol-4-yl)-1-(phenylsulfonyl)-1H-pyrrolo[2,3-b]pyridin-3-yl)-N,N-dimethylbenzamide (437.5 mg, 0.828 mmol) in dichloromethane (30.0 mL) was added pyridine (350 µL, 4.33 mmol) followed by a solution of diethyl (1,2-dichloro-2-oxoethyl)phosphonate (320.3 mg, 1.286 mmol) in dichloromethane (10.0 mL). After stirring at room temperature for 2 h, the reaction was quenched with water and extracted with EtOAc. The separated organic layer was dried over anhydrous Na$_2$SO$_4$, filtered and concentrated to give the desired product which was used directly in the next step without further purification. LCMS calculated for $C_{33}H_{33}ClN_6O_8PS$ (M+H)$^+$ m/z=741.2. found 741.2.

Step 10: 4-(8-chloro-2-(1-methyl-1H-pyrazol-4-yl)-7-oxo-3-(phenylsulfonyl)-6,7-dihydro-3H-pyrrolo[3,2-f][1,7]naphthyridin-1-yl)-N,N-dimethylbenzamide

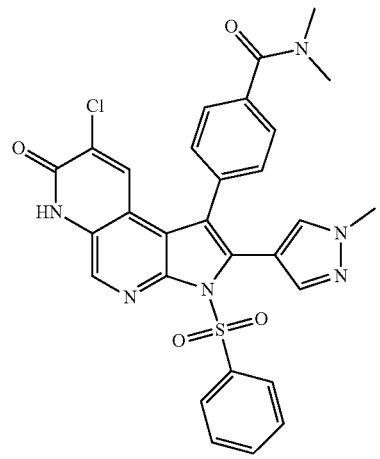 [SMILES: CN(C)C(=O)c1ccc(-c2c(-c3cnn(C)c3)n(S(=O)(=O)c3ccccc3)c3ncc4[nH]c(=O)c(Cl)cc4c23)cc1]

The diethyl (1-chloro-2-((3-(4-(dimethylcarbamoyl)phenyl)-4-formyl-2-(1-methyl-1H-pyrazol-4-yl)-1-(phenylsulfonyl)-1H-pyrrolo[2,3-b]pyridin-5-yl)amino)-2-oxoethyl)phosphonate from the above step was dissolved in tetrahydrofuran (12.0 mL). Lithium chloride (187.3 mg, 4.42 mmol) was added. Then a solution of DBU (642.1 mg, 4.22 mmol) in tetrahydrofuran (10.0 mL) was added slowly. After stirring at room temperature for 1 h, the reaction mixture was poured into water and extracted with EtOAc. The separated organic layer was dried over anhydrous $Na_2SO_4$, filtered and concentrated to give the desired product which was used directly in the next step without further purification. LCMS calculated for $C_{29}H_{24}ClN_6O_4S$ (M+H)$^+$ m/z=587.1; found 587.2.

Step 11: 4-(8-chloro-6-methyl-2-(1-methyl-1H-pyrazol-4-yl)-7-oxo-3-(phenylsulfonyl)-6,7-dihydro-3H-pyrrolo[3,2-j][1,7]naphthyridin-1-yl)-N,N-dimethylbenzamide

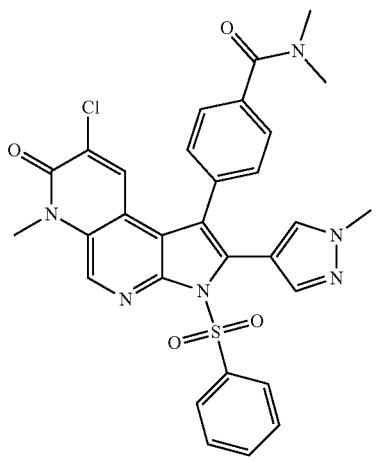 [SMILES: CN(C)C(=O)c1ccc(-c2c(-c3cnn(C)c3)n(S(=O)(=O)c3ccccc3)c3ncc4c(cc(Cl)c(=O)n4C)c23)cc1]

The 4-(8-chloro-2-(1-methyl-1H-pyrazol-4-yl)-7-oxo-3-(phenylsulfonyl)-6,7-dihydro-3H-pyrrolo[3,2-f][1,7]naphthyridin-1-yl)-N,N-dimethylbenzamide from the above step was dissolved in DMF (20.0 mL). $CS_2CO_3$ (957.4 mg, 2.94 mmol) was added followed by a solution of MeI (2.0 M in MTBE) (550.0 μL, 1.100 mmol). The mixture was stirred at room temperature for 1 h, and then concentrated. The residue was diluted with dichloromethane and filtered. The filtrate was concentrated. The resulting residue was purified on silica gel (40 g, 0-100% EtOAc in dichloromethane, then 5% methanol in dichloromethane) to afford desired product as a yellow foamy solid (308.1 mg, 61% over three steps). LCMS calculated for $C_{30}H_{26}ClN_6O_4S$ (M+H)$^+$ m/z=601.1. found 601.2.

Step 12: 4-(8-((3-(1H-tetrazol-5-yl)phenyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide

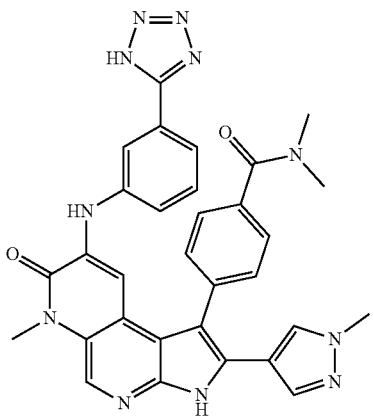 [SMILES: CN(C)C(=O)c1ccc(-c2c(-c3cnn(C)c3)[nH]c3ncc4c(cc(Nc5cccc(-c6nnn[nH]6)c5)c(=O)n4C)c23)cc1]

To a screw-cap vial equipped with a magnetic stir bar was added 4-(8-chloro-6-methyl-2-(1-methyl-1H-pyrazol-4-yl)-7-oxo-3-(phenylsulfonyl)-6,7-dihydro-3H-pyrrolo[3,2-f][1,7]naphthyridin-1-yl)-N,N-dimethylbenzamide (10.6 mg, 0.018 mmol), 3-(1H-tetrazol-5-yl)aniline (11.2 mg, 0.069 mmol), $CS_2CO_3$ (32.4 mg, 0.099 mmol) and BrettPhos Pd G3 (3.4 mg, 3.75 μmol). The vial was sealed with a Teflon-lined septum, evacuated and backfilled with nitrogen (this process was repeated a total of three times). t-Butanol (2.0 mL) was added. The reaction was stirred at 80° C. for 16 h. The reaction was cooled to room temperature, methanol (1 mL) was added followed by NaOH (5.0 N, aq) (500.0 μL). The mixture was stirred at room temperature for 30 min, then TFA (500.0 μL) was added. The resulting mixture was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{31}H_{28}N_{11}O_2$ (M+H)$^+$: m/z=586.2; found: 586.2.

Example 35. 4-(8-((4-((1H-tetrazol-5-yl)methyl)phenyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide

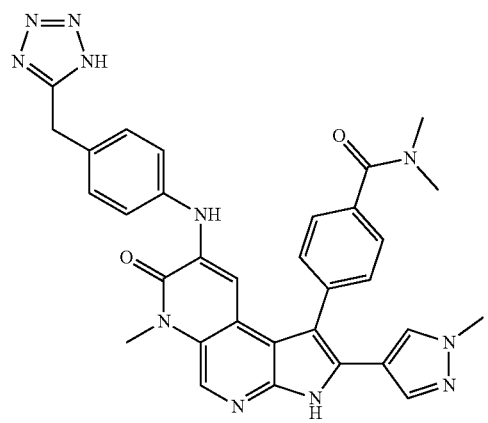 [SMILES: CN(C)C(=O)c1ccc(-c2c(-c3cnn(C)c3)[nH]c3ncc4c(cc(Nc5ccc(Cc6nnn[nH]6)cc5)c(=O)n4C)c23)cc1]

The title compound was prepared according to the procedure described in example 34 (step 12), using 4-((1H-tetrazol-5-yl)methyl)aniline instead of 3-(1H-tetrazol-5-yl)aniline as the starting material. LCMS calculated for $C_{32}H_{30}N_{11}O_2$ (M+H)$^+$: m/z=600.3; found: 600.2.

Example 36. N,N-dimethyl-4-(6-methyl-2-(1-methyl-1H-pyrazol-4-yl)-8-(4-methylpyridin-3-yl)-7-oxo-6,7-dihydro-3H-pyrrolo[3,2-f][1,7]naphthyridin-1-yl)benzamide

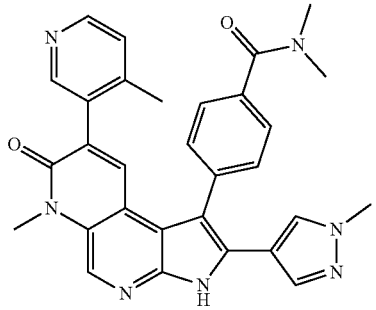 [SMILES: Cc1ccncc1-c1cc2c3c(-c4ccc(C(=O)N(C)C)cc4)c(-c4cnn(C)c4)[nH]c3ncc2n(C)c1=O]

To a screw-cap vial equipped with a magnetic stir bar was added 4-(8-chloro-6-methyl-2-(1-methyl-1H-pyrazol-4-yl)-7-oxo-3-(phenylsulfonyl)-6,7-dihydro-3H-pyrrolo[3,2-f][1,7]naphthyridin-1-yl)-N,N-dimethylbenzamide (10.0 mg, 0.017 mmol), 4-methyl-3-(4,4,5,5-tetramethyl-1,3,2-dioxaborolan-2-yl)pyridine (8.2 mg, 0.037 mmol), $CS_2CO_3$ (25.4 mg, 0.078 mmol) and XPhos Pd G2 (2.6 mg, 3.30 μmol). The vial was sealed with a Teflon-lined septum, evacuated and backfilled with nitrogen (this process was repeated a total of three times). 1,4-Dioxane (2.0 mL) was added, followed by water (200.0 μL, 11.10 mmol). The reaction was stirred at 80° C. for 16 h. The reaction was cooled to room temperature, methanol (1 mL) was added followed by NaOH (5.0 N, aq) (500.0 μL). The mixture was stirred at room temperature for 30 min, then TFA (500.0 μL) was added. The resulting mixture was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{30}H_{28}N_7O_2$ (M+H)$^+$: m/z=518.2; found: 518.2.

Example 37. (R)-8-(1-acetylpyrrolidin-3-yl)-6-methyl-2-(4-((4-(methylsulfonyl)piperidin-1-yl)methyl)phenyl)-1-phenyl-3,6-dihydro-7/7-pyrrolo[3,2-f][1,7]naphthyridin-7-one

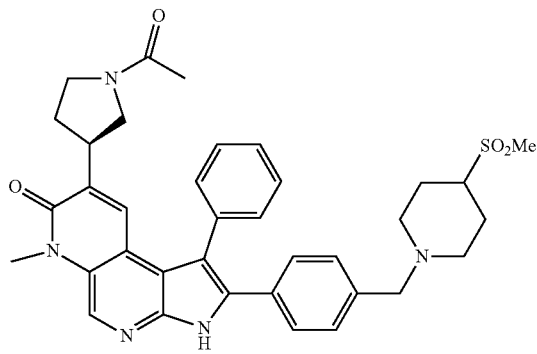 [SMILES: CC(=O)N1CC[C@H](c2cc3c4c(-c5ccccc5)c(-c5ccc(CN6CCC(S(C)(=O)=O)CC6)cc5)[nH]c4ncc3n(C)c2=O)C1]

Step 1. 5-nitro-1-(phenylsulfonyl)-4-vinyl-1H-pyrrolo[2,3-b]pyridine

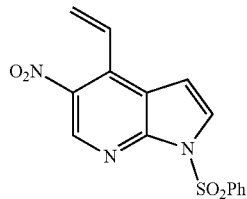

To a 250 mL flask was added 4-chloro-5-nitro-1-(phenylsulfonyl)-1H-pyrrolo[2,3-b]pyridine (10 g, 29.6 mmol), followed by [1,1'-bis(diphenylphosphino)ferrocene]dichloropalladium(II), complex with dichloromethane (4.83 g, 5.92 mmol) and cesium carbonate (28.9 g, 89 mmol). The flask was sealed with a rubber septum, evacuated, and backfilled with nitrogen three times. Then dioxane (140 mL) and water (28 mL) were added. The resulting solution was further degassed over 10 min. Then the mixture was heated to 60° C. and stirred for two hours. After that, the resulting solution was poured into the mixture of dichloromethane and water. The layers were separated, and the aqueous layer was extracted with dichloromethane twice. The combined organic layer was washed with brine and dried with anhydrous $Na_2SO_4$. The solution was then filtered and concentrated. The crude product was further purified by silica gel chromatography (ethyl acetate:dichloromethane 0 to 50%) to give 8.2 g (84% yield) desired product. LCMS calculated for $C_{15}H_{12}N_3O_4S$ (M+H)$^+$ m/z=330.1; found 330.

Step 2. 2-bromo-5-nitro-1-(phenylsulfonyl)-4-vinyl-1H-pyrrolo[2,3-b]pyridine

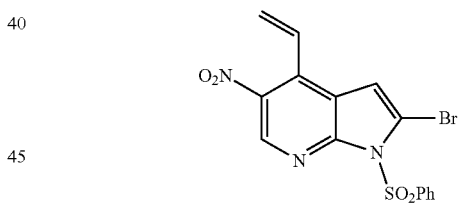

At –78° C., to a solution of diisopropylamine (4.47 mL, 31.9 mmol) in 60 mL tetrahydrofuran was added n-BuLi (1.6 M in hexanes, 18.98 mL, 30.4 mmol) dropwise. The resulting solution was stirred at the same temperature for 10 min, then 5-nitro-1-(phenylsulfonyl)-4-vinyl-1H-pyrrolo[2,3-b]pyridine (5 g, 15.18 mmol) in 60 mL tetrahydrofuran was added dropwise. The mixture was stirred at –78° C. for 50 min before a solution of 1,2-dibromotetrachloroethane. (7.91 g, 24.29 mmol) in 32 mL tetrahydrofuran was added. The resulting solution was stirred at the same temperature for 30 minutes then poured into the mixture of 1N HCl (aq) and ethyl acetate. The layers were separated and the aqueous layer was extracted with ethyl acetate 3 times. The combined organic layer was washed with brine and dried with anhydrous $Na_2SO_4$. The solution was filtered and concentrated and further purified by silica gel chromatography (ethyl acetate:dichloromethane 0 to 50%) to give 5.8 g desired product, 94% yield. LCMS calculated for $C_{15}H_{11}BrN_3O_4S$ (M+H)$^+$ m/z=410.0, 408.0. found 410.0, 408.0.

Step 3. 2-(4-((4-(methylsulfonyl)piperidin-1-yl)methyl)phenyl)-5-nitro-1-(phenylsulfonyl)-4-vinyl-1H-pyrrolo[2,3-b]pyridine

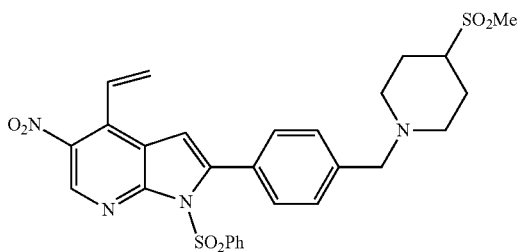

To a 250 mL round bottom flask was added 2-bromo-5-nitro-1-(phenylsulfonyl)-4-vinyl-1H-pyrrolo[2,3-b]pyridine (3 g, 7.35 mmol), 4-(methylsulfonyl)-1-(4-(4,4,5,5-tetramethyl-1,3,2-dioxaborolan-2-yl)benzyl)piperidine (3.07 g, 8.08 mmol), $CS_2CO_3$ (7.17 g, 22.05 mmol) and [1,1-bis(diphenylphosphino)ferrocene]dichloropalladium(II), complex with dichloromethane (0.600 g, 0.735 mmol). The flask was sealed with a rubber stopper, evacuated, and backfilled with nitrogen three times. Then dioxane (58.8 mL) and water (14.70 mL) were added. The solution was further degassed over 10 min, then heated to 80° C. for 1.5 h. After that, the solution was cooled down to r.t. and poured into the mixture of dichloromethane and water. The layers were separated, and the aqueous layer was washed with dichloromethane three times. The combined organic layer was washed with brine and dried with $Na_2SO_4$. Then the solution was filtered and concentrated. The crude product was further purified by silica gel chromatography (ethyl acetate:dichloromethane 0 to 0 to 100% then methanol:dichloromethane 0 to 10%) to give 4.1 g product, 96% yield. LCMS calculated for $C_{28}H_{29}N_4O_6S_2$ $(M+H)^+$ m/z=581.1; found 581.2.

Step 4. 2-(4-((4-(methylsulfonyl)piperidin-1-yl)methyl)phenyl)-5-nitro-1-(phenylsulfonyl)-1H-pyrrolo[2,3-b]pyridine-4-carbaldehyde

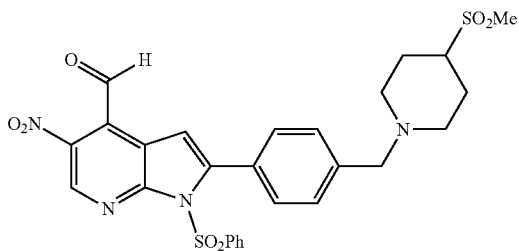

To a 250 mL round bottom flask was added 2-(4-((4-(methylsulfonyl)piperidin-1-yl)methyl)phenyl)-5-nitro-1-(phenylsulfonyl)-4-vinyl-1H-pyrrolo[2,3-b]pyridine (4.3 g, 7.41 mmol), sodium periodate (6.34 g, 29.6 mmol) and 2,6-dimethylpyridine (1.029 mL, 8.89 mmol). Then dioxane (40 mL) and water (10 mL) were added. To this mixture was injected osmium(VIII) oxide (4 wt % in water, 3.76 g, 0.592 mmol). The resulting solution was stirred at r.t. for 3h and then poured into the mixture of ethyl acetate and water. The layers were separated, and the aqueous layer was washed with ethyl acetate 3 times. The combined organic layer was washed with brine and dried with $Na_2SO_4$. Then the solution was filtered and concentrated. The crude product was further purified by silica gel chromatography (ethyl acetate:dichloromethane 0 to 100% then methanol:dichloromethane 0 to 10%) to give 2.66 g product. LCMS calculated for $C_{27}H_{27}N_4O_7S_2$ $(M+H)^+$ m/z=583.2. found 583.3.

Step 5. 3-bromo-2-(4-((4-(methylsulfonyl)piperidin-1-yl)methyl)phenyl)-5-nitro-1-(phenylsulfonyl)-1H-pyrrolo[2,3-b]pyridine-4-carbaldehyde

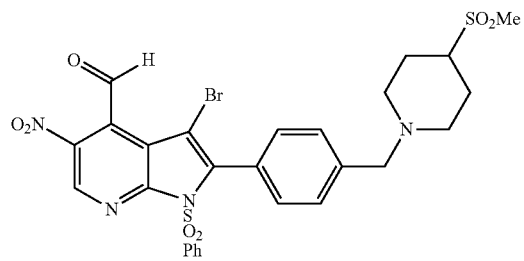

To a solution of 2-(4-((4-(methylsulfonyl)piperidin-1-yl)methyl)phenyl)-5-nitro-1-(phenylsulfonyl)-1H-pyrrolo[2,3-b]pyridine-4-carbaldehyde (2.66 g, 4.57 mmol) in acetonitrile (114 mL) was added bromine (0.94 mL, 18.26 mmol) dropwise. The resulting solution was stirred at r.t. for 15 minutes, and then the solution was concentrated. The residue was redissolved in ethyl acetate and washed with saturated $NaHCO_3$. The organic layer was washed with brine and dried over anhydrous $Na_2SO_4$. Then the mixture was filtered and concentrated. The crude product was further purified by silica gel chromatography (ethyl acetate:dichloromethane 0 to 0 to 100% then methanol:dichloromethane 0 to 10%) to give 2.04 g product, 68% yield. LCMS calculated for $C_{27}H_{26}BrN_4O_7S_2$ (M+H)+ m/z=663.0, 661.0; found 663.2, 661.2.

Step 6. 5-amino-3-bromo-2-(4-((4-(methylsulfonyl)piperidin-1-yl)methyl)phenyl)-1-(phenylsulfonyl)-1H-pyrrolo[2,3-b]pyridine-4-carbaldehyde

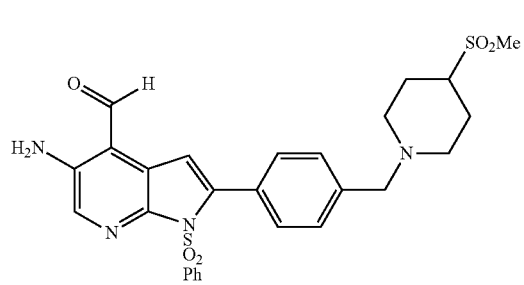

To a 100 mL round bottom flask was added 3-bromo-2-(4-((4-(methylsulfonyl)piperidin-1-yl)methyl)phenyl)-5-nitro-1-(phenylsulfonyl)-1H-pyrrolo[2,3-b]pyridine-4-carbaldehyde (2.04 g, 3.08 mmol), followed by iron powder (0.861 g, 15.42 mmol) and ammonium chloride (0.825 g, 15.42 mmol). Then methanol (11.42 mL), tetrahydrofuran (11.42 mL), and water (11.42 mL) were added. The flask was sealed with a rubber stopper. Then the mixture was heated to 70° C. and stirred for one hour. Then the solution was cooled down to r.t. and 50 mL acetonitrile was added. The mixture was stirred for 10 min before passing through a pad of Celite. The filtrate was concentrated and redissolved in 100 mL dichloromethane. The mixture was then washed with 1N $K_2CO_3$, brine, and dried with anhydrous $Na_2SO_4$. The solvent was removed under vacuum, and the crude product was further purified by silica gel chromatography (ethyl acetate:dichloromethane 0 to 0 to 100% then methanol:dichloromethane 0 to 50%) to give 1.4 g product, 72% yield. LCMS calculated for $C_{27}H_{28}BrN_4O_5S_2$ (M+H)$^+$ m/z=633.1, 631.1. found 633.1, 631.1.

Step 7. 5-amino-2-(4-((4-(methylsulfonyl)piperidin-1-yl)methyl)phenyl)-3-phenyl-1-(phenylsulfonyl)-1H-pyrrolo[2,3-b]pyridine-4-carbaldehyde

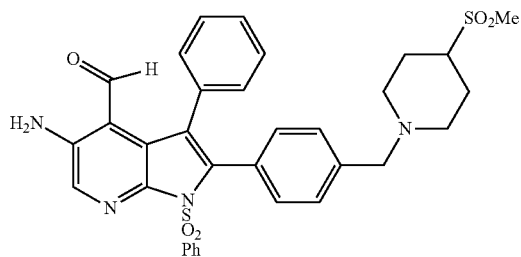

To a 100 mL round bottom flask was added 5-amino-3-bromo-2-(4-((4-(methylsulfonyl)piperidin-1-yl)methyl)phenyl)-1-(phenylsulfonyl)-1H-pyrrolo[2,3-b]pyridine-4-carbaldehyde (1.4 g, 2.217 mmol), phenylboronic acid (0.324 g, 2.66 mmol), [1,1-bis(diphenylphosphino)ferrocene]dichloropalladium(II), complex with dichloromethane (0.181 g, 0.222 mmol) and $CS_2CO_3$ (2.52 g, 7.76 mmol). The flask was sealed with a rubber stopper, evacuated, and backfilled with nitrogen three times. Then dioxane (17.73 mL) and water (4.43 mL) were added. The solution was further degassed over 10 min. The resulting solution was heated to 70° C. for 1.5 hour. After cooling down to r.t., the solution was poured into the mixture of dichloromethane and water. The layers were separated, and the aqueous layer was washed with dichloromethane 3 times. The combined organic layer was washed with brine and dried with anhydrous $Na_2SO_4$. Then the solution was filtered and concentrated. The crude product was further purified by silica gel chromatography (ethyl acetate:dichloromethane 0 to 0 to 100% then methanol:dichloromethane 0 to 50%) to give 0.96 g product. LCMS calculated for $C_{33}H_{33}N_4O_5S_2$ (M+H)$^+$ m/z=629.2. found 629.1.

Step 8. 2-((S)-1-(tert-butoxycarbonyl)pyrrolidin-3-yl)-2-(diethoxyphosphoryl)acetic acid

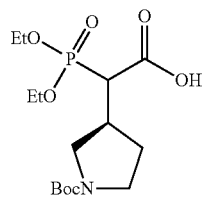 [SMILES: CCOP(=O)(OCC)C(C(=O)O)[C@H]1CCN(C(=O)OC(C)(C)C)C1]

To a solution of ethyl 2-(diethoxyphosphoryl)acetate (0.534 mL, 2.69 mmol) in 5 mL of DMSO at room temperature was added potassium 2-methylpropan-2-olate (0.302 g, 2.69 mmol). This resulted in a temperature rise to 60° C. for 50 min. Then tert-butyl (R)-3-iodopyrrolidine-1-carboxylate (1 g, 3.37 mmol) dissolved in 2 mL DMSO was added. The resulting solution was heated for 90 minutes then poured into the mixture of ethyl acetate and water. The layers were separated, and the aqueous layer was washed with ethyl acetate three times. The combined organic layer was washed with brine and dried with $Na_2SO_4$. The solution was filtered and concentrated. The residue was dissolved in 10 mL 1N NaOH solution, and stirred overnight. The reaction mixture was washed with 5 mL dichloromethane. The two layers were separated, and the aqueous layer was neutralized with 10 mL 1N HCl solution. Then 30 mL ethyl acetate was added to the aqueous solution. The resulting mixture was separated, and the aqueous layer was washed with ethyl acetate 3 times. The combined organic layer was washed with brine, dried with $Na_2SO_4$, and concentrated. The crude product was purified by silica gel chromatography (ethyl acetate:dichloromethane 0-100%) to give 534 mg acid, 43% yield. LCMS calculated for $C_{15}H_{28}NO_7PNa$ (M+Na)$^+$ m/z=388.2. found 388.3.

Step 9. tert-butyl (R)-3-(2-(4-((4-(methylsulfonyl)piperidin-1-yl)methyl)phenyl)-7-oxo-1-phenyl-3-(phenylsulfonyl)-6,7-dihydro-3H-pyrrolo[3,2-j][1,7]naphthyridin-8-yl)pyrrolidine-1-carboxylate

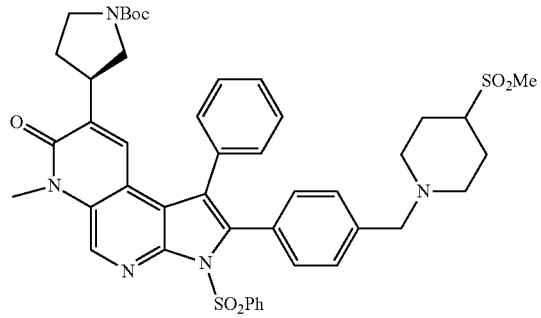

To a solution of 5-amino-2-(4-((4-(methylsulfonyl)piperidin-1-yl)methyl)phenyl)-3-phenyl-1-(phenylsulfonyl)-1H-pyrrolo[2,3-b]pyridine-4-carbaldehyde (80 mg, 0.127 mmol) in 4 mL DMF was added 2-((S)-1-(tert-butoxycarbonyl)pyrrolidin-3-yl)-2-(diethoxyphosphoryl)acetic acid (51.1 mg, 0.140 mmol), followed by diisopropylethylamine (48.7 μL, 0.280 mmol) and HATU (82 mg, 0.216 mmol). The resulting solution was heated to 50° C. for two hours then poured into the mixture of ethyl acetate and water. The layers were separated, and the aqueous layer was washed with ethyl acetate three times. The combined organic layer was washed with brine and dried with $Na_2SO_4$. The solution was filtered and concentrated to obtain the crude product, which was directly used in the next step.

The above crude product in 2 mL tetrahydrofuran was added LiCl (0.016 g, 0.390 mmol), followed by 1,8-diazabicyclo[5.4.0]undec-7-ene (0.043 mL, 0.286 mmol). The resulting solution was stirred at r.t. for two hours, then 50° C. for 1.5 h. Then the reaction was cooled down to r.t., and the mixture was diluted with ethyl acetate and methanol (10:1) and washed with water, combined organic layers, and dried with $Na_2SO_4$. The crude product was directly used in the next step.

To a solution of the above crude product in 2 mL DMF was added Cs₂CO₃ (0.127 g, 0.390 mmol), followed by methyl iodide (0.098 mL, 0.195 mmol). The resulting solution was stirred at r.t. for 1.5 h then diluted with ethyl acetate. The mixture was washed with water and dried with anhydrous Na₂SO₄. The crude product was concentrated and purified by silica gel chromatography (ethyl acetate:dichloromethane 0 to 100%, then methanol:dichloromethane 0 to 20%) to give 34.4 mg product, 31.7% yield for three step s.

Step 10. (R)-8-(1-acetylpyrrolidin-3-yl)-6-methyl-2-(4-((4-(methylsulfonyl)piperidin-1-yl)methyl)phenyl)-1-phenyl-3,6-dihydro-7H-pyrrolo[3,2-j][1,7]naphthyridin-7-one

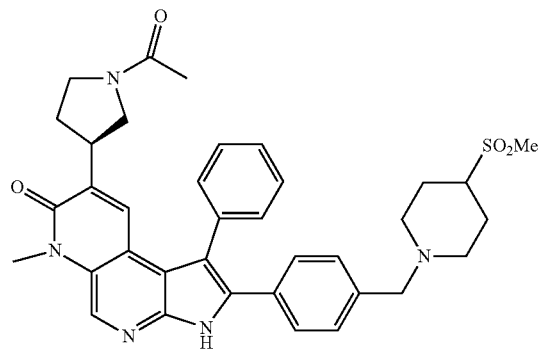 [SMILES: CC(=O)N1CC[C@H](c2cc3c4c(-c5ccccc5)c(-c5ccc(CN6CCC(S(C)(=O)=O)CC6)cc5)[nH]c4ncc3n(C)c2=O)C1]

To a solution of tert-butyl (R)-3-(6-methyl-2-(4-((4-(methylsulfonyl)piperidin-1-yl)methyl)phenyl)-7-oxo-1-phenyl-3-(phenylsulfonyl)-6,7-dihydro-3H-pyrrolo[3,2-f][1,7]naphthyridin-8-yl)pyrrolidine-1-carboxylate (34.4 mg, 0.041 mmol) in 2 mL dichloromethane was added 0.5 mL TFA, the resulting solution was stirred at r.t. for 30 min then concentrated under vacuum. The residue was redissolved in 10 mL dichloromethane and washed with 1N K₂CO₃ solution. The organic layer was dried with brine and Na₂SO₄, then filtered and concentrated to give 30 mg crude amine, which was directly used in the next step.

To a solution of 10 mg above product in 1 mL dichloromethane was added triethylamine (11.36 μL, 0.082 mmol), followed by addition of acetyl chloride (20.38 μL, 0.020 mmol). The resulting solution was stirred at r.t. for one hour then concentrated. The residue was redissolved in 1 mL methanol, then 1 mL 1N NaOH was added. The mixture was heated to 50° C. for 30 min before 1 mL 6N HCl was added. The resulting solution was further purified by prep-LCMS (XBridge C18 column, eluting with a gradient of acetonitrile/water containing 0.1% TFA, at flow rate of 60 mL/min) to get the title compound. LCMS calculated for $C_{36}H_{40}N_5O_4S$ (M+H)⁺ m/z=638.3. found 638.4.

Example 38. 4-(8-((4-(cyanomethyl)cyclohexyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide

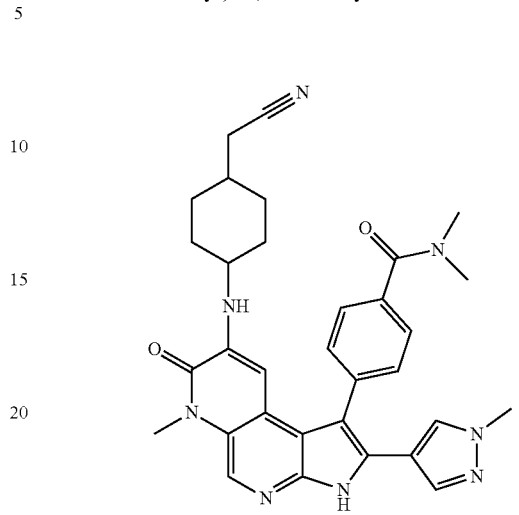

To a 2 dram vial was added 4-(8-chloro-6-methyl-2-(1-methyl-1H-pyrazol-4-yl)-7-oxo-3-(phenylsulfonyl)-6,7-dihydro-3H-pyrrolo[3,2-f][1,7]naphthyridin-1-yl)-N,N-dimethylbenzamide (10 mg, 0.017 mmol), 2-(4-aminocyclohexyl)acetonitrile (4.60 mg, 0.033 mmol), CS₂CO₃ (16.26 mg, 0.050 mmol) and (2-dicyclohexylphosphino-2',6'-diisopropoxy-1,1'-biphenyl)[2-(2'-amino-1,1'-biphenyl)]palladium(II) methanesulfonate (RuPhos Pd G3, 4.17 mg, 4.99 μmol). The vial was sealed with a Teflon screw-cap, evacuated, and backfilled with nitrogen three times. Then 1 mL dioxane was added. The solution was further degassed over 5 min. Then the mixture was heated to 90° C. for 16 h. After that, the solution was cooled down to r.t., 1 mL methanol, and 1 mL 1N NaOH was added. The mixture was heated to 50° C. for 30 min before 1 mL 6N HCl was added. The resulting solution was further purified by prep-LCMS to give the desired product. LCMS calculated for $C_{32}H_{35}N_8O_2$ (M+H)⁺ m/z=563.3. found 563.4.

Example 39. N,N-dimethyl-4-(6-methyl-2-(1-methyl-1H-pyrazol-4-yl)-8-(4-(methylsulfonyl)piperidin-1-yl)-7-oxo-6,7-dihydro-3H-pyrrolo[3,2-f][1,7]naphthyridin-1-yl)benzamide

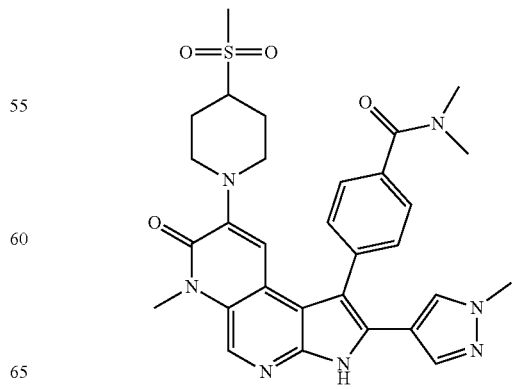

The title compound was prepared according to the procedure described in example 38, using 4-(methylsulfonyl)piperidine instead of 2-(4-aminocyclohexyl)acetonitrile. LCMS calculated for $C_{30}H_{34}N_7O_4S$ (M+H)$^+$ m/z=588.2; found 588.2.

Example 40. 4-(8-(4-((2-Methoxyethyl)sulfonyl)piperidin-1-yl)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide

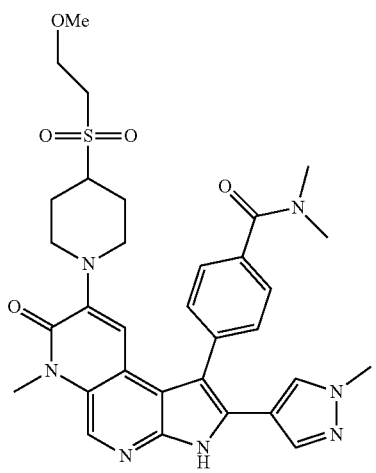 [SMILES: COCCS(=O)(=O)C1CCN(c2cc3c4c(-c5ccc(C(=O)N(C)C)cc5)c(-c5cnn(C)c5)[nH]c4ncc3n(C)c2=O)CC1]

The title compound was prepared according to the procedure described in example 38, using 4-((2-methoxyethyl)sulfonyl)piperidine instead of 2-(4-aminocyclohexyl)acetonitrile. LCMS calculated for $C_{32}H_{38}N_7O_5S$ (M+H)$^+$ m/z=632.3; found 632.3.

Example 41. N,N-dimethyl-4-(6-methyl-2-(1-methyl-1H-pyrazol-4-yl)-7-oxo-8-(2-oxa-8-azaspiro[4.5]decan-8-yl)-6,7-dihydro-3H-pyrrolo[3,2-f][1,7]naphthyridin-1-yl)benzamide

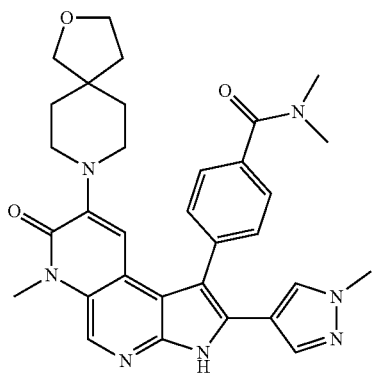 [SMILES: CN(C)C(=O)c1ccc(-c2c(-c3cnn(C)c3)[nH]c3ncc4c(cc(N5CCC6(CCOC6)CC5)c(=O)n4C)c23)cc1]

The title compound was prepared according to the procedure described in example 38, using 2-oxa-8-azaspiro[4.5]decane instead of 2-(4-aminocyclohexyl)acetonitrile. LCMS calculated for $C_{32}H_{36}N_7O_3$ (M+H)$^+$ m/z=566.3; found 566.3.

Example 42. 1-(4-Methoxyphenyl)-N,N,6-trimethyl-2-(1-methyl-1H-pyrazol-4-yl)-7-oxo-6,7-dihydro-3H-pyrrolo[3,2-f][1,7]naphthyridine-8-carboxamide

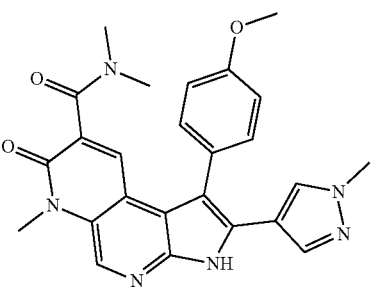 [SMILES: COc1ccc(-c2c(-c3cnn(C)c3)[nH]c3ncc4c(cc(C(=O)N(C)C)c(=O)n4C)c23)cc1]

Step 1. 4-chloro-2-(1-methyl-1H-pyrazol-4-yl)-5-nitro-1-(phenylsulfonyl)-1H-pyrrolo[2,3-b]pyridine

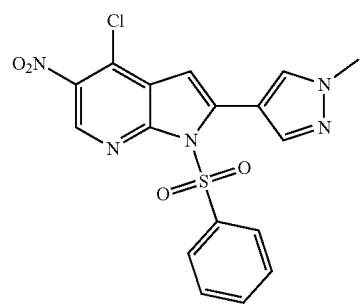

To a solution of 2-bromo-4-chloro-5-nitro-1-(phenylsulfonyl)-1H-pyrrolo[2,3-b]pyridine (example 1, Step 2) (2.0 g, 4.8 mmol) and 1-methyl-4-(4,4,5,5-tetramethyl-1,3,2-dioxaborolan-2-yl)-1H-pyrazole (1.0 g, 4.8 mmol) in dioxane (23 mL) and water (6 mL) was added cesium carbonate (3.9 g, 12 mmol) and [1,1'-bis(diphenylphosphino)ferrocene]dichloropalladium(II) (235 mg, 0.288 mmol). N$_2$ was bubbled through the mixture for 5 minutes then the mixture was stirred at 70° C. for 4 hours. The resulting solution was then cooled to r.t., the water was removed, the resulting mixture was concentrated to dryness and then purified by silica gel chromatography using 0-5% methanol in dichloromethane to afford the desired product (1.45 g, 3.47 mmol). LC-MS calculated for $C_{17}H_{13}ClN_5O_4S$ (M+H)$^+$: m/z=418.0. found 418.0.

Step 2. 2-(1-methyl-1H-pyrazol-4-yl)-5-nitro-1-(phenylsulfonyl)-4-vinyl-1H-pyrrolo[2,3-b]pyridine

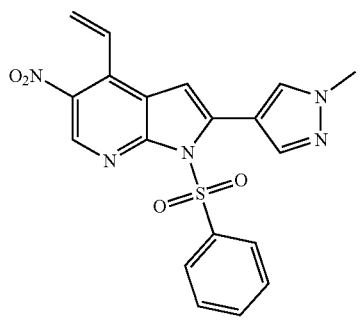

To a solution of 4-chloro-2-(1-methyl-1H-pyrazol-4-yl)-5-nitro-1-(phenylsulfonyl)-1H-pyrrolo[2,3-b]pyridine (1.45 g, 3.47 mmol) and 4,4,5,5-tetramethyl-2-vinyl-1,3,2-dioxaborolane (1.18 mL, 6.94 mmol, Combi Blocks cat #PN-8602) in dioxane (20 mL) and water (4 mL) was added [1,1'-bis(diphenylphosphino)ferrocene]dichloropalladium (II) dichloromethane adduct (283 mg, 0.347 mmol), and sodium carbonate (920 mg, 8.68 mmol). The solvent was sparged with nitrogen and stirred at 110° C. for 30 minutes. The crude reaction mixture was cooled to room temperature and was extracted 3×EtOAc. The combined organic layers were washed with brine, dried over magnesium sulfate, and concentrated under reduced pressure. The crude residue was purified by silica gel chromatography using 0-5% methanol in dichloromethane to afford the desired product (750 mg, 1.83 mmol). LC-MS calculated for $C_{19}H_{16}N_5O_4S$ (M+H)$^+$: m/z=410.1. found 410.0.

Step 3; 2-(1-methyl-1H-pyrazol-4-yl)-5-nitro-1-(phenylsulfonyl)-1H-pyrrolo[2,3-b]pyridine-4-carbaldehyde

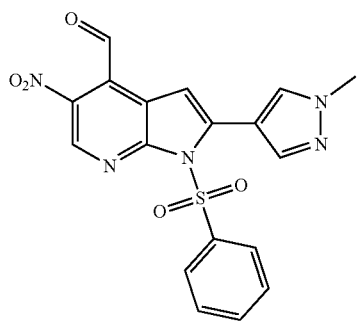

To a solution of 2-(1-methyl-1H-pyrazol-4-yl)-5-nitro-1-(phenylsulfonyl)-4-vinyl-1H-pyrrolo[2,3-b]pyridine (750 mg, 1.83 mmol) in a mixture of tetrahydrofuran (8 mL) and water (4 mL) was added sodium periodate (1.17 g, 5.5 mmol), and potassium osmate dehydrate (68 mg, 0.18 mmol). The reaction mixture was allowed to stir at room temperature for 1 hour after which time the crude reaction mixture was diluted with 5% methanol in dichloromethane followed by water. The resulting mixture was extracted 3× with 5% methanol in dichloromethane. The combined organic layers were washed with brine, dried over magnesium sulfate, and concentrated under reduced pressure. The crude residue was purified by silica gel chromatography using 0-5% methanol in dichloromethane to afford the desired product (608 mg, 1.48 mmol). LC-MS calculated for $C_{18}H_{14}N_5O_5S$ (M+H)$^+$: m/z=412.1. found 412.2.

Step 4: 5-amino-2-(1-methyl-1H-pyrazol-4-yl)-1-(phenylsulfonyl)-1H-pyrrolo[2,3-b]pyridine-4-carbaldehyde

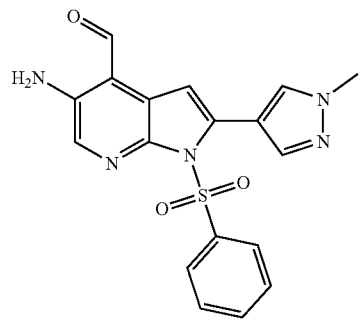

In a vial, 2-(1-methyl-1H-pyrazol-4-yl)-5-nitro-1-(phenylsulfonyl)-1H-pyrrolo[2,3-b]pyridine-4-carbaldehyde was diluted with a mixture of tetrahydrofuran/water/methanol (6 mL/6 mL/2 mL). To this was then sequentially added ammonium chloride (553 mg, 10.35 mmol) and iron (413 mg, 7.39 mmol). The reaction mixture was heated to reflux for one hour after which time it was cooled to room temperature and filtered over celite to remove the iron. The resulting filtrate was then extracted with 5% methanol in dichloromethane (3×). The combined organic layers were washed with brine, dried over magnesium sulfate, and concentrated under reduced pressure. The crude residue (424 mg, 1.11 mmol) was taken on as-is. LC-MS calculated for $C_{18}H_{16}N_5O_3S$ (M+H)$^+$: m/z=382.1. found 382.1.

Step 5. N,N-dimethyl-2-(1-methyl-1H-pyrazol-4-yl)-7-oxo-3-(phenylsulfonyl)-6,7-dihydro-3H-pyrrolo[3,2-f][1,7]naphthyridine-8-carboxamide

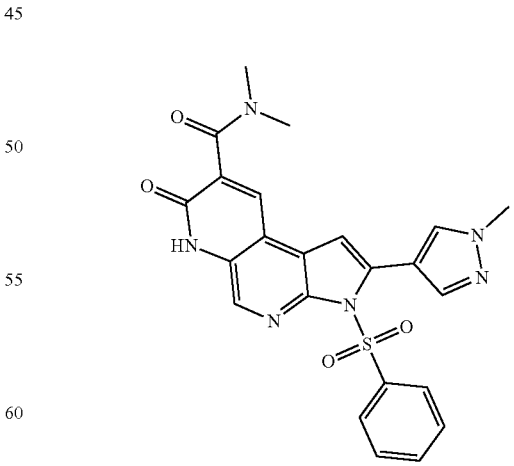

In a vial, 5-amino-2-(1-methyl-1H-pyrazol-4-yl)-1-(phenylsulfonyl)-1H-pyrrolo[2,3-b]pyridine-4-carbaldehyde was diluted with DMF (11 mL). To this was sequentially added 3-(dimethylamino)-3-oxopropanoic acid (729 mg, 5.56 mmol) and Hünig's base (1.9 mL, 11.1 mmol), and HATU (2.53 g, 6.67 mmol). The resulting solution was stirred at 50° C. for 3 hours. Once the starting material had been consumed the crude reaction mixture was diluted with water and extracted with EtOAc (3×). The combined organic layers were washed with brine, dried over magnesium sulfate, and concentrated under reduced pressure. The crude residue was purified by silica gel chromatography using 0-5% methanol in dichloromethane to afford the desired product as a partially purified mixture with other inseparable impurities, taken on as-is. LC-MS calculated for $C_{23}H_{21}N_6O_4S$ (M+H)$^+$: m/z=477.1. found 477.3.

Step 6. N,N,6-trimethyl-2-(1-methyl-1H-pyrazol-4-yl)-7-oxo-3-(phenylsulfonyl)-6,7-dihydro-3H-pyrrolo[3,2-f][1,7]naphthyridine-8-carboxamide

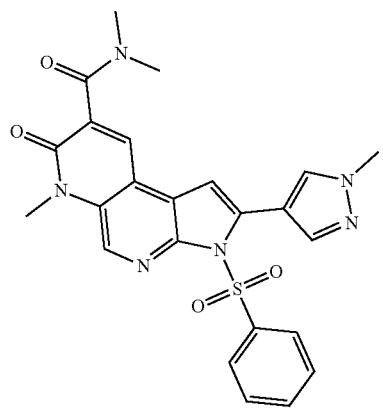

The partially purified N,N-dimethyl-2-(1-methyl-1H-pyrazol-4-yl)-7-oxo-3-(phenylsulfonyl)-6,7-dihydro-3H-pyrrolo[3,2-f][1,7]naphthyridine-8-carboxamide from the previous step (assumed to be 1.11 mmol) was diluted with tetrahydrofuran (11 mL). To this was sequentially added cesium carbonate (1.09 g, 3.33 mmol) and iodomethane (0.104 mL, 1.67 mmol). The reaction mixture was heated to 50° C. for 12 hours after which time the crude reaction mixture was cooled to room temperature and filtered. The filtrate was concentrated under reduced pressure. The crude residue was purified by silica gel chromatography using 0-5% methanol in dichloromethane to afford the desired product (260 mg, 0.530 mmol). LC-MS calculated for $C_{24}H_{23}N_6O_4S$ (M+H)$^+$: m/z=491.2. found 491.1.

Step 7. 1-bromo-N,N,6-trimethyl-2-(1-methyl-1H-pyrazol-4-yl)-7-oxo-3-(phenylsulfonyl)-6,7-dihydro-3H-pyrrolo[3,2-j][1,7]naphthyridine-8-carboxamide

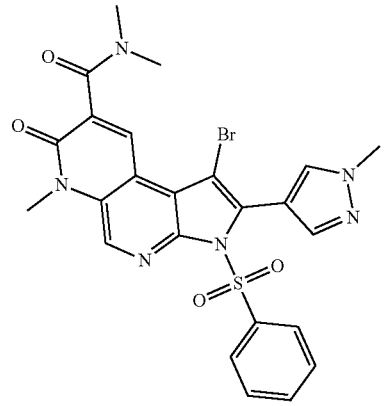

To a solution of N,N,6-trimethyl-2-(1-methyl-1H-pyrazol-4-yl)-7-oxo-3-(phenylsulfonyl)-6,7-dihydro-3H-pyrrolo[3,2-f][1,7]naphthyridine-8-carboxamide (260 mg, 0.530 mmol) in dichloromethane (5.3 mL) was added NBS (113 mg, 0.636 mmol) in a single portion. The desired bromination was complete in less than 5 minutes. The crude reaction mixture was diluted with water and extracted with dichloromethane (3×). The combined organic layers were washed with brine, dried over magnesium sulfate, and concentrated under reduced pressure. The crude residue was purified by silica gel chromatography using 0-5% methanol in dichloromethane to afford the desired product (203 mg, 0.356 mmol). LC-MS calculated for $C_{24}H_{22}BrN_6O_4S$ (M+H)$^+$: m/z=569.1, 571.1. found 569.1, 571.1.

Step 8. 1-(4-methoxyphenyl)-N,N,6-trimethyl-2-(1-methyl-1H-pyrazol-4-yl)-7-oxo-6,7-dihydro-3H-pyrrolo[3,2-f][1,7]naphthyridine-8-carboxamide

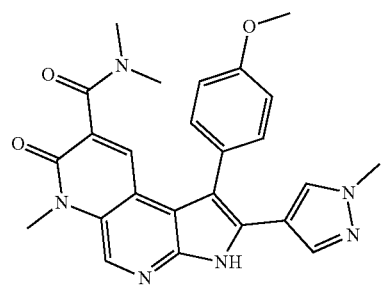 [SMILES: COc1ccc(-c2c(-c3cnn(C)c3)[nH]c3ncc4c(cc(C(=O)N(C)C)c(=O)n4C)c23)cc1]

In a vial 1-bromo-N,N,6-trimethyl-2-(1-methyl-1H-pyrazol-4-yl)-7-oxo-3-(phenylsulfonyl)-6,7-dihydro-3H-pyrrolo[3,2-f][1,7]naphthyridine-8-carboxamide (20 mg, 0.035 mmol) was combined with (4-methoxyphenyl)boronic acid (16.0 mg, 0.105 mmol), [1,1'bis(diphenylphosphino)ferrocene]dichloropalladium(II) dichloromethane adduct (3.23 mg, 0.00395 mmol), and potassium carbonate (21.8 mg, 0.158 mmol). The reagents were diluted with dioxane (0.42 mL) and water (0.10 mL). The solvent was sparged with nitrogen and stirred at 70° C. for 1 hour. The crude reaction mixture was cooled to 45° C. To this was added methanol (0.5 mL), and 2M NaOH (1 mL) and was stirred for an additional hour until deprotection was complete. The crude reaction mixture was cooled to room temperature and purified by prep-LCMS (XBridge C18 column, eluting with a gradient of acetonitrile/water containing 0.1% TFA, at flow rate of 60 mL/min) to afford the desired product. LC-MS calculated for $C_{25}H_{25}N_6O_3$ (M+H)$^+$: m/z=457.2. found 457.3.

Example 43. N,N,6-trimethyl-1-(1-methyl-1H-indazol-5-yl)-2-(1-methyl-1H-pyrazol-4-yl)-7-oxo-6,7-dihydro-3H-pyrrolo[3,2-f][1,7]naphthyridine-8-carboxamide

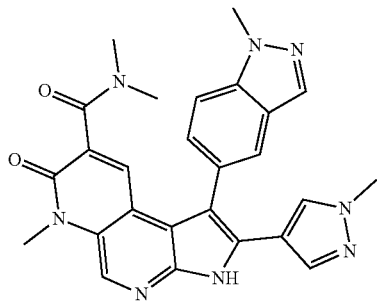 [SMILES: CN(C)C(=O)c1cc2c3c(-c4ccc5c(cnn5C)c4)c(-c4cnn(C)c4)[nH]c3ncc2n(C)c1=O]

The title compound was prepared according to the procedures described in example 42, using 1-Methylindazole-5-boronic acid instead of 4-methoxyphenyl boronic acid as reagent in Step 8. LC-MS calculated for $C_{26}H_{25}N_8O_2$ (M+H)$^+$: m/z=481.2; found 481.4.

Example 44. 1-(4-(1-cyanocyclopropyl)phenyl)-N,N,6-trimethyl-2-(1-methyl-1H-pyrazol-4-yl)-7-oxo-6,7-dihydro-3H-pyrrolo[3,2-f][1,7]naphthyridine-8-carboxamide

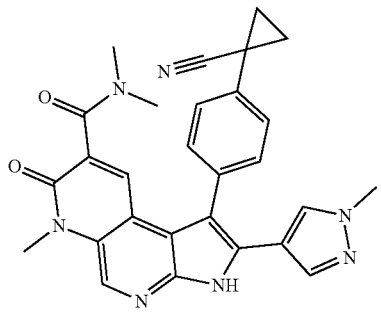 [SMILES: CN(C)C(=O)c1cc2c3c(-c4ccc(C5(C#N)CC5)cc4)c(-c4cnn(C)c4)[nH]c3ncc2n(C)c1=O]

The title compound was prepared according to the procedures described in example 42, using 4-(1-Cycanocyclopropyl)phenylboronic acid (Combi-Blocks BB-5904) instead of 4-methoxyphenyl boronic acid as reagent in Step 8. LC-MS calculated for $C_{28}H_{26}N_7O_2$ (M+H)$^+$: m/z=492.2. found 492.4.

Example A. JAK2 LanthaScreen JH1 Binding Assay

JAK2 JH1 binding assay utilizes catalytic domain (JH1, amino acids 826-1132) of human JAK2 expressed as N-terminal FLAG-tagged, biotinylated protein in a baculovirus expression system (Carna Biosciences, Product #08-445-20N). The assay was conducted in black 384-well polystyrene plates in a final reaction volume of 20 μL. JAK2 JH1 (1.5 nM) was incubated with compounds (100 nL serially diluted in DMSO) in the presence of 50 nM Fluorescent JAK2-JH1 Tracer and 0.5 nM Streptavidin-Tb cryptate (Cisbio Part #610SATLB) in assay buffer (50 mM Tris, pH=7.5, 10 mM MgCl$_2$, 0.01% Brij-35, 0.1% BSA, 1 mM EGTA, 5% Glycerol and 5 mM DTT). Non-specific binding was accessed in the presence of 2 mM ATP. After incubation for 2 hours at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example B. JAK2 LanthaScreen JH2-WT Binding Assay

JAK2 JH2-WT binding assay utilizes pseudo-kinase domain (JH2, amino-acids 536-812 with 3 surface mutations W659A, W777A, F794H) of human Wild Type JAK2 expressed as C-terminal His-Avi-tagged, biotinylated protein in a baculovirus expression system (BPS Bioscience, Catalog #79463). The assay was conducted in black 384-well polystyrene plates in a final reaction volume of 20 μL. JAK2 JH2-WT (0.145 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM MgCl$_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LAB TECH). Data was analyzed with IDBS XLfit and GraphPad Prism 5.0 software using a four parameter dose response curve to determine IC50 for each compound.

Example C. JAK2 LanthaScreen JH2-V617F Binding Assay

JAK2 JH2-V617F binding assay utilizes pseudo-kinase domain (JH2, amino-acids 536-812 with 3 surface mutations W659A, W777A, F794H) of human V617F mutant JAK2 expressed as C-terminal His-Avi-tagged, biotinylated protein in a baculovirus expression system (BPS Bioscience, Catalog #79498). The assay was conducted in black 384-well polystyrene plates in a final reaction volume of 20 μL. JAK2 JH2-V617F (0.26 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM MgCl$_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example D. JAK2 HTRF Enzyme Activity Assay

JAK2 enzyme activity assays utilize catalytic domain (JH1, amino acids 808-1132) of human JAK2 expressed as N-terminal His-tagged protein in a baculovirus expression system (BPS Bioscience, Catalog #40450). The assays was conducted in black 384-well polystyrene plates in a final reaction volume of 20 μL. JAK2 (0.015 nM) was incubated with compounds (100 nL serially diluted in DMSO) in the presence of ATP (30 μM or 1 mM) and 500 nM Biotin-labeled EQEDEPEGDYFEWLE (SEQ ID NO.: 1) peptide (BioSource International, custom synthesis) in assay buffer (50 mM Tris, pH=7.5, 10 mM $MgCl_2$, 0.01% Brij-35, 0.1% BSA, 1 mM EGTA, 5% Glycerol and 5 mM DTT) for 60 minutes at 25° C. The reactions were stopped by the addition of 10 μL of detection buffer (50 mM Tris, pH 7.8, 0.5 mg/mL BSA, 150 mM NaCl), supplemented with EDTA, LANCE Eu-W1024 anti-phosphotyrosine (PY20), (PerkinElmer, Catalog #AD0067) and Streptavidin SureLight APC (PerkinElmer Catalog #CR130-100), for a final concentration of 15 mM, 1.5 nM and 75 nM, respectively. HTRF signals were read after 30 minutes incubation at room temperature on a PHERAstar FS plate reader (BMG LAB TECH). Data was analyzed with IDBS XLfit and GraphPad Prism 5.0 software using a four parameter dose response curve to determine IC50 for each compound.

The compounds of the disclosure were tested in one or more of the assays described in Examples A-D, and the resulting data are shown in Table A.

TABLE A

| Ex. No. | JH1 BIND $IC_{50}$ (nM) | JH2 BIND WT $IC_{50}$ (nM) | JH2 BIND V617F $IC_{50}$ (nM) | ENZYME $IC_{50}$ (nM) |
|---|---|---|---|---|
| 1 | ++++ | ++++ | ++++ | +++++ |
| 2 | +++++ | + | + | +++++ |
| 3 | +++++ | ++++ | ++++ | +++++ |
| 4 | ++++ | ++++ | ++++ | ++++ |
| 5 | +++++ | +++ | ++++ | ++++ |
| 6 | +++++ | + | + | +++++ |
| 7 | ++++ | ++ | ++++ | ++++ |
| 8 | ++ | + | + | ++ |
| 9 | + | + | + | + |
| 10 | ++ | + | + | ++ |
| 11 | + | + | + | + |
| 12 | ++ | + | + | + |
| 13 | ++ | + | + | ++ |
| 14 | ++ | + | + | ++ |
| 15 | ++++ | +++ | ++++ | ++++ |
| 16 | ++ | + | + | ++ |
| 17 | ++++ | ++++ | ++++ | ++++ |
| 18 | ++++ | +++ | ++++ | ++++ |
| 19 | ++++ | ++++ | ++++ | ++++ |
| 20 | + | + | ++ | + |
| 21 | ++ | + | + | ++ |
| 22 | ++ | + | + | ++ |
| 23 | ++ | + | + | ++ |
| 24 | + | + | + | + |
| 25 | +++ | + | + | ++ |
| 26 | ++ | + | + | ++ |
| 27 | ++ | + | + | ++ |
| 28 | ++ | + | + | ++ |
| 29 | ++ | + | + | ++ |
| 30 | +++ | + | + | +++ |
| 31 | +++ | + | + | +++ |
| 32 | ++ | + | + | ++ |
| 33 | ++ | + | + | ++ |
| 34 | ++ | + | + | ++ |
| 35 | + | + | + | + |
| 36 | + | + | + | + |
| 37 | + | + | + | + |
| 38 | ++ | + | + | + |
| 39 | ++ | + | + | ++ |
| 40 | ++++ | ++ | ++ | ++++ |
| 41 | ++++ | ++ | +++ | ++++ |
| 42 | ++++ | + | + | ++++ |
| 43 | ++++ | + | + | ++++ |
| 44 | ++++ | + | + | ++++ |

+ refers to $IC_{50}$ of ≤100 nM

++ refers to $IC_{50}$ of >100 nM to ≤500 nM

+++ refers to $IC_{50}$ of >500 nM to ≤1000 nM

++++ refers to $IC_{50}$ of >1000 nM to ≤10000 nM

+++++ refers to $IC_{50}$ of >10000 nM

Example E. Cell Culture and STAT5 (Tyr694) Phosphorylation Cell Based Assay

Ba/F3 cells expressing human JAK2 V617F/EPOR (mouse JAK2 WT knocked out by CRISPR) are cultured in RPMI media with 10% FBS, 1 μg/mL Puromycin, 1 mg/mL Geneticin (Thermo Fisher). Ba/F3 cells expressing human JAK2 WT/EPOR are cultured in RPMI media with 10% FBS, 1 μg/mL Puromycin, 1 mg/mL Geneticin and 2 ng/mL EPO. 24 hours before the assay, the culture medium for JAK2 V617F/EPOR Ba/F3 cells are changed to RPMI with 10% FBS without antibiotic (assay medium 1). Culture medium for Ba/F3 cells expressing human JAK2 WT/EPOR are changed to RPMI with 10% FBS and 2 ng/mL EPO (R&D systems) without antibiotic (assay medium 2). 50 nL/well test compounds in DMSO are transferred to the 384 white low volume cell culture plate (Greiner Bio-one) by ECHO liquid handler (Labcyte). The cells are centrifuged, resuspended in the corresponding fresh assay medium and dispensed at 10 μL/well ($6\times10^6$ cells/mL) with 0.5% DMSO in the final assay. After the treated cells are incubated at 37° C., 5% $CO_2$ for 2 hours, 4 μL/well supplemented lysis buffer (100× blocking buffer diluted 25 fold in 4× lysis buffer, Perkin-Elmer) are added and incubated at room temperature for 60 min with gentle shaking on orbital shaker at 600 rpm. Phospho-STAT5 Cryptate antibody and Phospho-STAT5 d2 antibody (1:1 vol/vol, Perkin-Elmer) are premixed and diluted 20 fold within the detection buffer. 4 μL of the premixed antibody solution are added to each well followed with 16 hours incubation at room temperature. The product activity is determined by measuring the fluorescence at 620 nm and 665 nm on Pherastar microplate reader (BMG Labtech). A ratio is calculated (665/620 nm) for each well. Wells with DMSO serve as the positive controls and wells containing high concentration of control compound are used as negative controls. $IC_{50}$ determination is performed by fitting the curve of percent control activity versus the log of the compound concentration using the Genedata Screener software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

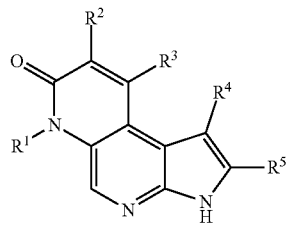

I or a pharmaceutically acceptable salt thereof, wherein:

$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^M$ substituents;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^2(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{e2}C(=NR^{e2})R^{b2}$, $NR^{c2}S(O)R^{b2}$, $NR^{c2}S(O)NR^{c2}R^{d2}$, $NR^{e2}S(O)_2 R^{b2}$, $NR^{c2}S(O)(=NR^{e2})R^{b2}$, $NR^{c2}S(O)_2 NR^{c2}R^{d2}$, $S(O)R^{b2}$, $S(O)NR^{c2}R^{d2}$, $S(O)_2 R^{b2}$, $S(O)_2 NR^{c2}R^{d2}$, $OS(O)(=NR^{e2})R^{b2}$, and $OS(O)_2 R^{b2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{e2}$, and $R^{d21}$s independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$ C(O)

OR$^{a21}$, OC(O)R$^{b21}$, OC(O)NR$^{c21}$R$^{d21}$, NR$^{c21}$R$^{d21}$, NR$^{c21}$R$^{d21}$, NR$^{e21}$C(O)R$^{b21}$, NR$^{21}$C(O)OR$^{a21}$NR$^{c21}$C(O)NR$^{c21}$R$^{d21}$, C(=NR$^{e21}$)R$^{b21}$, C(=NR$^{e21}$)NR$^{c21}$R$^{d21}$, NR$^{c21}$C(=NR$^{e21}$)NR$^{c21}$R$^{d21}$, NR$^{c21}$C(=NR$^{e21}$)R$^{b21}$, NR$^{c21}$S(O)R$^{b21}$, NR$^{c21}$S(O)NR$^{c21}$R$^{d21}$, NR$^{c21}$S(O)$_2$R$^{b21}$, NR$^{c21}$S(O)(=NR$^{e21}$)R$^{b21}$, NR$^{c21}$S(O)$_2$NR$^{c21}$R$^{d21}$, S(O)R$^{b21}$, S(O)NR$^{c21}$R$^{d21}$, S(O)$_2$R$^{b21}$, S(O)$_2$NR$^{c2}$R$^{d21}$, OS(O)(=NR$^{e21}$)R$^{b21}$, and OS(O)$_2$R$^{b21}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{2A}$ are each optionally substituted with 1, 2, 3, 4, 5, 6, 7, or 8 independently selected R$^{2B}$ substituents;

each R$^{a21}$, R$^{c21}$, and R$^{d21}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a21}$, R$^{c21}$ and R$^{d21}$ are each optionally substituted with 1, 2, 3, 4, 5, 6, 7, or 8 independently selected R$^{2B}$ substituents;

or, any R$^{c21}$ and R$^{d21}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected R$^{2B}$ substituents;

each R$^{b21}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b21}$ are each optionally substituted with 1, 2, 3, 4, 5, 6, 7, or 8 independently selected R$^{2B}$ substituents;

each R$^{e21}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{2B}$ is independently selected from halo, oxo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a22}$, SR$^{a22}$, NHOR$^{a22}$, C(O)R$^{b22}$, C(O)NR$^{c22}$R$^{d22}$, C(O)NR$^{c22}$(OR$^{a22}$), C(O)

OR$^{a22}$, OC(O)R$^{b22}$, OC(O)NR$^{c22}$R$^{d22}$, NR$^{c22}$R$^{d22}$, NR$^{c22}$NR$^{d22}$, NR$^{c22}$C(O)R$^{b22}$, NR$^{c22}$C(O)OR$^{a22}$, NR$^{c22}$C(O)NR$^{c22}$R$^{d22}$, C(=NR$^{e22}$)R$^{b22}$, C(=NR$^{e22}$)NR$^{c22}$R$^{d2}$, NR$^{22}$C(=NR$^{e22}$)NR$^{c22}$R$^{d22}$, NR$^{c22}$C(=NR$^{e22}$)R$^{b22}$, NR$^{c22}$S(O)R$^{b22}$, NR$^{c22}$S(O)NR$^{c22}$R$^{d22}$, NR$^{c22}$S(O)$_2$R$^{b22}$, NR$^{c22}$S(O)(=NR$^{e22}$)R$^{b22}$, NR$^{c22}$S(O)$_2$NR$^{c22}$R$^{d22}$, S(O)R$^{b22}$, S(O)NR$^{c22}$R$^{d22}$, S(O)$_2$R$^{b22}$, S(O)$_2$NR$^{c22}$R$^{d22}$, OS(O)(=NR$^{e22}$)R$^{b22}$, and OS(O)$_2$R$^{b22}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{2B}$ are each optionally substituted with 1, 2, 3, 4, 5, 6, 7, or 8 independently selected R$^{2C}$ substituents;

each R$^{a22}$, R$^{c22}$, and R$^{d22}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a22}$, R$^{c22}$ and R$^{d22}$ are each optionally substituted with 1, 2, 3, 4, 5, 6, 7, or 8 independently selected R$^{2C}$ substituents;

or, any R$^{c22}$ and R$^{d22}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected R$^{2C}$ substituents;

each R$^{b22}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b22}$ are each optionally substituted with 1, 2, 3, 4, 5, 6, 7, or 8 independently selected R$^{2C}$ substituents;

each R$^{e22}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{2C}$ is independently selected from halo, oxo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a23}$, SR$^{a23}$, NHOR$^{a23}$, C(O)R$^{b23}$, C(O)NR$^{23}$R$^{d23}$, C(O)NR$^{23}$(OR$^{a23}$), C(O)OR$^{a23}$, OC(O)

$R^{b23}$, OC(O)NR$^{c23}$R$^{d23}$, NR$^{c23}$R$^{d23}$, NR$^{c23}$NR$^{c23}$R$^{d23}$, NR$^{c23}$C(O)R$^{b23}$, NR$^{c23}$C(O)OR$^{a23}$, NR$^{c23}$C(O)NR$^{c23}$R$^{23}$, C(=NR$^{e23}$)R$^{b23}$, C(=NR$^{e23}$)R$^{23}$R$^{d23}$, NR$^{c23}$C(=NR$^{e23}$)NR$^{c23}$R$^{d23}$, NR$^{c23}$C(=NR$^{e23}$)R$^{b23}$, NR$^{c23}$S(O)R$^{b23}$, NR$^{c23}$S(O)NR$^{c23}$R$^{23}$, NR$^{e23}$S(O)$_2$R$^{b23}$, NR$^{e23}$S(O)(=NR$^{e23}$)R$^{b23}$, NR$^{c23}$S(O)$_2$NR$^{c23}$R$^{d23}$, S(O)R$^{b23}$, S(O)NR$^{c23}$R$^{d23}$, S(O)$_2$R$^{b23}$, S(O)$_2$NR$^{c23}$R$^{d23}$, OS(O)(=NR$^{e23}$)R$^{b23}$, and OS(O)$_2$R$^{b23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{2C}$ are each optionally substituted with 1, 2, 3, or 4 independently selected $R^M$ substituents;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a23}$, $R^{e23}$ and $R^{d23}$ are each optionally substituted with 1, 2, 3, or 4 independently selected $R^M$ substituents;

or, any $R^{c23}$ and $R^{d23}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b23}$ are each optionally substituted with 1, 2, 3, or 4 independently selected $R^M$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a3}$, SR$^{a3}$, NHOR$^{a3}$, C(O)R$^{b3}$, C(O)NR$^{c3}$R$^{d3}$, C(O)NR$^{c3}$(OR$^{a3}$), C(O)OR$^{a3}$, OC(O)R$^{b3}$, OC(O)NR$^{c3}$R$^{d3}$, NR$^{c3}$R$^{d3}$, NR$^{c3}$NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(NR$^{e3}$)NR$^{c3}$R$^{d3}$, NR$^{c3}$C(=NR$^{e3}$)R$^{b3}$, NR$^{c3}$S(O)R$^{b3}$, NR$^{c3}$S(O)NR$^{c3}$R$^{d3}$, NR$^{c3}$S(O)$_2$R$^{b3}$, NR$^{c3}$S(O)(=NR$^{e3}$)R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, OS(O)(=NR$^{e3}$)R$^{b3}$, and OS(O)$_2$R$^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a31}$, SR$^{a31}$, NHOR$^{a31}$, C(O)R$^{b31}$, C(O)NR$^{c31}$R$^{d31}$, C(O)NR$^{c31}$(OR$^{a31}$), C(O)OR$^{a31}$, OC(O)R$^{b31}$, OC(O)NR$^{c31}$R$^{d31}$, NR$^{b31}$R$^{d31}$, NR$^{c31}$NR$^{c31}$R$^{d31}$, NR$^{c31}$C(O)R$^{b31}$, NR$^{c31}$C(O)OR$^{a31}$, NR$^{c31}$C(O)NR$^{c31}$R$^{d31}$, C(=NR$^{e31}$)R$^{b31}$, C(=NR$^{e31}$)NR$^{c31}$R$^{d31}$, NR$^{c31}$C(=NR$^{e31}$NR$^{c31}$R$^{d31}$, NR$^{c31}$C(=NR$^{e31}$)R$^{b31}$, NR$^{c31}$S(O)R$^{b31}$, NR$^{c31}$S(O) NR$^{b31}$R$^{d31}$, NR$^{c31}$S(O)$_2$R$^{b31}$, NR$^{c31}$S(O)(=NR$^{e31}$)

$R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$C(O)$R^{b32}$, C(O)NR$^{c32}$R$^{d32}$, C(O)NR$^{32}$(OR$^{a32}$), C(O)OR$^{a32}$, OC(O)R$^{b32}$, OC(O)NR$^{c32}$R$^{d32}$ NR$^{c32}$R$^{d32}$, NR$^{c32}$NR$^{c32}$R$^{d32}$, NR$^{b32}$C(O)R$^{b32}$, NR$^{c62}$C(O)OR$^{a32}$, NR$^{32}$C(O)NR$^{c32}$R$^{d32}$, C(=NR$^{e32}$)R$^{b32}$, C(=NR$^{e32}$)NR$^{c32}$R$^{d32}$, NR$^{c32}$C(=NR$^{e32}$NR$^{c32}$R$^{d32}$, NR$^{e32}$C(=NR$^{e32}$)R$^{b32}$, NR$^{e32}$S(O)R$^{b32}$, NR$^{e32}$S(O)NR$^{e32}$R$^{d32}$, NR$^{e32}$S(O)$_2$R$^{b32}$, NR$^{c32}$S(O)(=NR$^{e32}$) $R^{b32}$, NR$^{c32}$S(O)$_2$NR$^{c32}$R$^{d32}$, S(O)R$^{b32}$, S(O)NR$^{c32}$R$^{d32}$, S(O)$_2$R$^{b32}$, S(O)$_2$NR$^{c32}$R$^{d32}$, OS(O)(=NR$^{e32}$)R$^{b32}$, and OS(O)$_2$R$^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, OR$^{a33}$, SR$^{a33}$, NHOR$^{a33}$, C(O)R$^{b33}$, C(O)NR$^{c33}$R$^{d33}$, C(O)NR$^{c33}$(OR$^{a33}$), C(O)OR$^{a33}$, OC(O)R$^{b33}$, OC(O)NR$^{c33}$R$^{d33}$, NR$^{c33}$R$^{d33}$, NR$^{c33}$NR$^{c33}$R$^{d33}$, NR$^{c33}$C(O)R$^{b33}$, NR$^{c33}$C(O)OR$^{a33}$, NR$^{c33}$C(O) NR$^{c33}$R$^{d33}$, C(=NR$^{e33}$)R$^{b33}$, C(=NR$^{e33}$)NR$^{c33}$R$^{d33}$, NR$^{c33}$C(=NR$^{e33}$)NR$^{c33}$R$^{d33}$, NR$^{b33}$C(=NR$^{e33}$)R$^{b33}$, NR$^{c33}$S(O)R$^{b33}$, NR$^{c33}$S(O)NR$^{b33}$R$^{d33}$, NR$^{c33}$S(O)$_2$R$^{b33}$, NR$^{c33}$S(O)(=NR$^{e33}$)R$^{b33}$, NR$^{c33}$S(O)$_2$ $NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, 6, 7, or 8 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{c4}$ and $R^{d4}$ are each optionally substituted with 1, 2, 3, 4, 5, 6, 7, or 8 independently selected $R^{4A}$ substituents;

or, any $R^{c4}$ and $R^{d4}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4A}$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b4}$ are each optionally substituted with 1, 2, 3, 4, 5, 6, 7, or 8 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}C(=NR^{e41})R^{b41}$, $NR^{c41}S(O)R^{b41}$, $NR^{c41}S(O)NR^{c41}R^{d41}$, $NR^{c41}S(O)_2R^{41}$, $NR^{c41}S(O)(=NR^{e41})R^{41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, $OS(O)(=NR^{e41})R^{41}$, and $OS(O)_2R^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, 4, 5, 6, 7, or 8 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, 4, 5, 6, 7, or 8 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b41}$ are each optionally substituted with 1, 2, 3, 4, 5, 6, 7, or 8 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $NHOR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}NR^{c42}R^{d42}$, $NR^{c42}C(O)R^{b42}$, $NR^{c42}C(O)OR^{a42}$, $NR^{c42}C(O)NR^{c42}R^{d42}$, $C(=NR^{e42})R^{b42}$, $C(=NR^{e42})NR^{c42}R^{d42}$, $NR^{42}C(=NR^{e42})NR^{c42}R^{d42}$, $NR^{c42}C(=NR^{e42})R^{b42}$, $NR^{c42}S(O)R^{b42}$, $NR^{c42}S(O)NR^{e42}R^{d42}$, $NR^{c42}S(O)_2R^{b42}$, $NR^{c42}S(O)(=NR^{e42})R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, $OS(O)(=NR^{e42})R^{b42}$, and $OS(O)_2R^{b42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, 4, 5, 6, 7, or 8 independently selected $R^{4C}$ substituents;

each $R^{a42}$, $R^{42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{c42}$ and $R^{a42}$ are each optionally substituted with 1, 2, 3, 4, 5, 6, 7, or 8 independently selected $R^{4C}$ substituents;

or, any $R^{c42}$ and $R^{d42}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{4C}$ substituents;

each $R^{b42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b42}$ are each optionally substituted with 1, 2, 3, 4, 5, 6, 7, or 8 independently selected $R^{4C}$ substituents;

each $R^{e42}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a43}$, $SR^{a43}$, $NHOR^{a43}$, $C(O)R^{b43}$, $C(O)NR^{c43}R^{d43}$, $C(O)NR^{c43}(OR^{a43})$, $C(O)OR^{a43}$, $OC(O)R^{b43}$, $OC(O)NR^{c43}R^{d43}$, $NR^{c43}R^{d43}$ $NR^{c43}NR^{c43}R^{d43}$, $NR^{c43}C(O)R^{b43}$, $NR^{c43}C(O)OR^{a43}$, $NR^{c43}C(O)NR^{c43}R^{d43}$, $C(=NR^{e43})R^{b43}$, $C(=NR^{e43})NR^{c43}R^{d43}$, $NR^{c43}C(=NR^{e43})NR^{c43}R^{d43}$, $NR^{c43}C(=NR^{e43})R^{b43}$, $NR^{c43}S(O)R^{b43}$, $NR^{c43}S(O)NR^{c43}R^{d43}$, $NR^{c43}S(O)_2R^{b43}$, $NR^{c43}S(O)(=NR^{e43})R^{b43}$, $NR^{c43}S(O)_2NR^{c43}R^{d43}$, $S(O)R^{b43}$, $S(O)NR^{c43}R^{d43}$, $S(O)_2R^{b43}$, $S(O)_2NR^{c43}R^{d43}$, $OS(O)(=NR^{e43})R^{b43}$, and $OS(O)_2R^{b43}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{4C}$ are each optionally substituted with 1, 2, 3, or 4 independently selected $R^M$ substituents;

each $R^{a43}$, $R^{c43}$, and $R^{d43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a43}$, $R^{c43}$ and $R^{d43}$ are each optionally substituted with 1, 2, 3, or 4 independently selected $R^M$ substituents;

or, any $R^{c43}$ and $R^{d43}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected $R^M$ substituents;

each $R^{b43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{43}$ are each optionally substituted with 1, 2, 3, or 4 independently selected $R^M$ substituents;

each $R^{e43}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^5$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{5A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a51}$, SR$^{a51}$, NHOR$^{a51}$, C(O)R$^{b51}$, C(O)NR$^{c51}$R$^{d51}$, C(O)NR$^{c51}$(OR$^{a51}$), C(O)OR$^{a51}$, OC(O)R$^{b51}$, OC(O)NR$^{c51}$R$^{d51}$, NR$^{c51}$R$^{d51}$, NR$^{c51}$NR$^{c51}$R$^{d51}$, NR$^{c51}$C(O)R$^{b51}$, NR$^{c51}$C(O)OR$^{a51}$, NR$^{c51}$C(O)NR$^{c51}$R$^{d51}$, C(=NR$^{e51}$)R$^{b51}$, C(=NR$^{e51}$)NR$^{c51}$R$^{d51}$, NR$^{c51}$C(=NR$^{e51}$)NR$^{c51}$R$^{d51}$, NR$^{c51}$C(=NR$^{e51}$)R$^{b51}$, NR$^{c51}$S(O)R$^{b51}$, NR$^{c51}$S(O)NR$^{c51}$R$^{d51}$, NR$^{c51}$S(O)$_2$R$^{b51}$, NR$^{c51}$S(O)(=NR$^{e51}$)R$^{b51}$, NR$^{c51}$S(O)$_2$NR$^{c51}$R$^{d51}$, S(O)R$^{b51}$, S(O)NR$^{c51}$R$^{d51}$, S(O)$_2$R$^{b51}$, S(O)$_2$NR$^{c51}$R$^{d51}$, OS(O)(=NR$^{e51}$)R$^{b51}$, and OS(O)$_2$R$^{b51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, 4, 5, 6, 7, or 8 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, 4, 5, 6, 7, or 8 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, 4, 5, 6, 7, or 8 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a52}$, SR$^{a52}$, NHOR$^{a52}$, C(O)R$^{b52}$, C(O)NR$^{c52}$R$^{d52}$, C(O)NR$^{c52}$(OR$^{a52}$), C(O)OR$^{a52}$, OC(O)R$^{b52}$, OC(O)NR$^{c52}$R$^{d52}$, NR$^{c52}$R$^{d52}$, NR$^{c52}$NR$^{c52}$R$^{d52}$, NR$^{c52}$C(O)R$^{b52}$, NR$^{c52}$C(O)OR$^{a52}$, NR$^{c52}$C(O)NR$^{c52}$R$^{d52}$, C(=NR$^{e52}$)R$^{b52}$, C(=NR$^{e52}$)NR$^{c52}$R$^{d52}$, NR$^{c52}$C(=NR$^{e52}$)NR$^{c52}$R$^{d52}$ NR$^{c52}$C (=NR$^{e52}$)R$^{b52}$, NR$^{c52}$S(O)R$^{b52}$, NR$^{c52}$S(O)NR$^{c52}$R$^{d52}$, NR$^{c52}$S(O)$_2$R$^{b52}$, NR$^{c52}$S(O)(=NR$^{e52}$)R$^{b52}$, NR$^{c52}$S(O)$_2$NR$^{c52}$R$^{d52}$, S(O)R$^{b52}$, S(O)NR$^{c52}$R$^{d52}$, S(O)$_2$R$^{b52}$, S(O)$_2$NR$^{c52}$R$^{d52}$, OS(O)(=NR$^{e52}$)R$^{b52}$, and OS(O)$_2$R$^{b52}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{5B}$ are each optionally substituted with 1, 2, 3, 4, 5, 6, 7, or 8 independently selected R$^{5C}$ substituents;

each R$^{a52}$, R$^{c52}$, and R$^{d52}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a52}$, R$^{c52}$ and R$^{d52}$ are each optionally substituted with 1, 2, 3, 4, 5, 6, 7, or 8 independently selected R$^{5C}$ substituents;

or, any R$^{e52}$ and R$^{d52}$ attached to the same N atom, together with the N atom to which they are attached, form a 5-10 membered heteroaryl or a 4-10 membered heterocycloalkyl group, wherein the 5-10 membered heteroaryl and 4-10 membered heterocycloalkyl group are each optionally substituted with 1, 2, 3, or 4 independently selected R$^{5C}$ substituents;

each R$^{b52}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b52}$ are each optionally substituted with 1, 2, 3, 4, 5, 6, 7, or 8 independently selected R$^{5C}$ substituents;

each R$^{e52}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{5C}$ is independently selected from halo, oxo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a53}$, SR$^{a53}$, NHOR$^{a53}$, C(O)R$^{b53}$, C(O)NR$^{c53}$R$^{d53}$, C(O)NR$^{c53}$(OR$^{a53}$), C(O)OR$^{a53}$, OC(O)R$^{b53}$, OC(O)NR$^{c53}$R$^{d53}$, NR$^{c53}$R$^{d53}$, NR$^{c53}$NR$^{c53}$R$^{d53}$, NR$^{c53}$C(O)R$^{b53}$, NR$^{c53}$C(O)OR$^{a53}$, NR$^{c53}$C(O)NR$^{c53}$R$^{d53}$, C(=NR$^{e53}$)R$^{b53}$, C(=NR$^{e53}$)NR$^{c53}$R$^{d53}$, NR$^{c53}$C(=NR$^{e53}$NR$^{c53}$R$^{d53}$, NR$^{c53}$C(=NR$^{e53}$)R$^{b53}$, NR$^{c53}$S(O)R$^{b53}$, NR$^{c53}$S(O)NR$^{c53}$R$^{d53}$, NR$^{c53}$S(O)$_2$R$^{b53}$, NR$^{c53}$S(O)(=NR$^{e53}$)R$^{53}$, NR$^{c53}$S(O)$_2$NR$^{c53}$R$^{d53}$, S(O)R$^{b53}$, S(O)NR$^{c53}$R$^{d53}$, S(O)$_2$R$^{b53}$, S(O)$_2$NR$^{c53}$R$^{d53}$, OS(O)(=NR$^{e53}$)R$^{b53}$, and OS(O)$_2$R$^{b53}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{5C}$ are each optionally substituted with 1, 2, 3, or 4 independently selected R$^{M}$ substituents;

each R$^{a53}$, R$^{c53}$, and R$^{d53}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a53}$, R$^{c53}$ and R$^{d53}$ are each optionally substituted with 1, 2, 3, or 4 independently selected R$^{M}$ substituents;

or, any R$^{c53}$ and R$^{d53}$ attached to the same N atom, together with the N atom to which they are attached, form a 5-6 membered heteroaryl or a 4-7 membered heterocycloalkyl group, wherein the 5-6 membered heteroaryl and 4-7 membered heterocycloalkyl group are each optionally substituted with 1, 2, 3, or 4 independently selected R$^{M}$ substituents;

each R$^{b53}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{b53}$ are each optionally substituted with 1, 2, 3, or 4 independently selected R$^{M}$ substituents;

each R$^{e53}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-; and each R$^{M}$ is independently selected from H, OH, halo, oxo, CN, C(O)OH, NH$_2$, NO$_2$, SF$_5$, C$_{1-6}$ alkyl, C$_{1-6}$ alkoxy, C$_{1-6}$ haloalkoxy, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-.

2. The compound of claim 1, or a pharmaceutically acceptable salt thereof, wherein R$^1$ is selected from H, C$_{1-6}$ alkyl, C$_{1-6}$ haloalkyl, C$_{2-6}$ alkenyl, and C$_{2-6}$ alkynyl.

3. The compound of claim 1, or a pharmaceutically acceptable salt thereof, wherein R$^1$ is selected from H and C$_{1-6}$ alkyl.

4. The compound of claim 1, or a pharmaceutically acceptable salt thereof, wherein $R^1$ is selected from H, methyl, and ethyl.

5. The compound of claim 1, or a pharmaceutically acceptable salt thereof, wherein $R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, $C(O)OR^{a2}$, and $NR^{c2}R^{d2}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents.

6. The compound of claim 1, or a pharmaceutically acceptable salt thereof, wherein $R^2$ is selected from H, phenyl, $C_{3-6}$ cycloalkyl, 5-6 membered heteroaryl, 5-6 membered heterocycloalkyl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (8-10 membered heterocycloalkyl)-$C_{1-6}$ alkyl-, CN, $C(O)NR^{c2}R^{d2}$, and $NR^{c2}R^{d2}$, wherein the phenyl, $C_{3-6}$ cycloalkyl, 5-6 membered heteroaryl, 5-6 membered heterocycloalkyl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (8-10 membered heterocycloalkyl)-$C_{1-6}$ alkyl- of $R^2$ are each optionally substituted with 1, 2, 3, or 4 independently selected $R^{2A}$ substituents.

7. The compound of claim 1, or a pharmaceutically acceptable salt thereof, wherein $R^2$ is selected from H, phenyl, pyrrolidinyl, piperidinyl, benzodioxolyl, dihydrobenzodioxinyl, pyrazolyl, tetrazolyl, oxa-azaspiro[4.5]decanyl, isoxazolyl, pyridinyl, CN, $C(O)NR^{c2}R^{d2}$, and $NR^{c2}R^{d2}$, wherein the phenyl, pyrrolidinyl, piperidinyl, benzodioxolyl, dihydrobenzodioxinyl, oxa-azaspiro[4.5]decanyl, isoxazolyl, and pyridinyl of $R^2$ are each optionally substituted with 1, 2, 3, or 4 independently selected $R^{2A}$ substituents.

8. The compound of claim 1, or a pharmaceutically acceptable salt thereof, wherein each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $C(O)R^{b21}$, $C(O)NR^{c21}R^{d21}$, $C(O)OR^{a21}$, and $S(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents.

9. The compound of claim 1, or a pharmaceutically acceptable salt thereof, wherein each $R^{2A}$ is independently selected from halo, $C_{1-6}$ alkyl, $C_{1-6}$ haloalkyl, 5-6 membered heteroaryl, CN, $NO_2$, $OR^{a1}$, $C(O)R^{b21}$, $C(O)OR^{a21}$, and $S(O)_2R^{b21}$, wherein the $C_{1-6}$ alkyl and 5-6 membered heteroaryl of $R^{2A}$ are each optionally substituted with 1, 2, 3, or 4 independently selected $R^{2B}$ substituents, wherein each $R^{a21}$ and $R^{b21}$ is independently selected from H, $C_{1-6}$ alkyl, $C_{1-6}$ haloalkyl, $C_{2-6}$ alkenyl, and $C_{2-6}$ alkynyl, and wherein the $C_{1-6}$ alkyl of $R^{a1}$ and $R^{b21}$ are each optionally substituted with 1, 2, 3, 4, 5, 6, 7, or 8 independently selected $R^{2B}$ substituents.

10. The compound of claim 1, or a pharmaceutically acceptable salt thereof, wherein each $R^{2A}$ is independently selected from chloro, fluoro, methyl, trifluoromethyl, methoxy, cyanomethyl, pyrazolyl, tetrazolyl, tetrazolylmethyl, CN, $NO_2$, $C(O)CH_3$, $C(O)OH$, methylsulfonyl, and methoxyethylsulfonyl, wherein the pyrazolyl and tetrazolyl of $R^{2A}$ are each optionally substituted with 1 or 2 independently selected $C_{1-6}$ alkyl substituents.

11. The compound of claim 1, or a pharmaceutically acceptable salt thereof, wherein $R^2$ is selected from H, phenyl, benzodioxolyl, dihydrobenzodioxinyl, and CN, wherein the phenyl, benzodioxolyl, and dihydrobenzodioxinyl of $R^2$ are each optionally substituted with 1, 2, 3, or 4 $R^{2A}$ substituents independently selected from chloro, fluoro, methyl, trifluoromethyl, methoxy, pyrazolyl, tetrazolyl, CN, $NO_2$, and $C(O)OH$, wherein the pyrazolyl and tetrazolyl of $R^{2A}$ are each optionally substituted with 1 or 2 independently selected $C_{1-6}$ alkyl substituents.

12. The compound of claim 1, or a pharmaceutically acceptable salt thereof, wherein $R^3$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 4-10 membered heterocycloalkyl, and $OR^{a3}$, wherein the $C_{6-10}$ aryl, $C_{3-10}$ cycloalkyl, and 4-10 membered heterocycloalkyl of $R^3$ are each optionally substituted with 1, 2, 3, 4, 5, 6, 7, or 8 independently selected $R^{3A}$ substituents.

13. The compound of claim 1, or a pharmaceutically acceptable salt thereof, wherein $R^3$ is selected from H, methyl, ethyl, methoxy, phenyl, cyclohexyl, pyrrolidino, and tetrahydropyranyl, wherein the phenyl, cyclohexyl, and pyrrolidino of $R^3$ are each optionally substituted with 1, 2, 3, or 4 independently selected $R^{3A}$ substituents.

14. The compound of claim 1, or a pharmaceutically acceptable salt thereof, wherein $R^3$ is selected from H, methyl, ethyl, and methoxy.

15. The compound of claim 1, or a pharmaceutically acceptable salt thereof, wherein $R^4$ is selected from H, $C_{1-6}$ alkyl, $C_{1-6}$ haloalkyl, $C_{2-6}$ alkenyl, $C_{2-6}$ alkynyl, $C_{6-10}$ aryl, and 5-10 membered heteroaryl, wherein the $C_{1-6}$ alkyl, $C_{2-6}$ alkenyl, $C_{2-6}$ alkynyl, $C_{6-10}$ aryl, and 5-10 membered heteroaryl of $R^4$ are each optionally substituted with 1, 2, 3, 4, 5, 6, 7, or 8 independently selected $R^{4A}$ substituents.

16. The compound of claim 1, or a pharmaceutically acceptable salt thereof, wherein $R^4$ is selected from H, $C_{1-6}$ alkyl, phenyl, and indazolyl, wherein the phenyl and indazolyl of $R^4$ are each optionally substituted with methyl, methoxy, cyanocyclopropyl, or $C(O)N(CH_3)_2$.

17. The compound of claim 1, or a pharmaceutically acceptable salt thereof, wherein $R^4$ is H.

18. The compound of claim 1, or a pharmaceutically acceptable salt thereof, wherein $R^5$ is selected from phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of $R^5$ are each optionally substituted with 1, 2, 3, or 4 independently selected $R^{5A}$ substituents.

19. The compound of claim 1, or a pharmaceutically acceptable salt thereof, wherein $R^5$ is selected from phenyl and pyrazolyl, wherein the phenyl and pyrazolyl of $R^5$ are each optionally substituted by 1 or 2 independently selected $R^{5A}$ substituents.

20. The compound of claim 1, or a pharmaceutically acceptable salt thereof, wherein each $R^{5A}$ is independently selected from $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents.

21. The compound of claim 1, or a pharmaceutically acceptable salt thereof, wherein each $R^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1, 2, 3, or 4 independently selected $R^{5B}$ substituents.

22. The compound of claim 1, or a pharmaceutically acceptable salt thereof, wherein each $R^{5A}$ is piperidinylmethyl, which is optionally substituted by 1 or 2 independently selected $R^{5B}$ groups.

23. The compound of claim 1, or a pharmaceutically acceptable salt thereof, wherein each $R^{5B}$ is independently selected from $C(O)R^{b52}$, $C(O)NR^{e52}R^{d52}$, $C(O)OR^{a52}$, $NR^{c52}S(O)R^{b52}$, $NR^{c52}S(O)_2R^{b52}$, $S(O)R^{b52}$, $S(O)NR^{e52}R^{d52}$, $S(O)_2R^{b52}$, and $S(O)_2NR^{e52}R^{d52}$.

24. The compound of claim 1, or a pharmaceutically acceptable salt thereof, wherein each $R^{a52}$, $R^{b52}$, $R^{c52}$, and $R^{d52}$ is independently selected from H and $C_{1-6}$ alkyl.

25. The compound of claim 1, or a pharmaceutically acceptable salt thereof, wherein each $R^{5B}$ is $S(O)_2R^{b52}$, wherein each $R^{b52}$ is independently selected from H and $C_{1-6}$ alkyl.

26. The compound of claim 1, or a pharmaceutically acceptable salt thereof, wherein each $R^{5B}$ is methylsulfonyl.

27. The compound of claim 1, or a pharmaceutically acceptable salt thereof, wherein $R^5$ is selected from pyrazolyl and phenyl, wherein the pyrazolyl and phenyl are each optionally substituted by methyl or piperidinylmethyl, wherein the piperidinylmethyl is optionally substituted by methylsulfonyl.

28. The compound of claim 1, or a pharmaceutically acceptable salt thereof, wherein:
$R^1$ is selected from H, $C_{1-6}$ alkyl, $C_{1-6}$ haloalkyl, $C_{2-6}$ alkenyl, and $C_{2-6}$ alkynyl;
$R^2$ is selected from H, halo, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $C(O)R^{b2}$, $C(O)NR^{c2}R^{d2}$, and $C(O)OR^{a}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;
each $R^{a2}$, $R^{b2}$, $R^{c3}$, and $R^{d2}$ is independently selected from H, $C_{1-6}$ alkyl, $C_{1-6}$ haloalkyl, $C_{2-6}$ alkenyl, and $C_{2-6}$ alkynyl;
each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $C(O)R^{b21}$, $C(O)NR^{c21}R^{d21}$, and $C(O)OR^{a21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;
each $R^{a21}$, $R^{b21}$, $R^{e21}$, and $R^{d21}$ is independently selected from H, $C_{1-6}$ alkyl, $C_{1-6}$ haloalkyl, $C_{2-6}$ alkenyl, and $C_{2-6}$ alkynyl;
each $R^{2B}$ is independently selected from $C_{1-6}$ alkyl, $C_{1-6}$ haloalkyl, $C_{2-6}$ alkenyl, and $C_{2-6}$ alkynyl;
$R^3$ is selected from H, $C_{1-6}$ alkyl, $C_{1-6}$ haloalkyl, $C_{2-6}$ alkenyl, $C_{2-6}$ alkynyl, and $OR^{a3}$;
$R^{a3}$ is selected from H, $C_{1-6}$ alkyl, $C_{1-6}$ haloalkyl, $C_{2-6}$ alkenyl, and $C_{2-6}$ alkynyl;
$R^4$ is selected from H, $C_{1-6}$ alkyl, $C_{1-6}$ haloalkyl, $C_{2-6}$ alkenyl, and $C_{2-6}$ alkynyl;
$R^5$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;
each $R^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;
each $R^{5B}$ is independently selected from $C(O)R^{b52}$, $C(O)NR^{e52}R^{d52}$, $C(O)OR^{a52}$, $NR^{c52}S(O)R^{b52}$, $NR^{c52}S(O)_2R^{b52}$, $S(O)R^{b52}$, $S(O)NR^{e52}R^{d52}$, $S(O)_2R^{b52}$, and $S(O)_2NR^{e52}R^{d52}$; and
each $R^{a52}$, $R^{b52}$, $R^{c52}$, and $R^{d52}$ is independently selected from H and $C_{1-6}$ alkyl.

29. The compound of claim 1, or a pharmaceutically acceptable salt thereof, wherein:
$R^1$ is selected from H, $C_{1-6}$ alkyl, $C_{1-6}$ haloalkyl, $C_{2-6}$ alkenyl, and $C_{2-6}$ alkynyl;
$R^2$ is selected from H, phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (8-10 membered heterocycloalkyl)-$C_{1-6}$ alkyl-, and CN, wherein the phenyl, $C_{3-6}$ cycloalkyl, 5-6 membered heteroaryl, 8-10 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (8-10 membered heterocycloalkyl)-$C_{1-6}$ alkyl- of $R^2$ are each optionally substituted with 1, 2, 3, or 4 independently selected $R^{2A}$ substituents;

each R$^{2A}$ is independently selected from halo, C$_{1-6}$ alkyl, C$_{1-6}$ haloalkyl, 5-6 membered heteroaryl, CN, NO$_2$, OR$^{a21}$, and C(O)OR$^{a21}$, wherein the C$_{1-6}$ alkyl and 5-6 membered heteroaryl of R$^{2A}$ are each optionally substituted with 1, 2, 3, or 4 independently selected R$^{2B}$ substituents;

each R$^{a21}$ is independently selected from H, C$_{1-6}$ alkyl, C$_{1-6}$ haloalkyl, C$_{2-6}$ alkenyl, and C$_{2-6}$ alkynyl;

R$^3$ is selected from H, C$_{1-6}$ alkyl, C$_{1-6}$ haloalkyl, C$_{2-6}$ alkenyl, C$_{2-6}$ alkynyl, and OR$^{a3}$;

R$^{a3}$ is selected from H, C$_{1-6}$ alkyl, C$_{1-6}$ haloalkyl, C$_{2-6}$ alkenyl, and C$_{2-6}$ alkynyl;

R$^4$ is selected from H, C$_{1-6}$ alkyl, C$_{1-6}$ haloalkyl, C$_{2-6}$ alkenyl, and C$_{2-6}$ alkynyl;

R$^5$ is selected from phenyl, C$_{3-6}$ cycloalkyl, 5-6 membered heteroaryl, and 4-6 membered heterocycloalkyl, wherein the phenyl, C$_{3-6}$ cycloalkyl, 5-6 membered heteroaryl, and 4-6 membered heterocycloalkyl of R$^5$ are each optionally substituted with 1, 2, 3, or 4 independently selected R$^{5A}$ substituents;

each R$^{5A}$ is independently selected from phenyl-C$_{1-6}$ alkyl-, C$_{3-6}$ cycloalkyl-C$_{1-6}$ alkyl-, (5-6 membered heteroaryl)-C$_{1-6}$ alkyl-, and (4-6 membered heterocycloalkyl)-C$_{1-6}$ alkyl-, wherein the phenyl-C$_{1-6}$ alkyl-, C$_{3-6}$ cycloalkyl-C$_{1-6}$ alkyl-, (5-6 membered heteroaryl)-C$_{1-6}$ alkyl-, and (4-6 membered heterocycloalkyl)-C$_{1-6}$ alkyl- of R$^{5A}$ are each optionally substituted with 1, 2, 3, or 4 independently selected R$^{51}$ substituents;

each R$^{5B}$ is independently selected from S(O)R$^{b52}$ and S(O)$_2$R$^{b52}$; and each R$^{b52}$ is independently selected from H and C$_{1-6}$ alkyl.

30. The compound of claim 1, or a pharmaceutically acceptable salt thereof, wherein:

R$^1$ is selected from H and C$_{1-6}$ alkyl;

R$^2$ is selected from H, phenyl, benzodioxolyl, dihydrobenzodioxinyl, and CN, wherein the phenyl, benzodioxolyl, and dihydrobenzodioxinyl of R$^2$ are each optionally substituted with 1, 2, 3, or 4 independently selected R$^{2A}$ substituents;

R$^{2A}$ is independently selected from chloro, fluoro, methyl, trifluoromethyl, methoxy, pyrazolyl, tetrazolyl, CN, NO$_2$, and C(O)OH, wherein the pyrazolyl and tetrazolyl of R$^{2A}$ are each optionally substituted with 1 or 2 independently selected C$_{1-6}$ alkyl substituents;

R$^3$ is selected from H, C$_{1-6}$ alkyl, and C$_{1-6}$ alkoxy;

R$^4$ is selected from H and C$_{1-6}$ alkyl;

R$^5$ is phenyl, which is optionally substituted by piperidinylmethyl, wherein the piperidinylmethyl is optionally substituted by S(O)$_2$R$^{b52}$; and each R$^{b52}$ is independently selected from H and C$_{1-6}$ alkyl.

31. The compound of claim 1, wherein the compound of Formula I is a compound of Formula II:

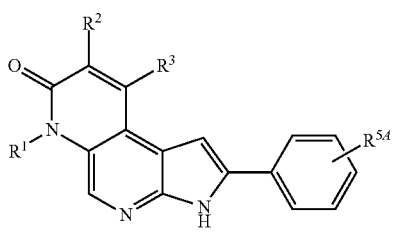

II or a pharmaceutically acceptable salt thereof.

32. The compound of claim 1, wherein the compound of Formula I is a compound of Formula III:

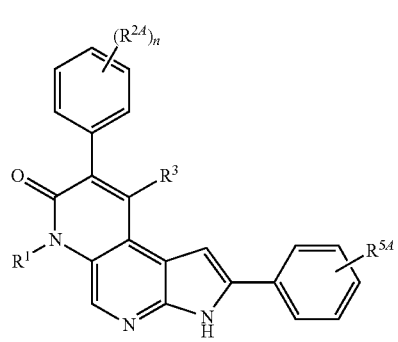

III or a pharmaceutically acceptable salt thereof, wherein n is 0, 1, 2, 3, or 4.

33. The compound of claim 1, wherein the compound of Formula I is a compound of Formula IV:

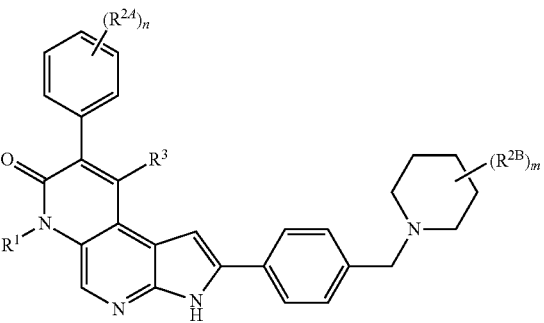

IV or a pharmaceutically acceptable salt thereof, wherein:

n is 0, 1, 2, 3, or 4; and m is 0, 1 or 2.

34. The compound of claim 1, which is selected from:

2-(4-((4-(methylsulfonyl)piperidin-1-yl)methyl)phenyl)-8-phenyl-3,6-dihydro-7H-pyrrolo[3,2-f][1,7]naphthyridin-7-one;

4-(2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

2-(4-((4-(methylsulfonyl)piperidin-1-yl)methyl)phenyl)-7-oxo-6,7-dihydro-3H-pyrrolo[3,2-f][1,7]naphthyridine-8-carbonitrile;

8-(1-methyl-1H-pyrazol-5-yl)-2-(4-((4-(methylsulfonyl)piperidin-1-yl)methyl)phenyl)-3,6-dihydro-7H-pyrrolo[3,2-f][1,7]naphthyridin-7-one;

2-(4-((4-(methylsulfonyl)piperidin-1-yl)methyl)phenyl)-8-(1H-tetrazol-5-yl)-3,6-dihydro-7H-pyrrolo[3,2-f][1,7]naphthyridin-7-one;

4-(9-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

8-(4-(1H-tetrazol-1-yl)phenyl)-9-methyl-2-(4-((4-(methylsulfonyl)piperidin-1-yl)methyl)phenyl)-3,6-dihydro-7H-pyrrolo[3,2-f][1,7]naphthyridin-7-one;

4-(6,9-dimethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;

6,9-dimethyl-2-(4-((4-(methylsulfonyl)piperidin-1-yl)methyl)phenyl)-8-(p-tolyl)-3,6-dihydro-7H-pyrrolo[3,2-f][1,7]naphthyridin-7-one;
8-(4-chlorophenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one;
8-(3-chlorophenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one;
8-(4-methoxyphenyl)-6,9-dimethyl-2-(4-((4-(methylsulfonyl)piperidin-1-yl)methyl)phenyl)-3,6-dihydro-7H-pyrrolo[3,2-f][1,7]naphthyridin-7-one;
4-(6,9-dimethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzonitrile;
4-(6-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;
4-(6-ethyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;
4-(9-ethyl-6-methyl-2-(4-((4-(methylsulfonyl)piperidin-1-yl)methyl)phenyl)-7-oxo-6,7-dihydro-3H-pyrrolo[3,2-f][1,7]naphthyridin-8-yl)benzoic acid;
9-methyl-2-(4-((4-(methylsulfonyl)piperidin-1-yl)methyl)phenyl)-3,6-dihydro-7H-pyrrolo[3,2-f][1,7]naphthyridin-7-one;
9-methyl-2-(4-((4-(methylsulfonyl)piperidin-1-yl)methyl)phenyl)-8-(4-nitrophenyl)-3,6-dihydro-7H-pyrrolo[3,2-f][1,7]naphthyridin-7-one;
8-(2,3-dihydrobenzo[b][1,4]dioxin-6-yl)-9-methyl-2-(4-((4-(methylsulfonyl)piperidin-1-yl)methyl)phenyl)-3,6-dihydro-7H-pyrrolo[3,2-f][1,7]naphthyridin-7-one; and
9-methoxy-6-methyl-2-(4-((4-(methylsulfonyl)piperidin-1-yl)methyl)phenyl)-8-phenyl-3,6-dihydro-7H-pyrrolo[3,2-f][1,7]naphthyridin-7-one;
or a pharmaceutically acceptable salt thereof.

35. The compound of claim 1, which is selected from:
6-Methyl-8-(3-methylisoxazol-5-yl)-2-(4-((4-(methylsulfonyl)piperidin-1-yl)methyl)phenyl)-9-(tetrahydro-2H-pyran-4-yl)-3,6-dihydro-7H-pyrrolo[3,2-f][1,7]naphthyridin-7-one;
9-(4-Methoxycyclohexyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;
6-methyl-2-(1-methyl-1H-pyrazol-4-yl)-8-(3-methylisoxazol-5-yl)-9-phenyl-3,6-dihydro-7H-pyrrolo[3,2-f][1,7]naphthyridin-7-one;
9-(4-methoxycyclohexyl)-6-methyl-2-(1-methyl-1H-pyrazol-4-yl)-3,6-dihydro-7H-pyrrolo[3,2-f][1,7]naphthyridin-7-one;
N-(2-hydroxyethyl)-4-(6-methyl-2-(1-methyl-1H-pyrazol-4-yl)-8-(3-methylisoxazol-5-yl)-7-oxo-6,7-dihydro-3H-pyrrolo[3,2-f][1,7]naphthyridin-9-yl)benzamide;
4-(6-Methyl-2-(1-methyl-1H-pyrazol-4-yl)-8-(3-methylisoxazol-5-yl)-7-oxo-6,7-dihydro-3H-pyrrolo[3,2-f][1,7]naphthyridin-9-yl)-N-(2-methylbenzo[d]oxazol-5-yl)benzamide;
9-(4-(Methoxymethyl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;
6-Methyl-2-(1-methyl-1H-pyrazol-4-yl)-8-(3-methylisoxazol-5-yl)-9-(4-(((tetrahydro-2H-pyran-3-yl)amino)methyl)phenyl)-3,6-dihydro-7H-pyrrolo[3,2-f][1,7]naphthyridin-7-one;
9-(4-((2-Methoxyethyl)(methyl)amino)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;
6-Methyl-2-(1-methyl-1H-pyrazol-4-yl)-8-(3-methylisoxazol-5-yl)-9-(4-((tetrahydro-2H-pyran-4-yl)amino)phenyl)-3,6-dihydro-7H-pyrrolo[3,2-f][1,7]naphthyridin-7-one;
9-(4-(1,5-Dimethyl-1H-pyrazol-4-yl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;
9-(4-(5-(Hydroxymethyl)-1-methyl-1H-pyrazol-4-yl)phenyl)-6-methyl-2-(1-methyl-1H-pyrazol-4-yl)-8-(3-methylisoxazol-5-yl)-3,6-dihydro-7H-pyrrolo[3,2-f][1,7]naphthyridin-7-one;
6-Methyl-2-(1-methyl-1H-pyrazol-4-yl)-8-(3-methylisoxazol-5-yl)-9-(1-(methylsulfonyl)pyrrolidin-3-yl)-3,6-dihydro-7H-pyrrolo[3,2-f][1,7]naphthyridin-7-one;
4-(8-((3-(1H-tetrazol-5-yl)phenyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide;
4-(8-((4-((1H-tetrazol-5-yl)methyl)phenyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide;
N,N-dimethyl-4-(6-methyl-2-(1-methyl-1H-pyrazol-4-yl)-8-(4-methylpyridin-3-yl)-7-oxo-6,7-dihydro-3H-pyrrolo[3,2-f][1,7]naphthyridin-1-yl)benzamide;
(R)-8-(1-acetylpyrrolidin-3-yl)-6-methyl-2-(4-((4-(methylsulfonyl)piperidin-1-yl)methyl)phenyl)-1-phenyl-3,6-dihydro-7H-pyrrolo[3,2-f][1,7]naphthyridin-7-one;
4-(8-((4-(cyanomethyl)cyclohexyl)amino)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide;
N,N-dimethyl-4-(6-methyl-2-(1-methyl-1H-pyrazol-4-yl)-8-(4-(methylsulfonyl)piperidin-1-yl)-7-oxo-6,7-dihydro-3H-pyrrolo[3,2-f][1,7]naphthyridin-1-yl)benzamide;
4-(8-(4-((2-Methoxyethyl)sulfonyl)piperidin-1-yl)-6-methyl-2-(1-methyl-1H-pyrazol-4-yl)-7-oxo-6,7-dihydro-3H-pyrrolo[3,2-f][1,7]naphthyridin-1-yl)-N,N-dimethylbenzamide;
N,N-dimethyl-4-(6-methyl-2-(1-methyl-1H-pyrazol-4-yl)-7-oxo-8-(2-oxa-8-azaspiro[4.5]decan-8-yl)-6,7-dihydro-3H-pyrrolo[3,2-f][1,7]naphthyridin-1-yl)benzamide;
1-(4-Methoxyphenyl)-N,N,6-trimethyl-2-(1-methyl-1H-pyrazol-4-yl)-7-oxo-6,7-dihydro-3H-pyrrolo[3,2-f][1,7]naphthyridine-8-carboxamide;
N,N,6-trimethyl-1-(1-methyl-1H-indazol-5-yl)-2-(1-methyl-1H-pyrazol-4-yl)-7-oxo-6,7-dihydro-3H-pyrrolo[3,2-f][1,7]naphthyridine-8-carboxamide; and
1-(4-(1-cyanocyclopropyl)phenyl)-N,N,6-trimethyl-2-(1-methyl-1H-pyrazol-4-yl)-7-oxo-6,7-dihydro-3H-pyrrolo[3,2-f][1,7]naphthyridine-8-carboxamide;
or a pharmaceutically acceptable salt thereof.

36. The compound of claim 1, or a pharmaceutically acceptable salt thereof, which is deuterated.

37. A pharmaceutical composition, comprising a compound of claim 1, or a pharmaceutically acceptable salt thereof, and a pharmaceutically acceptable carrier.

\* \* \* \* \*

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Biotin-labeled peptide, custom synthesis

<400> SEQUENCE: 1

Glu Gln Glu Asp Glu Pro Glu Gly Asp Tyr Phe Glu Trp Leu Glu
1               5                   10                  15